(12) United States Patent
Desantis et al.

(10) Patent No.: US 11,787,778 B2
(45) Date of Patent: Oct. 17, 2023

(54) BI-FUNCTIONAL COMPOUNDS AND METHODS FOR TARGETED UBIQUITINATION OF ANDROGEN RECEPTOR

(71) Applicant: MONTELINO THERAPEUTICS, INC., Southborough, MA (US)

(72) Inventors: Jenny Desantis, Foligno (IT); Roy Joseph Vaz, Southborough, MA (US)

(73) Assignee: MONTELINO THERAPEUTICS, INC., Southborough, MA (US)

( * ) Notice: Subject to any disclaimer, the term of this patent is extended or adjusted under 35 U.S.C. 154(b) by 32 days.

(21) Appl. No.: 17/331,940

(22) Filed: May 27, 2021

(65) Prior Publication Data
US 2021/0292298 A1  Sep. 23, 2021

Related U.S. Application Data

(63) Continuation of application No. 16/777,294, filed on Jan. 30, 2020, now Pat. No. 11,098,025.

(60) Provisional application No. 62/798,554, filed on Jan. 30, 2019.

(51) Int. Cl.
| | |
|---|---|
| *C07D 401/04* | (2006.01) |
| *C07D 417/14* | (2006.01) |
| *C07D 417/04* | (2006.01) |
| *C07D 417/12* | (2006.01) |
| *A61K 45/06* | (2006.01) |

(52) U.S. Cl.
CPC ......... *C07D 401/04* (2013.01); *C07D 417/04* (2013.01); *C07D 417/12* (2013.01); *C07D 417/14* (2013.01); *A61K 45/06* (2013.01)

(58) Field of Classification Search
CPC .................. C07D 401/04; C07D 417/04
See application file for complete search history.

(56) References Cited

U.S. PATENT DOCUMENTS

| | | |
|---|---|---|
| 6,306,663 B1 | 10/2001 | Kenten et al. |
| 6,888,241 B1 | 5/2005 | Korn et al. |
| 9,993,514 B2 | 6/2018 | Campos et al. |
| 10,112,968 B2 | 10/2018 | Olhava et al. |
| 11,098,025 B2 | 8/2021 | Desantis et al. |
| 11,220,490 B2 | 1/2022 | Fan et al. |
| 2014/0356322 A1 | 12/2014 | Crews et al. |
| 2016/0214972 A1 | 7/2016 | Jin et al. |
| 2017/0008904 A1 | 1/2017 | Crew et al. |
| 2017/0183319 A1 | 6/2017 | Tcherkassov et al. |
| 2017/0218353 A1 | 8/2017 | Petter et al. |
| 2017/0327469 A1 | 11/2017 | Crew et al. |
| 2018/0099940 A1 | 4/2018 | Crew et al. |
| 2018/0118733 A1 | 5/2018 | Harling et al. |
| 2018/0134688 A1 | 5/2018 | Casillas et al. |
| 2018/0346461 A1 | 12/2018 | Arvinas |
| 2019/0192668 A1 | 6/2019 | Mainolfi et al. |
| 2020/0095205 A1 | 3/2020 | Crew et al. |
| 2020/0172927 A1 | 6/2020 | Tsang et al. |
| 2020/0142228 A1 | 7/2020 | Hong et al. |
| 2020/0239430 A1 | 7/2020 | Desantis et al. |
| 2020/0282068 A1 | 9/2020 | Desantis et al. |
| 2021/0171470 A1 | 6/2021 | Crew et al. |
| 2021/0198280 A1 | 7/2021 | Kelly et al. |
| 2021/0292298 A1 | 9/2021 | Desantis et al. |
| 2023/0132823 A1 | 5/2023 | Desantis et al. |

FOREIGN PATENT DOCUMENTS

| | | |
|---|---|---|
| WO | WO 2015/120543 | 8/2015 |
| WO | WO 2016/105518 A1 | 6/2016 |
| WO | WO 2017/007612 | 1/2017 |
| WO | WO 2017/176957 A1 | 10/2017 |
| WO | WO 2017/197056 | 11/2017 |
| WO | WO 2018/114781 | 6/2018 |
| WO | WO 2020/102575 | 5/2020 |

OTHER PUBLICATIONS

Antonarakis, E. et al., "AR-V7 and Resistance to Enzalutamide and Abiraterone in Prostate Cancer," New England, Journal of Medicine, 371(11):1028-1038 (2014).
Chamberlain, Philip P., "Cereblon modulators: Low molecular weight inducers of protein degradation," Drug Discovery Today: Technologies, vol. 31, 2019, pp. 29-34.
Chopra, Rajesh, "A critical evaluation of the approaches to targeted protein degradation for drug discovery," Drug Discovery Today: Technologies, vol. 31, 2019, pp. 5-13.
Churcher, Ian, "Protac-Induced Protein Degradation in Drug Discovery: Breaking the Rules or Just Making New Ones?," Journal of Medicinal Chemistry, 2018, 61, pp. 444-452.

(Continued)

*Primary Examiner* — Kamal A Saeed
(74) *Attorney, Agent, or Firm* — Hoxie & Associates LLC

(57) ABSTRACT

The present invention relates to bi-functional compounds which function to recruit endogenous proteins to an E3 ubiquitin ligase for degradation, and methods for using same. More specifically, the present disclosure provides specific proteolysis targeting chimera (PROTAC) molecules which find utility as modulators of targeted ubiquitination of a variety of polypeptides and other proteins, in particular the androgen receptor of a slice variant of AR which lacks the LBD, labelled as AR-V7, which are then degraded and/or otherwise inhibited by the compounds as described herein.

19 Claims, 1 Drawing Sheet

(56) References Cited

OTHER PUBLICATIONS

Crews, Craig M., "Targeting the Undruggable Proteome: The Small Molecules of My Dreams," Chemistry & Biology 17, Jun. 25, 2010, pp. 551-555.
Dalal, Kush, "Selectively targeting the dimerization interface of human androgen receptor with small-molecules to treat castration-resistant prostate cancer," Elsevier, Cancer Letters 437, 2018, pp. 35-43.
Dalal, Kush, "Bypassing Drug Resistance Mechanisms of Prostate Cancer with Small Molecules that Target Androgen Receptor-Chromatin Interactions," Molecular Cancer Therapeutics, 2017, 16, 2281-2291.
Dehm, S.M. et al., "Alternatively Spliced Androgen Receptor Variants," Endocr Relat Cancer. 2011, 18(5): R183-R196.
Han, Ting, "Anticancer sulfonamides target splicing by inducing RBM39 degradation via recruitment to DCAF15," Science, 2017, 356, 397.
Hansen, Joshua D., "Protein Degradation via CRL4CRBN Ubiquitin Ligase: Discovery and Structure-Activity Relationships of Novel Glutarimide Analogs That Promote Degradation of Aiolos and/or GSPT1," Journal of Medicinal Chemistry, 2018, 61, 492-503.
Hines, John, "MDM2-Recruiting PROTAC Offers Superior, Synergistic Antiproliferative Activity via Simultaneous Degradation of BRD4 and Stabilization of p53," American Association for Cancer Research, 2019, 79, pp. 251-262.
Hunter, Allison M., "The inhibitors of apoptosis (IAPs) as cancer targets," Science+Business Media, 2007, 12, pp. 1543-1598.
International Search Report and Written Opinion of International Application No. PCT/US2020/15922, prepared by the International Searching Authority, dated Mar. 30, 2020, 13 pages.
Itoh, Yukihiro, "Double protein knockdown of cIAP1 and CRABP-II using a hybrid molecule consisting of ATRA and APs antagonist," Bioorganic & Medicinal Chemistry Letters 22, 2012, 4453-4457.
Li, Huifang, "Discovery of Small-Molecule Inhibitors Selectively Targeting the DNA-Binding Domain of the Human Androgen Receptor," Journal of Medicinal Chemistry, 2014, 57, 6458-6467 {correction included}.
Li, Huifang, "Correction to Discovery of Small-Molecule Inhibitors Selectively Targeting the DNA-Binding Domain of the Human Androgen Receptor," Journal of Medicinal Chemistry, 2014, 57, pp. 6458-6467 (Correction).
Naito, Mikihiko, "SNIPERs—Hijacking IAP activity to induce protein degradation," Drug Discovery Today: Technologies, J019, vol. 31, pp. 35-42.
Ohoka, Nobumichi, "In Vivo Knockdown of Pathogenic Proteins via Specific and Nongenetic Inhibitor of Apoptosis Protein (IAP)—dependent Protein Erasers (SNIPERs)," Journal of Biological Chemistry, 2017, vol. 292, No. 11, 1556-4570.
Pettersson, Mariell, "PROteolysis Targeting Chimeras (PROTACs)—Past, present and future," Drug Discovery Today Technologies, 2019, vol. 31, pp. 15-27.
PubChem CID 132260110, Date Created: Jan. 29, 2018, Obtained from the Internet: May 27, 2020, 8 pages. URL: <https://pubchem.ncbi.nlm.nih.gov/compound/132260110>.
Rodriguez-Gonzalez, A., "Targeting steroid hormone receptors for ubiquitination and degradation in breast and prostate cancer," Oncogene, 2008, 27, pp. 7201-7211.
Shibata, Norihito, "Development of Protein Degradation Inducers of Androgen Receptor by Conjugation of Androgen Receptor Ligands and Inhibitor of Apoptosis Protein Ligands," Journal of Medicinal Chemistry, 2018, 61, 543-575.
Sievers, Quinlan, L., "Defining the human C2H2 zinc-finger degrome targeted by thalidomide analogs through CRBN," Science, 2018, 362.
Skalniak, Lukasz, A therapeutic patent overview of MDM2/X-targeted therapies (2014-2018), Expert Opinion on Therapeutic Patents, 2019.
Soares, Pedro, "Group-Based Optimization of Potent and Cell-Active Inhibitors of the von Hippel-Lindau (VHL) E3 Ubiquitin Ligase: Structure—Activity Relationships Leading to the Chemical Probe (2S,4R)-1-((S)-2-(1-Cyanocyclopropanecarboxamido)-3,3-dimethylbutanoyl-4-hydroxy-N-(4-(4-methylthiazol-5-yl)benzyl)pyrrolidine-2-carboxamide (VH298)," Journal of Medicinal Chemistry, 2018, 61, 599-618.
Alabi et al., "Major advances in targeted protein degradation: PROTACs, LYTACs, and MADTACs", J. Biol. Chem., 296:100647, (2021).
Bond et al., "Proteolysis targeting chimeras (PROTACs) come of age: entering the third decade of targeted protein degradation", RSC Chemical Biology, 2:725-742, (2021).
Li et al., "Protein degradation technology: a strategic paradigm shift in drug discovery", Journal of Hematology & Oncology, 14:138, (2021).
Roth et al., "Advances in targeted degradation of endogenous proteins", Cellular and Molecular Life Sciences, 76:2761-2777, (2019).
Edmondson, R. J. et al., "The human ovarian surface epithelium is an androgen responsive tissue", Br. J Cancer 2002 86, 879-885.
Fang, Y. F. et al., "Hsp90 Regulates Androgen Receptor Hormone Binding Affinity in Vivo", J Biol. Chem. 1996 271 :28697-28702.
Frost, et al., "Potent and selective chemical probe of hypoxic signaling downstream of HIF-a hydroxylation via VHL inhibition", Nature Communications, 7:13312; pp. 1-12, (2016).
Gao, W. Q. et al., "Chemistry and Structural Biology of Androgen Receptor", Chem. Rev. 2005 105:3352-3370.
Risch, H. A, "Hormonal Etiology of Epithelial Ovarian Cancer, With a Hypothesis Concerning the Role of Androgens and Progesterone", J Natl. Cancer Inst. 1998 90, 1774-1786.
Tilley, W. D. et al., "Mutations in the androgen receptor gene are associated with progression of human prostate cancer to androgen independence", Cancer Res. 1994 54:4096-4102.
Varfolomeev et al., "IAP Antagonists Induce Autoubiquitination of c-IAPs, NF-kB Activation, and TNFa-Dependent Apoptosis", Cell, 131:4; pp. 669-681, (2007).
Wong, C. I. et al., "Steroid requirement for androgen receptor dimerization and DNA binding. Modulation by intramolecular interactions between the NH2-terminal and steroid-binding domains.", J Biol. Chem. 1993 268: 19004-19012.
Zhou, X. E. et al., "Identification of SRC3/AIB1 as a Preferred Coactivator for Hormone-activated Androgen Receptor", J Biol. Chem. 2010 285:9161-9171.

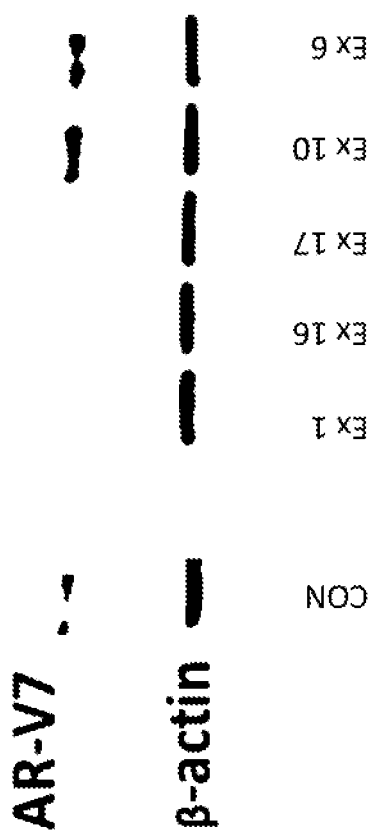

BI-FUNCTIONAL COMPOUNDS AND METHODS FOR TARGETED UBIQUITINATION OF ANDROGEN RECEPTOR

CROSS-REFERENCE TO RELATED APPLICATIONS

This application is a continuation of U.S. application Ser. No. 16/777,294, filed on Jan. 30, 2020, which claims priority to, and the benefit of, U.S. Provisional Application No. 62/798,554, filed on Jan. 30, 2019, the contents of each of which are hereby incorporated by reference in their entireties.

FIELD OF THE INVENTION

This invention relates to therapeutic compounds and compositions, and methods for their use in the treatment of various indications, including various cancers. In particular, the invention relates to therapies and methods of treatment for cancers such as prostate cancer.

BACKGROUND OF THE INVENTION

Prostate cancer is the most commonly diagnosed malignancy in males in the United States and the second leading cause of male cancer mortality. Numerous studies have shown that the androgen receptor (AR) is central not only to the development of prostate cancer, but also the progression of the disease to the castration resistance state (Taplin, M. E. et al., *J. Clin. Oncol.* 2003 21:2673-8; and Tilley, W. D. et al., *Cancer Res.* 1994 54:4096-4102). Thus, effective inhibition of human AR remains one of the most effective therapeutic approaches to the treatment of advanced, metastatic prostate cancer.

Androgens are also known to play a role in female cancers. One example is ovarian cancer where elevated levels of androgens are associated with an increased risk of developing ovarian cancer (Helzlsouer, K. J. et al., *JAMA* 1995 274, 1926-1930; Edmondson, R. J. et al., *Br. J. Cancer* 2002 86, 879-885). Moreover, AR has been detected in a majority of ovarian cancers (Risch, H. A., *J. Natl. Cancer Inst.* 1998 90, 1774-1786; Rao, B. R. et al., *Endocr. Rev.* 1991 12, 14-26; Clinton, G. M. et al., *Crit. Rev. Oncol. Hematol.* 1997 25, 1-9).

AR belongs to the nuclear hormone receptor family that is activated by androgens such as testosterone and dihydrotestosterone. These androgens, as well as antagonists such as enzalutamide, compete with the androgens that bind to the ligand binding domain (LBD). AR possesses a modular organization characteristic of all nuclear receptors. It is comprised of an N-terminal domain (NTD), a central DNA binding domain (DBD), a short hinge region, and C-terminal domain that contains a hormone ligand binding pocket (the LBD, which also comprises the hormone binding site (HBS)) and the Activation Function-2 (AF2) site (Gao, W. Q. et al., *Chem. Rev.* 2005 105:3352-3370). The latter represents a hydrophobic groove on the AR surface which is flanked with regions of positive and negative charges— "charge clamps" that are significant for binding AR activation factors (Zhou, X. E. et al., *J. Biol. Chem.* 2010 285: 9161-9171).

The activation of AR follows a well characterized pathway: in the cytoplasm, the receptor is associated with chaperone proteins that maintain agonist binding conformation of the AR (Georget, V. et al., *Biochemistry* 2002 41:11824-11831). Upon binding of an androgen, the AR undergoes a series of conformational changes, disassociation from chaperones, dimerization, and translocation into the nucleus (Fang, Y. F. et al., *J. Biol. Chem.* 1996 271: 28697-28702; and Wong, C. I. et al., *J. Biol. Chem.* 1993 268:19004-19012) where it further interacts with co-activator proteins at the AF2 site (Zhou, X. E. et al. *J. Biol. Chem.* 2010 285:9161-9171). This event triggers the recruitment of RNA polymerase II and other factors to form a functional transcriptional complex with the AR.

In castration-resistant prostate cancer (CRPC), drug resistance can manifest through AR-LBD mutations that convert AR-antagonists into agonists or by expression of AR-variants lacking the LBD. AR is a major driver of prostate cancer and inhibition of its transcriptional activity using competitive antagonists such as enzalutamide and apalutamide remains a frontline therapy for prostate cancer management. Another therapy is abiraterone which is an inhibitor of cytochrome P450 17A1 that impairs AR signaling by depleting adrenal and intratumoral testosterone and dihydrotestosterone. Recent work (Antonarakis, E. S. et al., *New Engl. J Med.* 2014 37, 1028-1038) has shown that patients on enzalutamide and abiraterone with a splice variant of AR, labelled as AR-V7, had lower PSA response rates, shorter PSA progression-free survival, and shorter overall survival.

AR-V7 lacks the LBD, which is the target of enzalutamide and testosterone, but AR-V7 remains constitutively active as a transcription factor. Accordingly, it is desirable to investigate other approaches to antagonize the AR receptor as well as AR-V7. The common domain between these two proteins is the DBD and compounds have been identified as discussed in Li, H. et al., *J. Med. Chem.* 2014 57, 6458-6467 (2014); Dalal, K. et al., *Mol. Cancer Ther.* 2017 vol. 16, 2281-2291; Xu, R. et al., *Chem. Biol. & Drug Design* 2018 91(1), 172-180; and WO 2015/120543.

Several methods are available for the manipulation of protein levels, including bi-functional proteolysis targeting chimeric molecules (PROTACs) which contain a ligand that recognizes the target protein that is linked to a ligand that binds to a specific E3 ubiquitin ligase. The ensuing bifunctional molecule binds to the target protein and the E3 ligase enabling the transfer of ubiquitin to the target protein from the Ligase provided there is a suitable acceptor on the target protein. Another method is the "molecular glue" process whereby the molecule together with the E3 ligase recruit the target protein to the E3 ligase followed by the ubiquitin transfer and degradation of the target (Chopra, R., Sadok, A., Collins, I., Drug Disc Today: Technologies, 2019, 31, 5-13.) In the case of a compound acting as a "molecular glue", the only requirement is the presence of an E3 ligase binding moiety. After binding to the E3 ligase, the ensuing moiety could recruit the protein to be degraded. The labelling of proteins with ubiquitin is implicated in the protein's turnover by the 26S proteasome.

Protein ubiquitination is a multi-step process whereby a ubiquitin protein is successively relayed between different classes of enzymes (E1, E2, E3) in order to eventually tag a cellular substrate. Initially, the C-terminal carboxylate of ubiquitin is adenylated by the E1 activating enzyme in an ATP-dependent step. Subsequently, a conserved nucleophilic cysteine residue of the E1 enzyme displaces the AMP from the ubiquitin adenylate resulting in a covalent ubiquitin thioester conjugate. The binding and ensuing adenylation of a second ubiquitin molecule promote the recruitment of an E2 conjugating enzyme to this ternary complex. An active site Cys on the E2 subsequently facilitates the transfer of the covalently linked ubiquitin from the E1 to a Cys residue on the E2 through a trans-thioesterification reaction. Concomitantly, an E3 ligase recruits a specific downstream target protein and mediates the transfer of the ubiquitin from the E2 enzyme to the terminal substrate through either a covalent or non-covalent mechanism. Each ubiquitin is ligated to a protein through either a peptide bond with the N-terminal amino group or an isopeptide bond formed between a side chain ε-amino group of a select Lys residue on the target protein and the ubiquitin.

Deubiquitinating enzymes (DUBs) are enzymes that specifically cleave the ubiquitin protein from the substrate thereby offering additional mechanisms of regulation over the entire labeling pathway. In the current human proteome there are eight known human E1s, about 40 E2s, over 600 E3s and over 100 DUBs. These enzymes are well described in Pavia, S. et al., *J. Med. Chem.* 2018 61(2), 405-421.

The E3 ligases originate in three major classes—the RING finger and U-box E3s, the HECT E3s, and the RING/HECT-hybrid type E3s. The E3 ligases are localized in various cell organelles and hence the effectiveness of the E3 ligase ligand depends at least in part on the location of the protein targeted for degradation, assuming that the full molecule is available within the appropriate location in the cell. In addition, for every combination of the target ligand and the ubiquitin recruiting ligand, the linker length and conformational flexibility also contributes to the effectiveness of the degradation molecule. The mechanism depends on the availability of a Lys residue on the surface of the protein close to the targeted protein ligand binding pocket. Ubiquitin binds at Lys residues and hence the "delivery" of ubiquitin for binding at the appropriate Lys influences the effectiveness of the degradation molecule. Crew et al. (US20170327469A1, US20180099940A1) are progressing a proposed treatment for castration-resistant prostate cancer based on bifunctional molecules coupling various E3 ligases to AR antagonists binding at the AR LBD site. Our approach is different in that we do not target the LBD site but the DBD site and, correspondingly, the chemical matter is quite different.

There exists a continuing need for effective treatments for diseases and conditions that are related to aberrant AR regulation or activity, for example, cancers such as prostate cancer, and Kennedy's Disease. In developing such treatments, it would be desirable to have a molecule which can simultaneously bind AR and an E3 ubiquitin ligase and which also promotes ubiquitination of AR-V7 and perhaps AR, and leads to degradation of AR-V7 and AR by the proteasome.

SUMMARY OF THE INVENTION

The present invention relates to bi-functional compounds which function to recruit endogenous proteins to an E3 ubiquitin ligase for degradation, and methods for using same. More specifically, the present disclosure provides specific proteolysis targeting chimera (PROTAC) molecules which find utility as modulators of targeted ubiquitination of a variety of polypeptides and other proteins, such as AR, which are then degraded and/or otherwise inhibited by the compounds as described herein.

In one aspect, these PROTAC molecules comprise an E3 ubiquitin ligase binding moiety (i.e., a ligand for an E3 ubiquitin ligase) linked to a moiety that binds a target protein (i.e., a protein/polypeptide targeting ligand) such that the target protein/polypeptide is placed in proximity to the ubiquitin ligase to effect degradation (and/or inhibition) of that protein. In addition, the description provides methods for using an effective amount of the compounds described herein for the treatment or amelioration of a disease condition including cancer, e.g., prostate cancer, and Kennedy's Disease.

Suitable ligands that bind to the E3 ubiquitin ligase include cereblon binders such as immunomodulatory imide drugs (IMiDs) including thalidomide, pomalidomide, and lenalidomide (Deshales, R. J., *Nature Chem Biol.* 2015 11, 634-635), and analogs or derivatives thereof. The IMiDs themselves act as "molecular glues" and therefore have been shown to recruit a different set of proteins for degradation (reference). In addition, we have uncovered an intermediate molecule that acts via the "molecular glue" mechanism. Other suitable E3 ubiquitin ligase binders are E3 CRL2$^{VHL}$ compounds, also called Von-Hippel-Lindau or VHL ligands, the cellular inhibitor of apoptosis protein (IAP) as discussed in Shibata, N. et al., *J. Med. Chem.*, 2018 61(2), 543-575. Binders of the E3 ligase Mouse Double Minute 2 (MDM2) comprise the fourth class of E3 Ligase Binders (E3LBs) that are utilized (Skalniak, L., et al., *Expert Opin. Ther, Patents,* 2019, 29, 151-170).

In one aspect, there are provided compositions comprising such compounds which function to recruit proteins including AR-V7 and AR for targeted ubiquitination and degradation. In some embodiments, the structure of such compounds can be depicted as:

wherein ARB is an AR binding moiety and E3LB is a ubiquitin ligase binding moiety.

In some embodiments, the compounds may further comprise a chemical linker ("L"). The structure of such compounds can be depicted as:

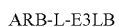

wherein ARB is an AR binding moiety, L is a bond or linker moiety, and E3LB is a ubiquitin ligase binding moiety.

In an additional aspect, the description provides therapeutic compositions comprising an effective amount of a compound as described herein or pharmaceutically acceptable salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation and/or inhibition of proteins of interest for the treatment or amelioration of a disease, e.g., cancer.

In another aspect, the present disclosure provides a method of ubiquitinating/degrading a target protein in a cell. In certain embodiments, the method comprises administering a bi-functional compound as described herein comprising an ARB moiety and a E3LB moiety, preferably linked through a linker moiety, as otherwise described herein, wherein the E3LB moiety is coupled to the ARB moiety and wherein the E3LB moiety recognizes an E3 ubiquitin ligase and the ARB moiety recognizes the target protein such that degradation of the target protein occurs when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In another aspect, the description provides methods for treating or ameliorating a disease, disorder or symptom thereof in a subject or a patient, e.g., an animal such as a human, comprising administering to a subject in need thereof a pharmaceutical composition comprising an effective amount, e.g., a therapeutically effective amount, of a compound as described herein or pharmaceutically acceptable salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present disclosure. The publications and other materials used herein to illuminate the background of the invention, and in particular cases, to provide additional details respecting the practice, are incorporated by reference. Where applicable or not specifically disclaimed, any one of the embodiments described herein are contemplated to be able to combine with any other one or more embodiments, even though the embodiments are described under different aspects of the disclosure.

BRIEF DESCRIPTION OF THE DRAWINGS

FIG. 1 is an immunoblot of certain exemplified compounds.

DETAILED DESCRIPTION

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

The present description relates to the surprising and unexpected discovery that an E3 ubiquitin ligase protein can ubiquitinate a target protein, in particular the androgen receptor of a slice variant of AR which lacks the LBD, labelled as AR-V7, once the E3 ubiquitin ligase protein and the target protein are brought into proximity by a chimeric construct (e.g., a PROTAC) as described herein, in which a moiety that binds the E3 ubiquitin ligase protein is coupled, e.g., covalently, to a moiety that binds the androgen receptor target protein. Accordingly, the present description provides compounds, compositions comprising the same, and associated methods of use for ubiquitination and degradation of a chosen target protein, e.g., androgen receptor AR-V7.

In one aspect, the present disclosure provides compounds useful for regulating protein activity. The composition comprises a ubiquitin pathway protein binding moiety (preferably for an E3 ubiquitin ligase, alone or in complex with an E2 ubiquitin conjugating enzyme which is responsible for the transfer of ubiquitin to targeted proteins) according to a defined chemical structure and a protein targeting moiety which are linked or coupled together, preferably through a linker, wherein the ubiquitin pathway protein binding moiety recognizes a ubiquitin pathway protein and the targeting moiety recognizes a target protein (e.g., androgen receptor). Such compounds may be referred to herein as PROTAC compounds or PROTACs.

In one aspect, the PROTACs of the present invention comprise an E3 ubiquitin ligase binding moiety ("E3LB"), and a moiety that binds a target protein (i.e. a protein/polypeptide targeting ligand) that is an AR binding moiety ("ARB"). In this embodiment, the structure of the bi-functional compound can be depicted as:

ARB-E3LB where ARB is an AR binding moiety as described herein, and E3LB is an E3 ligase binding moiety as described herein In certain embodiments the bi-functional compound further comprises a chemical linker ("L"). In these embodiments, the structure of the bi-functional compounds can be depicted as:

ARB-L-E3LB where ARB is an AR binding moiety as described herein, E3LB is an E3 ligase binding moiety as described herein, and L is a chemical linker moiety, e.g., a linker as described herein, or optionally a bond, that links the ARB and E3LB moieties.

The respective positions of the ARB and E3LB moieties as well as their number as illustrated herein is provided by way of example only and is not intended to limit the compounds in any way. As would be understood by the skilled artisan, the bi-functional compounds as described herein can be synthesized such that the number and position of the respective functional moieties can be varied as desired. In certain embodiments, the compounds as described herein comprise multiple E3LB moieties, multiple ARB moieties, multiple chemical linkers, or a combination thereof.

It will be understood that the general structures are exemplary and the respective moieties can be arranged spatially in any desired order or configuration, e.g., ARB-L-E3LB, and E3LB-L-ARB, respectively. The E3LB group and ARB group may be covalently linked to the linker group through any covalent bond which is appropriate and stable to the chemistry of the linker. It will be further understood that for all compounds described herein, one or more hydrogen atoms may be replaced with an equivalent number of deuterium atoms.

In certain embodiments, the ARB may be selected from the following structures:

ARB-a:

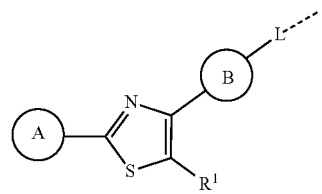

ARB-b:

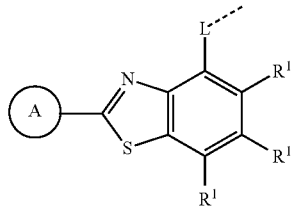

ARB-c:

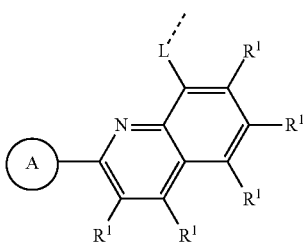

wherein L is the linker in the general formula above;

A is 3-7 membered alicyclic with 0-4 heteroatoms or aryl, heteroaryl independently substituted by 1 or more halo, hydroxyl, nitro, CN, C≡CH, $NR^2R^3$, $OCH_3$, $OC_{1-3}$ alkyl (optionally substituted by 1 or more halo), $CH_2F$, $CHF_2$, $CF_3$, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, 3-6 membered alicyclic with 0-4 heteroatoms and substituted by 1 or more halo, hydroxyl, nitro, CN, C≡CH, $CF_3$, $C_{1-6}$ alkyl (linear, branched, optionally substituted by 1 or more halo, $C_{1-6}$ alkoxy), $C_{1-6}$ alkoxy (linear, branched, optionally substituted by 1 or more halo), $C_{2-6}$ alkenyl, or $C_{2-6}$ alkynyl;

B is aryl, heteroaryl independently substituted by 1 or more halo, hydroxyl, nitro, CN, C≡CH, $NR^2R^3$, $OCH_3$, $OC_{1-3}$ alkyl (optionally substituted by 1 or more halo), $CF_3$, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, 3-6 membered alicyclic with 0-4 heteroatoms and substituted by 1 or more halo, hydroxyl, nitro, CN, C≡CH, $CF_3$, $C_{1-6}$ alkyl (linear, branched, optionally substituted by 1 or more halo, $C_{1-6}$ alkoxy), $C_{1-6}$ alkoxy (linear, branched, optionally substituted by 1 or more halo), $C_{2-6}$ alkenyl, or $C_{2-6}$ alkynyl, wherein the linker L is attached to B; and $R^1$ are independently H, OH, $CONH_2$, $CONR^2R^3$, $SONH_2$, $SONR^2R^3$, $SO_2NH_2$, $SO_2NR^2R^3$, NHCO $C_{1-3}$ alkyl (optionally substituted by 1 or more halo), $NR^2COC_{1-3}$ alkyl (optionally substituted by 1 or more halo), $NR^2SO_2C_{1-3}$ alkyl (optionally substituted by 1 or more halo), $NR^2SOC_{1-3}$ alkyl (optionally substituted by 1 or more halo), CN, C≡CH, $NH_2$, $NR^2R^3$, $OCH_3$, $OC_{1-3}$ alkyl (optionally substituted by 1 or more halo), $CHF_2$, $CH_2F$, $CF_3$, halo, $C_{1-6}$ alkyl (linear, branched, optionally substituted by 1 or more halo, $C_{1-6}$ alkoxyl) or, if applicable, taken together with an $R^1$ on an adjacent bonded atom, together with the atoms they are attached to, form a 3-6 membered ring alicyclic, aryl, or heteroaryl system containing 0-2 heteroatoms, and $R^2$, $R^3$ is independently H, halo, $C_{1-6}$ alkyl (optionally substituted by 1 or more F) or taken together with the atom they are attached to, form a 3-8 membered ring system containing 0-2 heteroatoms.

In one aspect, A is:

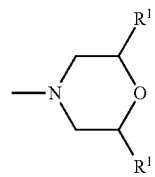

wherein $R^1$ is described above.

In another aspect, A is:

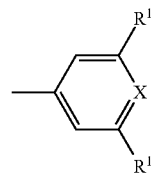

wherein $R^1$ is described above and X═C or N.

In yet another aspect, B is:

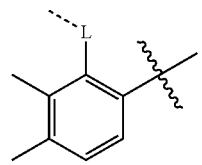

wherein L is the linker as described above, and $R^1$ is described above.

In still another aspect, B is:

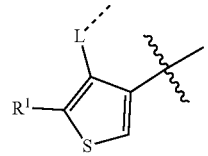

wherein L is the linker as described above, and $R^1$ is described above.

In yet another aspect, B is:

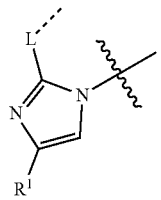

wherein L is the linker as described above, and $R^1$ is described above.

The linker group (L) comprises a chemical structural unit represented by the formula: $-A_q-$, in which q is an integer greater than 1; and A is independently selected from the group consisting of a bond, $CR^{L1}R^{L2}$, O, S, SO, $SO_2$, $NR^{L3}$ $SO_2NR^{L3}$ $SONR^{L3}$ $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^{L4}$, $C_{3-11}$ cycloalkyl optionally substituted with 0-6 $R^{L1}$ and/or $R^{L2}$ groups, and heteroaryl optionally substituted with 0-6 $R^{L1}$ and/or $R^{L2}$ groups, wherein $R^{L1}$, $R^{L2}$, $R^{L3}$, $R^{L4}$ and $R^{L5}$ are each independently selected from the group consisting of H, halo, $C_{1-8}$ alkyl, $OC_{1-8}$ alkyl, $SC_{1-8}$ alkyl, $NHC_{1-8}$ alkyl, $N(C_{1-8}$ alkyl$)_2$, $C_{3-11}$ cycloalkyl, aryl, heteroaryl, $C_{3-11}$ heterocyclyl, $OC_{1-8}$ cycloalkyl, $SC_{1-8}$ cycloalkyl, $NHC_{1-8}$ cycloalkyl, $N(C_{1-8}$cycloalkyl$)_2$, $N(C_{1-8}$ cycloalkyl)($C_{1-8}$ alkyl), OH, $NH_2$, SH, $SO_2C_{1-8}$ alkyl, $P(O)(OC_{1-8}$ alkyl)($C_{1-8}$ alkyl), $P(O)(OC_{1-8}$ alkyl$)_2$, CC—$C_{1-8}$ alkyl, CCH, CH=CH($C_{1-8}$ alkyl), $C(C_{1-8}$ alkyl)=CH($C_{1-8}$ alkyl), $C(C_{1-8}$ alkyl)=C($C_{1-8}$ alkyl$)_2$, $Si(OH)_3$, $SiC(i-s$ alkyl$)_3$, $Si(OH)(C_{1-8}$ alkyl$)_2$, $COC_{1-8}$ alkyl, $CO_2H$, CN, $CF_3$, $CHF_2$, $CH_2F$, $NO_2$, $SF_5$, $SO_2NHC_{1-8}$ alkyl, $SO_2NHC_{1-8}$ alkyl, $SO_2N(C_{1-8}$ alkyl$)_2$, $SONHC_{1-8}$ alkyl, $SON(C_{1-8}$ alkyl$)_2$, $CONHC_{1-8}$ alkyl, $CON(C_{1-8}$ alkyl$)_2$, $N(C_{1-8}$ alkyl)$CONH(C_{1-8}$ alkyl), $N(C_{1-8}$ alkyl)$CON(C_{1-8}$ alkyl$)_2$, $NHCONH(C_{1-8}$ alkyl), $NHCON(C_{1-8}$ alkyl$)_2$, $NHCONH_2$, $N(C_{1-8}$ alkyl)$SO_2NH(C_{1-8}$ alkyl), $N(C_{1-8}$ alkyl)$SO_2N(C_{1-8}$ alkyl$)_2$, $NHSO_2NH(C_{1-8}$ alkyl), $NHSO_2N(C_{1-8}$ alkyl$)_2$ and $NHSO_2NH_2$. $R^{L1}$ and $R^{L2}$ each, independently can be linked to another A group to form a cycloalkyl and or heterocyclyl moiety that can be further substituted with 0-4 $R^{L5}$ groups.

In certain embodiments, the E3LB moiety may be selected from a variety of moieties, including the following structures:

E3LB-a:

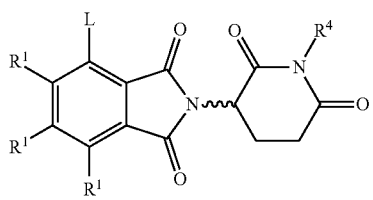

E3LB-b:

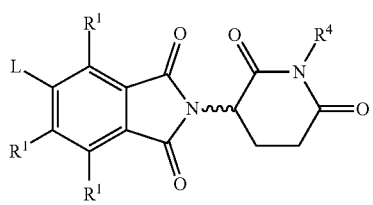

E3LB-c:

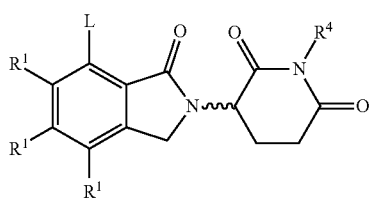

E3LB-d:

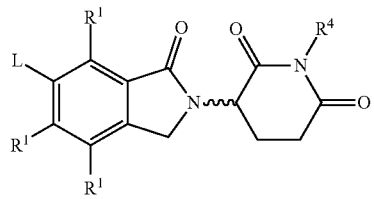

wherein "⁓" in the above structures, represents a bond that may be stereospecific ((R) or (S)), or non-stereospecific;

$R^1$ is described above;

$R^4$ is selected from the group consisting of H, alkyl (linear, branched, optionally substituted with $R^5$), OH, $R^5OCOOR^6$, $R^5OCONR^5R^7$, $CH_2$-heterocyclyl optionally substituted with $R^5$, or benzyl optionally substituted with $R^5$;

$R^5$ and $R^7$ are each independently a bond, H, alkyl (linear, branched), cycloalkyl, aryl, hetaryl heterocyclyl, or —C(=O)$R^6$ each of which is optionally substituted; and $R^6$ is selected from $CONR^5R^7$, $OR^5$, $NR^5R^7$, $SR^5$, $SO_2R^5$, $SO_2NR^5R^7$, $CR^5R^7$, $CR^5NR^5R^7$, aryl, hetaryl, alkyl (linear, branched, optionally substituted), cycloalkyl, heterocyclyl, $P(O)(OR^5)R^7$, $P(O)R^5R^7$, $OP(O)(OR^5)R^7$, $OP(O)R^5R^7$, Cl, F, Br, I, $CF_3$, $CHF_2$, $CH_2F$, CN, $NR^5SO_2NR^5R^7$, $NR^5CONR^5R^7$, $CONR^5COR^7$, $NR^5C(=N—CN)NR^5R^7$, $C(=N—CN)NR^5R^7$, $NR^5C(—N=CN)R^7$, $NR^5C(=C—NO_2)NR^5R^7$, $SO_2NR^5COR^7$, $NO_2$, $CO_2R^5$, $C(C=N—OR^5)R^7$, $CR^5$, $CR^5R^7$, $CCR^5$, $S(C=O)(C=N—R^5)R^7$, $SF_5$, $R^5NR^5R^7$, $(R^5O)_nR^7$, or $OCF_3$, where n is an integer from 1 to 10.

The E3LB moiety may also be selected from E3LB-e and E3LB-f as described below:

E3LB-e:

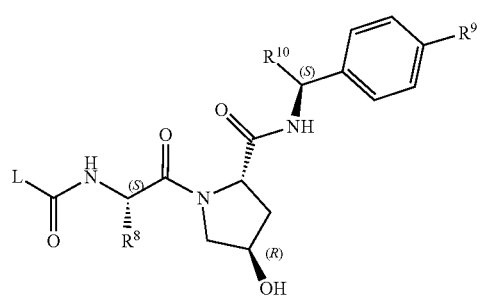

wherein L is the linker previously described; $R^8$ is H, a straight chain or branched $C_{1-8}$ alkyl, $C_{3-6}$ cycloalkyl, halo, $CFH_2$, $CF_2H$, or $CF_3$; and $R^9$ is a H, halo, 4-methylthiazol-5-ylm, or oxazol-5-yl.

E3LB-f:

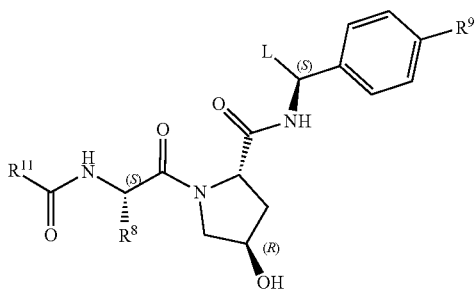

wherein L is the linker previously described and $R^{11}$ is independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heterocycloalkyl wherein the substituents are alkyl, halogen, or OH.

The E3LB moiety may also be selected from E3LB-g, E3LB-h, E3LB-i, E3LB-j, and E3LB-k as described below:

E3LB-g:

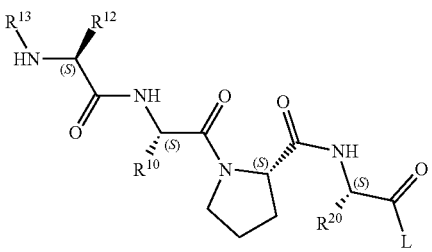

E3LB-h:

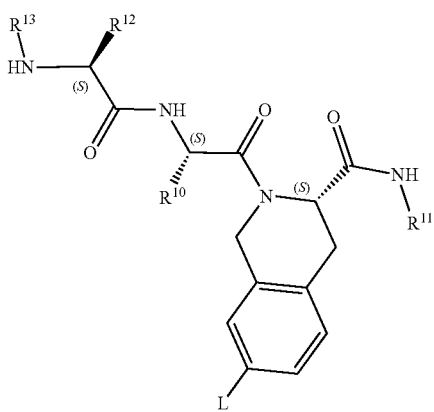

E3LB-i:

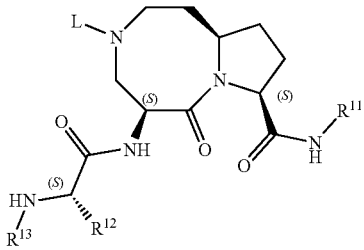

E3LB-j:

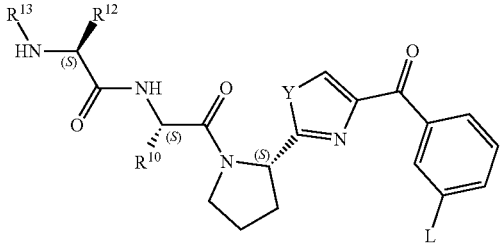

E3LB-k:

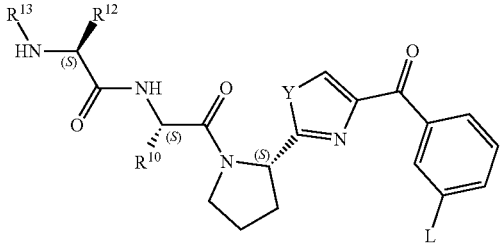

wherein L is the linker previously described;

$R^{10}$ are independently optionally substituted alkyl, optionally substituted cycloalkyl, optionally substituted cycloalkylalkyl, optionally substituted arylalkyl, optionally substituted aryl, optionally substituted thioalkyl wherein the substituents attached to the S atom of the thioalkyl are optionally substituted alkyl, optionally substituted branched alkyl, optionally substituted heterocyclyl, $(CH_2)_vCOR^{14}$, $CH_2CHR^{15}COR^{16}$ or $CH_2R^{17}$, where v=1 to 3; $R^{14}$ and $R^{16}$ are independently selected from OH, $NR^{18}R^{19}$, or $-OR^{20}$; $R^{15}$ is $-NR^{18}R^{19}$; $R^{17}$ is optionally substituted aryl or optionally substituted heterocyclyl, where the optional substituents include alkyl and halogen; $R^{18}$ is hydrogen or optionally substituted alkyl; $R^{19}$ is hydrogen, optionally substituted alkyl, optionally substituted branched alkyl, optionally substituted arylalkyl, optionally substituted heterocyclyl, $-CH_2(OCH_2CH_2O)_wCH_3$, or a polyamine chain, where w=1 to 8; and optional substituents may be OH, halo, or $NH_2$;

$R^{12}$ and $R^{13}$ are independently hydrogen, optionally substituted alkyl, or optionally substituted cycloalkyl;

X is $CH_2$, N, or O; Y is S or O;

D is a bond (direct bond between X and L) or a ring which may be aryl, heteroaryl independently substituted by 1 or more halo, hydroxyl, nitro, CN, C≡CH, $NR^2R^3$, $OCH_3$, $OC_{1-3}$ alkyl (optionally substituted by 1 or more halo), $CF_3$, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, 3-6 membered alicyclic with 0-4 heteroatoms and substituted by 1 or more halo, hydroxyl, nitro, CN, C≡CH, $CF_3$, $C_{1-6}$ alkyl (linear, branched, optionally substituted by 1 or more halo, $C_{1-6}$ alkoxy), $C_{1-6}$ alkoxy (linear, branched, optionally substituted by 1 or more halo), $C_{2-6}$ alkenyl, or $C_{2-6}$ alkynyl. $R^2$, $R^3$ is independently H, halo, $C_{1-6}$ alkyl (optionally substituted by 1 or more F) or taken together with the atom they are attached to, form a 3-8 membered ring system containing 0-2 heteroatoms; and $R^{20}$ is selected from the group consisting of:

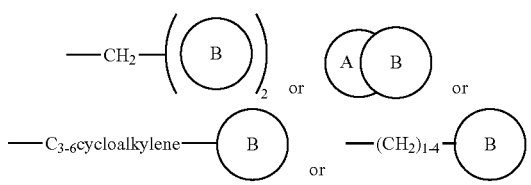

wherein A is a $C_{4-8}$ aliphatic ring, and B is an aryl or N-containing heteroaryl and optionally substituted by alkyl or haloalkyl.

Optionally, E3LB may be selected from the MDM2 class of E3 ligases represented by E3LB-1 below.

E3LB-1:

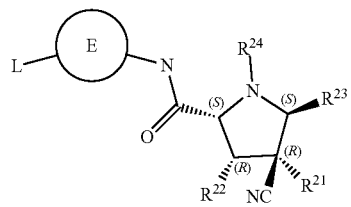

(R)

wherein $R^{22}$ is independently aryl or heteroaryl optionally substituted by halogen, mono-, di or tri-substituted halogen;

$R^{21}$ is independently aryl or heteroaryl, optionally substituted by mono-, di- or tri-substituted halogen, CN, ethynyl, cyclopropyl, methyl, ethyl, isopropyl, methoxy, ethoxy, isopropoxy, other $C_{1-6}$ alkyl, other $C_{1-6}$ alkenyl and $C_{1-6}$ alkynyl;

$R^{23}$ is selected from alkyl, substituted alkyl, alkenyl, substituted alkenyl, substituted alkynyl, aryl, substituted aryl, heteroaryl, substituted heteroaryl, cycloalkyl, substituted cycloalkyl, alkenyl and substituted cycloalkenyl;

$R^{24}$ is H, alkyl, aryl, substituted alkyl, cycloalkyl, aryl substituted cycloalkyl and alkoxy substituted cycloalkyl; and E is para-substituted aryl, single or multiple N containing heteroaryl optionally substituted by $-OCH_3$, $-OCH_2CH_3$ and halogen. L is the linker previously defined above.

The E3LB moiety is inclusive of all cereblon binders such as immunomodulatory imide drugs (IMiDs) including thalidomide, pomalidomide, and lenalidomide, and analogs or derivatives thereof, as well as E3 $CRL2^{VHL}$ compounds, the cellular inhibitor of apoptosis protein (IAP), and the mouse double minute 2 (MDM2) binders.

In certain embodiments, the compounds as described herein comprise a plurality of E3LB moieties and/or a plurality of ARB moieties. In certain additional embodiments, the compounds as described herein comprise multiple ARB moieties (targeting the same or different locations of the AR), multiple E3LB moieties, one or more moieties that bind specifically to another E3 ubiquitin ligase, e.g., VHL, IAP, MDM2, or a combination thereof. In any of the aspects of embodiments described herein, the ARB moieties, E3LB moieties, and other moieties that bind specifically to another E3 ubiquitin ligase can be coupled directly or via one or more chemical linkers or a combination thereof. In additional embodiments, where a compound has multiple moieties that bind specifically to another E3 ubiquitin ligase, the moieties can be for the same E3 ubiquitin ligase or each respective moiety can bind specifically to a different E3 ubiquitin ligase. In those embodiments where a compound has multiple ARB moieties, such moieties may be the same or, optionally, different.

In certain embodiments, where the compound comprises multiple E3LB moieties, the E3LB moieties are identical or, optionally, different. In additional embodiments, the compound comprising a plurality of E3LB moieties further comprises at least one ARB moiety coupled to a E3LB moiety directly or via a chemical linker ("L") or both. In certain additional embodiments, the compound comprising a plurality of E3LB moieties further comprises multiple ARB moieties. In still additional embodiments, the ARB moieties are the same or, optionally, different.

In certain embodiments, the compound is selected from the group consisting of the exemplary compounds as described below, and salts and polymorphs thereof:

Example 1

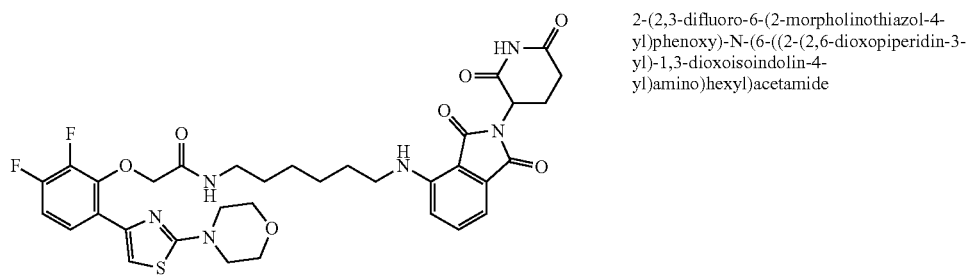

2-(2,3-difluoro-6-(2-morpholinothiazol-4-yl)phenoxy)-N-(6-((2-(2,6-dioxopiperidin-3-yl)-1,3-dioxoisoindolin-4-yl)amino)hexyl)acetamide -continued Example 2 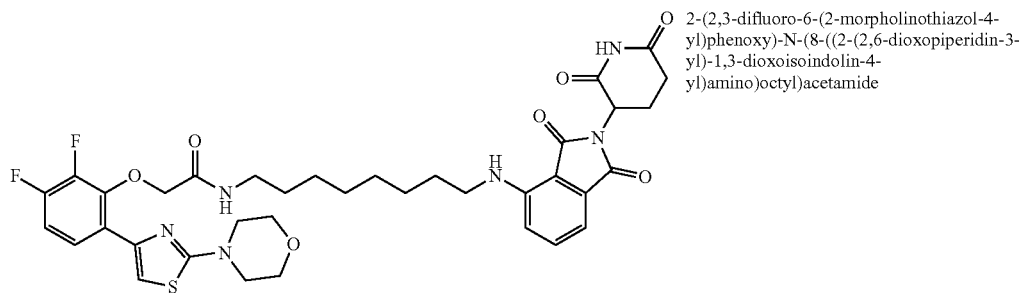 2-(2,3-difluoro-6-(2-morpholinothiazol-4-yl)phenoxy)-N-(8-((2-(2,6-dioxopiperidin-3-yl)-1,3-dioxoisoindolin-4-yl)amino)octyl)acetamide Example 3 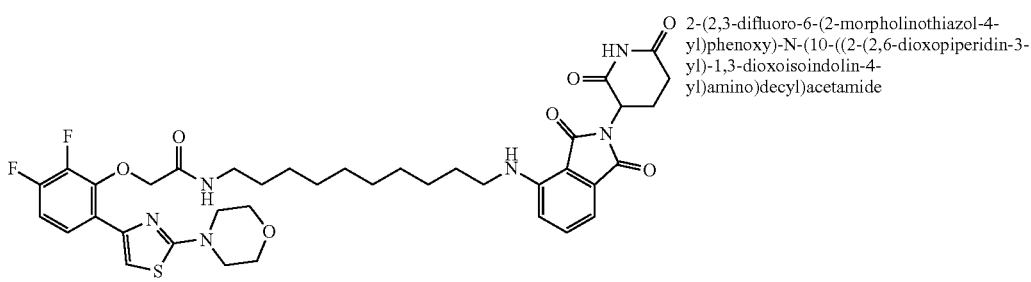 2-(2,3-difluoro-6-(2-morpholinothiazol-4-yl)phenoxy)-N-(10-((2-(2,6-dioxopiperidin-3-yl)-1,3-dioxoisoindolin-4-yl)amino)decyl)acetamide Example 4 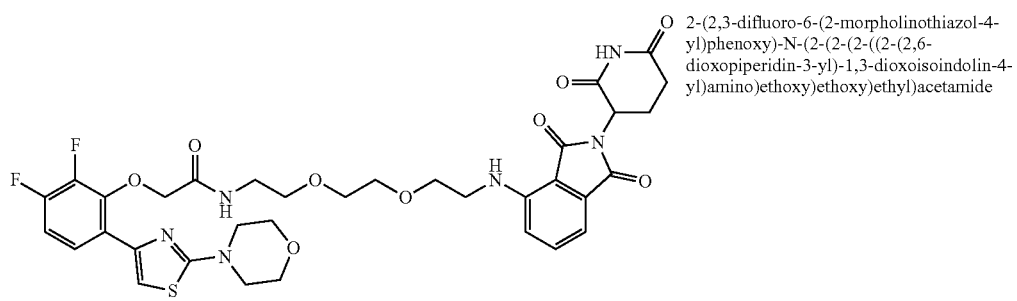 2-(2,3-difluoro-6-(2-morpholinothiazol-4-yl)phenoxy)-N-(2-(2-(2-((2-(2,6-dioxopiperidin-3-yl)-1,3-dioxoisoindolin-4-yl)amino)ethoxy)ethoxy)ethyl)acetamide Example 5 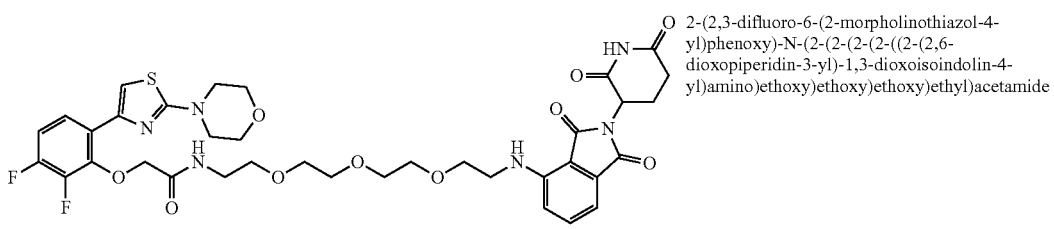 2-(2,3-difluoro-6-(2-morpholinothiazol-4-yl)phenoxy)-N-(2-(2-(2-(2-((2-(2,6-dioxopiperidin-3-yl)-1,3-dioxoisoindolin-4-yl)amino)ethoxy)ethoxy)ethoxy)ethyl)acetamide Example 6 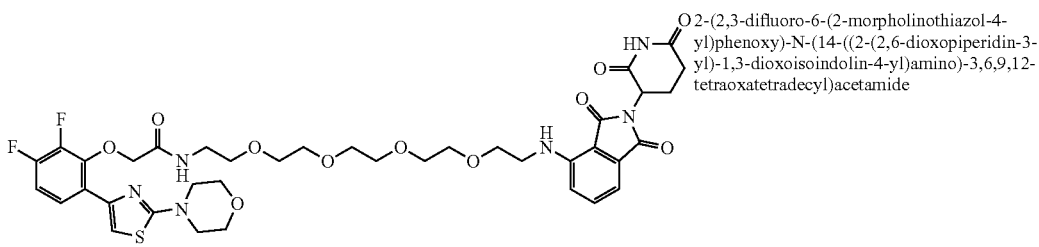 2-(2,3-difluoro-6-(2-morpholinothiazol-4-yl)phenoxy)-N-(14-((2-(2,6-dioxopiperidin-3-yl)-1,3-dioxoisoindolin-4-yl)amino)-3,6,9,12-tetraoxatetradecyl)acetamide Example 7 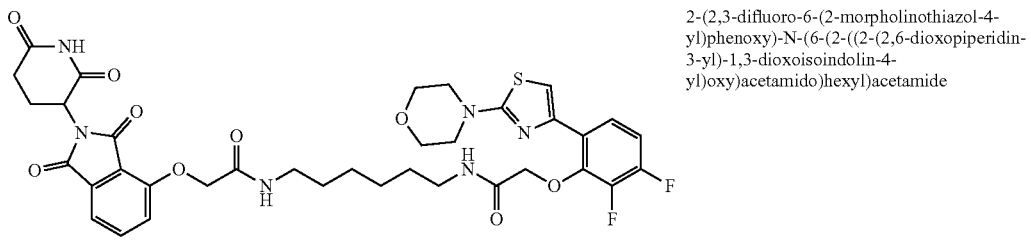 2-(2,3-difluoro-6-(2-morpholinothiazol-4-yl)phenoxy)-N-(6-(2-((2-(2,6-dioxopiperidin-3-yl)-1,3-dioxoisoindolin-4-yl)oxy)acetamido)hexyl)acetamide -continued

| | | |
|---|---|---|
| Example 8 | 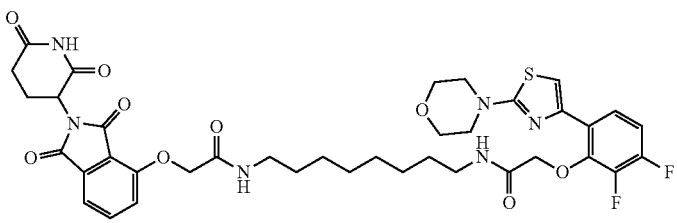 [SMILES: O=C(COc1cccc2c1C(=O)N(C1CCC(=O)NC1=O)C2=O)NCCCCCCCCNC(=O)COc1c(-c2csc(N3CCOCC3)n2)ccc(F)c1F] | 2-(2,3-difluoro-6-(2-morpholinothiazol-4-yl)phenoxy)-N-(8-(2-((2-(2,6-dioxopiperidin-3-yl)-1,3-dioxoisoindolin-4-yl)oxy)acetamido)octyl)acetamide |
| Example 9 | 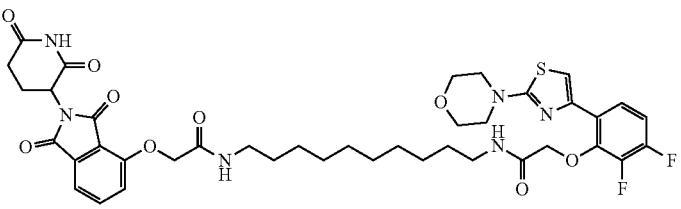 [SMILES: O=C(COc1cccc2c1C(=O)N(C1CCC(=O)NC1=O)C2=O)NCCCCCCCCCCNC(=O)COc1c(-c2csc(N3CCOCC3)n2)ccc(F)c1F] | 2-(2,3-difluoro-6-(2-morpholinothiazol-4-yl)phenoxy)-N-(10-(2-((2-(2,6-dioxopiperidin-3-yl)-1,3-dioxoisoindolin-4-yl)oxy)acetamido)decyl)acetamide |
| Example 10 | 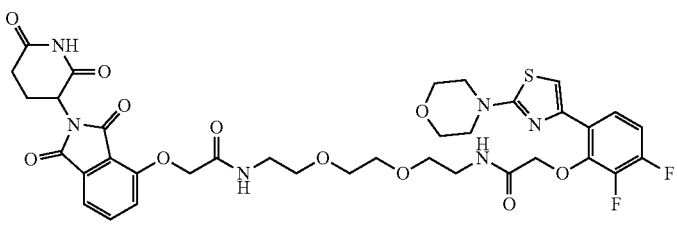 [SMILES: O=C(COc1cccc2c1C(=O)N(C1CCC(=O)NC1=O)C2=O)NCCOCCOCCNC(=O)COc1c(-c2csc(N3CCOCC3)n2)ccc(F)c1F] | 2-(2,3-difluoro-6-(2-morpholinothiazol-4-yl)phenoxy)-N-(2-(2-(2-((2-(2,6-dioxopiperidin-3-yl)-1,3-dioxoisoindolin-4-yl)oxy)acetamido)ethoxy)ethoxy)ethyl)acetamide |
| Example 11 | 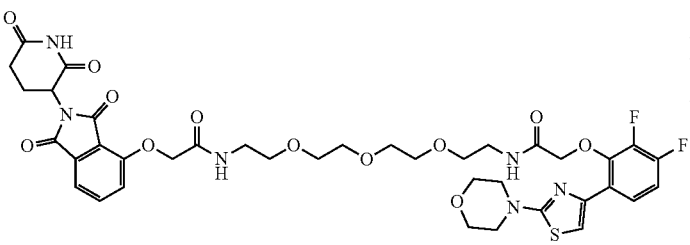 [SMILES: O=C(COc1cccc2c1C(=O)N(C1CCC(=O)NC1=O)C2=O)NCCOCCOCCOCCNC(=O)COc1c(-c2csc(N3CCOCC3)n2)ccc(F)c1F] | 2-(2,3-difluoro-6-(2-morpholinothiazol-4-yl)phenoxy)-N-(1-((2-(2,6-dioxopiperidin-3-yl)-1,3-dioxoisoindolin-4-yl)oxy)-2-oxo-6,9,12-trioxa-3-azatetradecan-14-yl)acetamide |
| Example 12 | 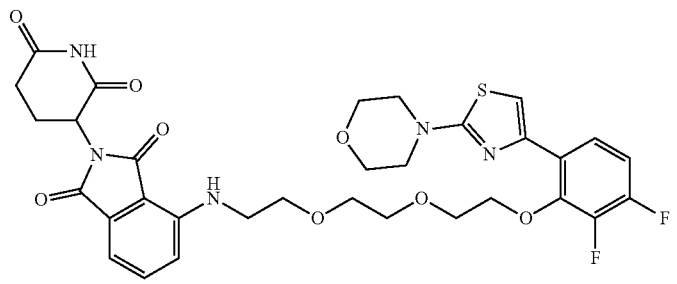 [SMILES: O=C1CCC(N2C(=O)c3cccc(NCCOCCOCCOc4c(-c5csc(N6CCOCC6)n5)ccc(F)c4F)c3C2=O)C(=O)N1] | 4-((2-(2-(2-(2,3-difluoro-6-(2-morpholinothiazol-4-yl)phenoxy)ethoxy)ethyl)amino)-2-(2,6-dioxopiperidin-3-yl)isoindoline-1,3-dione |
| Example 13 | 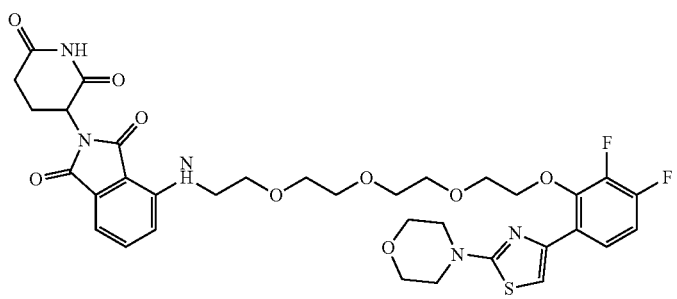 [SMILES: O=C1CCC(N2C(=O)c3cccc(NCCOCCOCCOCCOc4c(-c5csc(N6CCOCC6)n5)ccc(F)c4F)c3C2=O)C(=O)N1] | 4-((2-(2-(2-(2-(2,3-difluoro-6-(2-morpholinothiazol-4-yl)phenoxy)ethoxy)ethoxy)ethoxy)ethyl)amino)-2-(2,6-dioxopiperidin-3-yl)isoindoline-1,3-dione |

Example 14 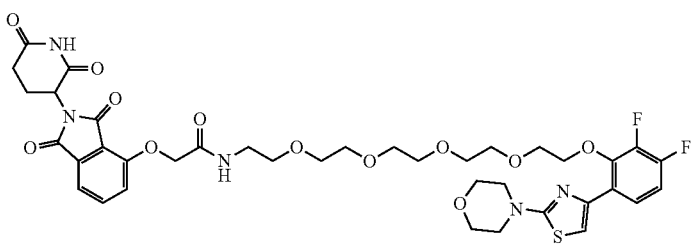 [SMILES: O=C(COc1cccc2c1C(=O)N(C1CCC(=O)NC1=O)C2=O)NCCOCCOCCOCCOCCOc1c(-c2csc(N3CCOCC3)n2)ccc(F)c1F] N-(14-(2,3-difluoro-6-(2-morpholinothiazol-4-yl)phenoxy)-3,6,9,12-tetraoxatetradecyl)-2-((2-(2,6-dioxopiperidin-3-yl)-1,3-dioxoisoindolin-4-yl)oxy)acetamide Example 15 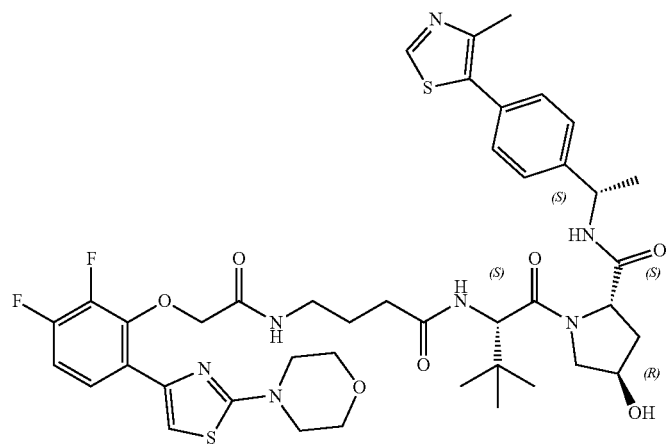 (2S,4R)-1-((S)-2-(4-(2-(2,3-difluoro-6-(2-morpholinothiazol-4-yl)phenoxy)acetamido)butanamido)-3,3-dimethylbutanoyl)-4-hydroxy-N-((S)-1-(4-(4-methylthiazol-5-yl)phenyl)ethyl)pyrrolidine-2-carboxamide Example 16 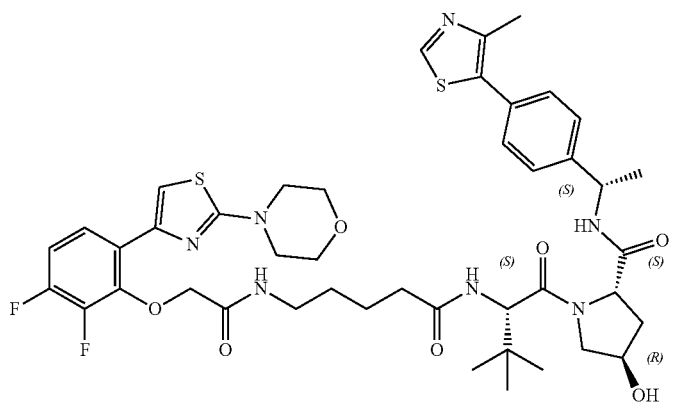 (2S,4R)-1-((S)-2-(5-(2-(2,3-difluoro-6-(2-morpholinothiazol-4-yl)phenoxy)acetamido)pentanamido)-3,3-dimethylbutanoyl)-4-hydroxy-N-((S)-1-(4-(4-methylthiazol-5-yl)phenyl)ethyl)pyrrolidine-2-carboxamide Example 17 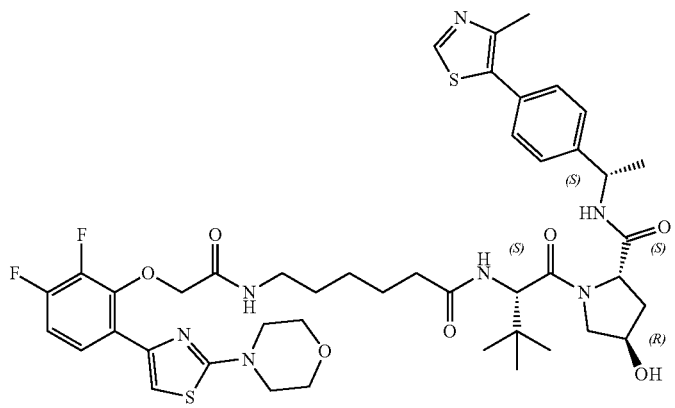 (2S,4R)-1-((S)-2-(6-(2-(2,3-difluoro-6-(2-morpholinothiazol-4-yl)phenoxy)acetamido)hexanamido)-3,3-dimethylbutanoyl)-4-hydroxy-N-((S)-1-(4-(4-methylthiazol-5-yl)phenyl)ethyl)pyrrolidine-2-carboxamide -continued

| | | |
|---|---|---|
| Example 18 | 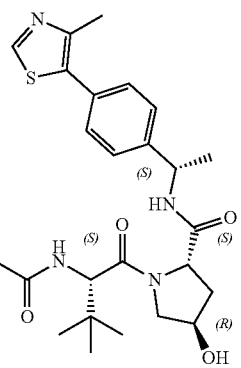 | (2S,4R)-1-((S)-2-(7-(2-(2,3-difluoro-6-(2-morpholinothiazol-4-yl)phenoxy)acetamido)heptanamido)-3,3-dimethylbutanoyl)-4-hydroxy-N-((S)-1-(4-(4-methylthiazol-5-yl)phenyl)ethyl)pyrrolidine-2-carboxamide |
| Example 19 | 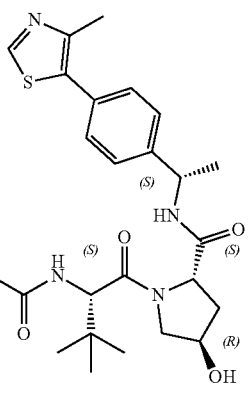 | (2S,4R)-1-((S)-2-(2-(3-(2-(2,3-difluoro-6-(2-morpholinothiazol-4-yl)phenoxy)acetamido)propoxy)acetamido)-3,3-dimethylbutanoyl)-4-hydroxy-N-((S)-1-(4-(4-methylthiazol-5-yl)phenyl)ethyl)pyrrolidine-2-carboxamide |
| Example 20 | 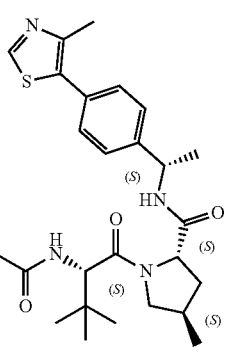 | (2S,4R)-1-((S)-2-(tert-butyl)-14-(2,3-difluoro-6-(2-morpholinothiazol-4-yl)phenoxy)-4,13-dioxo-6,9-dioxa-3,12-diazatetradecanoyl)-4-hydroxy-N-((S)-1-(4-(4-methylthiazol-5-yl)phenyl)ethyl)pyrrolidine-2-carboxamide |
| Example 21 | 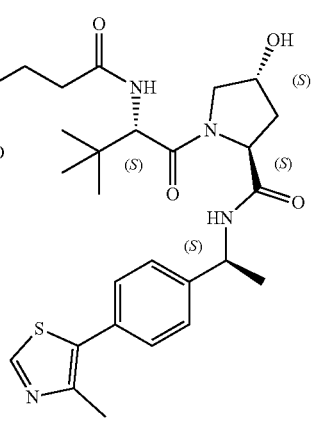 | (2S,4R)-1-((S)-2-(8-(2,3-difluoro-6-(2-morpholinothiazol-4-yl)phenoxy)octanamido)-3,3-dimethylbutanoyl)-4-hydroxy-N-((S)-1-(4-(4-methylthiazol-5-yl)phenyl)ethyl)pyrrolidine-2-carboxamide |

| | | -continued |
|---|---|---|
| Example 22 | 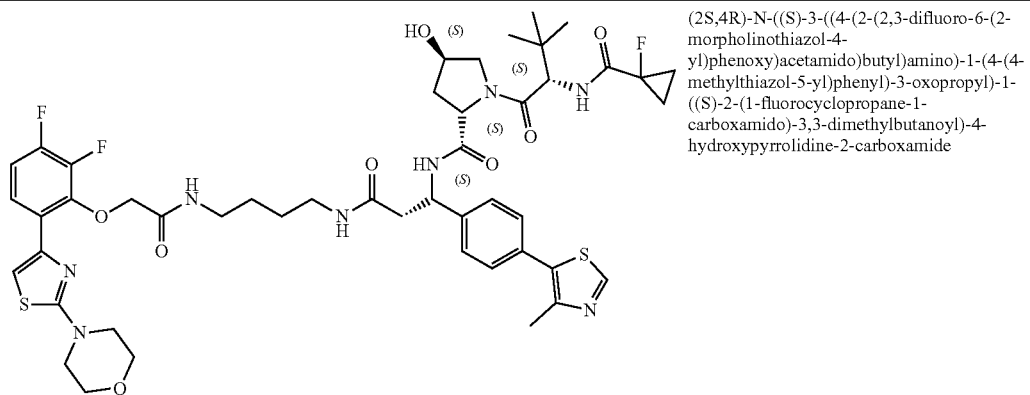 | (2S,4R)-N-((S)-3-((4-(2-(2,3-difluoro-6-(2-morpholinothiazol-4-yl)phenoxy)acetamido)butyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide |
| Example 23 | 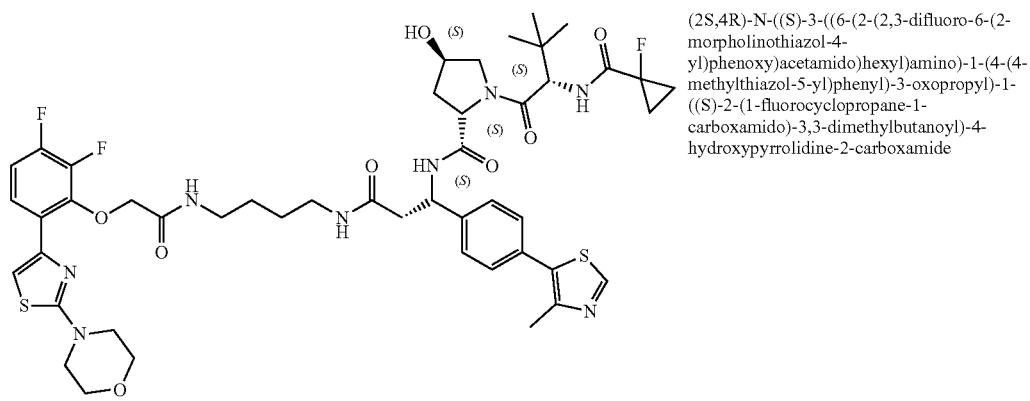 | (2S,4R)-N-((S)-3-((6-(2-(2,3-difluoro-6-(2-morpholinothiazol-4-yl)phenoxy)acetamido)hexyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide |
| Example 24 | 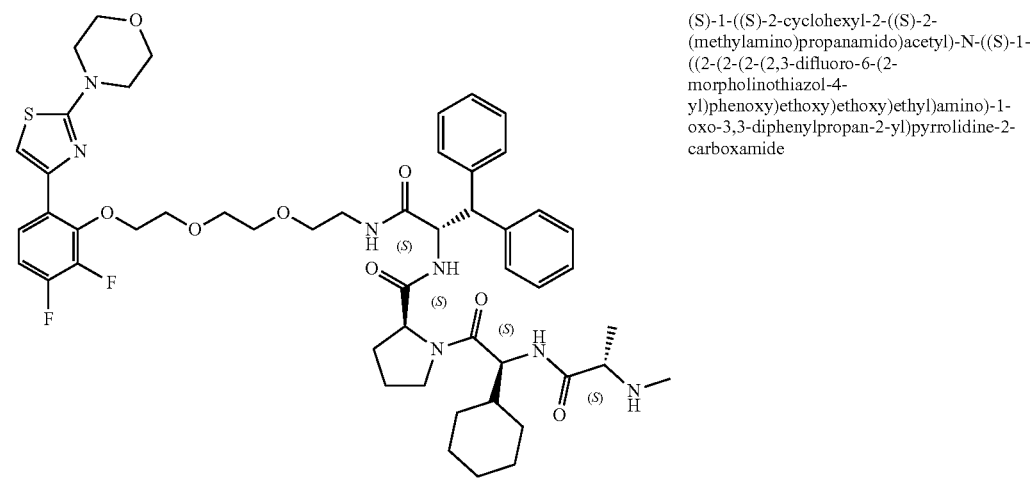 | (S)-1-((S)-2-cyclohexyl-2-((S)-2-(methylamino)propanamido)acetyl)-N-((S)-1-((2-(2-(2-(2,3-difluoro-6-(2-morpholinothiazol-4-yl)phenoxy)ethoxy)ethoxy)ethyl)amino)-1-oxo-3,3-diphenylpropan-2-yl)pyrrolidine-2-carboxamide |

-continued

| Example 25 | 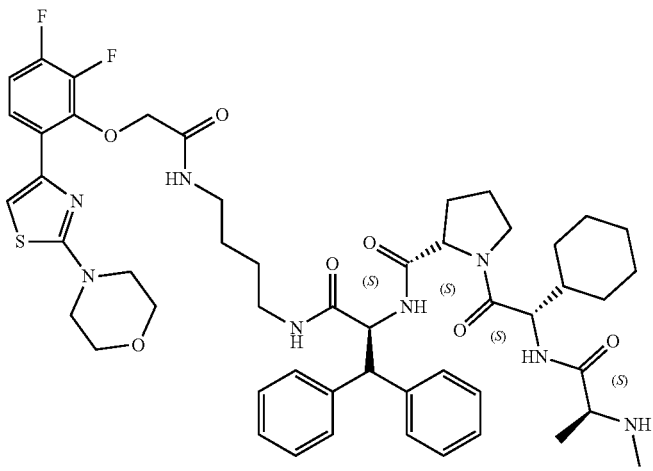 | (S)-1-((S)-2-cyclohexyl-2-((S)-2-(methylamino)propanamido)acetyl)-N-((S)-1-((4-(2-(2,3-difluoro-6-(2-morpholinothiazol-4-yl)phenoxy)acetamido)butyl)amino)-1-oxo-3,3-diphenylpropan-2-yl)pyrrolidine-2-carboxamide |
| --- | --- | --- |
| Example 26 | 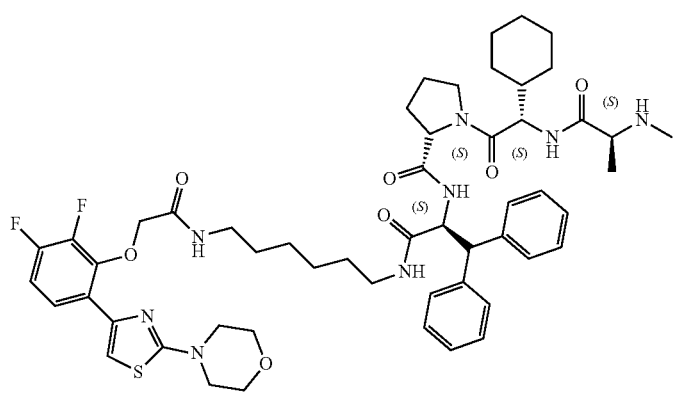 | (S)-1-((S)-2-cyclohexyl-2-((S)-2-(methylamino)propanamido)acetyl)-N-((S)-1-((6-(2-(2,3-difluoro-6-(2-morpholinothiazol-4-yl)phenoxy)acetamido)hexyl)amino)-1-oxo-3,3-diphenylpropan-2-yl)pyrrolidine-2-carboxamide |
| Example 27 | 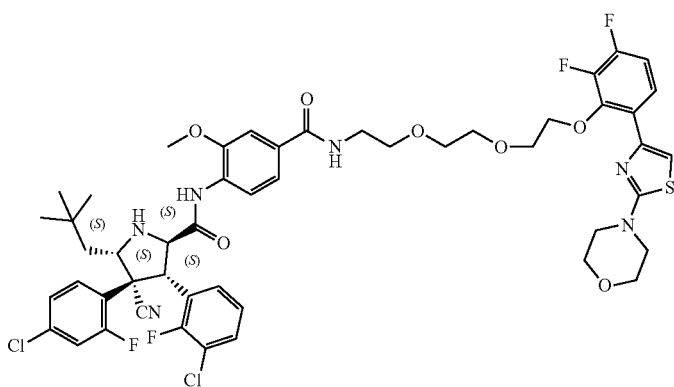 | (2R,3S,4R,5S)-3-(3-chloro-2-fluorophenyl)-4-(4-chloro-2-fluorophenyl)-4-cyano-N-(4-((2-(2-(2-(2,3-difluoro-6-(2-morpholinothiazol-4-yl)phenoxy)ethoxy)ethoxy)ethyl)carbamoyl)-2-methoxyphenyl)-5-neopentylpyrrolidine-2-carboxamide |
| Example 28 | 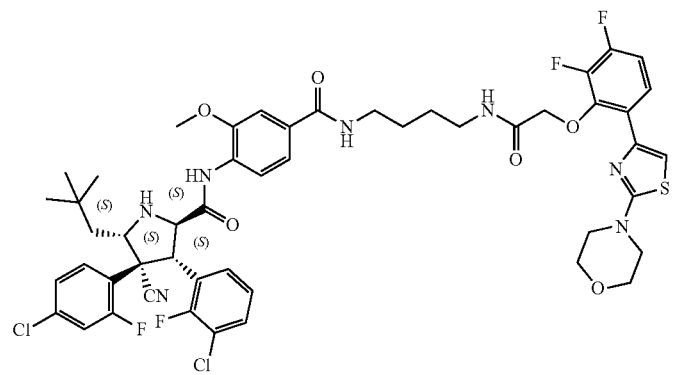 | (2R,3S,4R,5S)-3-(3-chloro-2-fluorophenyl)-4-(4-chloro-2-fluorophenyl)-4-cyano-N-(4-((4-(2-(2,3-difluoro-6-(2-morpholinothiazol-4-yl)phenoxy)acetamido)butyl)carbamoyl)-2-methoxyphenyl)-5-neopentylpyrrolidine-2-carboxamide |

| | | |
|---|---|---|
| Example 29 | 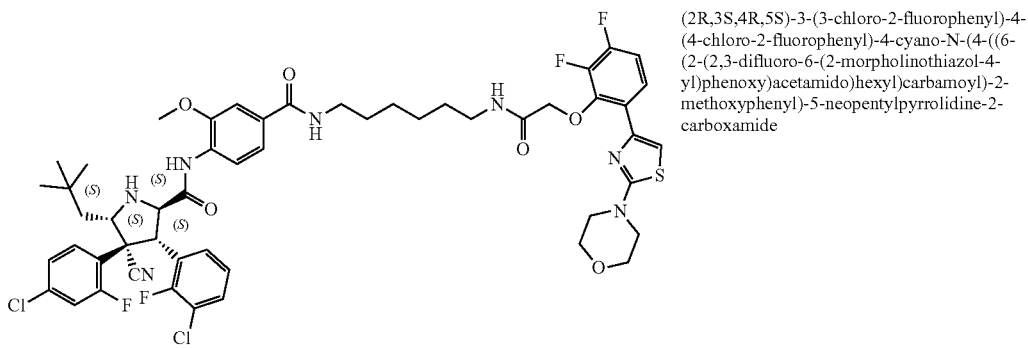 | (2R,3S,4R,5S)-3-(3-chloro-2-fluorophenyl)-4-(4-chloro-2-fluorophenyl)-4-cyano-N-(4-((6-(2-(2,3-difluoro-6-(2-morpholinothiazol-4-yl)phenoxy)acetamido)hexyl)carbamoyl)-2-methoxyphenyl)-5-neopentylpyrrolidine-2-carboxamide |
| Example 30 | 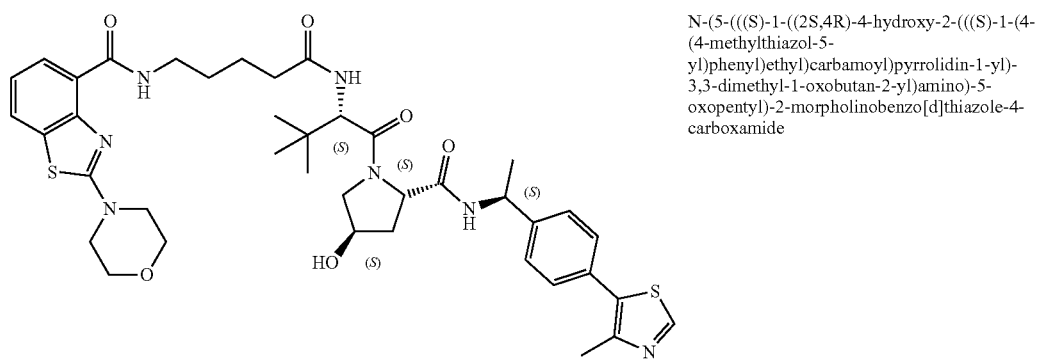 | N-(5-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-5-oxopentyl)-2-morpholinobenzo[d]thiazole-4-carboxamide |
| Example 31 | 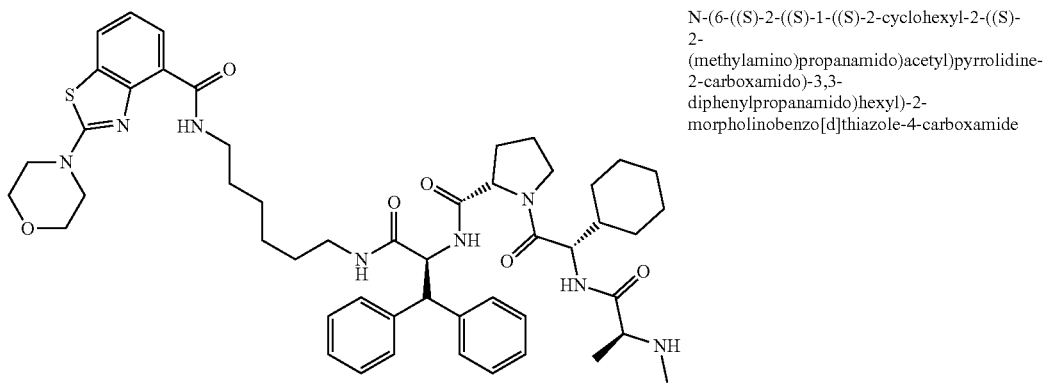 | N-(6-((S)-2-((S)-1-((S)-2-cyclohexyl-2-((S)-2-(methylamino)propanamido)acetyl)pyrrolidine-2-carboxamido)-3,3-diphenylpropanamido)hexyl)-2-morpholinobenzo[d]thiazole-4-carboxamide |
| Example 32 | 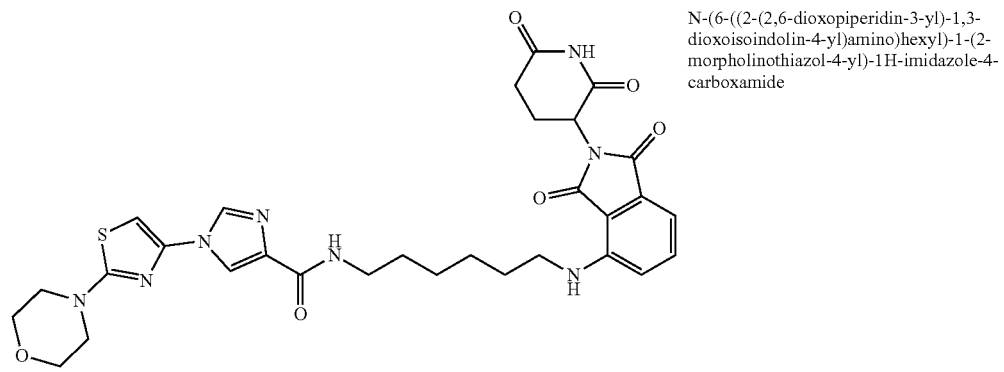 | N-(6-((2-(2,6-dioxopiperidin-3-yl)-1,3-dioxoisoindolin-4-yl)amino)hexyl)-1-(2-morpholinothiazol-4-yl)-1H-imidazole-4-carboxamide |

Example 33

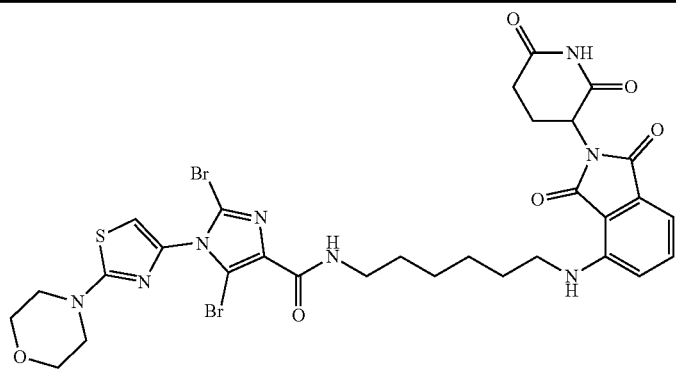

2,5-dibromo-N-(6-((2-(2,6-dioxopiperidin-3-yl)-1,3-dioxoisoindolin-4-yl)amino)hexyl)-1-(2-morpholinothiazol-4-yl)-1H-imidazole-4-carboxamide Example 34

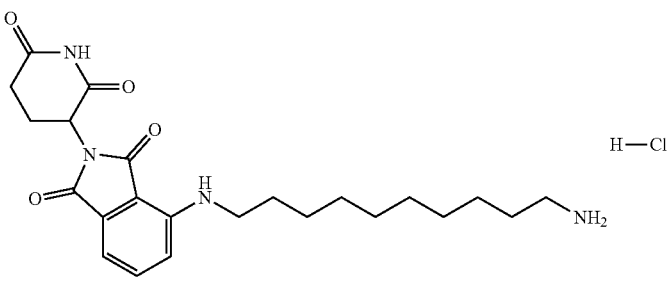 [SMILES: NCCCCCCCCCCNc1cccc2c1C(=O)N(C1CCC(=O)NC1=O)C2=O ; Cl]

4-((10-aminodecyl)amino)-2-(2,6-dioxopiperidin-3-yl)isoindoline-1,3-dione hydrochloride In one aspect the disclosure provides compounds of formula (I):

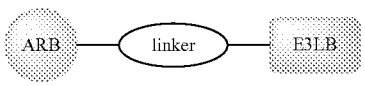

which is referred to as Androgen Receptor Binder-Linker-E3 Ligase Binder (I).

Examples

Unless otherwise noted, starting materials, reagents, and solvents were obtained from commercial suppliers (e.g. Acros Organics, Sigma-Aldrich, Alfa Aesar, Fluorochem, and Merck) and were used without further purification. Reactions were routinely monitored by thin-layer chromatography (TLC) performed on silica gel 60 $F_{254}$ (layer 0.2 mm) pre-coated aluminium foil (with fluorescent indicator UV254) (Sigma-Aldrich). Developed plates were air-dried and visualized under UV light (254/365 nm) or by using $KMnO_4$ or ninhydrin solutions. Flash column chromatography was performed on Merck silica gel 60 (mesh 230-400). $^1$H NMR and $^{13}$C NMR spectra were recorded at room temperature at 400 and 101 MHz, respectively, on a Bruker Avance 400 spectrometer by using TMS or residual solvent peak as internal standard. Chemical shifts are reported in ppm (δ) and the coupling constants (J) are given in Hertz (Hz). Peak multiplicities are abbreviated as follow: s (singlet), bs (broad singlet), d (doublet), dd (double doublet), t (triplet), dt (double triplet), q (quartet), p (pentet), and m (multiplet).

High-Resolution Mass Spectroscopy (HRMS) spectra were registered on Agilent Technologies 6540 UHD Accurate Mass Q-TOF LC-MS system. The purity of all final compounds that were evaluated in biological assays was assessed as >95%, using LC-MS. The analyses were carried out according to the method listed below. The mobile phase was a mixture of water (solvent A) and acetonitrile (solvent B), both containing formic acid at 0.1%. Method: Acquity UPLC BEH C18 1.7 μm (C18, 150×2.1 mm) column at 40° C. using a flow rate of 0.65 mL/min in a 10 min gradient elution. Gradient elution was as follows: 99.5:0.5 (A/B) to 5:95 (A/B) over 8 min, 5:95 (A/B) for 2 min, and then reversion back to 99.5:0.5 (A/B) over 0.1 min. The UV detection is an averaged signal from wavelength of 190 nm to 640 nm and mass spectra are recorded on a mass spectrometer using positive mode electro spray ionization. The chemical names were generated using ChemBioDraw 12.0 from CambridgeSoft.

Compounds described herein may be synthesized as described herein, using modified methods described herein or by methods known to a person of skill in the art.

Chemistry Abbreviations:

ACN, acetonitrile; AcOH, acetic acid; AcOK, potassium acetate; Boc, tert-butoxycarbonyl; $CD_3OD$, deuterated methanol; $CDCl_3$, deuterated chloroform; DCE, dichloroethane; DCM, dichloromethane; DEE, diethyl ether; DIAD, diisopropyl azodicarboxylate; DIPEA, N,N'-diisopropylethylamine; DMA, dimethylacetamide; DMF, dimethylformamide; DMSO, dimethylsulfoxide; DMSO-$d_6$, deuterated dimethylsulfoxide; EA, ethyl acetate; h, hour; EDC, 1-Ethyl-3-(3-dimethylaminopropyl)carbodiimide; $Et_3N$, triethylamine; HATU, 2-(7-Aza-1H-benzotriazole-1-yl)-1,1,3,3-tetramethyluronium hexafluorophosphate; min, minutes; HOBt, 1-hydroxybenzotriazole; HRMS, high-resolution mass spectroscopy; MeOH, methanol; NMR, nuclear magnetic resonance; tBu, tert-butyl; THF, tetrahydrofuran; TLC, thin-layer chromatography; TMS, tetramethylsilane; PE, petroleum ether; rt, room temperature.

Chemical Synthesis

Compounds of general formula (I) may be prepared by the general synthetic approaches described below (General Scheme 1 and 2), together with synthetic methods known in the art of organic chemistry. In all methods, it is well-understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3' edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I).

ARB: Androgen Receptor (AR) Binder; E3LB: E3 Ligase Binder.

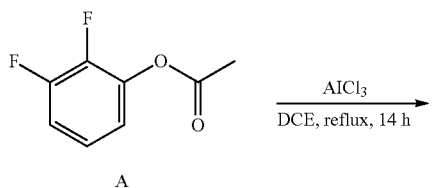

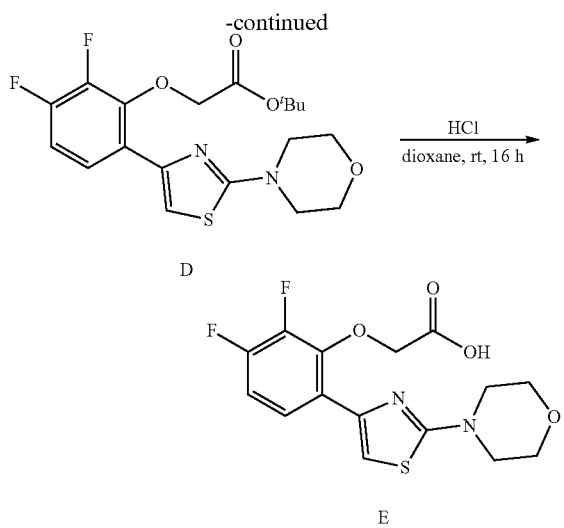

2,3-Difluorophenyl acetate (A)

The titled compound can be prepared according to the process described by Huifang Li et al. *J. Med. Chem.* 2014, 57, 6458-6467. Acetyl chloride (commercially available from, for example, Fluorochem) (6.01 mL, 6.63 g, 84.55 mmol) was slowly added at rt to a stirred solution of 2,3-difluorophenol (commercially available from, for example, Fluorochem) (10.0 g, 76.87 mmol) and pyridine (6.83 mL, 6.68 g, 84.55 mmol) in dry DCM (60.0 mL). After 2 h, the mixture was diluted with 2N HCl (60 mL) and the aqueous layer was separated and extracted with DCM (30 mL×3). The reunited organic phases were washed with brine (20 mL×2), dried over anhydrous $Na_2SO_4$, and concentrated under reduced pressure to afford the titled compound (13.26 g, 99% yield) as a colorless oil. $^1H$ NMR (400 MHz, $CDCl_3$): δ 7.16-7.03 (m, 2H), 6.99-6.83 (m, 1H), 2.37 (s, 3H); $^{13}C$ NMR (101 MHz, $CDCl_3$): δ 167.96, 151.26 (dd, J=10.9, 249.4 Hz), 143.29 (dd, J=14.3, 251.5 Hz), 139.55 (dd, J=2.3, 10.1 Hz), 123.36 (dd, J=5.0, 7.9 Hz), 118.78 (d, J=3.5 Hz), 114.71 (d, J=17.3 Hz), 20.44.

1-(3,4-Difluoro-2-hydroxyphenyl)ethan-1-one (B)

The titled compound can be prepared according to the process described by Gomtsyan, Arthur R. et al. PCT Int. Appl. WO2010045401. $AlCl_3$ (1.55 g, 11.62 mmol) was added under nitrogen at 0° C. in small portions to a stirred solution of 2,3-difluorophenyl acetate (A) (2.00 g, 11.62 mmol) in DCE (3.0 mL). After addition was completed, the mixture was refluxed for 14 h. After cooling at rt, the solvent was evaporated and the residue diluted with DCM (20 mL). 2N HCl (10 mL) was added, and the mixture was stirred for 20 min. Organic phase was separated, the water extracted with DCM (10 mL×2), and the reunited organic phases were dried over anhydrous $Na_2SO_4$ and concentrated under reduced pressure to give the titled compound (1.95 g, 97% yield) as a brownish solid. $^1H$ NMR (400 MHz, $CDCl_3$): δ 12.59 (d, J=1.4 Hz, 1H), 7.55 (ddd, J=2.3, 5.5, 9.1 Hz, 1H), 6.86-6.63 (m, 1H), 2.65 (s, 3H); $^{13}C$ NMR (101 MHz, $CDCl_3$): δ 203.66, 157.02, 154.88 (dd, J=9.7, 257.9 Hz), 139.98 (dd, J=13.7, 249.7 Hz), 125.92 (dd, J=4.5, 10.0 Hz), 117.77, 107.24 (d, J=18.7 Hz), 26.78.

2-Bromo-1-(3,4-difluoro-2-hydroxyphenyl)ethan-1-one (C)

The titled compound can be prepared according to the process described by Huifang Li et al. *J. Med. Chem.* 2014, 57, 6458-6467. A solution of 1-(3,4-difluoro-2-hydroxyphenyl)ethan-1-one (B) (1.95 g, 11.33 mmol) in EA (40.0 mL) was added dropwise at rt to a stirred suspension of $CuBr_2$ (3.03 g, 13.59 mmol) in EA (40 mL). After 24 h of reflux, the mixture was allowed to cool at rt, filtered over Celite, and the filtrate evaporated to dryness. The crude residue was purified by flash column chromatography on $SiO_2$ (PE/EA, 95:5) to give the titled compound (1.55 g, 69% yield) as yellow solid. $^1H$ NMR (400 MHz, $CDCl_3$): δ 12.10-11.84 (m, 1H), 7.58 (ddd, J=2.2, 5.4, 8.9 Hz, 1H), 6.93-6.65 (m, 1H), 2.65 (s, 2H); $^{13}C$ NMR (101 MHz, $CDCl_3$): δ 196.41, 155.36 (dd, J=9.7, 259.7 Hz), 154.11 (dd, J=5.6, 9.6 Hz), 140.29 (dd, J=13.9, 251.0 Hz), 125.92 (dd, J=4.6, 10.1 Hz), 115.13, 107.90 (d, J=19.1 Hz), 29.31.

2,3-Difluoro-6-(2-morpholinothiazol-4-yl)phenol (ARB-1)

The titled compound can be prepared according to the process described by Huifang Li et al. *J. Med. Chem.* 2014, 57, 6458-6467. Morpholine-4-carbothioamide (commercially available from, for example, Fluorochem) (0.330 g, 2.26 mmol) was added in small portions to a stirred solution of compound 2-bromo-1-(3,4-difluoro-2-hydroxyphenyl)ethan-1-one (C) (0.568 g, 2.26 mmol) in absolute EtOH (10 mL) at 0° C. When addition was completed, the mixture was refluxed for 4 h. After cooling at rt, the mixture was evaporated to dryness and $NaHCO_3$ saturated solution (20 mL) was added to pH 8. The aqueous phase was extracted with EA (10 mL×3), the reunited organic phases were dried over anhydrous $Na_2SO_4$ and concentered under reduced pressure to give a solid which was triturated with DEE and filtered affording the titled compound (0.590 g, 87% yield) as a light-yellow solid. $^1H$ NMR (400 MHz, $CDCl_3$): δ 12.43 (s, 1H), 7.24 (ddd, J=2.3, 5.6, 8.5 Hz, 1H), 6.76 (s, 1H), 6.66 (td, J=7.2, 9.3 Hz, 1H), 4.00-3.84 (m, 4H), 3.63-3.43 (m, 4H); $^{13}C$ NMR (101 MHz, $CDCl_3$): δ 171.13, 151.23 (dd, J=10.4, 247.9 Hz), 148.09, 147.25-146.05 (m), 140.72 (dd, J=14.2, 244.7 Hz), 119.63 (dd, J=4.5, 8.7 Hz), 115.71, 106.97 (d, J=18.4 Hz), 100.25 (d, J=1.7 Hz), 65.90 (2C), 48.31 (2C).

Tert-butyl 2-(2,3-difluoro-6-(2-morpholinothiazol-4-yl)phenoxy)acetate (D)

Tert-butyl bromoacetate (commercially available from, for example, Sigma-Aldrich) (0.434 mL, 0.575 g, 2.95 mmol) was added to a stirred suspension of 2,3-difluoro-6-(2-morpholinothiazol-4-yl)phenol (ARB-1) (0.800 g, 2.68 mmol) and $K_2CO_3$ (0.927 g, 6.71 mmol). The suspension was stirred for 18 h at rt, filtered, and the filtrate evaporated to dryness. Residue was purified by flash column chromatography on $SiO_2$ (PE/EA, 95:5 to 90:10) to afford the titled compound (0.800 g, 73% yield) as a yellow solid. $^1H$ NMR (400 MHz, $CDCl_3$): δ 7.92 (ddd, J=2.3, 6.2, 8.8 Hz, 1H), 7.68 (s, 1H), 7.10-6.87 (m, 1H), 4.67 (d, J=1.7 Hz, 2H), 4.00-3.79 (m, 4H), 3.68-3.47 (m, 4H), 1.53 (s, 9H); $^{13}C$ NMR (101 MHz, $CDCl_3$): δ 169.77, 167.40, 150.32 (dd, J=11.8, 249.8 Hz), 145.30, 144.64-144.23 (m), 143.98 (dd, J=14.4, 246.1 Hz), 124.35, 124.04 (dd, J=3.9, 7.8 Hz), 111.42 (d, J=17.0 Hz), 107.71, 82.55, 70.00 (d, J=7.5 Hz), 66.22 (2C), 48.61 (2C), 28.09 (3C).

2-(2,3-Difluoro-6-(2-morpholinothiazol-4-yl)phenoxy)acetic acid (E)

A solution of 4N HCl in dioxane (15 mL) was added to tert-butyl 2-(2,3-difluoro-6-(2-morpholinothiazol-4-yl)phenoxy)acetate (D) (0.780 g, 1.89 mmol) and the resulting suspension was stirred at rt for 16h. The solvent was evaporated to dryness and the residue was triturated with DEE. The solids were collected by filtration and dried under vacuo to afford the titled compound (0.672 g, 91% yield) as light-yellow solid. $^1$H NMR (400 MHz, CD$_3$OD): δ 7.48 (ddd, J=2.3, 5.7, 8.1 Hz, 1H), 7.27 (s, 1H), 7.18 (td, J=7.5, 9.2 Hz, 1H), 5.01 (d, J=1.5 Hz, 2H), 4.02-3.86 (m, 4H), 3.86-3.67 (m, 4H); $^{13}$C NMR (101 MHz, CD$_3$OD): δ 171.72, 169.44, 152.57 (dd, J=11.6, 252.2 Hz), 144.55 (d, J=1.7 Hz), 143.30 (dd, J=15.0, 248.0 Hz), 136.41 (d, J=13.3 Hz), 124.82 (dd, J=3.9, 8.6 Hz), 118.47, 111.66 (d, J=18.2 Hz), 106.15, 69.24 (d, J=9.0 Hz), 65.05 (2C), 49.17 (2C).

Scheme 2. Synthesis of pomalidomide-based E3LB-1 moiety and linker connection

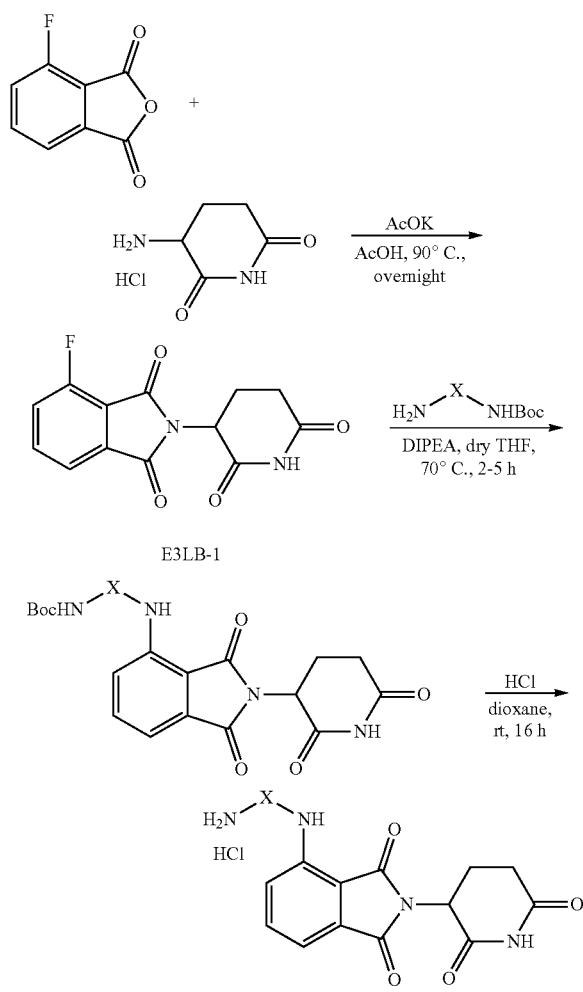

F X = (CH$_2$)$_6$
G X = (CH$_2$)$_8$
H X = (CH$_2$)$_{10}$
I X = CH$_2$CH$_2$(OCH$_2$CH$_2$)$_2$
J X = CH$_2$CH$_2$(OCH$_2$CH$_2$)$_3$
K X = CH$_2$CH$_2$(OCH$_2$CH$_2$)$_4$
L X = (CH$_2$)$_6$
M X = (CH$_2$)$_8$
N X = (CH$_2$)$_{10}$ (Example 34)
O X = CH$_2$CH$_2$(OCH$_2$CH$_2$)$_2$
P X = CH$_2$CH$_2$(OCH$_2$CH$_2$)$_3$
Q X = CH$_2$CH$_2$(OCH$_2$CH$_2$)$_4$

2-(2,6-Dioxopiperidin-3-yl)-4-fluoroisoindoline-1,3-dione (E3LB-1)

The titled compound can be prepared according to the process described by Bradner James et al. PCT Int. Appl., WO2016/105518. A mixture of 3-fluorophthalic anhydride (commercially available from, for example, Fluorochem) (1.00 g, 6.02 mmol), 3-aminopiperidine-2,6-dione hydrochloride (commercially available from, for example, Fluorochem) (1.09 g, 6.62 mmol), and potassium acetate (1.83 g, 18.66 mmol) in AcOH (20 mL) was stirred at 90° C. overnight. After cooling to rt, the black reaction mixture was poured in ice-water yielding a brown solid which was filtered and purified by flash column chromatography on SiO$_2$ (PE/EA, 4:6) to afford the titled compound as a white solid (1.22 g, 73% yield). $^1$H NMR (400 MHz, DMSO-d$_6$): δ 11.16 (s, 1H), 8.03-7.89 (m, 1H), 7.80 (d, J=7.3 Hz, 1H), 7.74 (t, J=8.9 Hz, 1H), 5.17 (dd, J=12.8, 5.4 Hz, 1H), 3.00-2.81 (m, 1H), 2.71-2.53 (m, 2H), 2.13-1.99 (m, 1H); $^{13}$C NMR (101 MHz, DMSO-d$_6$): δ 173.19, 170.14, 166.55 (d, J=2.9 Hz), 164.42, 157.25 (d, J=262.3 Hz), 138.51 (d, J=7.9 Hz), 133.90 (d, J=1.3 Hz), 123.46 (d, J=19.6 Hz), 120.50 (d, J=3.3 Hz), 117.48 (d, J=12.6 Hz), 49.54, 31.36, 22.30.

General Procedure I: Nucleophilic Substitution on Fluorothalidomide

Tert-butyl (6-((2-(2,6-dioxopiperidin-3-yl)-1,3-dioxoisoindolin-4-yl)amino)hexyl)carbamate (F)

The titled compound can be prepared according to the process described by Ishoey, M. et al. *ACS Chem. Biol.*, 2018, 13, 553-560. Under nitrogen atmosphere, a mixture of 2-(2,6-dioxopiperidin-3-yl)-4-fluoroisoindoline-1,3-dione (E3LB-1) (0.050 g, 0.181 mmol, 1.0 equiv), tert-butyl (6-aminohexyl)carbamate (commercially available from, for example, Fluorochem) (0.043 g, 0.199 mmol, 1.1 equiv), and DIPEA (0.061 mL, 0.362 mmol, 2.0 equiv) in dry THF (2.0 mL) was reacted at 70° C. for 4h (in this case, the reaction was performed in a pressure tube). After cooling to rt, the solvent was evaporated to dryness and the crude residue was purified by flash column chromatography on SiO$_2$ (DCM/Acetone, 8:2) to give a fluorescent yellow solid (0.040 g, 47% yield). $^1$H NMR (400 MHz, CDCl$_3$): δ 8.35 (bs, 1H), 7.50 (t, J=8.0 Hz, 1H), 7.10 (d, J=8.0 Hz, 1H), 6.90 (d, J=8.0 Hz, 1H), 6.25 (bs, 1H), 4.95 (dd, J=8.0 and 16 Hz, 1H), 4.55 (bs, 1H), 3.25 (t, J=8.0 Hz, 2H), 3.15-3.10 (m, 2H), 2.95-2.70 (m, 3H), 2.20-2.10 (m, 1H), 1.70-1.60 (m, 2H), 1.55-1.35 (m, 15H); $^{13}$C NMR (101 MHz, CDCl$_3$): δ 171.16, 169.52, 168.45, 167.64, 156.02, 146.97, 136.13, 132.49, 116.64, 111.41, 109.87, 79.15, 42.55, 40.45, 31.42, 30.02, 29.15, 28.43 (3C), 26.62, 26.47, 22.81.

Tert-butyl (8-((2-(2,6-dioxopiperidin-3-yl)-1,3-dioxoisoindolin-4-yl)amino)octyl)carbamate (G)

The titled compound can be prepared according to the process described by Remillard, D. et al. *Angew. Chem. Int. Ed. Engl.* 2017, 56, 5738-5743. General Procedure I (2h) was followed by using 2-(2,6-dioxopiperidin-3-yl)-4-fluoroisoindoline-1,3-dione (E3LB-1) (0.15 g, 0.543 mmol), tert-butyl (8-aminooctyl)carbamate (0.146 g, 0.597 mmol), and DIPEA (0.18 mL, 1.086 mmol) in NMP (5.0 mL) to afford the titled compound as fluorescent yellow solid (0.103 g, 39% yield) following purification by flash column chromatography on $SiO_2$ (DCM/MeOH 98:2). $^1$H NMR (400 MHz, $CDCl_3$): 8.05 (bs, 1H), 7.52 (dd, J=8.4 Hz, 1H), 7.11 (d, J=7.1 Hz, 1H), 6.90 (d, J=8.5 Hz, 1H), 6.25 (bs, 1H), 4.94 (dd, J=12.1 and 5.3 Hz, 1H), 4.55 (bs, 1H), 3.28 (t, J=6.9 Hz, 2H), 3.19-3.01 (m, 2H), 2.99-2.66 (m, 3H), 2.20-2.12 (m, 1H), 1.78-1.54 (m, 6H), 1.53-1.40 (m, 14H), 1.38-1.31 (m, 1H).

Tert-butyl (10-((2-(2,6-dioxopiperidin-3-yl)-1,3-dioxoisoindolin-4-yl)amino)decyl)carbamate (H)

General Procedure I (10h) was followed by using 2-(2,6-dioxopiperidin-3-yl)-4-fluoroisoindoline-1,3-dione (E3LB-1) (0.20 g, 0.724 mmol), tert-butyl (10-aminodecyl)carbamate (0.217 g, 0.796 mmol), and DIPEA (0.25 mL, 1.448 mmol) in dry DMF (4.0 mL) to afford the titled compound as fluorescent yellow film (0.122 g, 34% yield) following purification by flash column chromatography on $SiO_2$ (DCM/Acetone 9:1). $^1$H NMR (400 MHz, $CDCl_3$): δ 8.36 (bs, 1H), 7.50 (dd, J=8.3, 7.3 Hz, 1H), 7.09 (d, J=7.1 Hz, 1H), 6.89 (d, J=8.6 Hz, 1H), 6.25 (t, J=5.5 Hz, 1H), 4.93 (dd, J=12.0, 5.4 Hz, 1H), 4.56 (s, 1H), 3.27 (dd, J=12.8, 6.9 Hz, 2H), 3.16-3.03 (m, 2H), 2.94-2.68 (m, 3H), 2.17-2.07 (m, 1H), 1.72-1.59 (m, 2H), 1.52-1.38 (m, 11H), 1.36-1.24 (m, 12H); $^{13}$C NMR (101 MHz, $CDCl_3$): δ 171.17, 169.52, 168.46, 167.66, 155.99, 147.03, 136.10, 132.50, 116.65, 111.33, 109.80, 79.04, 48.86, 42.65, 40.62, 31.42, 30.05, 29.39 (2C), 29.23 (2C), 28.44 (3C), 26.89, 26.77, 22.81 (2C).

Tert-butyl (14-((2-(2,6-dioxopiperidin-3-yl)-1,3-dioxoisoindolin-4-yl)amino)-3,6,9,12-tetraoxatetradecyl)carbamate (I)

The titled compound can be prepared according to the process described by Remillard, D. et al. *Angew. Chem. Int. Ed. Engl.* 2017, 56, 5738-5743. General Procedure I (2h) was followed by using 2-(2,6-dioxopiperidin-3-yl)-4-fluoroisoindoline-1,3-dione (E3LB-1) (0.150 g, 0.597 mmol), tert-butyl (2-(2-(2-aminoethoxy)ethoxy)ethyl)carbamate (0.134 g, mmol), and DIPEA (0.18 mL, 0.108 mmol) in NMP (2.0 mL) to afford the titled compound as fluorescent yellow film (0.040 g, 14% yield) following double purification by flash column chromatography on $SiO_2$ (first: DCM/MeOH 98:2; second: PE/EA 6:4). $^1$H NMR (400 MHz, $CDCl_3$): 8.33 (s, 1H), 7.52 (dd, J=8.5, 7.2 Hz, 1H), 7.13 (d, J=7.0 Hz, 1H), 6.94 (d, J=8.5 Hz, 1H), 5.09 (s, 1H), 4.96 (s, 1H), 3.75 (t, J=5.3 Hz, 2H), 3.72-3.63 (m, 4H), 3.59 (t, J=5.2 Hz, 2H), 3.50 (t, J=5.2 Hz, 2H), 3.37-3.30 (m, 2H), 2.93-2.70 (m, 3H), 2.18-2.11 (m, J=9.2, 4.2 Hz, 1H), 1.45 (s, 9H); 13C NMR (101 MHz, $CDCl_3$): δ 170.97, 169.31, 168.32, 167.59, 156.08, 146.80, 136.06, 132.55, 116.71, 111.71, 110.41, 79.31, 70.80, 70.38, 70.15, 69.36, 48.89, 42.33, 40.41, 31.40, 28.42 (3C), 22.88.

Tert-butyl (2-(2-(2-(2-((2-(2,6-dioxopiperidin-3-yl)-1,3-dioxoisoindolin-4-yl)amino)ethoxy)ethoxy)ethoxy)ethyl)carbamate (J)

The titled compound can be prepared according to the process described by Peng, L. et al. *ACS Med. Chem. Lett.* 2019, 10, 767-772. General Procedure I (4h) was followed by using 2-(2,6-dioxopiperidin-3-yl)-4-fluoroisoindoline-1,3-dione (E3LB-1) (0.250 g, 0.905 mmol), tert-butyl (2-(2-(2-(2-aminoethoxy)ethoxy)ethoxy)ethyl)carbamate (0.291 g, 0.995 mmol), and DIPEA (0.31 mL, 1.810 mmol) in dry DMF (4.0 mL) to afford the titled compound as fluorescent yellow film (0.085 g, 15% yield) following purification by flash column chromatography on $SiO_2$ (DCM/MeOH 98:2). $^1$H NMR (400 MHz, $CDCl_3$): δ 8.61 (s, 1H), 7.52-7.43 (m, 1H), 7.15-7.06 (m, 1H), 6.92 (d, J=8.6 Hz, 1H), 6.52-6.46 (m, 1H), 5.08 (s, 1H), 4.93 (dd, J=11.8 and 5.4 Hz, 1H), 3.73 (t, J=5.2 Hz, 2H), 3.70-3.59 (m, J=18.3, 4.8 Hz, 8H), 3.58-3.51 (m, 2H), 3.51-3.42 (m, 2H), 3.37-3.23 (m, 2H), 2.93-2.65 (m, 3H), 2.15-2.07 (m, 1H), 1.44 (s, 9H); $^{13}$C NMR (101 MHz, $CDCl_3$): δ 171.38, 169.29, 168.56, 167.64, 156.05, 146.82, 136.03, 132.51, 116.78, 111.64, 110.29, 79.22, 70.73, 70.60, 70.59, 70.21, 70.18, 69.50, 48.87, 42.37, 40.34, 31.43, 28.42 (3C), 22.78.

Tert-butyl (14-((2-(2,6-dioxopiperidin-3-yl)-1,3-dioxoisoindolin-4-yl)amino)-3,6,9,12-tetraoxatetradecyl)carbamate (K)

General Procedure I (10h) was followed by using 2-(2,6-dioxopiperidin-3-yl)-4-fluoroisoindoline-1,3-dione (E3LB-1) (0.225 g, 0.814 mmol), tert-butyl (14-amino-3,6,9,12-tetraoxatetradec-1-yl)carbamate (0.301 g, 0.896 mmol), and DIPEA (0.28 mL, 1.629 mmol) in dry DMF (4.0 mL) to afford the titled compound as yellow film (0.060 g, 13% yield) following purification by flash column chromatography on $SiO_2$ (DCM/MeOH 98:5). $^1$H NMR (400 MHz, $CDCl_3$): δ 8.27 (bs, 1H), 7.58-7.42 (m, 1H), 7.13 (d, J=7.1 Hz, 1H), 6.94 (d, J=8.5 Hz, 1H), 6.52 (bs, 1H), 5.11 (bs, 1H), 4.93 (dd, J=5.3, 12.0 Hz, 1H), 3.85-3.43 (m, 18H), 3.32 (s, 2H), 2.89-2.63 (m, 3H), 2.26-2.06 (m, 1H), 1.46 (s, 9H); $^{13}$C NMR (101 MHz, $CDCl_3$): δ 171.00, 169.24, 168.30, 167.59, 156.03, 146.85, 136.05, 132.52, 116.78, 111.67, 110.31, 79.19, 70.79, 70.66, 70.59 (4C), 70.45, 70.28, 69.47, 48.86, 42.40, 31.42, 28.44 (3C), 22.83.

General Procedure II: Amine Boc-Deprotection

4-((6-Aminohexyl)amino)-2-(2,6-dioxopiperidin-3-yl)isoindoline-1,3-dione hydrochloride (L)

A solution of 4N HCl in dioxane (2.0 mL) was added to tert-butyl (6-((2-(2,6-dioxopiperidin-3-yl)-1,3-dioxoisoindolin-4-yl)amino)hexyl)carbamate (F) (0.10 g, 0.212 mmol, 1.0 equiv) and the resulting solution was stirred at rt for 16h. The solvent was evaporated to dryness and the residue was triturated with DEE, collected by filtration, and dried under vacuo to afford the titled compound as yellow solid (0.084 g, 97% yield), which was used in the successive step without further purification. $^1$H NMR (400 MHz, $CD_3OD$): δ 7.61-7.49 (m, 1H), 7.13-7.01 (m, 2H), 5.08 (dd, J=5.4, 12.3 Hz, 1H), 3.38 (t, J=7.0 Hz, 2H), 3.00-2.90 (m, 2H), 2.90-2.68 (m, 3H), 2.18-2.05 (m, 1H), 1.87-1.65 (m, 4H), 1.65-1.38 (m, 4H).

4-((8-Aminooctyl)amino)-2-(2,6-dioxopiperidin-3-yl)isoindoline-1,3-dione hydrochloride (M)

General Procedure II (16h) was followed by using tert-butyl (8-((2-(2,6-dioxopiperidin-3-yl)-1,3-dioxoisoindolin- 4-yl)amino)octyl)carbamate (G) (0.095 g, 0.189 mmol) and 4N HCl in dioxane (1.7 mL) to afford the titled compound as yellow solid (0.080 g, 96% yield). $^1$H NMR (400 MHz, MeOD): δ 7.62-7.46 (m, 1H), 7.14-6.92 (m, 2H), 5.08 (dd, J=5.5, 12.5 Hz, 1H), 3.36 (t, J=6.9 Hz, 2H), 2.99-2.90 (m, 2H), 2.90-2.66 (m, 3H), 2.17-2.09 (m, 1H), 1.81-1.61 (m, 4H), 1.61-1.40 (m, 8H).

4-((10-Aminodecyl)amino)-2-(2,6-dioxopiperidin-3-yl)isoindoline-1,3-dione hydrochloride (N) (Example 34)

General Procedure II (16h) was followed by using tert-butyl (10-((2-(2,6-dioxopiperidin-3-yl)-1,3-dioxoisoindolin-4-yl)amino)decyl)carbamate (H) (0.079 g, 0.149 mmol) and 4N HCl in dioxane (1.0 mL) to afford the titled compound as yellow solid (0.052 g, 75% yield). $^1$H NMR (400 MHz, MeOD): δ 7.57 (dd, J=8.3, 7.4 Hz, 1H), 7.09-7.03 (m, 2H), 5.08 (dd, J=12.7, 5.4 Hz, 1H), 2.96-2.67 (m, 5H), 2.19-2.07 (m, 1H), 1.74-1.61 (m, 4H), 1.51-1.35 (m, 14H). HRMS (ESI) m/z [M+H]+ calcd for $C_{23}H_{32}N_4O_4$ 429.24963, found 429.2497.

4-((2-(2-(2-Aminoethoxy)ethoxy)ethyl)amino)-2-(2,6-dioxopiperidin-3-yl)isoindoline-1,3-dione hydrochloride (O)

General Procedure II (16h) was followed by using tert-butyl (14-((2-(2,6-dioxopiperidin-3-yl)-1,3-dioxoisoindolin-4-yl)amino)-3,6,9,12-tetraoxatetradecyl)carbamate (I) (0.040 g, 0.079 mmol) and 4N HCl in dioxane (0.5 mL) to afford the titled compound as yellow solid (0.022 g, 83% yield). $^1$H NMR (400 MHz, MeOD): δ 7.59 (dd, J=8.6, 7.1 Hz, 1H), 7.11 (dd, J=10.6, 7.8 Hz, 2H), 5.08 (dd, J=12.6, 5.5 Hz, 1H), 3.80-3.66 (m, 8H), 3.55 (t, J=5.1 Hz, 2H), 3.18-3.08 (m, 2H), 2.95-2.64 (m, 3H), 2.22-2.08 (m, 1H).

4-((2-(2-(2-(2-Aminoethoxy)ethoxy)ethoxy)ethyl)amino)-2-(2,6-dioxopiperidin-3-yl)isoindoline-1,3-dione hydrochloride (P)

General Procedure II (16h) was followed by using tert-butyl (2-(2-(2-(2-((2-(2,6-dioxopiperidin-3-yl)-1,3-dioxoisoindolin-4-yl)amino)ethoxy)ethoxy)ethoxy)ethyl)carbamate (J) (0.075 g, 0.137 mmol) and 4N HCl in dioxane (0.8 mL) to afford the titled compound as yellow solid (0.055 g, 83% yield). $^1$H NMR (400 MHz, MeOD): δ 7.59 (dd, J=8.6 and 7.1 Hz, 1H), 7.11 (dd, J=12.5 and 7.9 Hz, 2H), 5.08 (dd, J=12.4 and 5.5 Hz, 1H), 3.80-3.63 (m, 12H), 3.54 (t, J=5.2 Hz, 2H), 3.21-3.07 (m, 3H), 2.97-2.65 (m, 3H), 2.19-2.08 (m, 1H).

4-((14-Amino-3,6,9,12-tetraoxatetradecyl)amino)-2-(2,6-dioxopiperidin-3-yl)isoindoline-1,3-dione hydrochloride (Q)

General Procedure II (3h) was followed by using tert-butyl (14-((2-(2,6-dioxopiperidin-3-yl)-1,3-dioxoisoindolin-4-yl)amino)-3,6,9,12-tetraoxatetradecyl)carbamate (K) (0.060 g, 0.101 mmol) and 4N HCl in dioxane (1.0 mL) to afford the titled compound as yellow solid (0.050 g, 94% yield). $^1$H NMR (400 MHz, MeOD): δ 7.58 (t, J=7.7 Hz, 1H), 7.30-6.86 (m, 2H), 5.08 (dd, J=5.5, 12.3 Hz, 1H), 3.86-3.58 (m, 16H), 3.58-3.41 (m, 2H), 3.19-3.05 (m, 2H), 2.88-2.64 (m, 3H), 2.21-1.98 (m, 1H).

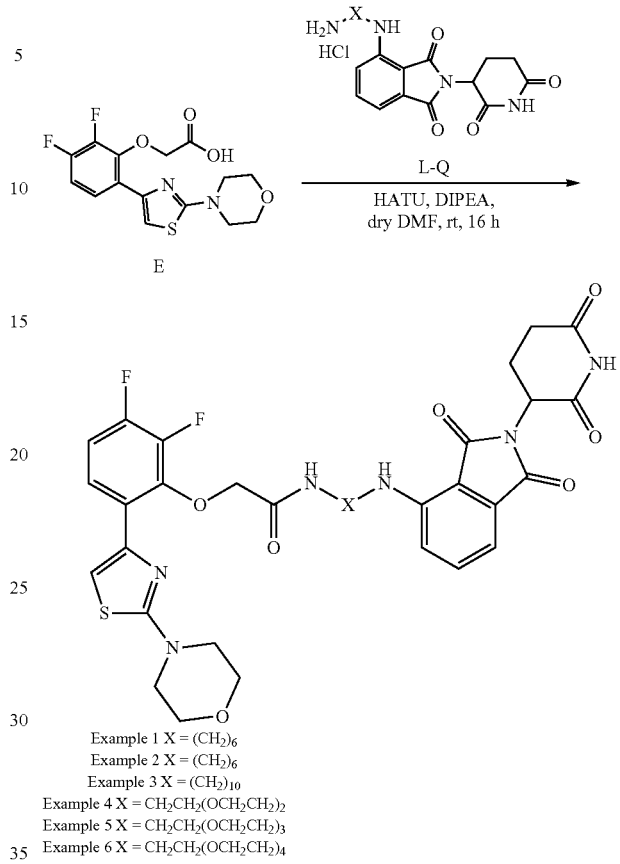

Scheme 3. Synthesis of Examples 1-6

Example 1 X = (CH$_2$)$_6$
Example 2 X = (CH$_2$)$_8$
Example 3 X = (CH$_2$)$_{10}$
Example 4 X = CH$_2$CH$_2$(OCH$_2$CH$_2$)$_2$
Example 5 X = CH$_2$CH$_2$(OCH$_2$CH$_2$)$_3$
Example 6 X = CH$_2$CH$_2$(OCH$_2$CH$_2$)$_4$

General Procedure III: HATU-Mediated Amidation Reaction

2-(2,3-Difluoro-6-(2-morpholinothiazol-4-yl)phenoxy)-N-(6-((2-(2,6-dioxopiperidin-3-yl)-1,3-dioxoisoindolin-4-yl)amino)hexyl)acetamide (Example 1)

In an oven-dried round-bottom flask, under nitrogen atmosphere, to a stirred solution of 2-(2,3-difluoro-6-(2-morpholinothiazol-4-yl)phenoxy)acetic acid (E) (0.048 g, 0.122 mmol, 1.0 equiv), 4-((6-aminohexyl)amino)-2-(2,6-dioxopiperidin-3-yl)isoindoline-1,3-dione hydrochloride (L) (0.050 g, 0.122 mmol, 1.0 equiv), and DIPEA (0.083 mL, 0.489 mmol, 4.0 equiv) in dry DMF (3.0 mL) was added HATU (0.058 g, 0.153 mmol, 1.25 equiv). Stirring was continued at rt for 16h. The reaction mixture was diluted with water (30 mL) and extracted with EA (15 mL×3). The reunited organic layers were washed with water (20 mL×3), brine (20 mL×3), dried over anhydrous Na$_2$SO$_4$ and then concentrated under reduced pressure to give a crude residue, which was purified by flash column chromatography on SiO$_2$ (DCM/Acetone/MeOH, 90:10:0 to 89:10:1) affording a yellow solid (0.015 g, 18% yield). $^1$H NMR (400 MHz, CDCl$_3$): δ 8.09 (s, 1H), 7.63-7.56 (m, 1H), 7.56-7.48 (m, 1H), 7.11 (d, J=7.0 Hz, 1H), 7.05 (s, 1H), 7.04-6.96 (m, 1H), 6.93 (s, 1H), 6.90 (d, J=8.5 Hz, 1H), 6.25 (s, 1H), 4.93 (dd, J=5.3, 11.9 Hz, 1H), 4.60 (s, 2H), 3.89-3.78 (m, 4H), 3.64-3.51 (m, 4H), 3.36 (q, J=6.8 Hz, 2H), 3.33-3.26 (m, 2H), 2.97-2.68 (m, 3H), 2.18-2.11 (m, 1H), 1.79-1.35 (m, 8H); $^{13}$C NMR (101 MHz, CDCl$_3$): δ 170.87, 170.74, 169.50, 168.25, 167.92, 167.59, 150.76 (dd, J=11.6, 251.4 Hz), 146.96, 146.37-146.09 (m), 144.62 (dd, J=1.5, 9.1 Hz), 144.15 (dd, J=14.0, 247.3 Hz), 136.15, 132.48, 125.04, 124.53 (dd, J=4.0, 7.8 Hz), 116.63, 112.43 (d, J=17.2 Hz), 111.46, 109.90, 105.96, 72.42 (d, J=4.9 Hz), 66.11 (2C), 48.87, 48.62 (2C), 42.52, 38.95, 31.41, 29.42, 29.13, 26.62, 26.55, 22.82. HRMS (ESI) m/z [M+H]+ calcd for C$_{34}$H$_{36}$F$_2$N$_6$O$_7$S 711.2407, found 711.2412.

2-(2,3-Difluoro-6-(2-morpholinothiazol-4-yl)phenoxy)-N-(8-((2-(2,6-dioxopiperidin-3-yl)-1,3-dioxoisoindolin-4-yl)amino)octyl)acetamide (Example 2)

General Procedure III was followed by using 2-(2,3-difluoro-6-(2-morpholinothiazol-4-yl)phenoxy)acetic acid (E) (0.02 g, 0.056 mmol), 4-((8-aminooctyl)amino)-2-(2,6-dioxopiperidin-3-yl)isoindoline-1,3-dione hydrochloride (M) (0.024 g, 0.056 mmol), DIPEA (0.03 mL, 0.224 mmol), and HATU (0.027 g, 0.70 mmol) in dry DMF (1.0 mL) to afford the titled compound as yellow solid (0.016 g, 50% yield) following purification by flash column chromatography on SiO$_2$ (DCM/MeOH, 99:1 to 96:4) followed by further HPLC purification (Agilent Technologies 1200; column, Eclipse XDB-C18 4.6×150 mm (5 m); flow rate, 1.0 mL/min; DAD 190-650 nm; isocratic eluent, ACN/H$_2$O 70:30). $^1$H NMR (400 MHz, CDCl$_3$): δ 8.14 (s, 1H), 7.64-7.55 (m, 1H), 7.55-7.45 (m, 1H), 7.11 (d, J=7.1 Hz, 1H), 7.04 (s, 1H), 7.04-6.97 (m, 1H), 6.93 (s, 1H), 6.90 (d, J=8.6 Hz, 1H), 6.25 (s, 1H), 5.02-4.86 (m, 1H), 4.60 (s, 2H), 3.97-3.76 (m, 4H), 3.64-3.48 (m, 4H), 3.34 (q, J=6.8 Hz, 2H), 3.28 (q, J=6.6 Hz, 2H), 2.99-2.67 (m, 3H), 2.21-2.08 (m, 1H), 1.81-1.31 (m, 12H); $^{13}$C NMR (101 MHz, CDCl$_3$): δ 170.90, 170.71, 169.50, 168.28, 167.88, 167.61, 150.78 (dd, J=10.5, 249.5 Hz), 147.01, 146.45-145.86 (m), 144.63 (d, J=10.5 Hz), 144.14 (dd, J=14.0, 247.4 Hz), 136.12, 132.49, 124.99, 124.52 (dd, J=3.8, 7.8 Hz), 116.65, 112.41 (d, J=17.2 Hz), 111.39, 109.86, 105.96, 72.41 (d, J=5.1 Hz), 66.11 (2C), 48.86, 48.62 (2C), 42.59, 39.10, 31.42, 29.45, 29.14, 29.12, 29.11, 26.78, 26.72, 22.84. HRMS (ESI) m/z [M+H]+ calcd for C$_{36}$H$_{40}$F$_2$N$_6$O$_7$S 739.27200, found 739.27369.

2-(2,3-Difluoro-6-(2-morpholinothiazol-4-yl)phenoxy)-N-(10-((2-(2,6-dioxopiperidin-3-yl)-1,3-dioxoisoindolin-4-yl)amino)decyl)acetamide (Example 3)

General Procedure III was followed by using 2-(2,3-difluoro-6-(2-morpholinothiazol-4-yl)phenoxy)acetic acid (E) (0.04 g, 0.086 mmol), 4-((10-aminodecyl)amino)-2-(2,6-dioxopiperidin-3-yl)isoindoline-1,3-dione hydrochloride (N) (0.04 g, 0.086 mmol), DIPEA (0.05 mL, 0.44 mmol) and HATU (0.041 g, 0.107 mmol) in dry DMF (2.0 mL) to afford the titled compound as yellow solid (0.026 g, 39% yield) following purification by flash column chromatography on SiO$_2$ (DCM/Acetone, 95:5 to 85:15). $^1$H NMR (400 MHz, CDCl$_3$): δ 8.16 (s, 1H), 7.61 (ddd, J=8.4, 6.0, 2.1 Hz, 1H), 7.55-7.47 (m, 1H), 7.10 (d, J=7.1 Hz, 1H), 7.06-6.95 (m, 2H), 6.94 (s, 1H), 6.90 (d, J=8.5 Hz, 1H), 6.25 (t, J=5.6 Hz, 1H), 4.93 (dd, J=12.1, 5.3 Hz, 1H), 4.59 (s, 2H), 3.93-3.78 (m, 4H), 3.59-3.50 (m, 4H), 3.38-3.23 (m, 4H), 2.97-2.69 (m, 3H), 2.20-2.08 (m, 1H), 1.74-1.64 (m, 2H), 1.59-1.48 (m, 2H), 1.47-1.39 (m, 2H), 1.37-1.29 (m, 10H); $^{13}$C NMR (101 MHz, CDCl$_3$): δ 170.97, 170.79, 169.51, 168.32, 167.89, 167.65, 150.71 (dd, J=251.9, 10.9 Hz), 147.04, 146.51-146.34 (m), 144.21 (dd, J=247.4, 14.0 Hz), 144.63 (d, J=10.7 Hz), 136.12, 132.49, 125.32-125.17 (m), 124.50 (dd, J=7.8, 4.0 Hz), 116.66, 112.45 (d, J=17.1 Hz), 111.36, 109.82, 106.06, 72.43 (d, J=5.1 Hz), 66.14 (2C), 48.86, 48.57 (2C), 42.65, 39.15, 31.43, 29.49, 29.39 (2C), 29.25, 29.22, 29.21, 26.90, 26.84, 22.83. HRMS (ESI) m/z [M+H]+ calcd for C$_{38}$H$_{44}$F$_2$N$_6$O$_7$S 767.30330, found 767.30327.

2-(2,3-Difluoro-6-(2-morpholinothiazol-4-yl)phenoxy)-N-(2-(2-(2-((2-(2,6-dioxopiperidin-3-yl)-1,3-dioxoisoindolin-4-yl)amino)ethoxy)ethoxy)ethyl)acetamide (Example 4)

General Procedure III was followed by using 2-(2,3-difluoro-6-(2-morpholinothiazol-4-yl)phenoxy)acetic acid (E) (0.018 g, 0.049 mmol), 4-((2-(2-(2-aminoethoxy)ethoxy)ethyl)amino)-2-(2,6-dioxopiperidin-3-yl)isoindoline-1,3-dione hydrochloride (O) (0.022 g, 0.049 mmol), DIPEA (0.034 mL, 0.199 mmol) and HATU (0.024 g, 0.062 mmol) in dry DMF (1.0 mL) to afford the titled compound as yellow solid (4.5 mg, 12% yield) following purification by flash column chromatography on SiO$_2$ (DCM/MeOH, 97:3) followed by HPLC purification (Agilent Technologies 1200; column, Eclipse XDB-C18 4.6×150 mm (5 m); flow rate, 0.8 mL/min; DAD 190-650 nm; isocratic eluent, ACN/H$_2$O 70:30). $^1$H NMR (400 MHz, CDCl$_3$): δ 8.44 (bs, 1H), 7.64 (t, J=6.5 Hz, 1H), 7.46 (t, J=7.8 Hz, 1H), 7.36 (bs, 1H), 7.09 (d, J=7.1 Hz, 1H), 7.05-6.95 (m, 2H), 6.83 (d, J=8.5 Hz, 1H), 6.51 (bs, 1H), 4.98-4.85 (m, 1H), 4.56 (s, 2H), 3.93-3.80 (m, 4H), 3.77-3.64 (m, 8H), 3.62-3.51 (m, 6H), 3.45-3.34 (m, 2H), 2.96-2.66 (m, 3H), 2.20-2.05 (m, 1H). HRMS (ESI) m/z [M+H]+ calcd for C$_{34}$H$_{36}$F$_2$N$_6$O$_9$S 743.23053, found 743.23191.

2-(2,3-Difluoro-6-(2-morpholinothiazol-4-yl)phenoxy)-N-(2-(2-(2-(2-((2-(2,6-dioxopiperidin-3-yl)-1,3-dioxoisoindolin-4-yl)amino)ethoxy)ethoxy)ethoxy)ethyl)acetamide (Example 5)

General Procedure III was followed by using 2-(2,3-difluoro-6-(2-morpholinothiazol-4-yl)phenoxy)acetic acid (E) (0.027 g, 0.076 mmol), 4-((2-(2-(2-(2-aminoethoxy)ethoxy)ethoxy)ethyl)amino)-2-(2,6-dioxopiperidin-3-yl)isoindoline-1,3-dione hydrochloride (P) (0.037 g, 0.076 mmol), DIPEA (0.053 mL, 0.305 mmol) and HATU (0.036 g, 0.095 mmol) in dry DMF (1.0 mL) to afford the titled compound as yellow solid (0.041 g, 69% yield) following purification by flash column chromatography on SiO$_2$ (DCM/MeOH, 98:2). $^1$H NMR (400 MHz, CDCl$_3$): δ 8.31 (s, 1H), 7.66 (t, J=6.6 Hz, 1H), 7.50 (t, J=7.8 Hz, 1H), 7.12 (d, J=7.1 Hz, 1H), 7.09-6.96 (m, 3H), 6.91 (d, J=8.5 Hz, 1H), 6.48 (t, J=4.8 Hz, 1H), 4.92 (dd, J=5.3, 11.9 Hz, 1H), 4.56 (s, 2H), 3.97-3.81 (m, 6H), 3.81-3.22 (m, 18H), 3.07-2.58 (m, 3H), 2.16-2.06 (m, 1H); $^{13}$C NMR (101 MHz, CDCl$_3$): δ 171.00, 170.63, 169.24, 168.30, 168.05, 167.58, 150.54 (dd, J=11.4, 251.2 Hz), 146.79, 146.23-145.77 (m), 144.52 (d, J=9.3 Hz), 144.29 (dd, J=13.9, 247.2 Hz), 136.02, 132.51, 125.28, 124.43, 116.72, 112.53 (d, J=17.0 Hz), 111.66, 110.30, 106.35, 72.26 (d, J=4.6 Hz), 70.77, 70.64, 70.60, 70.37, 69.58, 69.42, 66.14 (2C), 48.86, 48.56 (2C), 42.37, 38.88, 31.42, 22.82. IRMS (ESI) m/z [M+H]+ calcd for C$_{36}$H$_{40}$F$_2$N$_6$O$_{10}$S 787.25675, found 787.25712.

2-(2,3-Difluoro-6-(2-morpholinothiazol-4-yl)phenoxy)-N-(14-((2-(2,6-dioxopiperidin-3-yl)-1,3-dioxoisoindolin-4-yl)amino)-3,6,9,12-tetraoxatetradecyl)acetamide (Example 6)

General Procedure III was followed by using 2-(2,3-difluoro-6-(2-morpholinothiazol-4-yl)phenoxy)acetic acid (E) (0.031 g, 0.087 mmol), 4-((14-amino-3,6,9,12-tetraoxatetradecyl)amino)-2-(2,6-dioxopiperidin-3-yl)isoindoline-1,3-dione hydrochloride (Q) (0.036 g, 0.087 mmol), DIPEA (0.06 mL, 0.348 mmol) and HATU (0.041 g, 0.108 mmol) in dry DMF (1.0 mL) to afford the titled compound as yellow solid (0.03 g, 42% yield) following purification by flash column chromatography on $SiO_2$ (DCM/MeOH, 98:2). $^1$H NMR (400 MHz, $CDCl_3$): δ 8.37 (s, 1H), 7.67 (ddd, J=2.2, 6.0, 8.7 Hz, 1H), 7.53-7.47 (m, 1H), 7.39-7.32 (m, 1H), 7.12 (d, J=7.1 Hz, 1H), 7.05 (s, 1H), 7.04-6.96 (m, 1H), 6.92 (d, J=8.6 Hz, 1H), 6.50 (t, J=5.4 Hz, 1H), 4.94-4.85 (m, 1H), 4.56 (s, 2H), 3.92-3.80 (m, 4H), 3.71 (t, J=5.4 Hz, 2H), 3.69-3.50 (m, 16H), 3.54-3.50 (m, 4H), 3.46 (q, J=5.4 Hz, 2H), 2.92-2.65 (m, 3H), 2.17-2.09 (m, 1H); $^{13}$C NMR (101 MHz, $CDCl_3$): δ 171.09 (d, J=2.8 Hz), 170.60, 169.22, 168.38, 168.00, 167.57, 150.49 (dd, J=11.4, 250.9 Hz), 146.81, 145.99, 144.52 (d, J=9.5 Hz), 144.30 (dd, J=14.0, 247.3 Hz), 136.02, 132.51, 125.38, 124.41 (dd, J=4.1, 7.7 Hz), 116.74, 112.50 (d, J=17.1 Hz), 111.64, 110.29, 106.44, 72.22 (d, J=4.7 Hz), 70.75, 70.63, 70.59, 70.53, 70.43, 70.39, 69.67, 69.41, 66.15 (2C), 48.84, 48.52 (2C), 42.37, 38.86, 31.39, 22.82. HRMS (ESI) m/z [M+H]+ calcd for $C_{38}H_{44}F_2N_6O_{11}S$ 831.28296, found 831.28447.

Scheme 4. Synthesis of thalidomide-based E3LB-2 moiety and linker connection.

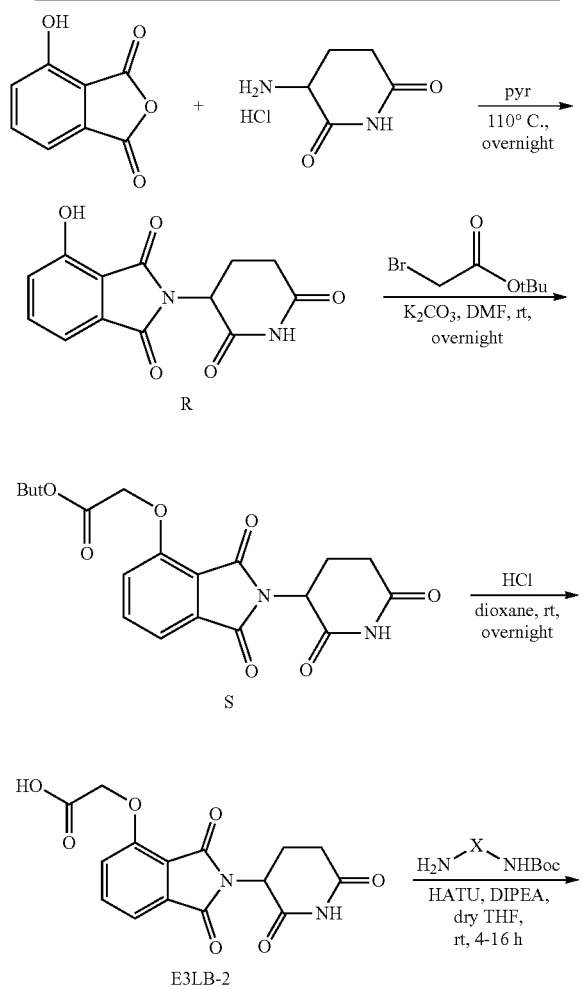

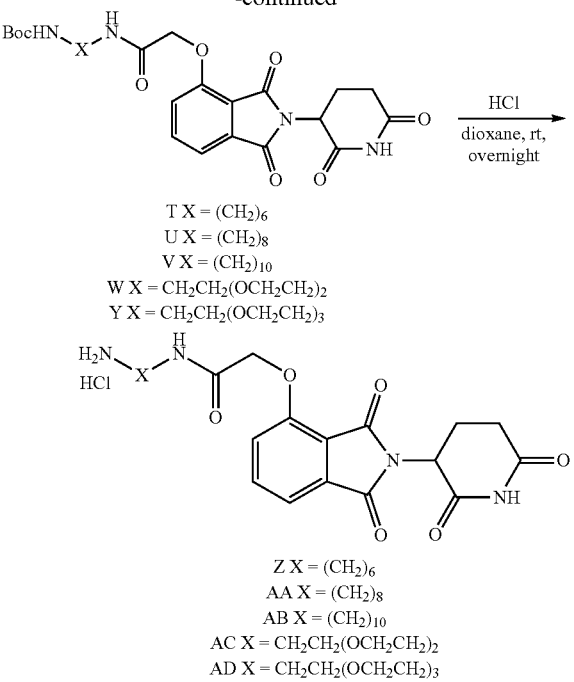

T X = $(CH_2)_6$
U X = $(CH_2)_8$
V X = $(CH_2)_{10}$
W X = $CH_2CH_2(OCH_2CH_2)_2$
Y X = $CH_2CH_2(OCH_2CH_2)_3$

Z X = $(CH_2)_6$
AA X = $(CH_2)_8$
AB X = $(CH_2)_{10}$
AC X = $CH_2CH_2(OCH_2CH_2)_2$
AD X = $CH_2CH_2(OCH_2CH_2)_3$ 2-(2,6-Dioxopiperidin-3-yl)-4-hydroxyisoindoline-1,3-dione (R)

The titled compound can be prepared according to the process described by Remillard, D. et al. *Angew. Chem. Int. Ed. Engl.* 2017, 56, 5738-5743. The solution of 3-hydroxyphthalic anhydride (0.50 g, 3.05 mmol) and 3-aminopiperidine-2,6-dione hydrochloride (0.50 g, 3.05 mmol) in pyridine (12.0 mL) was stirred at 110° C. overnight. After cooling, the mixture was cooled to rt and concentrated under reduced pressure. The crude was purified by flash column chromatography on $SiO_2$ (DCM/MeOH, 95:5) to give the titled compound as light-yellow solid (0.7 g, 84% yield). $^1$H NMR (400 MHz, DMSO-$d_6$): δ 11.16 (bs, 1H), 7.66 (dd, J=8.2 and 7.3 Hz, 1H), 7.32 (d, J=7.1 Hz, 1H), 7.26 (d, J=8.4 Hz, 1H), 5.08 (dd, J=12.8 and 5.4 Hz, 1H), 2.99-2.81 (m, 1H), 2.69-2.53 (m, 2H), 2.12-1.95 (m, 1H); $^{13}$C NMR (101 MHz, DMSO-$d_6$): δ 173.27, 170.48, 167.48, 166.27, 155.95, 136.84, 133.60, 124.02, 114.81, 114.73, 49.09, 31.42, 22.49.

Tert-butyl 2-((2-(2,6-dioxopiperidin-3-yl)-1,3-dioxoisoindolin-4-yl)oxy)acetate (S)

The titled compound can be prepared according to the process described by Remillard, D. et al. *Angew. Chem. Int. Ed. Engl.* 2017, 56, 5738-5743. To the solution of 2-(2,6-dioxopiperidin-3-yl)-4-hydroxyisoindoline-1,3-dione (R) (0.50 g, 1.82 mmol) in dry DMF (4.0 mL) were added $K_2CO_3$ (0.37 g, 2.73 mmol) and tert-butyl bromoacetate (0.27 mL, 1.82 mmol). The mixture was stirred at rt for 2 h. Then, it was poured in ice-water yielding a precipitate which was filtered and purified by flash column chromatography on $SiO_2$ (PE/EA, 6:4) to afford the titled compound as light-yellow solid (0.258 g, 42% yield). $^1$H NMR (400 MHz, $CDCl_3$): δ 8.37 (bs, 1H), 7.67 (t, J=7.9 Hz, 1H), 7.51 (d, J=7.3 Hz, 1H), 7.11 (d, J=8.4 Hz, 1H), 4.99 (dd, J=11.8 and 5.4 Hz, 1H), 4.80 (s, 2H), 2.95-2.71 (m, 3H), 2.19-2.06 (m, 1H), 1.49 (s, 9H); $^{13}$C NMR (101 MHz, $CDCl_3$): δ 171.09, 168.02, 166.88, 166.84, 165.46, 155.50, 136.29, 133.90, 119.75, 117.56, 116.90, 83.12, 77.37, 77.05, 76.73, 66.52, 49.17, 31.38, 28.03 (3C), 22.57.

2-((2-(2,6-Dioxopiperidin-3-yl)-1,3-dioxoisoindolin-4-yl)oxy)acetic acid (E3LB-2)

The titled compound can be prepared according to the process described by Remillard, D. et al. *Angew. Chem. Int. Ed. Engl.* 2017, 56, 5738-5743. Tert-butyl 2-((2-(2,6-dioxopiperidin-3-yl)-1,3-dioxoisoindolin-4-yl)oxy)acetate (S) (1.75 g, 4.51 mmol) was dissolved in 4N HCl in dioxane (15 mL, 0.1M) and stirred at rt overnight. The solvent was evaporated under reduced pressure and the crude residue was triturated with DEE affording the titled compound as white solid (1.26 g, 84% yield). $^{1}$H NMR (400 MHz, DMSO-$d_6$): δ 13.25 (s, 1H), 11.12 (s, 1H), 7.87-7.73 (m, 1H), 7.48 (d, J=7.2 Hz, 1H), 7.40 (d, J=8.6 Hz, 1H), 5.11 (dd, J=12.7 and 5.4 Hz, 1H), 5.00 (s, 2H), 2.96-2.82 (m, 1H), 2.72-2.54 (m, 2H), 2.11-1.98 (m, 1H); $^{13}$C NMR (101 MHz, DMSO-$d_6$): δ 173.27, 170.39, 169.98, 167.21, 165.64, 155.60, 137.23, 133.72, 120.33, 116.78, 116.23, 65.44, 49.25, 31.41, 22.43.

General Procedure IV: HATU-Mediated Amidation Reaction

Tert-butyl (6-(2-((2-(2,6-dioxopiperidin-3-yl)-1,3-dioxoisoindolin-4-yl)oxy)acetamido)hexyl)carbamate (T)

The titled compound can be prepared according to the process described by Bradner, J. et al. U.S. Pat. Appl. Publ., US20160176916. In an oven-dried round-bottom flask, under nitrogen atmosphere, to a stirred solution of 2-((2-(2,6-dioxopiperidin-3-yl)-1,3-dioxoisoindolin-4-yl)oxy)acetic acid (E3LB-2) (0.020 g, 0.060 mmol, 1.0 equiv), tert-butyl (6-aminohexyl)carbamate (0.014 g, 0.066 mmol, 1.1 equiv), and DIPEA (0.02 mL, 0.120 mmol, 2.0 equiv) in dry THF (1.5 mL) was added HATU (0.027 g, 0.072 mmol, 1.20 equiv). Stirring was continued at rt overnight. The reaction mixture was evaporated to dryness ad the crude residue was purified by flash column chromatography on SiO$_2$ (DCM/Acetone, 6:4) to give the titled compound as white solid (0.02 g, 62% yield). $^{1}$H NMR (400 MHz, CDCl$_3$): δ 8.80 (s, 1H), 7.77 (dd, J=8.4, 7.4 Hz, 1H), 7.58 (d, J=7.3 Hz, 1H), 7.51-7.44 (m, 1H), 7.22 (d, J=8.3 Hz, 1H), 5.01 (dd, J=12.3, 5.5 Hz, 1H), 4.66 (s, 2H), 3.52-3.29 (m, 2H), 3.23-3.02 (m, J=18.9 Hz, 2H), 3.00-2.79 (m, 3H), 2.26-2.14 (m, 1H), 1.65-1.57 (m, 2H), 1.54-1.35 (m, 15H); $^{13}$C NMR (101 MHz, CDCl$_3$): δ 171.03, 168.12, 166.64, 166.61, 166.05, 156.21, 154.52, 137.05, 133.60, 119.55, 118.20, 117.41, 87.18, 68.05, 49.34, 40.62, 39.09, 31.49, 30.01, 29.05, 28.43 (3C), 26.50 (2C), 22.68.

Tert-butyl (8-(2-((2-(2,6-dioxopiperidin-3-yl)-1,3-dioxoisoindolin-4-yl)oxy)acetamido)octyl)carbamate (U)

The titled compound can be prepared according to the process described by Remillard, D. et al. *Angew. Chem. Int. Ed. Engl.* 2017, 56, 5738-5743. General Procedure IV (4 h) was followed by using 2-((2-(2,6-dioxopiperidin-3-yl)-1,3-dioxoisoindolin-4-yl)oxy)acetic acid (E3LB-2) (0.250 g, 0.752 mmol), tert-butyl (8-aminooctyl)carbamate (0.202 g, 0.827 mmol), DIPEA (0.26 mL, 1.505 mmol) and HATU (0.343 g, 0.903 mmol) in dry DMF (3.0 mL) to afford the titled compound as light-yellow solid (0.140 g, 33% yield) following purification by flash column chromatography on SiO$_2$ (DCM/Acetone, 85:15 to 70:30). $^{1}$H NMR (400 MHz, CDCl$_3$): δ 8.46 (s, 1H), 7.77 (t, J=7.9 Hz, 1H), 7.58 (d, J=7.2 Hz, 1H), 7.42 (t, J=5.3 Hz, 1H), 7.22 (d, J=8.3 Hz, 1H), 4.99 (dd, J=12.1, 5.4 Hz, 1H), 4.66 (s, 2H), 4.62 (s, 1H), 3.39 (dd, J=12.9, 6.7 Hz, 2H), 3.20-3.04 (m, 2H), 3.02-2.73 (m, 3H), 2.25-2.11 (m, 1H), 1.71-1.57 (m, 4H), 1.46 (s, 11H), 1.37-1.27 (m, 6H); $^{13}$C NMR (101 MHz, CDCl$_3$): δ 170.81, 167.94, 166.63, 166.57, 165.95, 156.05, 154.51, 137.05, 133.59, 119.47, 118.12, 117.38, 68.00, 49.34, 39.18 (2C), 31.50, 30.01, 29.24, 29.15, 29.13, 28.43 (3C), 26.92, 26.68, 26.63, 22.58.

Tert-butyl (10-(2-((2-(2,6-dioxopiperidin-3-yl)-1,3-dioxoisoindolin-4-yl)oxy)acetamido)decyl)carbamate (V)

General Procedure IV (overnight) was followed by using 2-((2-(2,6-dioxopiperidin-3-yl)-1,3-dioxoisoindolin-4-yl)oxy)acetic acid (E3LB-2) (0.250 g, 0.752 mmol), tert-butyl (10-aminodecyl)carbamate (0.205 g, 0.752 mmol), DIPEA (0.25 mL, 1.505 mmol) and HATU (0.343 g, 0.903 mmol) in dry THF (5.0 mL) to afford the titled compound as white solid (0.220 g, 50% yield) following double purification by flash column chromatography on SiO$_2$ (first: DCM/Acetone, 80:20; second: DCM/MeOH, 96:4). $^{1}$H NMR (400 MHz, CDCl$_3$): δ 8.25 (bs, 1H), 7.83-7.74 (m, 1H), 7.58 (d, J=7.3 Hz, 1H), 7.43-7.36 (m, 1H), 7.22 (d, J=8.4 Hz, 1H), 4.99 (dd, J=12.3 and 5.2 Hz, 1H), 4.66 (s, 2H), 4.57 (s, 1H), 3.46-3.32 (m, 2H), 3.19-3.04 (m, 2H), 3.02-2.72 (m, 3H), 2.29-2.08 (m, 1H), 1.71-1.55 (m, 4H), 1.46 (s, 9H), 1.42-1.20 (m, 12H); $^{13}$C NMR (101 MHz, CDCl$_3$): δ 171.56, 170.69, 167.85, 166.61, 166.53, 165.93, 154.52, 137.06, 133.58, 119.45, 118.09, 117.37, 68.01, 49.31, 40.59, 39.24, 31.47, 30.05, 29.45, 29.42, 29.34, 29.24, 29.22, 28.44 (3C), 26.79, 26.73, 22.58.

Tert-butyl (1-((2-(2,6-dioxopiperidin-3-yl)-1,3-dioxoisoindolin-4-yl)oxy)-2-oxo-6,9,12-trioxa-3-azatetradecan-14-yl)carbamate (Y)

General Procedure IV (overnight) was followed by using 2-((2-(2,6-dioxopiperidin-3-yl)-1,3-dioxoisoindolin-4-yl)oxy)acetic acid (E3LB-2) (0.129 g, 0.388 mmol), tert-butyl (14-amino-3,6,9,12-tetraoxatetradec-1-yl)carbamate (0.130 g, 0.388 mmol), DIPEA (0.132 mL, 0.776 mmol) and HATU (0.177 g, 0.466 mmol) in dry THF (2.5 mL) to afford the titled compound as white solid (0.124 g, 49% yield) following purification by flash column chromatography on SiO$_2$ (DCM/MeOH, 97:3). $^{1}$H NMR (400 MHz, CDCl$_3$): δ 8.90 (bs, 1H), 7.77 (t, J=7.9 Hz, 1H), 7.68 (bs, 1H), 7.58 (d, J=7.3 Hz, 1H), 7.21 (d, J=8.4 Hz, 1H), 5.23 (bs, 1H), 4.98 (dd, J=11.9 and 5.3 Hz, 1H), 4.67 (s, 2H), 3.79-3.55 (m, 14H), 3.31 (t, J=4.8 Hz, 2H), 2.99-2.69 (m, 3H), 2.27-2.11 (m, 1H), 1.46 (s, 9H); $^{13}$C NMR (101 MHz, CDCl$_3$): δ 171.27, 168.28, 166.92, 166.65, 165.83, 156.10, 154.44, 137.03, 133.64, 119.40, 118.02, 117.31, 79.24, 70.34 (2C), 70.28 (2C), 70.23, 69.43, 67.88, 55.75, 43.68, 39.11, 31.38, 28.42 (3C), 22.71.

N-(6-Aminohexyl)-2-((2-(2,6-dioxopiperidin-3-yl)-1,3-dioxoisoindolin-4-yl)oxy)acetamide hydrochloride (Z)

General Procedure II (overnight) was followed by using tert-butyl (6-(2-((2-(2,6-dioxopiperidin-3-yl)-1,3-dioxoisoindolin-4-yl)oxy)acetamido)hexyl)carbamate (T) (0.090 g, 0.169 mmol) and 4N HCl in dioxane (1.0 mL) to afford the titled compound as white solid (0.070 g, 89% yield). $^1$H NMR (400 MHz, MeOD): δ 7.84 (dd, J=8.4 and 7.4 Hz, 1H), 7.57 (d, J=7.3 Hz, 1H), 7.46 (d, J=8.5 Hz, 1H), 5.16 (dd, J=12.5 and 5.5 Hz, 1H), 4.79 (s, 2H), 3.40-3.34 (m, 2H), 2.98-2.63 (m, 5H), 2.23-2.12 (m, 1H), 1.72-1.58 (m, 4H), 1.50-1.39 (m, 4H).

N-(8-Aminooctyl)-2-((2-(2,6-dioxopiperidin-3-yl)-1,3-dioxoisoindolin-4-yl)oxy)acetamide hydrochloride (AA)

General Procedure II (4 h) was followed by using tert-butyl (8-(2-((2-(2,6-dioxopiperidin-3-yl)-1,3-dioxoisoindolin-4-yl)oxy)acetamido)octyl)carbamate (U) (0.116 g, 0.208 mmol) and 4N HCl in dioxane (1.1 mL) to afford the titled compound as white solid (0.096 g, 93% yield). $^1$H NMR (400 MHz, MeOD): δ 7.83 (t, J=7.9 Hz, 1H), 7.56 (d, J=7.4 Hz, 1H), 7.46 (d, J=8.5 Hz, 1H), 5.16 (dd, J=12.5, 5.5 Hz, 1H), 4.78 (s, 2H), 3.00-2.67 (m, 5H), 2.25-2.12 (m, 1H), 1.73-1.54 (m, 4H), 1.47-1.37 (m, 10H).

N-(10-Aminodecyl)-2-((2-(2,6-dioxopiperidin-3-yl)-1,3-dioxoisoindolin-4-yl)oxy)acetamide hydrochloride (AB)

General Procedure II (5 h) was followed by using tert-butyl (10-(2-((2-(2,6-dioxopiperidin-3-yl)-1,3-dioxoisoindolin-4-yl)oxy)acetamido)decyl)carbamate (V) (0.210 g, 0.358 mmol) and 4N HCl in dioxane (2.0 mL) to afford the titled compound as white solid (0.175 g, 93% yield). $^1$H NMR (400 MHz, MeOD): δ 8.07 (t, J=5.6 Hz, 1H), 7.88-7.80 (m, 1H), 7.56 (d, J=7.3 Hz, 1H), 7.45 (d, J=8.5 Hz, 1H), 5.16 (dd, J=12.6, 5.4 Hz, 1H), 4.78 (s, 2H), 3.00-2.68 (m, 5H), 2.26-2.11 (m, 1H), 1.75-1.53 (m, 4H), 1.47-1.27 (m, 12H).

N-(2-(2-(2-Aminoethoxy)ethoxy)ethyl)-2-((2-(2,6-dioxopiperidin-3-yl)-1,3-dioxoisoindolin-4-yl)oxy)acetamide hydrochloride (AC)

General Procedure II (overnight) was followed by using tert-butyl (2-(2-(2-(2-((2-(2,6-dioxopiperidin-3-yl)-1,3-dioxoisoindolin-4-yl)oxy)acetamido)ethoxy)ethoxy)ethyl)carbamate (W) (synthesized according to the process described by Bradner, J. et al. U.S. Pat. Appl. Publ., US20160176916) (0.125 g, 0.222 mmol) and 4N HCl in dioxane (1.0 mL) to afford the titled compound as white solid (0.076 g, 70% yield). $^1$H NMR (400 MHz, MeOD): δ 7.83 (t, J=7.9 Hz, 1H), 7.54 (d, J=7.3 Hz, 1H), 7.46 (d, J=8.4 Hz, 1H), 5.16 (dd, J=12.7, 5.5 Hz, 1H), 4.80 (s, 2H), 3.77-3.63 (m, 8H), 3.54 (t, J=5.2 Hz, 2H), 3.18-3.10 (m, 2H), 2.99-2.66 (m, 3H), 2.25-2.13 (m, 1H).

N-(2-(2-(2-(2-Aminoethoxy)ethoxy)ethoxy)ethyl)-2-((2-(2,6-dioxopiperidin-3-yl)-1,3-dioxoisoindolin-4-yl)oxy)acetamide hydrochloride (AD)

General Procedure II (overnight) was followed by using tert-butyl (1-((2-(2,6-dioxopiperidin-3-yl)-1,3-dioxoisoindolin-4-yl)oxy)-2-oxo-6,9,12-trioxa-3-azatetradecan-14-yl)carbamate (Y) (0.145 g, 0.239 mmol) and 4N HCl in dioxane (1.0 mL) to afford the titled compound as light-yellow solid (0.104 g, 80% yield). $^1$H NMR (400 MHz, MeOD): δ 7.95-7.77 (m, 1H), 7.67-7.54 (m, 1H), 7.51-7.38 (m, 1H), 5.23-5.11 (m, 1H), 4.80 (s, 2H), 3.59-3.49 (m, 2H), 3.33 (s, 4H), 3.14 (s, 2H), 3.04-2.62 (m, 3H), 2.29-2.06 (m, 1H).

Scheme 5. Synthesis of Examples 7-11.

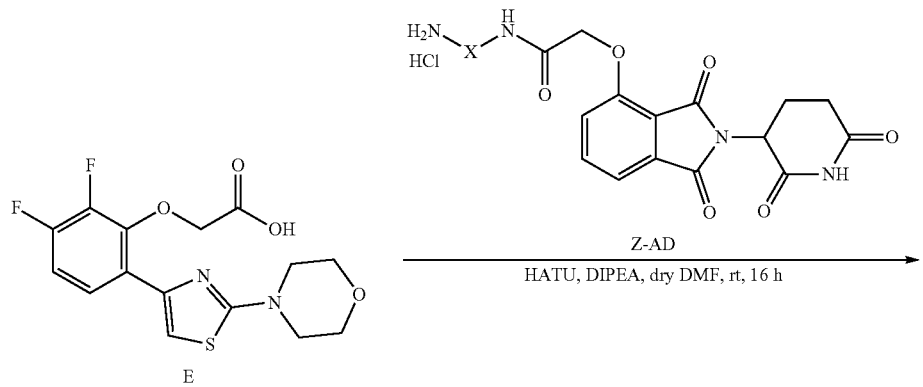

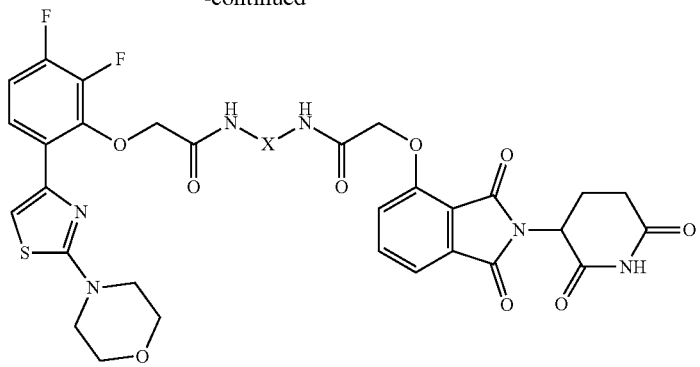

Example 7 X = (CH$_2$)$_6$
Example 8 X = (CH$_2$)$_8$
Example 9 X = (CH$_2$)$_{10}$
Example 10 X = CH$_2$CH$_2$(OCH$_2$CH$_2$)$_2$
Example 11 X = CH$_2$CH$_2$(OCH$_2$CH$_2$)$_3$ 2-(2,3-Difluoro-6-(2-morpholinothiazol-4-yl)phenoxy)-N-(6-(2-((2-(2,6-dioxopiperidin-3-yl)-1,3-dioxoisoindolin-4-yl)oxy)acetamido)hexyl)acetamide (Example 7)

General Procedure III (16h) was followed by using 2-(2,3-difluoro-6-(2-morpholinothiazol-4-yl)phenoxy)acetic acid (E) (0.023 g, 0.064 mmol), N-(6-aminohexyl)-2-((2-(2,6-dioxopiperidin-3-yl)-1,3-dioxoisoindolin-4-yl)oxy)acetamide hydrochloride (Z) (0.030 g, 0.064 mmol), DIPEA (0.044 mL, 0.257 mmol), and HATU (0.030 g, 0.080 mmol) in dry DMF (1.0 mL) to afford the titled compound as white solid (0.002 g, 4.6% yield) following purification by flash column chromatography on SiO$_2$ (DCM/MeOH, 97:3). $^1$H NMR (400 MHz, CDCl$_3$): δ 9.03 (bs, 1H), 7.82-7.73 (m, 1H), 7.65-7.47 (m, 3H), 7.21 (d, J=8.4 Hz, 1H), 7.14 (bs, 1H), 6.99 (dd, J=16.7, 9.1 Hz, 1H), 6.93 (s, 1H), 4.99 (dd, J=12.1, 5.3 Hz, 1H), 4.65 (s, 2H), 4.60 (s, 2H), 3.91-3.80 (m, 4H), 3.59-3.50 (m, 4H), 3.50-3.22 (m, 4H), 3.03-2.70 (m, 3H), 2.24-2.09 (m, 1H), 1.53-1.16 (m, 8H). HRMS (ESI) m/z [M+H]+ calcd for C$_{36}$H$_{38}$F$_2$N$_6$O$_9$S 769.24618, found 769.24848.

2-(2,3-Difluoro-6-(2-morpholinothiazol-4-yl)phenoxy)-N-(8-(2-((2-(2,6-dioxopiperidin-3-yl)-1,3-dioxoisoindolin-4-yl)oxy)acetamido)octyl)acetamide (Example 8)

General Procedure III (16h) was followed by using 2-(2,3-difluoro-6-(2-morpholinothiazol-4-yl)phenoxy)acetic acid (E) (0.032 g, 0.091 mmol), N-(8-aminooctyl)-2-((2-(2,6-dioxopiperidin-3-yl)-1,3-dioxoisoindolin-4-yl)oxy)acetamide hydrochloride (AA) (0.045 g, 0.091 mmol), DIPEA (0.062 mL, 0.363 mmol), and HATU (0.043 g, 0.114 mmol) in dry DMF (2.0 mL) to afford the titled compound as yellow solid (0.012 g, 17% yield) following purification by flash column chromatography on SiO$_2$ (DCM/Acetone, 75:25). $^1$H NMR (400 MHz, CDCl$_3$): δ 8.66 (bs, 1H), 7.76 (t, J=7.8 Hz, 1H), 7.66-7.53 (m, 2H), 7.49-7.39 (m, 1H), 7.21 (d, J=8.4 Hz, 1H), 7.08-6.90 (m, 3H), 4.98 (dd, J=12.0, 5.0 Hz, 1H), 4.65 (s, 2H), 4.60 (s, 2H), 3.94-3.78 (m, 4H), 3.60-3.47 (m, 4H), 3.40-3.25 (m, 4H), 3.02-2.73 (m, 3H), 2.26-2.12 (m, 1H), 1.56-1.47 (m, 2H), 1.45-1.28 (m, 10H); $^{13}$C NMR (101 MHz, CDCl$_3$): δ 170.91, 170.82, 168.05, 167.97, 166.64, 166.57, 165.99, 154.51, 150.69 (dd, J=251.69 and 11.5 Hz), 146.51-146.44 (m), 144.19 (dd, J=47.3, 14.0 Hz), 144.63 (d, J=10.6 Hz), 137.04, 133.60, 125.25 (d, J=3.5 Hz), 124.47 (dd, J=7.6, 4.3 Hz), 119.47, 118.14, 117.38, 112.41 (d, J=17.1 Hz), 106.11, 72.41 (d, J=5.1 Hz), 68.01, 66.13 (2C), 49.34, 48.55 (2C), 39.16, 39.10, 31.49, 29.44, 29.23, 29.13, 29.06, 26.70, 26.68, 22.59. HRMS (ESI) m/z [M+H]+ calcd for C$_{38}$H$_{42}$F$_2$N$_6$O$_9$S 797.27748, found 797.27834.

2-(2,3-Difluoro-6-(2-morpholinothiazol-4-yl)phenoxy)-N-(10-(2-((2-(2,6-dioxopiperidin-3-yl)-1,3-dioxoisoindolin-4-yl)oxy)acetamido)decyl)acetamide (Example 9)

General Procedure III (6h) was followed by using 2-(2,3-difluoro-6-(2-morpholinothiazol-4-yl)phenoxy)acetic acid (E) (0.031 g, 0.086 mmol), N-(10-aminodecyl)-2-((2-(2,6-dioxopiperidin-3-yl)-1,3-dioxoisoindolin-4-yl)oxy)acetamide hydrochloride (AB) (0.045 g, 0.086 mmol), DIPEA (0.059 mL, 0.344 mmol), and HATU (0.041 g, 0.107 mmol) in dry DMF (1.0 mL) to afford the titled compound as white solid (0.041 g, 58% yield) following purification by flash column chromatography on SiO$_2$ (DCM/MeOH, 97:3). $^1$H NMR (400 MHz, CDCl$_3$): δ 8.42 (s, 1H), 7.77 (t, J=7.9 Hz, 1H), 7.69-7.48 (m, 2H), 7.40 (s, 1H), 7.21 (d, J=8.4 Hz, 1H), 7.13-6.96 (m, 2H), 6.94 (s, 1H), 4.98 (dd, J=5.1, 12.2 Hz, 1H), 4.65 (s, 2H), 4.60 (s, 2H), 4.04-3.71 (m, 4H), 3.71-3.45

(m, 4H), 3.35 (dq, J=6.2, 6.7, 20.5 Hz, 4H), 3.12-2.68 (m, 3H), 2.27-2.03 (m, 1H), 1.55-1.44 (m, 4H), 1.44-1.16 (m, 12H); $^{13}$C NMR (101 MHz, CDCl$_3$): δ 170.77 (2C), 167.90 (2C), 166.61, 166.55, 165.95, 154.51, 150.71 (dd, J=11.5, 251.2 Hz), 146.39 (d, J=2.5 Hz), 144.62 (d, J=9.7 Hz), 144.17 (dd, J=14.1, 247.4 Hz), 137.05, 133.58, 125.18 (d, J=2.8 Hz), 124.47 (dd, J=4.0, 7.7 Hz), 119.46, 118.09, 117.37, 112.38 (d, J=17.1 Hz), 106.06, 72.40 (d, J=5.2 Hz), 68.01, 66.12 (2C), 49.32, 48.56 (2C), 39.25, 39.08, 31.47, 29.46, 29.41, 29.40, 29.33, 29.21, 29.20, 26.79, 26.77, 22.58. HRMS (ESI) m/z [M+H]+ calcd for C$_{40}$H$_{46}$F$_2$N$_6$O$_9$S 825.30878, found 825.30942.

2-(2,3-Difluoro-6-(2-morpholinothiazol-4-yl)phenoxy)-N-(2-(2-(2-(2-((2-(2,6-dioxopiperidin-3-yl)-1,3-dioxoisoindolin-4-yl)oxy)acetamido)ethoxy)ethoxy)ethyl)acetamide (Example 10)

General Procedure III (16h) was followed by using 2-(2,3-difluoro-6-(2-morpholinothiazol-4-yl)phenoxy)acetic acid (E) (0.025 g, 0.070 mmol), N-(2-(2-(2-aminoethoxy)ethoxy)ethyl)-2-((2-(2,6-dioxopiperidin-3-yl)-1,3-dioxoisoindolin-4-yl)oxy)acetamide hydrochloride (AC) (0.035 g, 0.070 mmol), DIPEA (0.048 mL, 0.280 mmol), and HATU (0.033 g, 0.087 mmol) in dry DMF (2.0 mL) to afford the titled compound as light-yellow solid (0.009 g, 17% yield) following purification by flash column chromatography on SiO$_2$ (DCM/MeOH, 97:3). $^1$H NMR (400 MHz, CDCl$_3$): δ 8.75 (bs, 1H), 7.75 (t, J=7.8 Hz, 1H), 7.68-7.52 (m, 3H), 7.40 (bs, 1H), 7.18 (d, J=8.3 Hz, 1H), 7.07-6.91 (m, 2H), 4.96 (dd, J=11.7, 5.1 Hz, 1H), 4.63 (s, 2H), 4.58 (s, 2H), 3.94-3.80 (m, 4H), 3.79-3.63 (m, 8H), 3.60-3.43 (m, 8H), 2.97-2.64 (m, 3H), 2.22-2.10 (m, 1H). HRMS (ESI) m/z [M+H]+ calcd for C$_{36}$H$_{38}$F$_2$N$_6$O$_{11}$S 801.23601, found 801.23745.

2-(2,3-Difluoro-6-(2-morpholinothiazol-4-yl)phenoxy)-N-(1-((2-(2-(2,6-dioxopiperidin-3-yl)-1,3-dioxoisoindolin-4-yl)oxy)-2-oxo-6,9,12-trioxa-3-azatetradecan-14-yl)acetamide (Example 11)

General Procedure III (16h) was followed by using 2-(2,3-difluoro-6-(2-morpholinothiazol-4-yl)phenoxy)acetic acid (E) (0.033 g, 0.092 mmol), N-(2-(2-(2-(2-aminoethoxy)ethoxy)ethoxy)ethyl)-2-((2-(2,6-dioxopiperidin-3-yl)-1,3-dioxoisoindolin-4-yl)oxy)acetamide hydrochloride (AD) (0.050 g, 0.092 mmol), DIPEA (0.063 mL, 0.368 mmol), and HATU (0.043 g, 0.115 mmol) in dry DMF (2.0 mL) to afford the titled compound as light-yellow solid (0.012 g, 16% yield) following purification by flash column chromatography on SiO$_2$ (DCM/MeOH, 97:3). $^1$H NMR (400 MHz, CDCl$_3$): δ 8.96 (bs, 1H), 7.75 (t, J=7.9 Hz, 1H), 7.70-7.59 (m, 2H), 7.55 (d, J=7.3 Hz, 1H), 7.46 (bs, 1H), 7.18 (d, J=8.4 Hz, 1H), 7.08 (s, 1H), 6.98 (dd, J=16.7, 9.0 Hz, 1H), 4.92 (dd, J=12.1, 5.3 Hz, 1H), 4.64 (s, 2H), 4.56 (s, 2H), 3.90-3.82 (m, 4H), 3.71-3.47 (m, 20H), 2.92-2.61 (m, 3H), 2.19-2.07 (m, 1H). HRMS (ESI) m/z [M+H]+ calcd for C$_{38}$H$_{42}$F$_2$N$_6$O$_{12}$S 845.26222, found 845.26303.

Scheme 6. Synthesis of Examples 12-14.

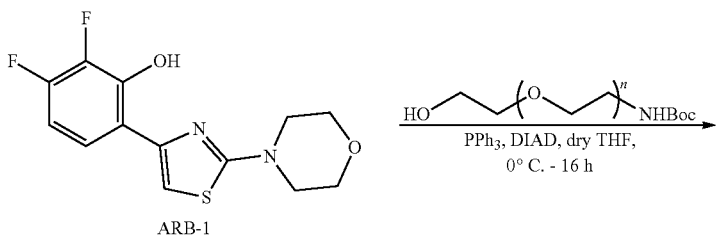

ARB-1

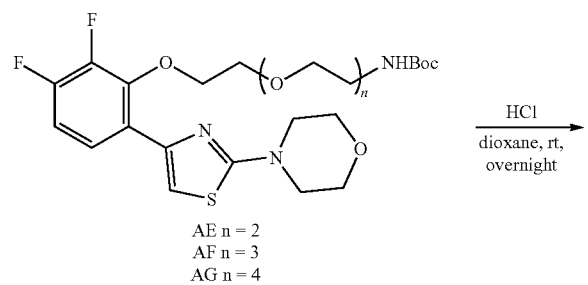

AE n = 2
AF n = 3
AG n = 4

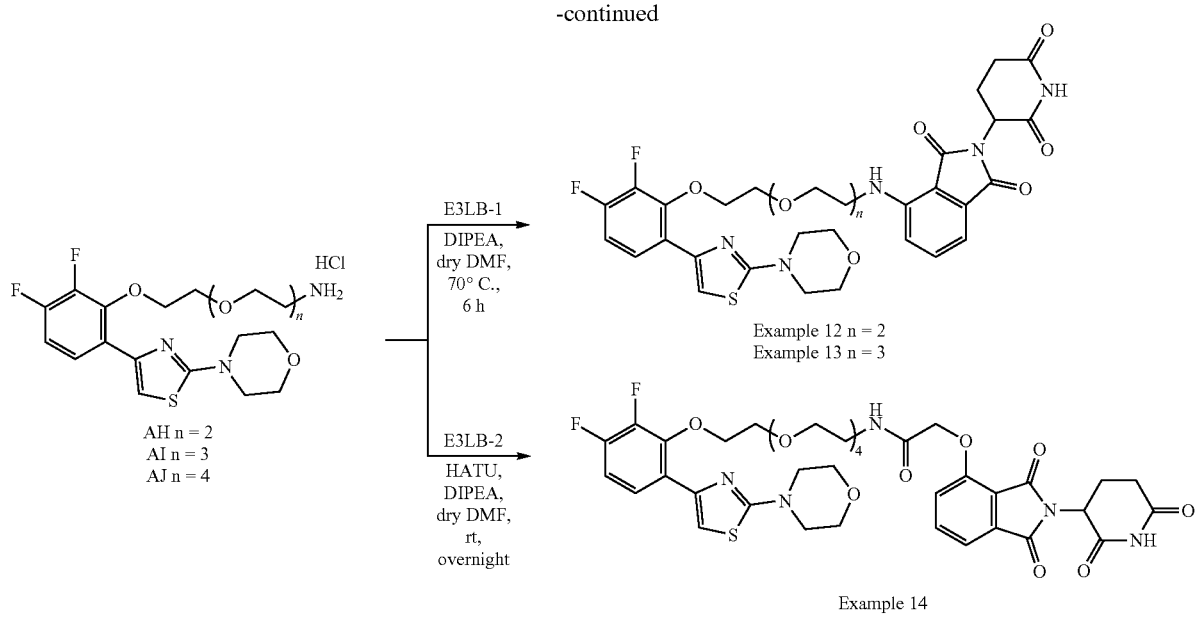

General Procedure V: Mitsunobu Reaction

Tert-butyl (2-(2-(2-(2,3-difluoro-6-(2-morpholinothiazol-4-yl)phenoxy)ethoxy)ethoxy)ethyl)carbamate (AE)

DIAD (0.087 mL, 0.442 mmol, 1.1 equiv) was slowly added to a stirred ice-cooled solution of 2,3-difluoro-6-(2-morpholinothiazol-4-yl)phenol (ARB-1) (0.120 g, 0.402 mmol, 1.0 equiv), tert-butyl (2-(2-(2-hydroxyethoxy)ethoxy)ethyl)carbamate (0.110 g, 0.442 mmol, 1.1 equiv), and PPh$_3$ (0.116 g, 0.442 mmol, 1.1 equiv) in dry THF (5.0 mL). The solution was stirred at 0° C. for 30 min, then at rt for 16 h. The reaction mixture was quenched with water (20 mL) and extracted with EA (10 mL×3). Reunited organic phases were dried over anhydrous Na$_2$SO$_4$ and concentrated under reduced pressure to afford a crude residue which was purified by flash column chromatography on SiO$_2$ (DCM/EA, 9:1 to 8:2) to give the titled compound as yellow oil (0.100 g, 70% yield). $^1$H NMR (400 MHz, DMSO-d$_6$): δ 7.89 (ddd, J=8.8, 6.3, 2.3 Hz, 1H), 7.58 (s, 1H), 7.00-6.88 (m, 1H), 5.10-4.94 (m, 1H), 4.35-4.24 (m, 2H), 3.92-3.79 (m, 6H), 3.72-3.61 (m, 4H), 3.60-3.48 (m, 6H), 3.39-3.25 (m, 2H), 1.43 (s, 9H); $^{13}$C NMR (101 MHz, CDCl$_3$): δ 169.71, 155.99, 150.35 (dd, J=11.6, 249.5 Hz), 145.52, 144.65 (dd, J=13.6, 246.2 Hz), 125.04 (d, J=2.1 Hz), 123.84 (dd, J=4.0, 7.8 Hz), 111.42 (d, J=17.0 Hz), 107.47, 79.17, 72.56 (d, J=6.0 Hz), 70.46, 70.34, 70.30 (2C), 66.22 (2C), 48.60 (2C), 40.35, 28.39 (3C).

Tert-butyl (2-(2-(2-(2-(2,3-difluoro-6-(2-morpholinothiazol-4-yl)phenoxy)ethoxy)ethoxy)ethoxy)ethyl) carbamate (AF)

General Procedure V was followed by using DIAD (0.087 mL, 0.442 mmol), 2,3-difluoro-6-(2-morpholinothiazol-4-yl)phenol (ARB-1) (0.120 g, 0.402 mmol), tert-butyl (2-(2-(2-(2-hydroxyethoxy)ethoxy)ethoxy)ethyl)carbamate (0.130 g, 0.442 mmol), and PPh$_3$ (0.116 g, 0.442 mmol) in dry THF (5.0 mL) to afford the titled compound as yellow oil, which solidified upon standing at rt (0.148 g, 93% yield) following purification by flash column chromatography on SiO$_2$ (DCM/EA, 7:3). $^1$H NMR (400 MHz, DMSO-d$_6$): δ 7.90 (ddd, J=8.9, 6.3, 2.3 Hz, 1H), 7.57 (s, 1H), 6.99-6.90 (m, 1H), 5.02 (s, 1H), 4.36-4.26 (m, 2H), 3.93-3.82 (m, 6H), 3.75-3.59 (m, 8H), 3.58-3.49 (m, 6H), 3.39-3.25 (m, 2H), 1.46 (s, 9H); $^{13}$C NMR (101 MHz, CDCl$_3$): δ 169.70, 155.98, 150.35 (dd, J=11.7, 249.5 Hz), 145.54, 144.63 (dd, J=13.7, 246.3 Hz), 125.02 (d, J=3.2 Hz), 123.83 (dd, J=3.9, 7.8 Hz), 111.38 (d, J=17.0 Hz), 107.48, 79.16, 72.60 (d, J=6.0 Hz), 70.64, 70.60, 70.58, 70.28, 70.23 (2C), 66.21 (2C), 48.59 (2C), 40.35, 28.41 (3C).

Tert-butyl (14-(2,3-difluoro-6-(2-morpholinothiazol-4-yl)phenoxy)-3,6,9,12-tetraoxatetradecyl) carbamate (AG)

General Procedure V was followed by using DIAD (0.040 mL, 0.201 mmol), 2,3-difluoro-6-(2-morpholinothiazol-4-yl)phenol (ARB-1) (0.05 g, 0.167 mmol), tert-butyl (14-hydroxy-3,6,9,12-tetraoxatetradecyl)carbamate (0.062 g, 0.184 mmol), and PPh$_3$ (0.526 g, 0.201 mmol) in dry THF (2.0 mL) to afford the titled compound as white solid (0.039 g, 37% yield) following double purification by flash column chromatography (first on SiO$_2$: DCM/Acetone, 95:5 to 90:10; second on Silica RP-18: water/ACN, 5:5). $^1$H NMR (400 MHz, CDCl$_3$): δ 7.89 (ddd, J=2.3, 6.3, 8.8 Hz, 1H), 7.57 (s, 1H), 7.03-6.85 (m, 1H), 5.06 (s, 1H), 4.41-4.14 (m, 2H), 3.95-3.77 (m, 6H), 3.77-3.59 (m, 12H), 3.53 (q, J=4.9, 5.3 Hz, 6H), 3.31 (d, J=5.1 Hz, 2H), 1.45 (s, 9H); $^{13}$C NMR (101 MHz, CDCl$_3$): δ 169.69, 155.99, 150.33 (dd, J=11.7, 249.5 Hz), 145.53, 144.62 (dd, J=13.7, 246.3 Hz), 125.00, 123.81 (dd, J=4.0, 7.8 Hz), 111.36 (d, J=17.0 Hz), 107.51, 79.15, 72.60 (d, J=6.0 Hz), 70.65, 70.63, 70.59, 70.55, 70.52, 70.26, 70.23 (2C), 66.21 (2C), 48.59 (2C), 40.35, 28.42 (3C).

2-(2-(2-(2,3-Difluoro-6-(2-morpholinothiazol-4-yl)phenoxy)ethoxy)ethoxy)ethan-1-amine hydrochloride (AH)

General Procedure II (overnight) was followed by using tert-butyl (2-(2-(2-(2,3-difluoro-6-(2-morpholinothiazol-4- yl)phenoxy)ethoxy)ethyl)carbamate (AE) (0.100 g, 0.189 mmol) and 4N HCl in dioxane (2.0 mL) to afford the titled compound as white solid (0.080 g, 91% yield). $^1$H NMR (400 MHz, MeOD): δ 7.49-7.40 (m, 1H), 7.28 (s, 1H), 7.04 (dd, J=16.9, 9.0 Hz, 1H), 4.25 (s, 1H), 3.86-3.50 (m, 18H), 3.02 (s, 2H).

2-(2-(2-(2-(2,3-Difluoro-6-(2-morpholinothiazol-4-yl)phenoxy)ethoxy)ethoxy)ethoxy)ethan-1-amine hydrochloride (AI)

General Procedure II (overnight) was followed by using tert-butyl (2-(2-(2-(2-(2,3-difluoro-6-(2-morpholinothiazol-4-yl)phenoxy)ethoxy)ethoxy)ethoxy)ethyl)carbamate (AF) (0.140 g, 0.244 mmol) and 4N HCl in dioxane (2.0 mL) to afford the titled compound as white solid (0.115 g, 93% yield). $^1$H NMR (400 MHz, MeOD): δ 7.59 (s, 1H), 7.43 (s, 1H), 7.15 (dd, J=16.8, 8.8 Hz, 1H), 4.39 (s, 2H), 3.91 (s, 4H), 3.82 (s, 2H), 3.77-3.55 (m, 14H), 3.15 (s, 2H).

4-((2-(2-(2-(2,3-Difluoro-6-(2-morpholinothiazol-4-yl)phenoxy)ethoxy)ethoxy)ethyl)amino)-2-(2,6-dioxopiperidin-3-yl)isoindoline-1,3-dione (Example 12)

General Procedure I (6h) was followed by using 2-(2-(2-(2,3-difluoro-6-(2-morpholinothiazol-4-yl)phenoxy)ethoxy)ethoxy)ethan-1-amine hydrochloride (AH) (0.044 g, 0.095 mmol), 2-(2,6-dioxopiperidin-3-yl)-4-fluoroisoindoline-1,3-dione (E3LB-1) (0.024 g, 0.086 mmol), and DIPEA (0.044 mL, 0.256 mmol) in dry DMF (0.6 mL) to afford the titled compound as yellow solid (0.06 g, 54% yield) following purification by flash column chromatography on SiO$_2$ (DCM/Acetone, 9:1). $^1$H NMR (400 MHz, CDCl$_3$): δ 8.21 (s, 1H), 7.89 (ddd, J=8.7, 6.3, 2.1 Hz, 1H), 7.58 (s, 1H), 7.52-7.44 (m, 1H), 7.11 (d, J=7.1 Hz, 1H), 6.99-6.88 (m, 2H), 6.51 (t, J=5.3 Hz, 1H), 4.90 (dd, J=12.1, 5.3 Hz, 1H), 4.40-4.24 (m, 2H), 3.98-3.81 (m, 6H), 3.79-3.62 (m, 6H), 3.59-3.38 (m, 6H), 2.96-2.65 (m, 3H), 2.19-2.03 (m, 1H). HRMS (ESI) m/z [M+H]+ calcd for C$_{32}$H$_{33}$F$_2$N$_5$O$_8$S 686.20907, found 686.20855.

4-((2-(2-(2-(2-(2,3-Difluoro-6-(2-morpholinothiazol-4-yl)phenoxy)ethoxy)ethoxy)ethoxy)ethyl)amino)-2-(2,6-dioxopiperidin-3-yl)isoindoline-1,3-dione (Example 13)

General Procedure I (6h) was followed by using 2-(2-(2-(2-(2,3-difluoro-6-(2-morpholinothiazol-4-yl)phenoxy)ethoxy)ethoxy)ethoxy)ethan-1-amine hydrochloride (AI) (0.050 g, 0.098 mmol), 2-(2,6-dioxopiperidin-3-yl)-4-fluoroisoindoline-1,3-dione (E3LB-1) (0.024 g, 0.086 mmol) and DIPEA (0.044 mL, 0.256 mmol) in dry DMF (0.6 mL) to afford the titled compound as yellow solid (0.034 g, 53% yield) following purification by flash column chromatography on SiO$_2$ (DCM/Acetone, 9:1). $^1$H NMR (400 MHz, CDCl$_3$): δ 8.19 (s, 1H), 7.88 (ddd, J=8.7, 6.3, 2.1 Hz, 1H), 7.57 (s, 1H), 7.52-7.44 (m, 1H), 7.11 (d, J=7.1 Hz, 1H), 6.98-6.87 (m, 2H), 6.49 (t, J=5.4 Hz, 1H), 4.91 (dd, J=12.0, 5.3 Hz, 1H), 4.34-4.22 (m, 2H), 3.92-3.81 (m, 6H), 3.79-3.60 (m, 10H), 3.58-3.40 (m, 6H), 2.96-2.62 (m, 3H), 2.15-2.06 (m, 1H); $^{13}$C NMR (101 MHz, CDCl$_3$): δ 170.98, 169.73, 169.25, 168.29, 167.60, 150.36 (dd, J=11.5, 249.7 Hz), 146.85, 145.64-145.34 (m), 144.64 (dd, J=13.6, 246.2 Hz), 136.04, 132.49, 124.99 (d, J=2.8 Hz), 123.84 (dd, J=4.0, 7.8 Hz), 116.77, 111.66, 111.40 (d, J=17.0 Hz), 110.27, 107.55, 72.65 (d, J=6.0 Hz), 70.73 (3C), 70.57, 70.26, 69.54, 66.21 (2C), 48.86, 48.60 (2C), 42.42, 31.41, 22.77. HRMS (ESI) m/z [M+H]+ calcd for C$_{34}$H$_{37}$F$_2$N$_5$O$_9$S 730.23528, found 730.23653.

N-(14-(2,3-Difluoro-6-(2-morpholinothiazol-4-yl)phenoxy)-3,6,9,12-tetraoxatetradecyl)-2-((2-(2,6-dioxopiperidin-3-yl)-1,3-dioxoisoindolin-4-yl)oxy)acetamide (Example 14)

General Procedure II (overnight) was followed by using tert-butyl (14-(2,3-difluoro-6-(2-morpholinothiazol-4-yl)phenoxy)-3,6,9,12-tetraoxatetradecyl) carbamate (AG) (0.039 g, 0.063 mmol) and 4N HCl in dioxane (2.0 mL) to afford 14-(2,3-difluoro-6-(2-morpholinothiazol-4-yl)phenoxy)-3,6,9,12-tetraoxatetradecan-1-amine hydrochloride (AJ) as white solid (0.034 g, 98% yield). Then, under nitrogen atmosphere, to the solution of 2-((2-(2,6-dioxopiperidin-3-yl)-1,3-dioxoisoindolin-4-yl)oxy)acetic acid (E3LB-2) (0.023 g, 0.069 mmol), 14-(2,3-difluoro-6-(2-morpholinothiazol-4-yl)phenoxy)-3,6,9,12-tetraoxatetradecan-1-amine hydrochloride (AJ) (0.035 g, 0.063 mmol), and DIPEA (0.035 mL, 0.205 mmol) in dry DMF was added HATU (0.046 g, 0.08 mmol) and the mixture was stirred at rt overnight. The reaction mixture was poured in ice-water and extracted with EA (10 mL×3). Reunited organic phases were dried over anhydrous Na$_2$SO$_4$ and concentrated under reduced pressure to afford a crude residue which was purified by HPLC (Agilent Technologies 1200; column, Eclipse XDB-C18 4.6×150 mm (5 m); flow rate, 1.0 mL/min; DAD 190-650 nm; isocratic eluent, ACN/H$_2$O 70:30) to afford the titled compound as white solid (5.5 mg, 10% yield). $^1$H NMR (400 MHz, CDCl$_3$): δ 8.82 (s, 1H), 7.89 (ddd, J=2.3, 6.2, 8.8 Hz, 1H), 7.82-7.70 (m, 1H), 7.70-7.61 (m, 1H), 7.56 (d, J=7.0 Hz, 1H), 7.54 (s, 1H), 7.20 (d, J=8.2 Hz, 1H), 7.04-6.85 (m, 1H), 4.99-4.81 (m, 1H), 4.66 (s, 2H), 4.42-4.20 (m, 2H), 3.91-3.79 (m, 6H), 3.79-3.44 (m, 20H), 3.01-2.67 (m, 3H), 2.28-2.01 (m, 1H); $^{13}$C NMR (101 MHz, CDCl$_3$): δ 170.94, 169.73, 168.03, 166.75, 166.60, 165.75, 154.40, 150.35 (dd, J=11.6, 249.7 Hz), 145.63-145.21 (m), 144.63 (dd, J=13.7, 246.2 Hz), 136.93, 133.68, 125.00, 123.82 (dd, J=3.9, 7.9 Hz), 119.23, 118.04, 117.26, 111.42 (d, J=17.0 Hz), 107.50, 72.62 (d, J=5.9 Hz), 70.77, 70.48, 70.46 (2C), 70.35, 70.29, 70.20, 69.45, 67.83, 66.22 (2C), 49.28, 48.59 (2C), 39.09, 31.41, 22.72. HRMS (ESI) m/z [M+H]+ calcd for C$_{38}$H$_{43}$F$_2$N$_5$O$_{12}$S 832.26698, found 832.26587.

Scheme 7. Synthesis of VHL-based E3LB-3 moiety and linker connection.

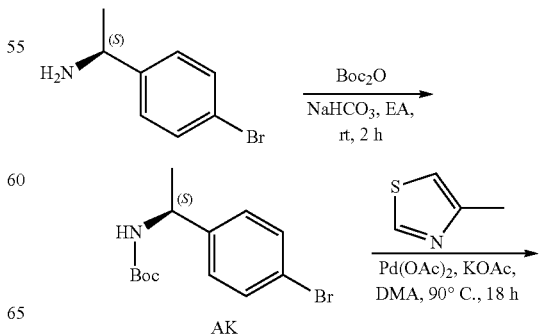

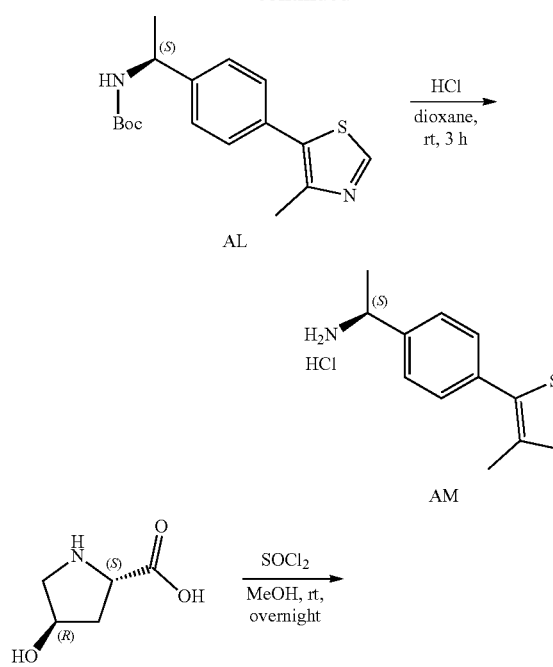
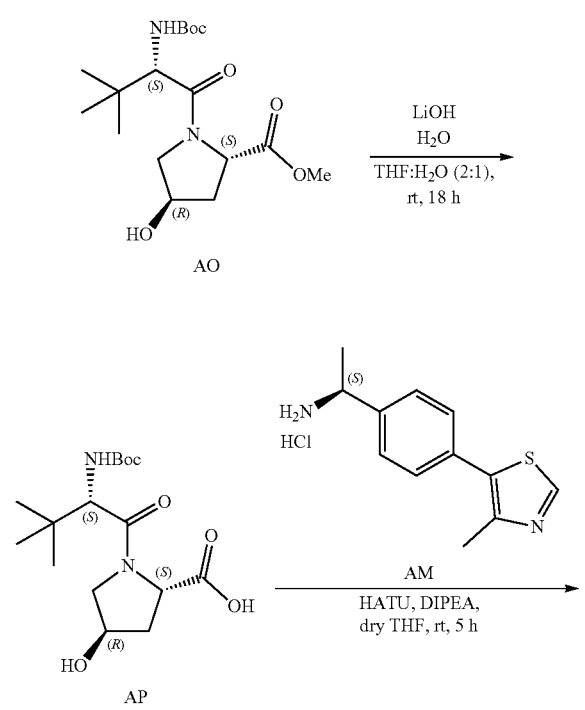
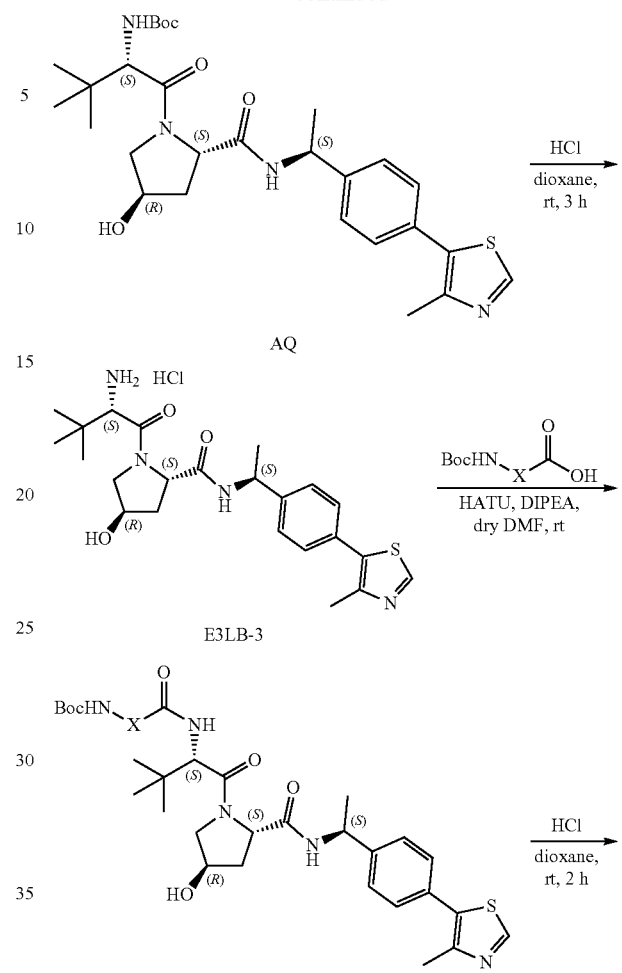

Tert-butyl (S)-1-(4-bromophenyl)ethyl)carbamate (AK)

The titled compound can be prepared according to the process described by Kanak Raina et al. *Proc. Natl. Acad. Sci. U.S.A.* 2016, 113, 7124-7129. To a mixture of (S)-1-(4-bromophenyl)ethanamine (commercially available from, for example, Fluorochem) (3.98 g, 19.89 mmol) and NaHCO$_3$ (1.25 g, 14.92 mmol) in water (10 mL) and EA (10 mL) was added (Boc)$_2$O (5.20 g, 23.87 mmol) by maintaining the temperature at 5° C. After stirring at rt for 2 h, the reaction mixture was filtered. The collected solid was suspended in a mixture of hexane (10 mL) and water (10 mL) for 30 min. The solid was filtered and dried in an oven at 50° C. to afford the titled compound as a white solid (5.41 g, 91% yield). $^1$H NMR (400 MHz, CDCl$_3$): δ 7.55-7.39 (m, 2H), 7.19 (d, J=8.3 Hz, 2H), 4.99-4.46 (m, 2H), 1.58-1.22 (m, 12H); $^{13}$C NMR (101 MHz, CDCl$_3$): δ 154.98, 143.26, 131.60 (2C), 127.60 (2C), 120.80, 79.61, 49.68, 28.36 (3C), 22.61.

Tert-butyl (S)-(1-(4-(4-methylthiazol-5-yl)phenyl)ethyl)carbamate (AL)

The titled compound can be prepared according to the process described by Raina K. et al. *Proc. Natl. Acad. Sci. U.S.A.* 2016, 113, 7124-7129. Under nitrogen atmosphere, a mixture of compound tert-butyl (S)-1-(4-bromophenyl)ethyl)carbamate (AK) (5.00 g, 16.65 mmol), 4-methylthiazole (commercially available from, for example, Fluorochem) (3.30 g, 33.31 mmol), palladium (II) acetate (0.037 g, 0.166 mmol), and potassium acetate (3.27 g, 33.31 mmol) in DMA (12.5 mL) was stirred at 90° C. for 18 h. After cooling, the reaction mixture was filtered. Water (60 mL) was added to the filtrate, and the resulting mixture was stirred at rt for 4 h. The solid was collected by filtration and dried in an oven at 50° C. to afford the titled compound (3.14 g, 74% yield) as a gray solid. $^1$H NMR (400 MHz, CDCl$_3$): δ 8.70 (s, 1H), 7.44-7.40 (m, 2H), 7.41-7.35 (m, 2H), 4.86 (bs, 2H), 2.56 (s, 3H), 1.50 (d, J=6.5 Hz, 3H), 1.46 (s, 9H); $^{13}$C NMR (101 MHz, CDCl$_3$): δ 155.06, 150.20, 148.48, 131.65, 130.72, 129.48 (2C), 127.60, 126.20 (2C), 79.60, 49.91, 28.39 (3C), 22.71, 16.11.

(S)-1-(4-(4-Methylthiazol-5-yl)phenyl)ethan-1-amine hydrochloride (AM)

The titled compound can be prepared according to the process described by Raina K. et al. *Proc. Natl. Acad. Sci. U.S.A.* 2016, 113, 7124-7129. A solution of 4N HCl in dioxane (10 mL) was added to tert-butyl (S)-(1-(4-(4-methylthiazol-5-yl)phenyl)ethyl)carbamate (AL) (3.00 g, 9.42 mmol). The reaction mixture was stirred at rt for 3 h. The solvent was evaporated to dryness, and the residue was triturated with DEE, filtered, and dried in an oven at 60° C. to afford the titled product (2.37 g, 99% yield) as a light-yellow solid. $^1$H NMR (400 MHz, DMSO-d$_6$): δ 9.19 (s, 1H), 8.78 (bs, 3H), 7.68 (d, J=8.1 Hz, 2H), 7.57 (d, J=8.3 Hz, 2H), 4.52-4.38 (m, 1H), 2.48 (s, 3H), 1.56 (d, J=6.8 Hz, 3H); $^{13}$C NMR (101 MHz, DMSO-d$_6$): δ 152.95, 147.68, 139.93, 131.97, 131.49, 129.64 (2C), 128.09 (2C), 50.11, 21.16, 16.03.

Methyl (2S,4R)-4-hydroxypyrrolidine-2-carboxylate hydrochloride (AN)

The titled compound can be prepared according to the process described by Gmez-Bengoa E. et al. *Chemistry* 2010, 16, 5333-5342. Thionyl chloride (2.12 mL, 3.48 g, 29.2 mmol) was slowly added dropwise under nitrogen atmosphere to a stirred suspension of (2S,4R)-4-hydroxypyrrolidine-2-carboxylic acid (commercially available from, for example, Fluorochem) (3.20 g, 24.4 mmol) in dry MeOH (60.0 mL) at 0° C. After stirring overnight at rt, the solvent was evaporated to dryness and the crude residue was triturated with DEE, filtered, and dried to afford the titled product as white solid (4.43 g, 100% yield). $^1$H NMR (400 MHz, DMSO-d$_6$): δ 9.78 (s, 2H), 5.58 (s, 1H), 4.48 (dd, J=7.5, 10.8 Hz, 1H), 4.45-4.39 (m, 1H), 3.77 (s, 3H), 3.39-3.34 (m, 1H), 3.11-3.01 (m, 1H), 2.26-2.01 (m, 1H); $^{13}$C NMR (101 MHz, DMSO-d$_6$): δ 169.54, 68.88, 57.87, 53.54, 53.47, 37.43.

Methyl (2S,4R)-1-((S)-2-((tert-butoxycarbonyl)amino)-3,3-dimethylbutanoyl)-4-hydroxypyrrolidine-2-carboxylate (AO)

The titled compound can be prepared according to the process described by Raina K. et al. *Proc. Natl. Acad. Sci. U.S.A.* 2016, 113, 7124-7129. Under nitrogen atmosphere, to a solution of (S)-2-(tert-butoxycarbonyl)amino-3,3-dimethylbutanoic acid (commercially available from, for example, Fluorochem) (5.09 g, 22.02 mmol), methyl (2S,4R)-4-hydroxypyrrolidine-2-carboxylate hydrochloride (AN) (4.00 g, 22.02 mmol), and DIPEA (13.43 mL, 9.97 g, 77.08 mmol) in dry DMF (40 mL) was added HATU (9.20 g, 21.2 mmol) at 0° C. The resulting mixture was allowed to warm to rt and stirred for 16 h. The reaction mixture was dropped in water (200 mL) and extracted with EA (100 mL×3). The combined organic phases were washed with water (100 mL×3), 1N HCl (100 mL×2), saturated NaHCO$_3$ solution (100 mL×2), brine (100 mL×2), dried over anhydrous Na$_2$SO$_4$, and concentrated under reduced pressure to afford the titled product as a light-yellow oil (7.66 g, 98% yield). $^1$H NMR (400 MHz, CDCl$_3$): δ 5.27 (d, J=9.4 Hz, 1H), 4.71 (t, J=8.6 Hz, 1H), 4.53 (s, 1H), 4.21 (d, J=9.5 Hz, 1H), 4.14-4.01 (m, 1H), 3.75 (s, 3H), 3.78-3.68 (m, 1H), 2.30 (s, 1H), 2.45-0.89 (m, 2H), 1.43 (s, 9H), 1.06 (s, 9H); $^{13}$C NMR (101 MHz, CDCl$_3$): δ 172.6, 171.2, 156.3, 80.0, 70.3, 58.7, 57.4, 56.3, 52.2, 37.6, 35.2, 28.3 (3C), 26.3 (3C).

(2S,4R)-1-((S)-2-((tert-butoxycarbonyl)amino)-3,3-dimethylbutanoyl)-4-hydroxypyrrolidine-2-carboxylic acid (AP)

The titled compound can be prepared according to the process described by Raina K. et al. *Proc. Natl. Acad. Sci. U.S.A.* 2016, 113, 7124-7129. To the solution of methyl (2S,4R)-1-((S)-2-((tert-butoxycarbonyl)amino)-3,3-dimethylbutanoyl)-4-hydroxypyrrolidine-2-carboxylate (AO) (2.00 g, 5.58 mmol) in THF (20 mL) at 0° C. was added the solution of lithium hydroxide monohydrate (2.34 g, 55.79 mmol) in water (10 mL). The resulting mixture was stirred at rt for 18 h. The organic solvent was removed under vacuo, the residue was diluted with ice-water (10 mL) and the pH was slowly adjusted to 2-3 with 2N HCl yielding a solid which was collected by filtration, washed with water (6 mL×2), and then dried in an oven at 50° C. to afford the titled compound as a white solid (1.45 g, 75% yield). $^1$H NMR (400 MHz, DMSO-d$_6$): δ 12.10 (bs, 1H), 6.49 (d, J=9.4 Hz, 1H), 5.19 (bs, 1H), 4.33 (bs, 1H), 4.26 (t, J=8.3 Hz, 1H), 4.16 (d, J=9.1 Hz, 1H), 3.69-3.51 (m, 2H), 2.19-1.82 (m, 2H), 1.38 (s, 9H), 0.94 (s, 9H); $^{13}$C NMR (101 MHz, DMSO-d$_6$): δ 173.76, 170.41, 155.77, 78.56, 69.28, 58.64, 58.17, 56.49, 37.75, 35.83, 28.64 (3C), 26.67 (3C).

Tert-butyl ((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate (AQ)

The titled compound can be prepared according to the process described by Raina K. et al. *Proc. Natl. Acad. Sci. U.S.A.* 2016, 113, 7124-7129. Under nitrogen atmosphere, to a stirred solution of (2S,4R)-1-((S)-2-((tert-butoxycarbonyl)amino)-3,3-dimethylbutanoyl)-4-hydroxypyrrolidine-2-carboxylic acid (AP) (1.40 g, 4.06 mmol), (S)-1-(4-(4-methylthiazol-5-yl)phenyl)ethan-1-amine hydrochloride (AM) (1.04 g, 4.06 mmol), and DIPEA (2.12 mL, 1.57 g, 12.19 mmol) in dry THF (20 mL) was added HATU (1.85 g, 4.88 mmol) at 0° C. The resulting mixture was allowed to warm to rt and stirred for 5 h. The organic solvent was removed under vacuo. Water (15 mL) was added to the residue, and the resulting mixture was stirred for 1 h and then was filtered. The solid was collected, dried in an oven at 50° C., and purified by flash column chromatography on SiO$_2$ (DCM/Acetone, 75:25) to give the titled product as a white solid (1.57 g, 71% yield). $^1$H NMR (400 MHz, CDCl$_3$): δ 8.70 (s, 1H), 7.62 (d, J=7.6 Hz, 1H), 7.45-7.37 (m, 4H), 5.23 (d, J=8.8 Hz, 1H), 5.14-5.02 (m, 1H), 4.82 (t, J=7.9 Hz, 1H), 4.53 (s, 1H), 4.22 (d, J=9.0 Hz, 1H), 4.17 (d, J=11.1 Hz, 1H), 3.58 (d, J=8.6 Hz, 1H), 2.83 (bs, 1H), 2.70-2.59 (m, 1H), 2.55 (s, 3H), 2.14-2.01 (m, 1H), 1.48 (d, J=7.0 Hz, 3H), 1.44 (s, 9H), 1.07 (s, 9H); $^{13}$C NMR (101 MHz, CDCl$_3$): δ 173.04, 169.45, 156.57, 150.29, 148.52, 143.14, 131.60, 130.91, 129.60 (2C), 126.43 (2C), 80.57, 70.09, 59.01, 58.10, 56.43, 48.89, 35.07, 34.68, 28.30 (3C), 26.47 (3C), 22.30, 16.10.

(2S,4R)-1-((S)-2-Amino-3,3-dimethylbutanoyl)-4-hydroxy-N—((S)-1-(4-(4-methylthiazol-5-yl)phenyl)ethyl)pyrrolidine-2-carboxamide hydrochloride (E3LB-3)

The titled compound can be prepared according to the process described by Raina K. et al. *Proc. Natl. Acad. Sci. U.S.A.* 2016, 113, 7124-7129. A solution of 4N HCl in dioxane (6.0 mL) was added to tert-butyl ((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)carbamate (AQ) (1.55 g, 2.85 mmol) and the mixture was stirred at rt for 3 h. The solvent was evaporated to dryness and the crude residue was triturated with DEE, filtered off, and dried in an oven at 50° C. to give the titled compound as a white solid (1.36 g, 99% yield). $^1$H NMR (400 MHz, DMSO-d$_6$): δ 9.11 (s, 1H), 8.62 (d, J=7.8 Hz, 1H), 8.16 (s, 3H), 7.50-7.34 (m, 4H), 6.83 (s, 1H), 4.91 (q, J=7.2 Hz, 1H), 4.55 (t, J=8.4 Hz, 1H), 4.31 (s, 1H), 3.89 (d, J=5.3 Hz, 1H), 3.75 (d, J=10.8 Hz, 1H), 3.50 (dd, J=3.7, 10.9 Hz, 1H), 2.47 (s, 3H), 2.21-1.65 (m, 2H), 1.38 (d, J=7.0 Hz, 3H), 1.03 (s, 9H); $^{13}$C NMR (101 MHz, DMSO-d$_6$): δ 170.68, 167.08, 151.52, 147.47, 145.31, 131.96, 129.84, 129.32 (2C), 126.85 (2C), 69.35, 59.30, 58.51, 56.94, 48.24, 38.39, 34.85, 26.53 (3C), 22.97, 16.14.

Tert-butyl (4-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-4-oxobutyl)carbamate (AR)

General Procedure III (1h) was followed by using (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (E3LB-3) (0.20 g, 0.416 mmol), 4-((tert-butoxycarbonyl)amino)butanoic acid (0.093 g, 0.458 mmol), DIPEA (0.29 mL, 1.666 mmol), and HATU (0.198 g, 0.521 mmol) in dry DMF (1.0 mL) to afford the titled compound as white solid (0.16 g, 61% yield) following purification by flash column chromatography on SiO$_2$ (DCM/MeOH, 99:1 to 96:4). $^1$H NMR (400 MHz, CDCl$_3$): δ 8.68 (s, 1H), 7.61 (d, J=7.3 Hz, 1H), 7.44-7.34 (m, 4H), 7.23 (d, J=7.0 Hz, 1H), 5.18-5.04 (m, 1H), 4.94 (s, 1H), 4.75 (t, J=8.1 Hz, 1H), 4.55-4.41 (m, 2H), 4.22-4.05 (m, 1H), 3.69-3.55 (m, 1H), 3.25-3.04 (m, 2H), 2.53 (s, 3H), 2.46-2.34 (m, 1H), 2.33-2.06 (m, 3H), 1.85-1.65 (m, 2H), 1.49 (d, J=6.9 Hz, 3H), 1.43 (s, 9H), 1.09 (s, 9H); $^{13}$C NMR (101 MHz, CDCl$_3$): δ 173.76, 172.06, 170.01, 156.76, 150.31, 148.44, 143.38, 131.62, 130.78, 129.51 (2C), 126.46 (2C), 79.62, 70.13, 58.64, 58.54, 56.74, 48.80, 39.40, 36.00, 34.74, 32.96, 28.40 (3C), 26.66, 26.56 (3C), 22.20, 16.08.

Tert-butyl (5-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-5-oxopentyl)carbamate (AS)

General Procedure III (2h) was followed by using (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (E3LB-3) (1.48 g, 3.08 mmol), 5-((tert-butoxycarbonyl)amino)pentanoic acid (0.735 g, 3.38 mmol), DIPEA (2.14 mL, 12.31 mmol), and HATU (1.46 g, 3.85 mmol) in dry DMF (6.0 mL) to afford the titled compound as white solid (1.60 g, 81% yield) following purification by flash column chromatography on SiO$_2$ (DCM/MeOH, 98:2 to 95:5). $^1$H NMR (400 MHz, CDCl$_3$): δ 8.69 (s, 1H), 7.51 (d, J=7.0 Hz, 1H), 7.41 (q, J=8.5 Hz, 4H), 6.31 (d, J=7.6 Hz, 1H), 5.18-5.04 (m, 1H), 4.76 (t, J=7.9 Hz, 2H), 4.58 (d, J=8.6 Hz, 1H), 4.53 (bs, 1H), 4.13 (d, J=11.4 Hz, 1H), 3.62 (d, J=10.4 Hz, 1H), 3.41 (bs, 1H), 3.18-3.00 (m, 2H), 2.55 (s, 4H), 2.33-2.04 (m, 3H), 1.72-1.57 (m, 2H), 1.55-1.38 (m, 14H), 1.06 (s, 9H); $^{13}$C NMR (101 MHz, CDCl$_3$): δ 173.59, 172.15, 169.63, 156.14, 150.28, 148.49, 143.15, 131.58, 130.88, 129.55 (2C), 126.45 (2C), 79.26, 70.06, 58.41, 57.69, 56.77, 48.84, 39.99, 35.73, 35.46, 34.95, 29.36, 28.44 (3C), 26.52 (3C), 22.59, 22.26, 16.10.

Tert-butyl (6-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-6-oxohexyl)carbamate (AT)

General Procedure III (1h) was followed by using (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (E3LB-3) (0.250 g, 0.521 mmol), 6-((tert-butoxycarbonyl)amino)hexanoic acid (0.132 g, 0.573 mmol), DIPEA (0.36 mL, 2.083 mmol), and HATU (0.247 g, 0.651 mmol) in dry DMF (1.0 mL) to afford the titled compound as white solid (0.213 g, 63% yield) following purification by flash column chromatography on SiO$_2$ (DCM/MeOH, 95:5). $^1$H NMR (400 MHz, CDCl$_3$): δ 8.70 (s, 1H), 7.49 (d, J=6.6 Hz, 1H), 7.46-7.36 (m, 4H), 6.16 (d, J=8.3 Hz, 1H), 5.16-5.06 (m, 1H), 4.78 (t, J=8.1 Hz, 1H), 4.70 (bs, 1H), 4.58 (d, J=9.1 Hz, 1H), 4.53 (s, 1H), 4.17 (d, J=11.6 Hz, 1H), 3.79-3.56 (m, 1H), 3.29-2.99 (m, 2H), 2.55 (s, 3H), 2.31-2.05 (m, 3H), 1.56-1.40 (m, 16H), 1.37-1.24 (m, 2H), 1.07 (s, 9H).

Tert-butyl (7-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-7-oxoheptyl)carbamate (AU)

General Procedure III (30 min) was followed by using (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (E3LB-3) (0.250 g, 0.521 mmol), 7-((tert-butoxycarbonyl)amino)heptanoic acid (0.14 g, 0.573 mmol), DIPEA (0.36 mL, 2.083 mmol), and HATU (0.247 g, 0.651 mmol) in dry DMF (1.0 mL) to afford the titled compound as white solid (0.244 g, 68% yield) following purification by flash column chromatography on $SiO_2$ (DCM/MeOH, 95:5). $^1H$ NMR (400 MHz, $CDCl_3$): δ 8.70 (s, 1H), 7.50 (d, J=6.2 Hz, 1H), 7.41 (q, J=8.3 Hz, 4H), 6.18 (d, J=8.5 Hz, 1H), 5.17-5.05 (m, 1H), 4.77 (t, J=8.0 Hz, 1H), 4.67-4.47 (m, 3H), 4.17 (d, J=11.5 Hz, 1H), 3.61 (d, J=10.6 Hz, 1H), 3.18-3.01 (m, 3H), 2.55 (s, 4H), 2.35-2.03 (m, 3H), 1.74-1.57 (m, 4H), 1.55-1.40 (m, 12H), 1.32 (s, 4H), 1.07 (s, 9H); $^{13}C$ NMR (101 MHz, $CDCl_3$): δ 173.9 (2C), 172.2, 169.6, 150.3, 148.4, 143.2, 130.8, 129.6 (2C), 126.5 (2C), 109.6, 79.2, 70.0, 58.3, 57.6, 56.7, 48.8, 40.3, 36.2, 35.3, 34.8, 29.7, 28.4 (3C), 28.4, 26.5 (3C), 26.2, 25.3, 22.2, 16.0.

Tert-butyl (2-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethoxy)ethyl)carbamate (AW)

General Procedure III (1h) was followed by using (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (E3LB-3) (0.10 g, 0.208 mmol), tert-butyl (2-(2-(2-aminoethoxy)ethoxy)ethyl)carbamate (0.06 g, 0.229 mmol), DIPEA (0.14 mL, 0.833 mmol), and HATU (0.099 g, 0.260 mmol) in dry DMF (0.5 mL) to afford the titled compound as white solid (0.072 g, 50% yield) following purification by flash column chromatography on $SiO_2$ (DCM/MeOH, 97:3 to 95:5). $^1H$ NMR (400 MHz, $CDCl_3$): δ 8.69 (s, 1H), 7.52 (d, J=8.6 Hz, 1H), 7.40 (d, J=7.3 Hz, 4H), 5.94 (s, 1H), 5.21-5.06 (m, 1H), 4.66 (dd, J=35.2, 26.9 Hz, 3H), 4.22-3.05 (m, 14H), 2.54 (s, 3H), 2.37-2.01 (m, 2H), 1.54-1.37 (m, 12H), 1.06 (s, 9H).

(2S,4R)-1-((S)-2-(4-Aminobutanamido)-3,3-dimethylbutanoyl)-4-hydroxy-N—((S)-1-(4-(4-methylthiazol-5-yl)phenyl)ethyl)pyrrolidine-2-carboxamide hydrochloride (AY)

General Procedure II (2h) was followed by using tert-butyl (4-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-4-oxobutyl)carbamate (AR) (0.120 g, 0.190 mmol) and 4N HCl in dioxane (1.2 mL) to afford the titled compound as light-yellow solid (0.10 g, 92% yield). $^1H$ NMR (400 MHz, MeOD): δ 9.84 (s, 1H), 7.55 (dd, J=16.3, 8.3 Hz, 4H), 5.04 (q, J=7.0 Hz, 1H), 4.63-4.53 (m, 2H), 4.46 (s, 1H), 3.95-3.88 (m, 1H), 3.79-3.71 (m, 1H), 2.99 (t, J=7.3 Hz, 2H), 2.61 (s, 3H), 2.52-2.43 (m, 2H), 2.24 (dd, J=13.0, 7.6 Hz, 1H), 2.01-1.89 (m, 3H), 1.53 (d, J=7.0 Hz, 3H), 1.07 (s, J=7.3 Hz, 9H).

(2S,4R)-1-((S)-2-(5-Aminopentanamido)-3,3-dimethylbutanoyl)-4-hydroxy-N—((S)-1-(4-(4-methylthiazol-5-yl)phenyl)ethyl)pyrrolidine-2-carboxamide hydrochloride (AZ)

General Procedure II (2h) was followed by using tert-butyl (5-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-5-oxopentyl)carbamate (AS) (1.35 g, 2.09 mmol) and 4N HCl in dioxane (10.0 mL) to afford the titled compound as white solid (1.11 g, 91% yield). $^1H$ NMR (400 MHz, $CD_3OD$): δ 10.03 (s, 1H), 7.57 (d, J=8.3 Hz, 4H), 5.10-5.01 (m, 1H), 4.73-4.56 (m, 2H), 4.46 (s, 1H), 3.91 (d, J=10.5 Hz, 1H), 3.76 (d, J=10.5 Hz, 1H), 3.33 (s, 1H), 3.02-2.84 (m, 2H), 2.64 (s, 3H), 2.48-2.33 (m, 2H), 2.33-2.23 (m, 1H), 2.00-1.90 (m, 1H), 1.80-1.68 (m, 4H), 1.53 (d, J=6.6 Hz, 3H), 1.05 (s, 9H); $^{13}C$ NMR (101 MHz, DMSO-$d_6$): δ 172.12, 171.08, 169.96, 152.39, 147.48, 145.34, 131.97, 129.80, 129.29 (2C), 126.88 (2C), 69.19, 59.01, 56.88, 56.73, 48.17, 38.90, 38.20, 35.69, 34.70, 27.09, 26.94 (3C), 22.91, 22.80, 16.13.

(2S,4R)-1-((S)-2-(6-Aminohexanamido)-3,3-dimethylbutanoyl)-4-hydroxy-N—((S)-1-(4-(4-methylthiazol-5-yl)phenyl)ethyl)pyrrolidine-2-carboxamide hydrochloride (BA)

General Procedure II (1h) was followed by using tert-butyl (6-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-6-oxohexyl)carbamate (AT) (0.20 g, 0.304 mmol) and 4N HCl in dioxane (2.0 mL) to afford the titled compound as white solid (0.128 g, 71% yield). $^1H$ NMR (400 MHz, MeOD): δ 10.06 (s, 1H), 7.57 (dd, J=16.4, 7.8 Hz, 4H), 5.08-5.02 (m, 1H), 4.67-4.56 (m, 2H), 4.46 (s, 1H), 3.90 (d, J=10.8 Hz, 1H), 3.81-3.72 (m, 1H), 2.95 (t, J=7.2 Hz, 2H), 2.65 (s, 3H), 2.46-2.20 (m, 3H), 2.02-1.89 (m, 1H), 1.75-1.63 (m, 4H), 1.54 (d, J=6.9 Hz, 3H), 1.41 (t, J=6.8 Hz, 2H), 1.07 (s, 9H).

(2S,4R)-1-((S)-2-(7-Aminoheptanamido)-3,3-dimethylbutanoyl)-4-hydroxy-N—((S)-1-(4-(4-methylthiazol-5-yl)phenyl)ethyl)pyrrolidine-2-carboxamide hydrochloride (BB)

General Procedure II (1h) was followed by using tert-butyl (7-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-7-oxoheptyl)carbamate (AU) (0.22 g, 0.327 mmol) and 4N HCl in dioxane (2.0 mL) to afford the titled compound as white solid (0.199 g, 100% yield). $^1H$ NMR (400 MHz, MeOD): δ 9.82 (s, 1H), 7.74-7.26 (m, 4H), 5.04 (q, J=7.0 Hz, 1H), 4.64 (s, 1H), 4.60 (t, J=8.4 Hz, 1H), 4.46 (s, 1H), 3.90 (d, J=11.3 Hz, 1H), 3.84-3.71 (m, 1H), 2.94 (t, J=7.5 Hz, 2H), 2.61 (s, 3H), 2.37-2.21 (m, 3H), 2.05-1.92 (m, 1H), 1.79-1.62 (m, 4H), 1.54 (d, J=7.0 Hz, 3H), 1.50-1.33 (m, 4H), 1.06 (s, 9H); $^{13}C$ NMR (101 MHz, MeOD): δ 175.86, 173.28, 172.25, 155.50, 147.60, 143.50, 136.81, 130.62 (2C), 128.52, 128.10 (2C), 70.96, 68.11, 60.53, 59.04, 57.98, 49.63, 40.64, 38.82, 36.44, 36.32, 29.58, 28.31, 27.03 (3C), 26.58, 22.40, 13.48.

(2S,4R)-1-((S)-2-(2-(3-Aminopropoxy)acetamido)-3,3-dimethylbutanoyl)-4-hydroxy-N—((S)-1-(4-(4-methylthiazol-5-yl)phenyl)ethyl)pyrrolidine-2-carboxamide hydrochloride (BC)

General Procedure III (30 min) was followed by using (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (E3LB-3) (0.250 g, 0.521 mmol), 2-(3-((tert-butoxycarbonyl)amino)propoxy) acetic acid (0.134 g, 0.573 mmol), DIPEA (0.36 mL, 2.083 mmol), and HATU (0.247 g, 0.651 mmol) in dry DMF (1.0 mL) to afford tert-butyl (3-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)propyl)carbamate (AV) as white solid (0.215 g, 63% yield) after purification by flash column chromatography on SiO$_2$ (DCM/MeOH, 95:5). Then, following general Procedure II (1h) by using tert-butyl (3-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)propyl)carbamate (AV) (0.210 g, 0.318 mmol) and 4N HCl in dioxane (2.0 mL) the titled compound was obtained as white solid (0.196 g, 100% yield). $^1$H NMR (400 MHz, MeOD): δ 9.88 (s, 1H), 7.55 (q, J=8.4 Hz, 4H), 5.04 (q, J=6.9 Hz, 1H), 4.75-4.67 (m, 1H), 4.65-4.53 (m, 1H), 4.47 (s, 1H), 4.10 (d, J=3.6 Hz, 2H), 3.90 (d, J=10.9 Hz, 1H), 3.80-3.70 (m, 2H), 3.37 (s, 2H), 3.13 (t, J=6.6 Hz, 2H), 2.62 (s, 3H), 2.33-2.17 (m, 1H), 2.08-1.88 (m, 3H), 1.54 (d, J=7.1 Hz, 3H), 1.40 (dd, J=4.3, 6.7 Hz, 2H), 1.07 (d, J=6.9 Hz, 9H); $^{13}$C NMR (101 MHz, MeOD): δ 173.2, 172.4, 171.9, 156.4, 147.7, 143.1, 137.1, 130.6 (2C), 128.3, 128.1 (2C), 71.0, 70.4, 60.6, 58.6, 58.1, 50.2, 49.0, 39.4, 38.9, 36.8, 28.2, 26.9 (3C), 22.4, 13.3.

(2S,4R)-1-((S)-2-(2-(2-(2-Aminoethoxy)ethoxy) acetamido)-3,3-dimethylbutanoyl)-4-hydroxy-N—((S)-1-(4-(4-methylthiazol-5-yl)phenyl)ethyl)pyrrolidine-2-carboxamide hydrochloride (BD)

General Procedure II (2h) was followed by using tert-butyl (2-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethoxy)ethyl)carbamate (AW) (0.06 g, 0.087 mmol) and 4N HCl in dioxane (1.0 mL) to afford the titled compound as white solid (0.054 g, 100% yield). $^1$H NMR (400 MHz, MeOD): δ 9.76 (s, 1H), 7.54 (q, J=8.1 Hz, 4H), 5.10-5.00 (m, 1H), 4.75 (s, 1H), 4.66-4.53 (m, 1H), 4.46 (s, 1H), 4.20-3.96 (m, 2H), 3.88 (d, J=11.1 Hz, 1H), 3.82-3.72 (m, 8H), 3.27-3.16 (m, 2H), 2.60 (s, 3H), 2.34-2.23 (m, 1H), 2.00-1.87 (m, 1H), 1.55 (d, J=7.1 Hz, 3H), 1.11-1.01 (m, 9H).

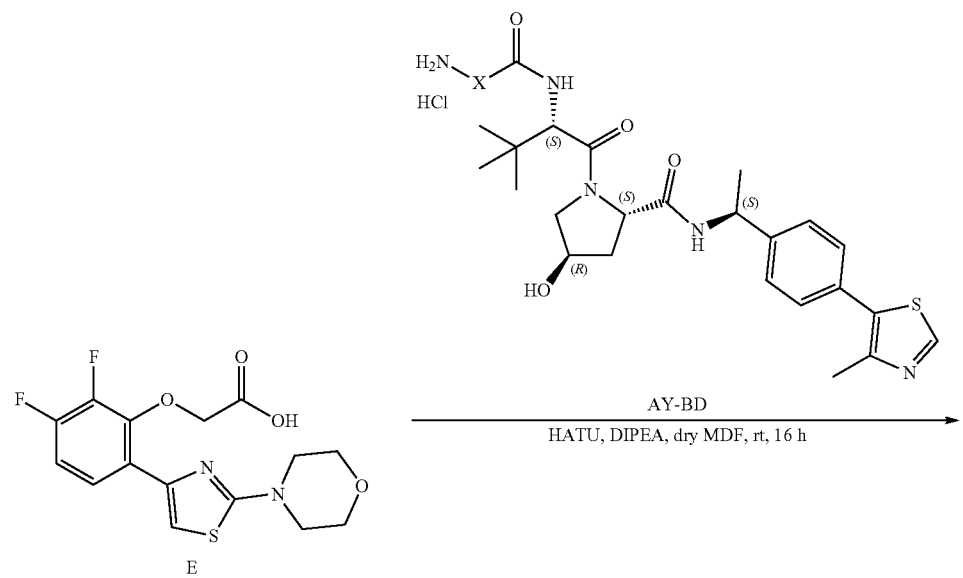

Scheme 8. Synthesis of Examples 15-20.

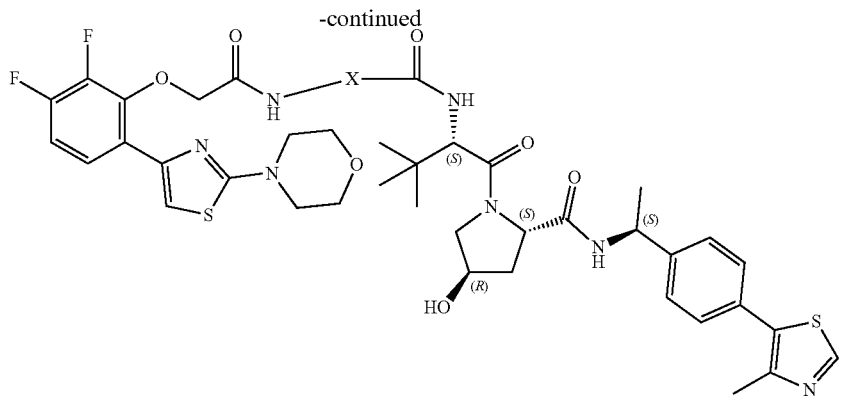

Example 15 X = (CH$_2$)$_3$
Example 16 X = (CH$_2$)$_4$
Example 17 X = (CH$_2$)$_5$
Example 18 X = (CH$_2$)$_6$
Example 19 X = (CH$_2$)$_3$OCH$_2$
Example 20 X = (CH$_2$CH$_2$O)$_2$CH$_2$

(2S,4R)-1-((S)-2-(4-(2-(2,3-Difluoro-6-(2-morpholinothiazol-4-yl)phenoxy)acetamido)butanamido)-3,3-dimethylbutanoyl)-4-hydroxy-N—((S)-1-(4-(4-methylthiazol-5-yl)phenyl)ethyl)pyrrolidine-2-carboxamide (Example 15)

General Procedure III (3h) was followed by using (2-(2,3-difluoro-6-(2-morpholinothiazol-4-yl)phenoxy)acetic acid (E) (0.035 g, 0.089 mmol), (2S,4R)-1-((S)-2-(4-aminobutanamido)-3,3-dimethylbutanoyl)-4-hydroxy-N—((S)-1-(4-(4-methylthiazol-5-yl)phenyl)ethyl)pyrrolidine-2-carboxamide hydrochloride (AY) (0.05 g, 0.089 mmol), DIPEA (0.062 mL, 0.356 mmol), and HATU (0.042 g, 0.111 mmol) in dry DMF (0.6 mL) to afford the titled compound as white solid (0.046 g, 60% yield) following purification by flash column chromatography on SiO$_2$ (DCM/MeOH, 98:2 to 95:5). $^1$H NMR (400 MHz, CDCl$_3$): δ 8.69 (s, 1H), 7.62-7.55 (m, 1H), 7.49 (d, J=7.8 Hz, 1H), 7.40 (q, J=8.3 Hz, 4H), 7.27-7.24 (m, 1H), 7.01 (dd, J=16.6, 9.0 Hz, 1H), 6.95-6.89 (m, 2H), 5.16-5.02 (m, 1H), 4.78 (t, J=8.1 Hz, 1H), 4.61 (s, 2H), 4.53 (d, J=8.2 Hz, 1H), 4.47 (s, 1H), 4.15 (d, J=11.6 Hz, 1H), 3.92-3.79 (m, 4H), 3.63-3.40 (m, 8H), 3.36-3.24 (m, 1H), 2.63-2.51 (m, 4H), 2.33-2.17 (m, 2H), 2.12-2.03 (m, 1H), 1.89-1.77 (m, 1H), 1.48 (d, J=7.0 Hz, 3H), 1.07 (s, 9H); $^{13}$C NMR (101 MHz, CDCl$_3$): δ 173.03, 172.34, 170.98, 169.59, 168.90, 150.73 (dd, J=251.3, 11.4 Hz), 150.28, 148.51, 146-73-146.38 (m), 144.58 (dd, J=8.9, 1.6 Hz,), 144.21 (dd, J=247.3, 14.1 Hz,), 143.17, 131.61, 130.87, 129.57 (2C), 126.46 (2C), 125.34 (d, J=3.4 Hz,), 124.52 (dd, J=7.7, 3.8 Hz), 112.54 (d, J=17.1 Hz), 106.25, 72.36 (d, J=5.2 Hz), 70.11, 66.11 (2C), 58.25, 58.09, 56.75, 48.85, 48.55 (2C), 37.82, 35.35, 34.80, 32.93, 26.54 (3C), 25.89, 22.22, 16.10. HRMS (ESI) m/z [M+H]+ calcd for C$_{42}$H$_{51}$F$_2$N$_7$O$_7$S$_2$ 868.33322, found 868.3327.

(2S,4R)-1-((S)-2-(5-(2-(2,3-Difluoro-6-(2-morpholinothiazol-4yl)phenoxy)acetamido)pentanamido)-3,3-dimethylbutanoyl)-4-hydroxy-N—((S)-1-(4-(4-methylthiazol-5-yl)phenyl)ethyl)pyrrolidine-2-carboxamide (Example 16)

General Procedure III (4h) was followed by using (2-(2,3-difluoro-6-(2-morpholinothiazol-4-yl)phenoxy)acetic acid (E) (0.67 g, 1.71 mmol), (2S,4R)-1-((S)-2-(5-aminopentanamido)-3,3-dimethylbutanoyl)-4-hydroxy-N—((S)-1-(4-(4-methylthiazol-5-yl)phenyl)ethyl)pyrrolidine-2 carboxamide hydrochloride (AZ) (0.99 g, 1.71 mmol), DIPEA (1.19 mL, 6.82 mmol), and HATU (0.81 g, 2.13 mmol) in dry DMF (7.5 mL) to afford the titled compound as white solid (0.604 g, 40% yield) following purification by flash column chromatography on SiO$_2$ (DCM/Acetone/MeOH, 60:37:3). $^1$H NMR (400 MHz, CDCl$_3$): δ 8.70 (s, 1H), 7.60 (ddd, J=8.5, 6.0, 2.1 Hz, 1H), 7.48-7.34 (m, 5H), 7.12 (t, J=5.6 Hz, 1H), 7.05-6.92 (m, 2H), 6.32 (d, J=8.6 Hz, 1H), 5.15-5.05 (m, 1H), 4.75 (t, J=8.0 Hz, 1H), 4.66-4.53 (m, 3H), 4.49 (bs, 1H), 4.11 (d, J=11.4 Hz, 1H), 3.90-3.80 (m, 4H), 3.59 (dd, J=11.4, 3.5 Hz, 1H), 3.55-3.46 (m, 4H), 3.45-3.17 (m, 3H), 2.61-2.50 (m, 4H), 2.39-2.21 (m, 2H), 2.07 (dd, J=13.6, 8.3 Hz, 1H), 1.83-1.52 (m, 4H), 1.48 (d, J=6.9 Hz, 3H), 1.06 (s, 9H); $^{13}$C NMR (101 MHz, CDCl$_3$): δ 173.34, 172.25, 170.85, 169.54, 168.31, 150.64 (dd, J=251.3, 11.3 Hz), 150.26, 148.50, 146.40 (d, J=1.7 Hz), 144.69-144.42 (m), 144.19 (dd, J=247.5, 14.0 Hz), 143.11, 131.58, 130.88, 129.56 (2C), 126.41 (2C), 125.32 (d, J=3.4 Hz), 124.48 (dd, J=7.7, 3.9 Hz), 112.49 (d, J=17.1 Hz), 106.25, 72.29 (d, J=5.0 Hz), 70.03, 66.13 (2C), 58.24, 57.67, 56.72, 48.86, 48.55 (2C), 38.35, 35.47, 35.35, 34.92, 28.73, 26.51 (3C), 22.40, 22.24, 16.10. HRMS (ESI) m/z [M+H]+ calcd for C$_{43}$H$_{53}$F$_2$N$_7$O$_7$S$_2$ 882.34887, found 882.3458.

(2S,4R)-1-((S)-2-(6-(2-(2,3-Difluoro-6-(2-morpholinothiazol-4-yl)phenoxy)acetamido)hexanamido)-3,3-dimethylbutanoyl)-4-hydroxy-N—((S)-1-(4-(4-methylthiazol-5-yl)phenyl)ethyl)pyrrolidine-2-carboxamide (Example 17)

General Procedure III (1.5h) was followed by using (2-(2,3-difluoro-6-(2-morpholinothiazol-4-yl)phenoxy)acetic acid (E) (0.036 g, 0.102 mmol), (2S,4R)-1-((S)-2-(6-aminohexanamido)-3,3-dimethylbutanoyl)-4-hydroxy-N—((S)-1-(4-(4-methylthiazol-5-yl)phenyl)ethyl)pyrrolidine-2-carboxamide hydrochloride (BA) (0.061 g, 0.102 mmol), DIPEA (0.07 mL, 0.407 mmol), and HATU (0.048 g, 0.127 mmol) in dry DMF (0.5 mL) to afford the titled compound as white solid (0.024 g, 26% yield) following purification by flash column chromatography on SiO$_2$ (DCM/MeOH, 98:2 to 96:4). ¹H NMR (400 MHz, CDCl₃): δ 8.69 (s, 1H), 7.60 (ddd, J=8.6, 6.0, 2.3 Hz, 1H), 7.50-7.34 (m, 5H), 7.08-6.97 (m, 2H), 6.95 (s, 1H), 6.16 (d, J=8.6 Hz, 1H), 5.10 (p, J=7.3 Hz, 1H), 4.76 (t, J=8.0 Hz, 1H), 4.61-4.54 (m, 3H), 4.51 (s, 1H), 4.12 (d, J=11.6 Hz, 1H), 3.89-3.81 (m, 4H), 3.58 (dd, J=11.4, 3.5 Hz, 1H), 3.55-3.50 (m, 4H), 3.32 (dd, J=14.2, 7.1 Hz, 2H), 3.22-3.12 (m, 1H), 2.61-2.50 (m, 4H), 2.31-2.16 (m, 2H), 2.14-2.04 (m, 1H), 1.69-1.59 (m, 2H), 1.57-1.46 (m, 5H), 1.39-1.26 (m, 2H), 1.06 (s, 9H); ¹³C NMR (101 MHz, CDCl₃): δ 173.50, 172.22, 170.85, 169.57, 169.47, 168.04, 150.67 (dd, J=251.3, 11.4 Hz), 150.26, 148.51, 146.52 (dd, J=6.4, 1.7 Hz), 144.18 (dd, J=246.8, 14.7 Hz), 143.13, 131.57, 130.90, 129.57 (2C), 126.42 (2C), 125.31 (d, J=3.6 Hz), 124.49 (dd, J=7.7, 3.8 Hz), 112.46 (d, J=17.1 Hz), 106.16, 72.37 (d, J=5.2 Hz), 70.01, 66.13 (2C), 58.27, 57.58, 56.71, 48.86, 48.54 (2C), 38.87, 36.15, 35.41, 34.87, 29.20, 26.50 (3C), 26.18, 25.07, 22.25, 16.11. HRMS (ESI) m/z [M+H]+ calcd for $C_{44}H_{55}F_2N_7O_7S_2$ 896.36452, found 896.3645.

(2S,4R)-1-((S)-2-(7-(2-(2,3-Difluoro-6-(2-morpholinothiazol-4-yl)phenoxy)acetamido)heptanamido)-3,3-dimethylbutanoyl)-4-hydroxy-N—((S)-1-(4-(4-methylthiazol-5-yl)phenyl)ethyl)pyrrolidine-2-carboxamide (Example 18)

General Procedure III (1h) was followed by using (2-(2,3-difluoro-6-(2-morpholinothiazol-4-yl)phenoxy)acetic acid (E) (0.036 g, 0.100 mmol), (2S,4R)-1-((S)-2-(7-aminoheptanamido)-3,3-dimethylbutanoyl)-4-hydroxy-N—((S)-1-(4-(4-methylthiazol-5-yl)phenyl)ethyl)pyrrolidine-2-carboxamide hydrochloride (BB) (0.061 g, 0.100 mmol), DIPEA (0.069 mL, 0.401 mmol), and HATU (0.048 g, 0.127 mmol) in dry DMF (0.5 mL) to afford the titled compound as white solid (0.045 g, 49% yield) following purification by flash column chromatography on SiO₂ (DCM/Acetone/MeOH, 60:40:1.5). ¹H NMR (400 MHz, CDCl₃): δ 8.68 (s, 1H), 7.60 (ddd, J=2.2, 6.0, 8.6 Hz, 1H), 7.52 (d, J=7.9 Hz, 1H), 7.47-7.34 (m, 4H), 7.10-6.81 (m, 3H), 6.28 (d, J=8.8 Hz, 1H), 5.09 (p, J=7.1 Hz, 1H), 4.73 (t, J=7.9 Hz, 1H), 4.59 (d, J=8.8 Hz, 1H), 4.56 (s, 2H), 4.50 (s, 1H), 4.07 (d, J=11.4 Hz, 1H), 3.89-3.80 (m, 4H), 3.76-3.66 (m, 1H), 3.61 (dd, J=3.6, 11.3 Hz, 1H), 3.54-3.47 (m, 4H), 3.30 (q, J=5.9 Hz, 2H), 2.53 (s, 3H), 2.50-2.40 (m, 1H), 2.32-2.01 (m, 3H), 1.69-1.49 (m, 4H), 1.48 (d, J=6.9 Hz, 3H), 1.38-1.28 (m, 4H), 1.05 (s, 9H); ¹³C NMR (101 MHz, CDCl₃): δ 173.50, 171.99, 170.78, 169.83, 167.99, 150.62 (dd, J=11.5, 251.1 Hz), 150.30, 148.45, 146.93-146.03 (m), 144.57 (dd, J=1.5, 9.1 Hz), 144.16 (dd, J=14.0, 247.2 Hz), 143.24, 131.58, 130.83, 129.52 (2C), 126.43 (2C), 125.28 (d, J=3.4 Hz), 124.48 (dd, J=4.0, 7.7 Hz), 114.06, 112.43 (d, J=17.1 Hz), 106.14, 72.34 (d, J=5.1 Hz), 69.90, 66.12, 58.48, 57.46, 56.74, 53.85, 48.80, 48.52, 38.89, 36.19, 35.69, 35.12, 29.15, 28.44, 26.51 (3C), 26.31, 25.34, 22.24, 16.09. HRMS (ESI) m/z [M+H]+ calcd for $C_{45}H_{57}F_2N_7O_7S_2$ 910.38017, found 910.3802.

(2S,4R)-1-((S)-2-(2-(3-(2-(2,3-Difluoro-6-(2-morpholinothiazol-4-yl)phenoxy)acetamido)propoxy)acetamido)-3,3-dimethylbutanoyl)-4-hydroxy-N—((S)-1-(4-(4-methylthiazol-5-yl)phenyl)ethyl)pyrrolidine-2-carboxamide (Example 19)

General Procedure III (1h) was followed by using (2-(2,3-difluoro-6-(2-morpholinothiazol-4-yl)phenoxy)acetic acid (E) (0.035 g, 0.098 mmol), (2S,4R)-1-((S)-2-(2-(3-aminopropoxy)acetamido)-3,3-dimethylbutanoyl)-4-hydroxy-N—((S)-1-(4-(4-methylthiazol-5-yl)phenyl)ethyl)pyrrolidine-2-carboxamide hydrochloride (BC) (0.059 g, 0.098 mmol), DIPEA (0.069 mL, 0.395 mmol), and HATU (0.048 g, 0.127 mmol) in dry DMF (0.5 mL) to afford the titled compound as white solid (0.09 g, 53% yield) following purification by flash column chromatography on SiO₂ (DCM/MeOH, 95:5). ¹H NMR (400 MHz, CDCl₃): δ 8.68 (s, 1H), 7.61 (ddd, J=2.2, 6.0, 8.7 Hz, 1H), 7.45-7.32 (m, 5H), 7.25 (t, J=5.9 Hz, 1H), 7.21 (d, J=8.8 Hz, 1H), 7.03-6.96 (m, 1H), 6.96 (s, 1H), 5.07 (p, J=7.0 Hz, 1H), 4.71 (t, J=7.7 Hz, 1H), 4.63-4.53 (m, 3H), 4.50 (s, 1H), 4.04-3.87 (m, 3H), 3.86-3.78 (m, 4H), 3.67-3.53 (m, 4H), 3.53-3.48 (m, 4H), 3.46 (q, J=6.4 Hz, 2H), 2.53 (s, 3H), 2.54-2.45 (m, 1H), 2.12-1.98 (m, 1H), 1.87 (p, J=6.5 Hz, 2H), 1.47 (d, J=6.9 Hz, 3H), 1.06 (s, 9H); ¹³C NMR (101 MHz, CDCl₃): δ 171.45, 170.78, 169.97, 169.69, 168.21, 150.61 (dd, J=251.3, 11.4 Hz), 150.32, 148.47, 146.40-146.32 (m), 144.56 (dd, J=9.1, 1.4 Hz), 144.22 (dd, J=247.1, 14.0 Hz), 143.16, 131.60, 130.85, 129.54 (2C), 126.43 (2C), 125.35 (d, J=3.4 Hz), 124.53 (dd, J=7.7, 4.0 Hz), 112.56 (d, J=17.0 Hz), 106.19, 72.34 (d, J=4.9 Hz), 70.12, 70.03, 69.21, 66.11 (2C), 58.42, 56.96, 56.61, 48.87, 48.54 (2C), 36.18, 35.54, 35.36, 29.45, 26.47 (3C), 22.22, 16.09. HRMS (ESI) m/z [M+H]+ calcd for $C_{43}H_{53}F_2N_7O_8S_2$ 898.34379, found 898.3438.

(2S,4R)-1-((S)-2-(tert-butyl)-14-(2,3-difluoro-6-(2-morpholinothiazol-4-yl)phenoxy)-4,13-dioxo-6,9-dioxa-3,12-diazatetradecanoyl)-4-hydroxy-N—((S)-1-(4-(4-methylthiazol-5-yl)phenyl)ethyl)pyrrolidine-2-carboxamide (Example 20)

General Procedure III (3h) was followed by using (2-(2,3-difluoro-6-(2-morpholinothiazol-4-yl)phenoxy)acetic acid (E) (0.026 g, 0.072 mmol), (2S,4R)-1-((S)-2-(2-(2-(2-aminoethoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide hydrochloride (BD) (0.045 g, 0.072 mmol), DIPEA (0.05 mL, 0.287 mmol), and HATU (0.034 g, 0.089 mmol) in dry DMF (0.6 mL) to afford the titled compound as white solid (0.038 g, 57% yield) following purification by flash column chromatography on SiO₂ (DCM/MeOH, 97:3 to 95:5). ¹H NMR (400 MHz, CDCl₃): δ 8.70 (s, 1H), 7.79-7.67 (m, 2H), 7.42 (dt, J=24.5, 8.6 Hz, 5H), 7.23 (d, J=7.5 Hz, 1H), 7.07-6.92 (m, 2H), 5.09 (p, J=7.2 Hz, 1H), 4.66-4.53 (m, 4H), 4.49 (s, 1H), 4.10-3.92 (m, 3H), 3.89-3.80 (m, 4H), 3.80-3.55 (m, 9H), 3.54-3.45 (m, 4H), 2.90 (s, 1H), 2.55 (s, 3H), 2.50-2.38 (m, 1H), 1.98-1.86 (m, 1H), 1.49 (d, J=6.9 Hz, 3H), 1.06 (s, 9H); ¹³C NMR (101 MHz, CDCl₃): δ 171.35, 170.59, 170.29, 169.63, 168.34, 150.47 (dd, J=251.0, 11.4 Hz), 150.31, 148.55, 145.91-145.78 (m), 144.43 (d, J=8.4 Hz), 144.26 (dd, J=246.8, 14.0 Hz), 143.00, 131.56, 130.98, 129.60 (2C), 126.46 (2C), 125.25 (d, J=3.5 Hz), 124.64-124.40 (m), 112.63 (d, J=17.0 Hz), 106.39, 72.29 (d, J=4.6 Hz), 71.31, 70.44, 70.35, 70.10, 70.08, 66.14 (2C), 58.44, 56.91, 56.72, 48.86, 48.53 (2C), 39.18, 35.75, 35.57, 26.52 (3C), 21.98, 16.12. HRMS (ESI) m/z [M+H]+ calcd for $C_{44}H_{55}F_2N_7O_9S_2$ 928.35435, found 928.3540.

Scheme 9. Synthesis of Example 21.

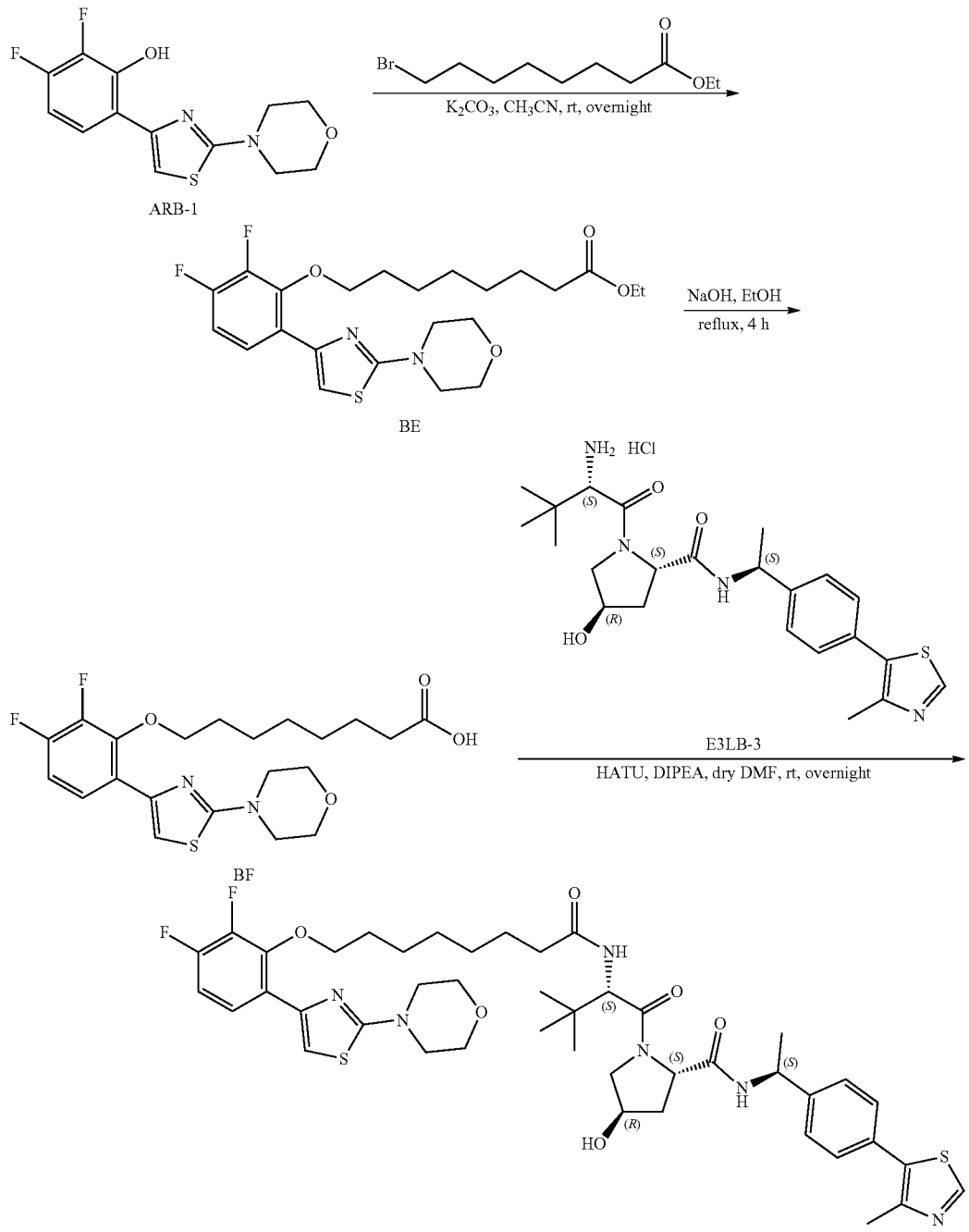

Example 21

Ethyl 8-(2,3-difluoro-6-(2-morpholinothiazol-4-yl)phenoxy)octanoate (BE)

To the solution of 2,3-difluoro-6-(2-morpholinothiazol-4-yl)phenol (ARB-1) (0.1 g, 0.335 mmol) in ACN (3.0 mL) $K_2CO_3$ (0.115 g, 0.834 mmol) and ethyl 8-bromooctanoate (commercially available from, for example, Fluorochem) (0.084 g, 0.335 mmol) were added and the mixture was stirred at rt overnight. Then, the solvent was evaporated under vacuo and the crude residue diluted with water (10 mL) and extracted with EA (5 mL×3). The reunited organic phases were washed with brine (10 mL), dried over $Na_2SO_4$, and concentrated under reduced pressure to afford a yellow oil which was purified by flash column chromatography on $SiO_2$ (PE/EA, 95:5 to 8:2) affording the titled compound as white solid (0.135 g, 86% yield). $^1H$ NMR (400 MHz, $CDCl_3$): δ 7.80 (ddd, J=8.8, 6.3, 2.3 Hz, 1H), 7.25 (s, 1H), 6.90 (td, J=9.2, 7.4 Hz, 1H), 2.29 (t, J=7.5 Hz, 2H), 1.84-1.74 (m, 2H), 1.63 (dd, J=14.6, 7.3 Hz, 2H), 1.51-1.31 (m, 6H), 1.25 (t, J=7.1 Hz, 3H); $^{13}C$ NMR (101 MHz, $CDCl_3$): δ 173.80, 169.86, 150.52 (dd, J=249.4, 11.7 Hz), 146.11-146.03 (m), 144.50 (d, J=2.7 Hz), 144.65 (dd, J=246.3, 13.7 Hz), 125.11-125.01 (m), 123.80 (dd, J=8.0, 4.0 Hz), 111.12 (d, J=17.1 Hz), 106.34, 74.12 (d, J=5.6 Hz), 66.22 (2C), 60.20, 48.57 (2C), 34.33, 30.21, 29.04, 28.96, 25.67 (2C), 24.89, 14.27. HRMS (ESI) m/z [M+Na]+ calcd for $C_{44}H_{56}F_2N_6O_6S_2$ 889.35630, found 889.35713.

8-(2,3-Difluoro-6-(2-morpholinothiazol-4-yl)phenoxy)octanoic acid (BF)

To the solution of ethyl 8-(2,3-difluoro-6-(2-morpholinothiazol-4-yl)phenoxy)octanoate (BE) (0.095 g, 0.203 mmol) in EtOH (1.0 mL) was added 1M NaOH solution (1.0 mL, 1.014 mmol) and the mixture was stirred at reflux for 4 h. After cooling, the mixture was poured in ice-water, the pH was slowly adjusted to 2 with 2N HCl and the reaction mixture was extracted with EA (15 mL×3). The combined organic layers were washed with brine (10 mL×2), dried over anhydrous $Na_2SO_4$, and concentrated under reduced pressure yielding the titled compound as a white solid (0.072 g, 81% yield). $^1$H NMR (400 MHz, DMSO-$d_6$): δ 7.79 (ddd, J=8.9, 6.3, 2.4 Hz, 1H), 7.24 (s, 1H), 6.90 (td, J=9.2, 7.4 Hz, 1H), 4.13-4.03 (m, 2H), 3.90-3.79 (m, 4H), 3.58-3.46 (m, 4H), 2.35 (t, J=7.5 Hz, 2H), 1.85-1.72 (m, 2H), 1.71-1.56 (m, 2H), 1.51-1.33 (m, 6H); $^{13}$C NMR (101 MHz, CDCl$_3$): δ 178.64, 169.92, 150.54 (dd, J=249.5, 11.7 Hz), 146.15-146.02 (m), 144.74, 144.67 (dd, J=246.4, 13.5 Hz), 125.09 (d, J=3.6 Hz), 123.82 (dd, J=7.9, 3.9 Hz), 111.14 (d, J=17.1 Hz), 106.38, 74.11 (d, J=5.6 Hz), 66.22 (2C), 48.57 (2C), 33.78, 30.19, 28.94, 28.91, 25.65, 24.59.

(2S,4R)-1-((S)-2-(8-(2,3-Difluoro-6-(2-morpholinothiazol-4-yl)phenoxy)octanamido)-3,3-dimethylbutanoyl)-4-hydroxy-N—((S)-1-(4-(4-methylthiazol-5-yl)phenyl)ethyl)pyrrolidine-2-carboxamide (Example 21)

Under nitrogen atmosphere, to a stirred solution of 8-(2,3-difluoro-6-(2-morpholinothiazol-4-yl)phenoxy)octanoic acid (BF) (0.018 g, 0.041 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (E3LB-3) (0.020 g, 0.041 mmol), and DIPEA (0.029 mL, 0.166 mmol) in dry DMF (0.5 mL) was added HATU (0.0197 g, 0.051 mmol) and the stirring was continued at rt overnight. The reaction mixture was poured in ice-water (10 mL) yielding a precipitate which was collected by filtration, dried, and purified by flash column chromatography on SiO$_2$ (DCM/MeOH, 97:3) to afford the titled compound as light-yellow solid (0.018 g, 51% yield). $^1$H NMR (400 MHz, CDCl$_3$): δ 8.74 (s, 1H), 7.85-7.77 (m, 1H), 7.48-7.35 (m, 5H), 7.24 (s, 1H), 6.93 (dd, J=16.9, 8.4 Hz, 1H), 6.13 (d, J=7.6 Hz, 1H), 5.14-5.04 (m, 1H), 4.76 (t, J=8.1 Hz, 1H), 4.61-4.49 (m, 2H), 4.16 (d, J=11.8 Hz, 1H), 4.10 (t, J=6.1 Hz, 2H), 3.94-3.79 (m, 4H), 3.64-3.51 (m, 5H), 2.56 (s, 4H), 2.23 (t, J=7.3 Hz, 2H), 2.12-2.02 (m, 1H), 1.85-1.73 (m, 2H), 1.71-1.56 (m, 2H), 1.53-1.40 (m, 5H), 1.35 (s, 4H), 1.07 (s, 9H); $^{13}$C NMR (101 MHz, CDCl$_3$): δ 173.88, 172.27, 169.84, 169.55, 150.71 (dd, J=250.0, 11.9 Hz), 150.58, 149.22, 147.60, 146.03 (dd, J=9.1, 1.0 Hz), 144.62 (dd, J=246.5, 13.5 Hz), 143.53, 132.22, 130.29, 129.59 (2C), 126.55 (2C), 124.49-124.36 (m), 124.22-123.95 (m), 111.21 (d, J=17.2 Hz), 106.15, 74.18 (d, J=5.6 Hz), 70.02, 66.19 (2C), 58.30, 57.57, 48.88, 48.82 (2C), 36.41, 35.22, 34.82, 30.14, 29.02, 28.90, 26.53 (3C), 25.62, 25.43, 22.26, 15.72. HRMS (ESI) m/z [M+Na]+ calcd for $C_{44}H_{56}F_2N_6O_6S_2$ 889.35685, found 889.35713.

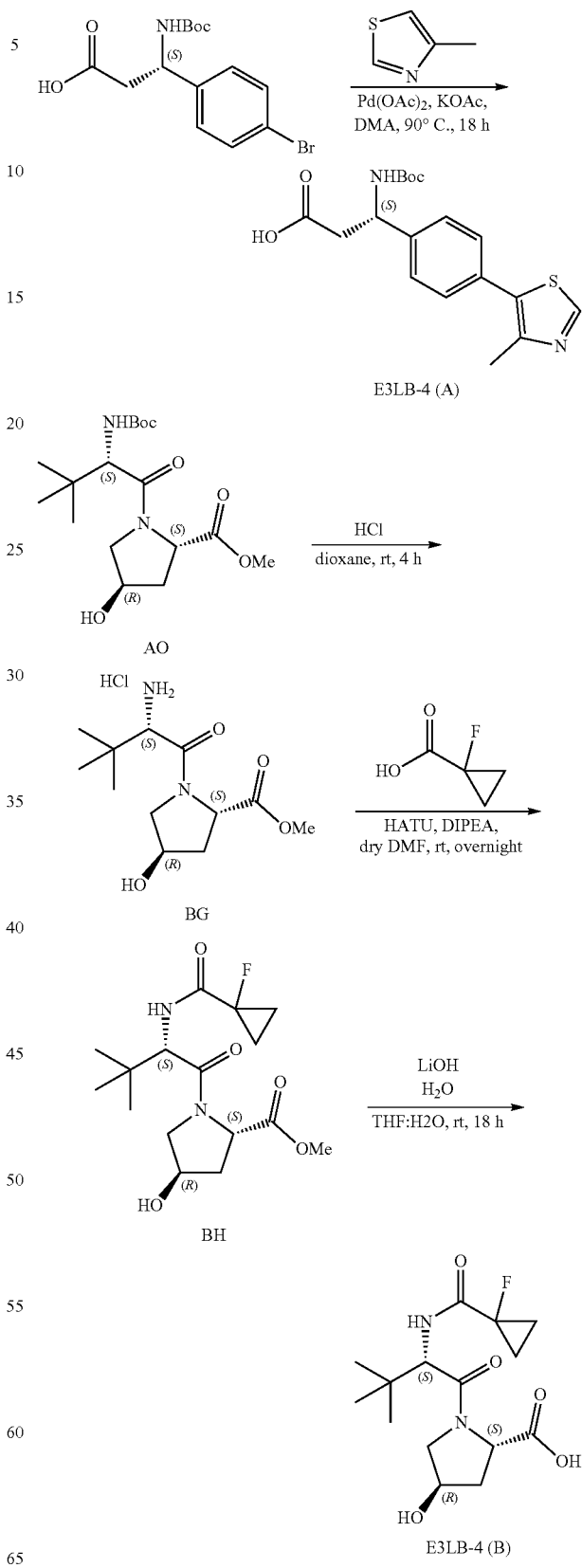

Scheme 10. Synthesis of VHL-based E3LB-4 moieties.

(S)-3-((Tert-butoxycarbonyl)amino)-3-(4-(4-methyl-thiazol-5-yl)phenyl)propanoic acid (E3LB-4 (A))

The titled compound can be prepared according to the process described by Han, X et al. *J Med Chem.* 2019, 62, 941-964. Under nitrogen atmosphere, a mixture of (S)-3-(4-bromophenyl)-3-((tert-butoxycarbonyl)amino)propanoic acid (0.25 g, 0.726 mmol), 4-methylthiazole (commercially available from, for example, Fluorochem) (0.132 ml, 1.453 mmol), palladium (II) acetate (1.63 mg, 7.26×10⁻³ mmol), and potassium acetate (0.142 g, 1.453 mmol) in dry DMA (0.8 mL) was stirred at 90° C. for 18 h. After cooling, the reaction mixture was extracted with EA (15 mL×4). The combined organic layers were washed with water (20 mL×3), brine (20 mL×2), dried over anhydrous $Na_2SO_4$, and concentrated under reduced pressure yielding an oil which was purified by flash column chromatography on $SiO_2$ (DCM/MeOH, 98:2 to 97:3) to afford the titled compound as a white solid (0.072 g, 81% yield). The solid was collected by filtration and dried in an oven at 50° C. to afford the titled compound (0.070 g, 27% yield) as a gray solid. ¹H NMR (400 MHz, CDCl₃): δ 8.72 (s, 1H), 7.38 (s, 4H), 5.65 (bs, 1H), 5.16 (bs, 1H), 3.04-2.75 (m, 2H), 2.46 (s, 3H), 1.43 (s, 9H).

Methyl (2S,4R)-1-((S)-2-amino-3,3-dimethylbutanoyl)-4-hydroxypyrrolidine-2-carboxylate hydrochloride (BG)

The titled compound can be prepared according to the process described by Laurent, A. et al. PCT Int. Appl. WO 2011098904. To the solution of methyl (2S,4R)-1-((S)-2-((tert-butoxycarbonyl)amino)-3,3-dimethylbutanoyl)-4-hydroxypyrrolidine-2-carboxylate (AO) (6.80 g, 18.971 mmol) in dry DCM (10.0 mL) at 0° C. a solution of 4N HCl in dioxane (10.0 mL) was added. The mixture was stirred at rt for 4 h. The solvent was evaporated to dryness and the crude residue was triturated with DEE and filtered off to afford the titled compound as a white solid (5.15 g, 92% yield). ¹H NMR (400 MHz, DMSO-d₆): δ 8.21 (bs, 3H), 4.42 (t, J=8.7 Hz, 1H), 4.36 (s, 1H), 3.94 (s, 1H), 3.81 (d, J=11.1 Hz, 1H), 3.64 (s, 3H), 3.60-3.48 (m, 2H), 2.24-2.11 (m, 1H), 1.98-1.85 (m, 1H), 1.03 (s, 9H); ¹³C NMR (101 MHz, DMSO-d₆): δ 172.30, 167.73, 69.30, 58.41, 58.36, 56.64, 52.33, 37.71, 34.81, 26.40 (3C).

Methyl (2S,4R)-1-((S)-2-(1-fluorocyclopropane-1-carboxamido)-3,3-dimethylbutanoyl)-4-hydroxypyrrolidine-2-carboxylate (BH)

In an oven-dried round-bottom flask, under nitrogen atmosphere, to a stirred solution of 1-fluorocyclopropane-1-carboxylic acid (commercially available from, for example, Fluorochem) (0.60 g, 5.765 mmol), methyl (2S,4R)-1-((S)-2-amino-3,3-dimethylbutanoyl)-4-hydroxypyrrolidine-2-carboxylate hydrochloride (BG) (1.545 g, 5.241 mmol), and DIPEA (4.564 mL, 26.207 mmol) in dry DMF (5.0 mL) was added HATU (2.391 g, 6.289 mmol). Stirring was continued at rt overnight. The reaction mixture was diluted with water (30 mL) and extracted with EA (20 mL×4). The reunited organic layers were washed with water (30 mL×2), brine (30 mL), dried over anhydrous $Na_2SO_4$ and then evaporated under reduced pressure to give an oil residue, which was purified by double flash column chromatography on $SiO_2$ (first: DCM/MeOH, 98:2; second: DCM/Acetone, 95:5 to 8:2) affording the titled compound as white solid (0.687 g, 38% yield). ¹H NMR (400 MHz, CDCl₃): δ 7.10 (d, J=5.9 Hz, 1H), 4.72-4.64 (m, 1H), 4.57 (d, J=9.1 Hz, 1H), 4.53 (s, 1H), 4.02 (d, J=11.2 Hz, 1H), 3.79-3.69 (m, 4H), 2.41-2.29 (m, 1H), 2.07-2.97 (m, 2H), 1.37-1.20 (m, 4H), 1.08 (s, 9H); ¹³C NMR (101 MHz, CDCl₃): δ 172.54, 170.26, 170.02, 78.27 (d, J=205.7 Hz), 70.39, 57.67, 57.34, 56.47, 52.26, 37.65, 35.75, 26.33 (3C), 13.68 (d, J=10.3 Hz).

(2S,4R)-1-((S)-2-(1-Fluorocyclopropane-1-carboxamido)-3,3-dimethylbutanoyl)-4-hydroxypyrrolidine-2-carboxylic acid (E3LB-4(B))

To the solution of methyl (2S,4R)-1-((S)-2-(1-fluorocyclopropane-1-carboxamido)-3,3-dimethylbutanoyl)-4-hydroxypyrrolidine-2-carboxylate (BH) (0.65 g, 1.887 mmol) in THF (5.0 mL) at 0° C. was added the solution of lithium hydroxide monohydrate (0.792 g, 18.874 mmol) in water (2.5 mL). The resulting mixture was stirred at rt for 18 h. The organic solvent was removed under vacuo, the residue was diluted with ice-water (15 mL) and the pH was slowly adjusted to 2-3 with 2N HCl. The mixture was then extracted with EA (5 mL×4). The reunited organic layers were washed with brine (10 mL), dried over anhydrous $Na_2SO_4$ and then evaporated under reduced pressure to give a residue which was triturated with DEE, filtered off, and dried to give the titled compound as a white solid (0.497 g, 80% yield). ¹H NMR (400 MHz, DMSO-d₆): δ 12.55 (bs, 1H), 7.27 (d, J=6.9 Hz, 1H), 5.21 (d, J=3.7 Hz, 1H), 4.60 (d, J=9.1 Hz, 1H), 4.3-4.25 (m, 2H), 3.70-3.54 (m, 2H), 2.21-2.06 (m, 1H), 1.96-1.84 (m, 1H), 1.44-1.10 (m, 4H), 0.96 (s, 9H); ¹³C NMR (101 MHz, DMSO-d₆): δ 173.56, 169.56, 168.53 (d, J=20.3 Hz), 78.55 (d, J=232.5 Hz), 69.28, 58.27, 56.88, 56.78, 37.69, 36.48, 26.57 (3C), 13.33 (dd, J=23.7, 10.3 Hz).

Scheme 11. Synthesis of Examples 22 and 23.

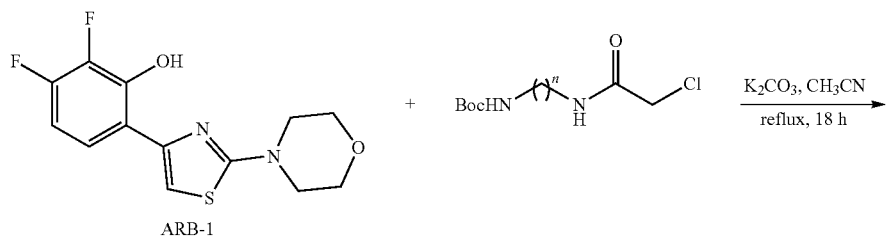

-continued
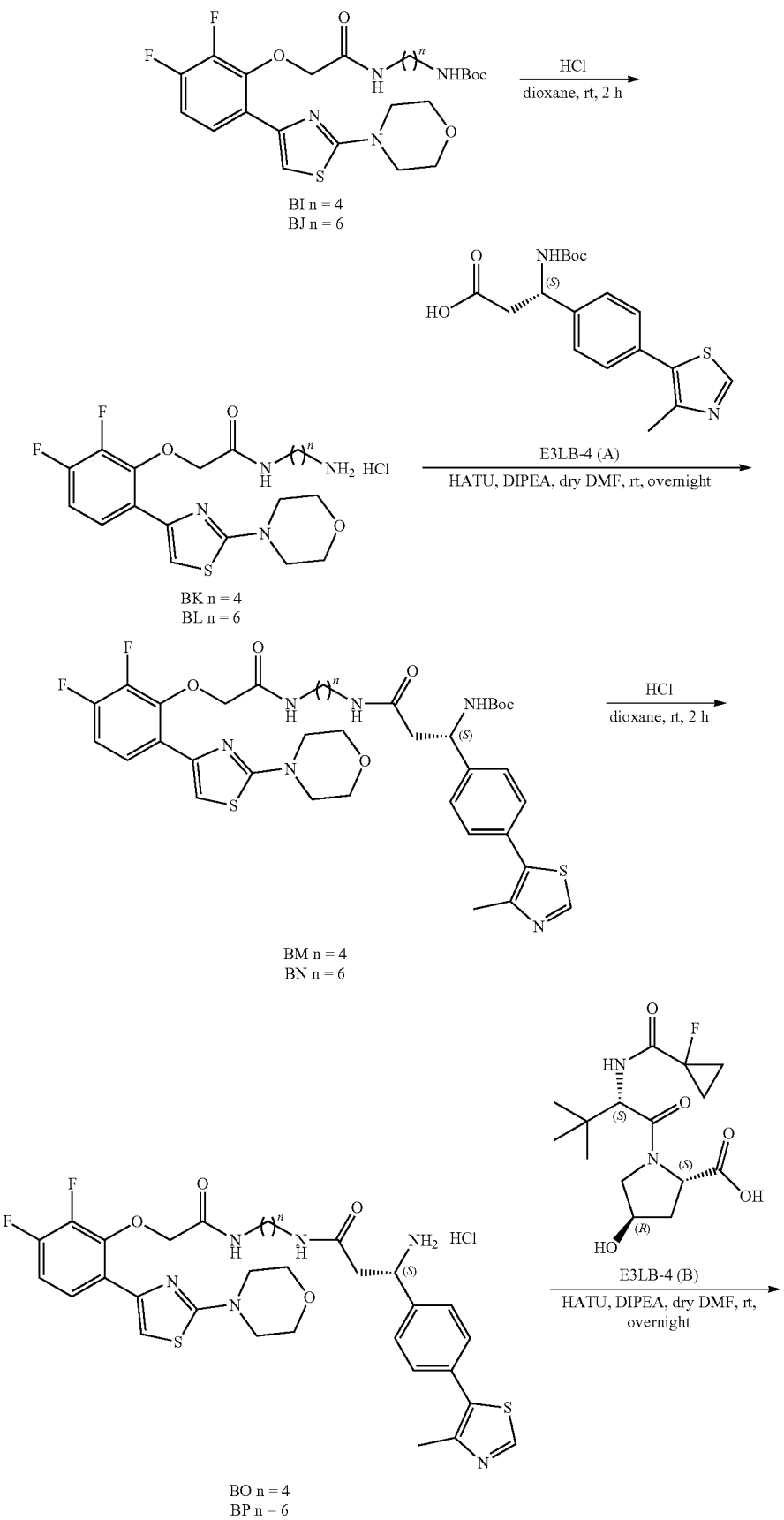
BI n = 4
BJ n = 6
BK n = 4
BL n = 6
BM n = 4
BN n = 6
BO n = 4
BP n = 6

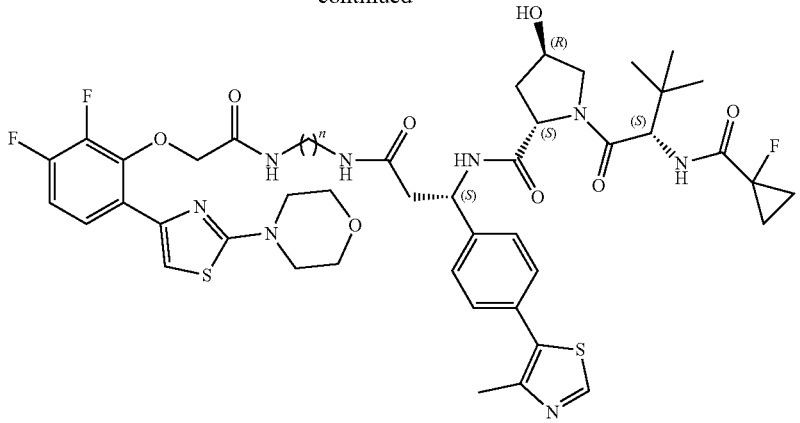

Example 22 n = 4
Example 23 n = 6

Tert-butyl (4-(2-(2,3-difluoro-6-(2-morpholinothiazol-4-yl)phenoxy)acetamido)butyl)carbamate (BI)

To the solution of 2,3-difluoro-6-(2-morpholinothiazol-4-yl)phenol (ARB-1) (0.250 g, 0.838 mmol) in ACN (3.5 mL) $K_2CO_3$ (0.289 g, 2.095 mmol) and tert-butyl (4-(2-chloroacetamido)butyl)carbamate (0.244 g, 0.922 mmol) were added and the mixture was refluxed for 18 h. Then, the solvent was evaporated under vacuo and the crude residue diluted with water (15 mL) yielding a solid which was collected by filtration, triturated by DEE and filtered off to afford the titled compound as white solid (0.366 g, 83% yield). $^1$H NMR (400 MHz, CDCl$_3$): δ 7.63-7.57 (m, 1H), 7.07 (s, 1H), 7.04-6.96 (m, 1H), 6.94 (s, 1H), 4.60 (s, 3H), 3.91-3.81 (m, 4H), 3.59-3.49 (m, 4H), 3.36 (dd, J=12.6, 6.4 Hz, 2H), 3.23-3.10 (m, 2H), 1.64-1.50 (m, 4H), 1.46 (s, 9H).

Tert-butyl (6-(2-(2,3-difluoro-6-(2-morpholinothiazol-4-yl)phenoxy)acetamido)hexyl)carbamate (BJ)

To the solution of 2,3-difluoro-6-(2-morpholinothiazol-4-yl)phenol (ARB-1) (0.06 g, 0.201 mmol) in ACN (1.0 mL) $K_2CO_3$ (0.069 g, 0.503 mmol) and tert-butyl (6-(2-chloroacetamido)hexyl)carbamate (0.065 g, 0.221 mmol) were added and the mixture was refluxed for 18 h. Then, the solvent was evaporated under vacuo and the crude residue diluted with water (10 mL) yielding a solid which was collected by filtration, triturated by DEE and filtered off to afford the titled compound as white solid (0.078 g, 70% yield). $^1$H NMR (400 MHz, CDCl$_3$): δ 7.60 (t, J=7.5 Hz, 1H), 7.06 (s, 1H), 7.00 (dd, J=16.6, 8.9 Hz, 1H), 6.94 (s, 1H), 4.60 (s, 2H), 4.55 (s, 1H), 3.90-3.84 (m, 4H), 3.59-3.51 (m, 4H), 3.39-3.29 (m, 2H), 3.18-3.08 (m, 2H), 1.59-1.48 (m, 4H), 1.46 (s, 9H), 1.40-1.31 (m, 4H).

N-(4-Aminobutyl)-2-(2,3-difluoro-6-(2-morpholinothiazol-4-yl)phenoxy)acetamide hydrochloride (BK)

To the solution of tert-butyl (4-(2-(2,3-difluoro-6-(2-morpholinothiazol-4-yl)phenoxy)acetamido)butyl)carbamate (BI) (0.093 g, 0.176 mmol) in dry dioxane (0.4 mL) at 0° C. a solution of 4N HCl in dioxane (0.44 mL) was added. The mixture was stirred at rt for 2 h. The solvent was evaporated to dryness and the crude residue was triturated with DEE and filtered off to afford the titled compound as a white solid (0.081 g, 100% yield). $^1$H NMR (400 MHz, DMSO-d$_6$): δ 8.42-8.34 (m, 1H), 8.03 (bs, 3H), 7.81 (t, J=7.2 Hz, 1H), 7.68 (s, 1H), 7.25 (dd, J=17.3, 9.1 Hz, 1H), 4.61 (s, 2H), 3.80-3.68 (m, 4H), 3.50-3.39 (m, 4H), 3.22-3.10 (m, 2H), 2.85-2.72 (m, 2H), 1.67-1.42 (m, 4H); $^{13}$C NMR (101 MHz, DMSO-d$_6$): δ 170.01, 167.60, 150.10 (dd, J=247.8, 11.3 Hz), 144.80 (d, J=8.6 Hz), 144.57-144.46 (m), 144.04 (dd, J=245.5, 14.0 Hz), 124.89 (d, J=2.6 Hz), 124.67 (d, J=7.9 Hz), 112.25 (d, J=17.0 Hz), 108.05, 72.08 (d, J=5.8 Hz), 65.83 (2C), 48.72 (2C), 38.83, 38.17, 26.48, 24.83.

N-(6-Aminohexyl)-2-(2,3-difluoro-6-(2-morpholinothiazol-4-yl)phenoxy)acetamide hydrochloride (BL)

To the solution of tert-butyl (6-(2-(2,3-difluoro-6-(2-morpholinothiazol-4-yl)phenoxy)acetamido)hexyl)carbamate (BJ) (0.067 g, 0.121 mmol) in dry dioxane (0.3 mL) at 0° C. a solution of 4N HCl in dioxane (0.3 mL) was added. The mixture was stirred at rt for 2 h. The solvent was evaporated to dryness and the crude residue was triturated with DEE and filtered off to afford the titled compound as a light-yellow solid (0.059 g, 100% yield). $^1$H NMR (400 MHz, DMSO-d$_6$): δ 8.30 (s, 1H), 7.96 (bs, 3H), 7.85-7.77 (m, 1H), 7.66 (s, 1H), 7.25 (dd, J=17.1, 9.4 Hz, 1H), 4.60 (s, 2H), 3.78-3.69 (m, 4H), 3.49-3.42 (m, 4H), 3.19-3.09 (m, 2H), 2.8-2.70 (m, 2H), 1.59-1.49 (m, 2H), 1.49-1.38 (m, 2H), 1.38-1.22 (m, 4H).

Tert-butyl (S)-(3-((4-(2-(2,3-difluoro-6-(2-morpholinothiazol-4-yl)phenoxy)acetamido)butyl)amino)-1-(4-(4-methylthiazol-5-yl)phenyl)-3-oxopropyl)carbamate (BM)

In an oven-dried round-bottom flask, under nitrogen atmosphere, to a stirred solution of (S)-3-((tert-butoxycarbonyl)amino)-3-(4-(4-methylthiazol-5-yl)phenyl)propanoic acid (E3LB-4 (A)) (0.030 g, 0.083 mmol), N-(4-aminobutyl)-2-(2,3-difluoro-6-(2-morpholinothiazol-4-yl)phenoxy)acetamide hydrochloride (BK) (0.038 g, 0.083 mmol), and DIPEA (0.072 mL, 0.414 mmol) in dry DMF (1.0 mL) was added HATU (0.038 g, 0.099 mmol). Stirring was continued at rt overnight. The reaction mixture was poured in ice-water yielding a precipitate which was collected by filtration, dried, and purified by flash column chromatography on SiO$_2$ (DCM/MeOH, 97:3) affording the titled compound as white solid (0.030 g, 48% yield). $^1$H NMR (400 MHz, CDCl$_3$): δ 8.67 (s, 1H), 7.58 (s, 1H), 7.45-7.35 (m, 4H), 7.08 (bs, 1H), 7.00 (dd, J=17.2, 8.8 Hz, 1H), 6.91 (s, 1H), 6.35 (bs, 1H), 6.17 (bs, 1H), 5.06 (bs, 1H), 4.60 (s, 2H), 3.91-3.81 (m, 4H), 3.59-3.50 (m, 4H), 3.32-3.11 (m, 4H), 2.82-2.59 (m, 2H), 2.53 (s, 3H), 1.59-1.33 (m, 13H).

Tert-butyl (S)-(3-((6-(2-(2,3-difluoro-6-(2-morpholinothiazol-4-yl)phenoxy)acetamido)hexyl)amino)-1-(4-(4-methylthiazol-5-yl)phenyl)-3-oxopropyl)carbamate (BN)

In an oven-dried round-bottom flask, under nitrogen atmosphere, to a stirred solution of (S)-3-((tert-butoxycarbonyl)amino)-3-(4-(4-methylthiazol-5-yl)phenyl)propanoic acid (E3LB-4 (A)) (0.043 g, 0.120 mmol), N-(6-aminohexyl)-2-(2,3-difluoro-6-(2-morpholinothiazol-4-yl)phenoxy)acetamide hydrochloride (BL) (0.059 g, 0.120 mmol), and DIPEA (0.105 mL, 0.60 mmol) in dry DMF (1.5 mL) was added HATU (0.055 g, 0.144 mmol). Stirring was continued at rt overnight. The reaction mixture was poured in ice-water and extracted with EA (10 mL×3). The reunited organic layers were washed with water (10 mL×2), brine (10 mL), dried over anhydrous Na$_2$SO$_4$ and then evaporated under reduced pressure to give a crude residue which was purified by flash column chromatography on SiO$_2$ (DCM/MeOH, 97:3 to 96:4) affording the titled compound as light-yellow solid (0.061 g, 63% yield). $^1$H NMR (400 MHz, CDCl$_3$): δ 8.70 (s, 1H), 7.62-7.55 (m, 1H), 7.44-7.35 (m, 4H), 7.11 (bs, 1H), 7.00 (dd, J=16.8, 9.0 Hz, 1H), 6.92 (s, 1H), 6.43 (bs, 1H), 5.94 (bs, 1H), 5.06 (s, 1H), 4.61 (s, 2H), 3.89-3.83 (m, 4H), 3.58-3.52 (m, 4H), 3.38-3.05 (m, 4H), 2.81-2.61 (m, 2H), 2.55 (s, 3H), 1.54-1.34 (m, 13H), 1.31-1.25 (m, 4H).

(S)-3-Amino-N-(4-(2-(2,3-difluoro-6-(2-morpholinothiazol-4-yl)phenoxy)acetamido)butyl)-3-(4-(4-methylthiazol-5-yl)phenyl)propanamide hydrochloride (BO)

To the solution of tert-butyl (S)-(3-((4-(2-(2,3-difluoro-6-(2-morpholinothiazol-4-yl)phenoxy)acetamido)butyl)amino)-1-(4-(4-methylthiazol-5-yl)phenyl)-3-oxopropyl)carbamate (BM) (0.03 g, 0.039 mmol) in dry DCM (0.3 mL) at 0° C. a solution of 4N HCl in dioxane (0.4 mL) was added. The mixture was stirred at rt overnight. The solvent was evaporated to dryness and the crude residue was triturated with DEE and filtered off to afford the titled compound as white solid (0.027 g, 100% yield). $^1$H NMR (400 MHz, MeOD): δ 9.71 (s, 1H), 7.70 (s, 4H), 7.57-7.36 (m, 1H), 7.35-7.09 (m, 2H), 5.07 (s, 2H), 4.82 (t, J=6.3 Hz, 1H), 4.00-3.86 (m, 4H), 3.86-3.71 (m, 4H), 3.28-3.08 (m, 4H), 3.08-2.93 (m, 2H), 2.60 (s, 3H), 1.52-1.36 (m, 4H).

(S)-3-Amino-N-(6-(2-(2,3-difluoro-6-(2-morpholinothiazol-4-yl)phenoxy)acetamido)hexyl)-3-(4-(4-methylthiazol-5-yl)phenyl)propanamide hydrochloride (BP)

To the solution of tert-butyl (S)-(3-((6-(2-(2,3-difluoro-6-(2-morpholinothiazol-4-yl)phenoxy)acetamido)hexyl)amino)-1-(4-(4-methylthiazol-5-yl)phenyl)-3-oxopropyl)carbamate (BN) (0.05 g, 0.062 mmol) in dry DCM (0.5 mL) at 0° C. a solution of 4N HCl in dioxane (0.6 mL) was added. The mixture was stirred at rt overnight. The solvent was evaporated to dryness and the crude residue was triturated with DEE and filtered off to afford the titled compound as light-yellow solid (0.044 g, 100% yield). $^1$H NMR (400 MHz, MeOD): δ 9.97 (s, 1H), 7.78-7.66 (m, 4H), 7.48-7.38 (m, 1H), 7.28-7.13 (m, 2H), 5.09 (s, 2H), 4.83 (t, J=6.9 Hz, 1H), 3.98-3.87 (m, 4H), 3.84-3.75 (m, 4H), 3.23 (t, J=6.7 Hz, 2H), 3.13 (t, J=6.8 Hz, 2H), 3.08-2.93 (m, 2H), 2.64 (s, 3H), 1.55-1.37 (m, 4H), 1.33-1.17 (m, 4H).

(2S,4R)—N—((S)-3-((4-(2-(2,3-Difluoro-6-(2-morpholinothiazol-4-yl)phenoxy)acetamido)butyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide (Example 22)

In an oven-dried round-bottom flask, under nitrogen atmosphere, to a stirred solution of (2S,4R)-1-((S)-2-(1-fluorocyclopropane-1-carboxamido)-3,3-dimethylbutanoyl)-4-hydroxypyrrolidine-2-carboxylic acid (E3LB-4 (B)) (0.013 g, 0.038 mmol), (S)-3-amino-N-(4-(2-(2,3-difluoro-6-(2-morpholinothiazol-4-yl)phenoxy)acetamido)butyl)-3-(4-(4-methylthiazol-5-yl)phenyl)propanamide hydrochloride (BO) (0.027 g, 0.038 mmol), and DIPEA (0.033 mL, 0.191 mmol) in dry DMF (0.5 mL) was added HATU (0.018 g, 0.048 mmol). Stirring was continued at rt overnight. The reaction mixture was poured in ice-water yielding a precipitate which was collected by filtration, dried, and purified by flash column chromatography on SiO$_2$ (DCM/MeOH, 95:5 to 93:7) affording the titled compound as white solid (0.004 g, 11% yield). $^1$H NMR (400 MHz, CDCl$_3$): δ 8.67 (s, 1H), 8.00 (d, J=7.8 Hz, 1H), 7.62-7.56 (m, 1H), 7.43-7.34 (m, 4H), 7.15 (bs, 1H), 7.10 (dd, J=8.8, 3.4 Hz, 1H), 6.99 (dd, J=16.7, 8.9 Hz, 1H), 6.93 (s, 1H), 6.73 (bs, 1H), 5.35 (dd, J=13.3, 6.1 Hz, 1H), 4.67 (t, J=8.1 Hz, 1H), 4.62 (d, J=9.1 Hz, 1H), 4.56 (d, J=4.0 Hz, 2H), 4.51 (s, 1H), 3.98 (d, J=11.2 Hz, 1H), 3.88-3.82 (m, 4H), 3.74 (dd, J=11.0, 3.6 Hz, 1H), 3.55-3.47 (m, 4H), 3.31-3.17 (m, 4H), 2.85-2.71 (m, 2H), 2.51 (s, 3H), 2.25-2.17 (m, 2H), 1.55-1.42 (m, 4H), 1.39-1.22 (m, 5H), 1.06 (s, 9H); $^{13}$C NMR (101 MHz, CDCl$_3$): δ 170.81, 170.77, 170.73, 170.11, 170.02, 169.81, 168.47, 150.68 (dd, J=251.3, 11.5 Hz), 150.34, 148.48, 146.19, 144.54 (d, J=9.0 Hz), 144.14 (dd, J=247.1, 14.1 Hz), 140.45, 131.49, 131.09, 129.45 (2C), 126.84 (2C), 125.11, 124.54 (dd, J=7.6, 3.9 Hz), 112.54 (d, J=17.1 Hz), 106.17, 78.27 (d, J=232.3 Hz), 72.26 (d, J=4.9 Hz), 70.17, 66.09 (2C), 59.41, 57.48, 56.76, 50.61, 48.58 (2C), 41.98, 39.10, 38.66, 37.22, 35.84, 27.10, 26.47 (3C), 26.08, 16.10, 13.64 (dd, J=17.9, 10.2 Hz) (2C). HRMS (ESI) m/z [M+H]+ calcd for C$_{47}$H$_{57}$F$_3$N$_8$O$_8$S$_2$ 983.37656, found 983.37691.

(2S,4R)—N—((S)-3-((6-(2-(2,3-Difluoro-6-(2-morpholinothiazol-4-yl)phenoxy)acetamido)hexyl)amino)-1-(4-(4-methylthiazol-5-yl)phenyl)-3-oxopropyl)-1-((S)-2-(1-fluorocyclopropane-1-carboxamido)-3,3-dimethylbutanoyl)-4-hydroxypyrrolidine-2-carboxamide (Example 23)

In an oven-dried round-bottom flask, under nitrogen atmosphere, to a stirred solution of (2S,4R)-1-((S)-2-(1-fluorocyclopropane-1-carboxamido)-3,3-dimethylbutanoyl)-4-hydroxypyrrolidine-2-carboxylic acid (E3LB-4 (B)) (0.018 g, 0.054 mmol), (S)-3-amino-N-(6-(2-(2,3-difluoro-6-(2-morpholinothiazol-4-yl)phenoxy)acetamido)hexyl)-3-(4-(4-methylthiazol-5-yl)phenyl)propanamide hydrochloride (BP) (0.040 g, 0.054 mmol), and DIPEA (0.047 mL, 0.272 mmol) in dry DMF (0.7 mL) was added HATU (0.026 g, 0.068 mmol). Stirring was continued at rt overnight. The reaction mixture was poured in ice-water yielding a precipitate which was collected by filtration, dried, and purified by flash column chromatography on SiO$_2$ (DCM/MeOH, 96:4 to 94:6) affording the titled compound as white solid (0.024 g, 44% yield). $^1$H NMR (400 MHz, CDCl$_3$): δ 8.70 (s, 1H), 7.96 (d, J=8.1 Hz, 1H), 7.58 (t, J=6.5 Hz, 1H), 7.40 (s, 4H), 7.16-7.05 (m, 2H), 7.00 (dd, J=16.6, 8.9 Hz, 1H), 6.92 (s, 1H), 6.38 (bs, 1H), 5.39-5.32 (m, 1H), 4.69 (t, J=7.9 Hz, 1H), 4.66-4.57 (m, 3H), 4.54 (s, 1H), 4.01 (d, J=11.1 Hz, 1H), 3.89-3.82 (m, 4H), 3.74 (dd, J=11.0, 3.6 Hz, 1H), 3.57-3.51 (m, 4H), 3.32-3.24 (m, 2H), 3.23-3.14 (m, 2H), 2.87-2.71 (m, 2H), 2.53 (s, 3H), 2.32-2.17 (m, 2H), 1.52-1.40 (m, 4H), 1.39-1.25 (m, 9H), 1.09 (s, 9H); $^{13}$C NMR (101 MHz, CDCl$_3$): δ 170.81, 170.74, 170.63, 170.01 (d, J=20.2 Hz), 169.95, 168.29, 150.86 (dd, J=251.6, 11.4 Hz), 150.36, 148.39, 146.08-145.96 (m), 144.58 (d, J=8.9 Hz), 144.20 (dd, J=247.36, 14.80 Hz), 140.55, 131.60, 131.02, 129.48 (2C), 126.82 (2C), 124.96-124.77 (m), 124.55 (dd, J=7.8, 4.0 Hz), 112.49 (d, J=17.1 Hz), 106.02, 78.32 (d, J=219.5 Hz), 72.28 (d, J=5.2 Hz), 70.20, 66.08 (2C), 59.33, 57.48, 56.67, 50.63, 48.63 (2C), 41.92, 39.06, 38.60, 37.08, 35.68, 29.28, 29.05, 26.48 (3C), 25.88, 25.82, 16.07, 13.68 (dd, J=10.2, 7.0 Hz) (2C). HRMS (ESI) m/z [M+H]+ calcd for C$_{49}$H$_{61}$F$_3$N$_8$O$_8$S$_2$ 1011.40786, found 1011.40793.

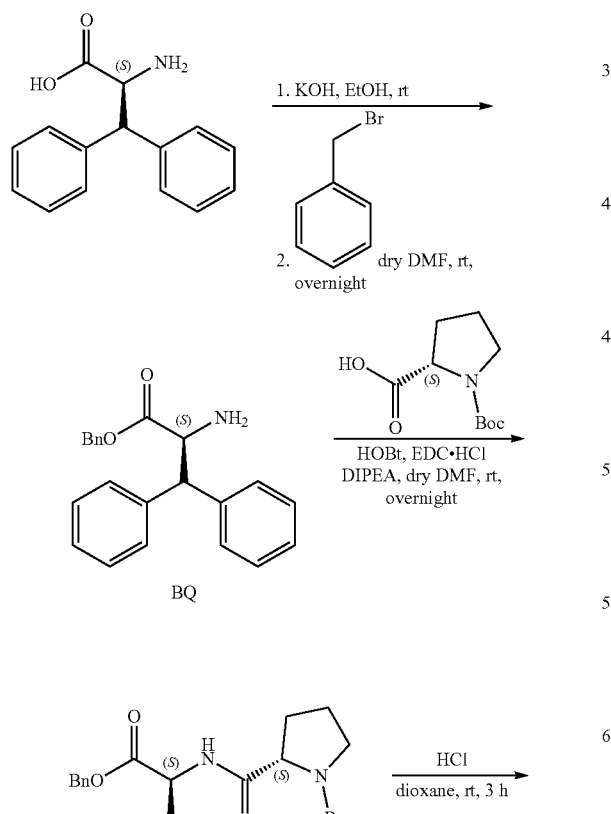

Scheme 12. Synthesis of IAP ligand-based E3LB-5 moiety.

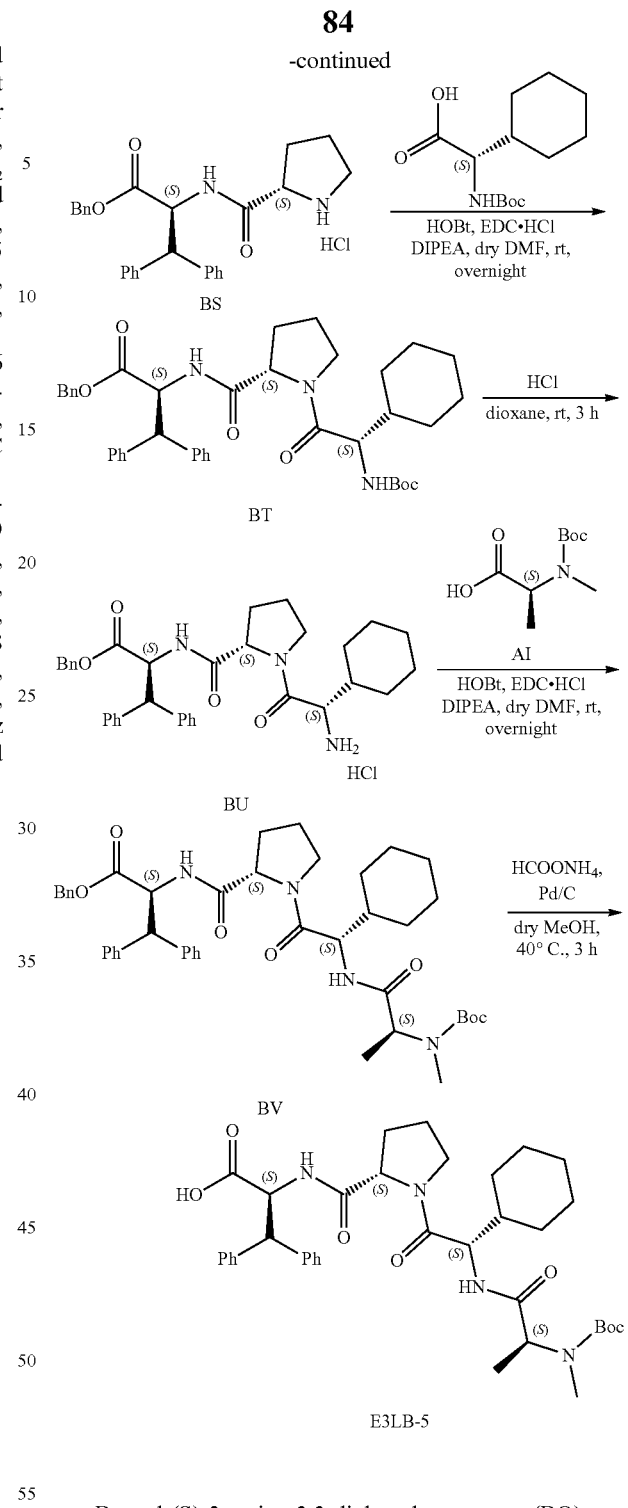

Benzyl (S)-2-amino-3,3-diphenylpropanoate (BQ)

(S)-2-amino-3,3-diphenylpropanoic acid (commercially available from, for example, Fluorochem) (1.00 g, 4.144 mmol) and KOH (0.256 g, 4.559 mmol) were stirred in EtOH (40.0 mL) at rt until complete dissolution of solids. Then, the reaction mixture was concentrated under vacuo to afford a white solid which was dissolved in dry DMF (40.0 mL) and benzyl bromide (commercially available from, for example, Sigma Aldrich) (0.542 mL, 4.559 mmol) was added. The mixture was stirred at rt overnight. The reaction mixture was quenched with saturated solution NaHCO$_3$ and extracted with EA (50 mL×3). The reunited organic phases were washed with brine (50 mL×2), dried over anhydrous $Na_2SO_4$, and concentrated under reduced pressure to afford a colorless oil which was purified by flash chromatography on $SiO_2$ (PE/EA, 9:1 to 7:3) to give the titled compound (0.325 g, 24% yield) as a clear oil, which turned white solid upon standing. $^1$H NMR (400 MHz, $CDCl_3$): δ 7.53-7.16 (m, 13H), 7.17-7.05 (m, 2H), 4.97 (dd, J=29.8, 12.2 Hz, 2H), 4.38-4.23 (m, 1H), 4.21-4.06 (m, 1H). HRMS (ESI) m/z [M+H]+ calcd for $C_{22}H_{21}NO_2$ 332.16451, found 332.16494.

Tert-butyl (S)-2-(((S)-1-(benzyloxy)-1-oxo-3,3-diphenylpropan-2-yl)carbamoyl)pyrrolidine-1-carboxylate (BR)

The titled compound can be prepared according to the process described by Shibata, N. et al. *J. Med Chem.* 2019, 61, 543-575. Under nitrogen atmosphere, to a solution of benzyl (S)-2-amino-3,3-diphenylpropanoate (BQ) (0.32 g, 0.965 mmol) and (tert-butoxycarbonyl)-L-proline (commercially available from, for example, Fluorochem) (0.291 g, 1.352 mmol) in dry DMF (3.0 mL) were added HOBt monohydrate (0.207 g, 1.352 mmol), DIPEA (0.336 mL, 1.931 mmol), and EDC HCl (0.259 g, 1.352 mmol) and the reaction mixture was stirred at rt overnight. The solution was poured in ice-water, yielding a precipitate which was collected by filtration and purified by flash chromatography on $SiO_2$ (PE/EA, 7:3 to 6:4) to give the titled compound (0.408 g, 80% yield) as a white solid. $^1$H NMR (400 MHz, $CDCl_3$): δ 7.53-7.15 (m, 14H), 7.04 (dd, J=7.2, 2.3 Hz, 2H), 5.50 (t, J=9.6 Hz, 1H), 5.02-4.85 (m, J=12.2 Hz, 2H), 4.37 (d, J=9.9 Hz, 1H), 4.30-0.07 (m, 1H), 3.38-3.00 (m, 2H), 2.25-1.52 (m, 4H), 1.42 (s, 9H).

Benzyl (S)-3,3-diphenyl-2-((S)-pyrrolidine-2-carboxamido)propanoate hydrochloride (BS)

The titled compound can be prepared according to the process slightly modified from that described by Shibata, N. et al. *J. Med. Chem.* 2019, 61, 543-575. To a solution of tert-butyl (S)-2-(((S)-1-(benzyloxy)-1-oxo-3,3-diphenylpropan-2-yl)carbamoyl)pyrrolidine-1-carboxylate (BR) (0.408 g, 0.772 mmol) in dry THF (2.0 mL) a solution of 4N HCl in dioxane (2.5 mL) was added. The mixture was stirred at rt for 3 h. The solvent was evaporated to dryness and the residue was triturated with DEE and filtered off to afford the titled product (0.344 g, 96% yield) as a white solid. $^1$H NMR (400 MHz, $CDCl_3$): δ 10.87 (bs, 1H), 8.45 (bs, 1H), 7.43-7.14 (m, 14H), 7.05 (d, J=3.8 Hz, 2H), 6.92 (s, 1H), 5.32 (s, 1H), 5.00-4.79 (m, 2H), 4.64 (d, J=10.0 Hz, 1H), 4.38 (s, 1H), 3.39-3.02 (m, 2H), 2.35 (s, 1H), 2.00-1.64 (m, 3H).

Benzyl (S)-2-((S)-1-((S)-2-((tert-butoxycarbonyl)amino)-2-cyclohexylacetyl)pyrrolidine-2-carboxamido)-3,3-diphenylpropanoate (BT)

The titled compound can be prepared according to the process described by Shibata, N. et al. *J. Med. Chem.* 2019, 61, 543-575. Under nitrogen atmosphere, to a solution of benzyl (S)-3,3-diphenyl-2-((S)-pyrrolidine-2-carboxamido)propanoate hydrochloride (BS) (0.338 g, 0.727 mmol) and (S)-2-((tert-butoxycarbonyl)amino)-2-cyclohexylacetic acid (commercially available from, for example, Fluorochem) (0.261 g, 1.018 mmol) in dry DMF (4.0 mL) were added HOBt monohydrate (0.156 g, 1.018 mmol), DIPEA (0.38 mL, 2.181 mmol), and EDC HCl (0.195 g, 1.018 mmol) and the reaction mixture was stirred at rt overnight. The solution was poured in ice-water, yielding a precipitate which was collected by filtration and purified by flash chromatography on $SiO_2$ (PE/EA, 7:3 to 6:4) to give the titled compound (0.36 g, 74% yield) as a white solid. $^1$H NMR (400 MHz, $CDCl_3$): δ 7.35-7.15 (m, 14H), 7.12-7.04 (m, 2H), 6.75 (d, J=8.7 Hz, 1H), 5.44 (t, J=8.7 Hz, 1H), 5.15 (d, J=9.3 Hz, 1H), 5.01-4.85 (m, 1H), 4.54-4.45 (m, 1H), 4.38 (d, J=8.7 Hz, 1H), 4.29-4.18 (m, 1H), 3.71-3.56 (m, 1H), 3.43-3.28 (m, 1H), 2.18-2.08 (m, 1H), 1.89-1.65 (m, 7H), 1.44 (s, 9H), 1.33-0.97 (m, 6H).

Benzyl (S)-2-((S)-1-((S)-2-((S)-2-((tert-butoxycarbonyl)(methyl)amino)propanamido)-2-cyclohexylacetyl)pyrrolidine-2-carboxamido)-3,3-diphenylpropanoate (BV)

The titled compound can be prepared according to the process described by Shibata, N. et al. *J. Med Chem.* 2019, 61, 543-575. A solution of 4N HCl in dioxane (2.5 mL) was added to benzyl (S)-2-((S)-1-((S)-2-((tert-butoxycarbonyl)amino)-2-cyclohexylacetyl)pyrrolidine-2-carboxamido)-3,3-diphenylpropanoate (BT) (0.345 g, 0.516 mmol) and the mixture was stirred at rt for 3 h. The solvent was evaporated to dryness and the residue was triturated with DEE and filtered to afford benzyl (S)-2-((S)-1-((S)-2-amino-2-cyclohexylacetyl)pyrrolidine-2-carboxamido)-3,3-diphenylpropanoate hydrochloride (BU) (0.290 g, 93% yield) as a white solid. Under nitrogen atmosphere, to a solution of the obtained (BU) (0.290 g, 0.480 mmol) and N-(tert-butoxycarbonyl)-N-methyl-L-alanine (commercially available from, for example, Fluorochem) (0.136 g, 0.672 mmol) in dry DMF (3.0 mL) were added HOBt monohydrate (0.103 g, 0.672 mmol), DIPEA (0.25 mL, 1.439 mmol), and EDC HCl (0.129 g, 0.672 mmol) and the reaction mixture was stirred at rt overnight. The solution was then poured in ice-water, yielding a precipitate which was collected by filtration and purified by flash chromatography on $SiO_2$ (DCM/MeOH, 98:2) to give the titled compound (0.287 g, 75% yield) as a colourless amorphous solid. $^1$H NMR (400 MHz, $CDCl_3$): δ 7.34-7.15 (m, 14H), 7.07 (dd, J=6.6, 2.8 Hz, 2H), 6.79-6.65 (m, 1H), 5.43 (t, J=8.6 Hz, 1H), 5.28 (s, 1H), 4.94 (s, 2H), 4.74-4.59 (m, 1H), 4.54-4.44 (m, 2H), 4.39 (d, J=8.6 Hz, 1H), 3.72-3.59 (m, 1H), 3.42-3.28 (m, 1H), 2.81 (s, 3H), 2.18-2.03 (m, 1H), 1.89-1.59 (m, 7H), 1.51 (d, J=6.0 Hz, 9H), 1.36-1.29 (m, 3H), 1.28-0.86 (m, 6H).

(S)-2-((S)-1-((S)-2-((S)-2-((Tert-butoxycarbonyl)(methyl)amino)propanamido)-2-cyclohexylacetyl)pyrrolidine-2-carboxamido)-3,3-diphenylpropanoic acid (E3LB-5)

The titled compound can be prepared according to the process slightly modified from that described by Shibata, N. et al. *J. Med. Chem.* 2019, 61, 543-575. Under nitrogen atmosphere, to a solution of benzyl (S)-2-((S)-1-((S)-2-((S)-2-((tert-butoxycarbonyl)(methyl)amino)propanamido)-2-cyclohexylacetyl)pyrrolidine-2-carboxamido)-3,3-diphenylpropanoate (BV) (0.280 g, 0.353 mmol) in dry MeOH (4.0 mL) were added 10% palladium on carbon (0.056 g) and anhydrous ammonium formate (0.089 g, 1.412 mmol). The reaction mixture was stirred at 40° C. for 3 h. After cooling, the reaction mixture was filtered over Celite and the filtrate was evaporated under vacuo yielding the titled compound as white solid (0.230 g, 98% yield). $^1$H NMR (400 MHz, MeOD): δ 7.41-7.10 (m, 10H), 5.19 (d, J=7.7 Hz, 1H), 4.66-4.30 (m, 5H), 3.85-3.73 (m, 1H), 3.68-3.56 (m, 1H), 2.87 (s, 3H), 2.10-1.98 (m, 1H), 1.92-1.66 (m, 9H), 1.51 (s, 9H), 1.39-1.24 (m, 5H), 1.15-0.96 (m, 2H). HRMS (ESI) m/z [M+H]+ calcd for $C_{37}H_{50}N_4O_7$ 663.37523, found 663.37700.

Scheme 13. Synthesis of Examples 24-26.

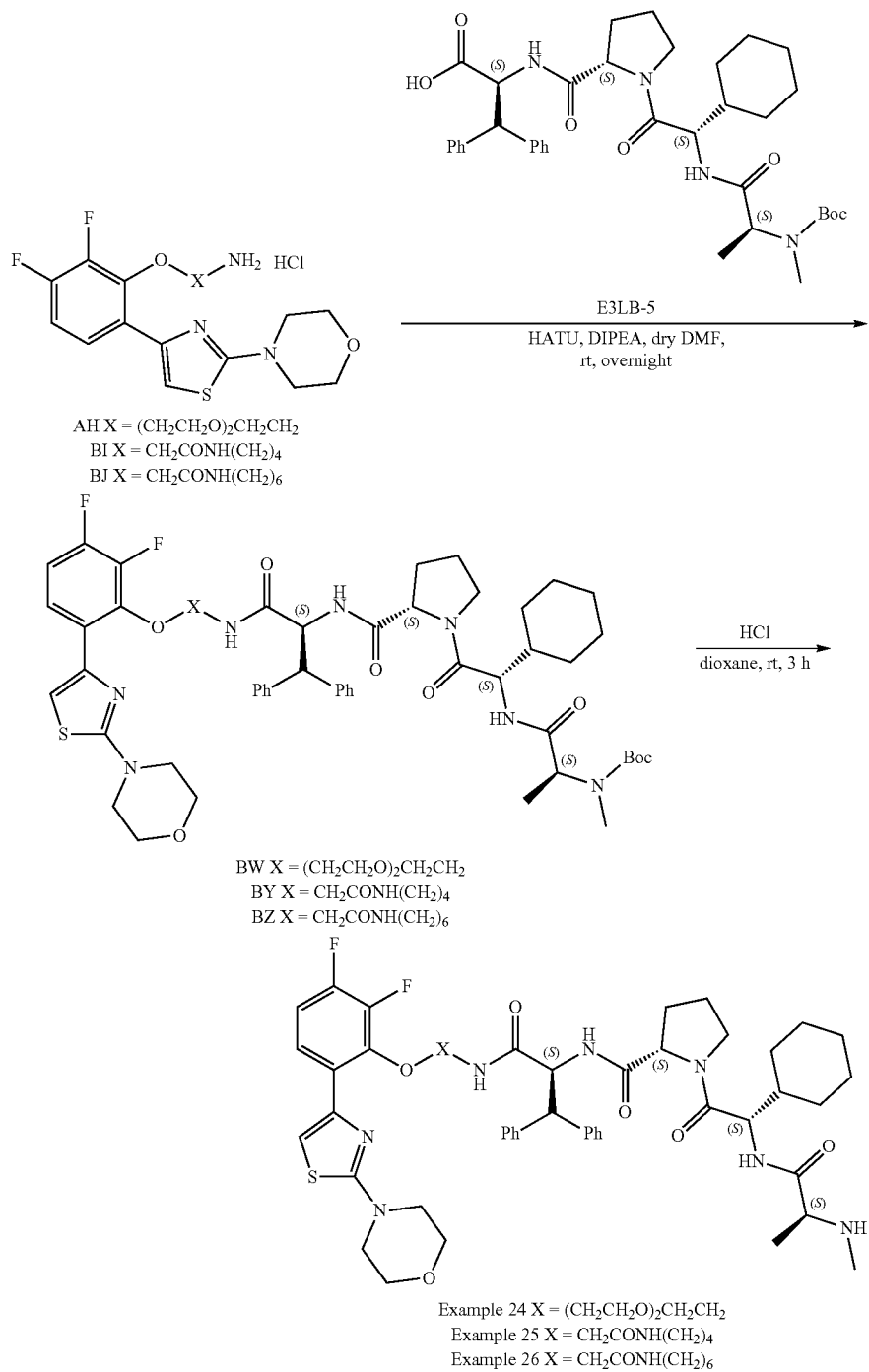

Example 24 X = (CH₂CH₂O)₂CH₂CH₂
Example 25 X = CH₂CONH(CH₂)₄
Example 26 X = CH₂CONH(CH₂)₆

Tert-butyl ((S)-1-(((S)-1-cyclohexyl-2-((S)-2-(((S)-1-((2-(2-(2-(2,3-difluoro-6-(2-morpholinothiazol-4-yl)phenoxy)ethoxy)ethoxy)ethyl)amino)-1-oxo-3,3-diphenylpropan-2-yl)carbamoyl)pyrrolidin-1-yl)-2-oxoethyl)amino)-1-oxopropan-2-yl)(methyl)carbamate (BW)

General Procedure III (overnight) was followed by using (S)-2-((S)-1-((S)-2-((S)-2-((tert-butoxycarbonyl)(methyl)amino)propanamido)-2-cyclohexylacetyl)pyrrolidine-2-carboxamido)-3,3-diphenylpropanoic acid (E3LB-5) (0.057 g, 0.086 mmol), 2-(2-(2-(2,3-difluoro-6-(2-morpholinothiazol-4-yl)phenoxy)ethoxy)ethoxy)ethan-1-amine hydrochloride (AH) (0.040 g, 0.086 mmol), DIPEA (0.06 mL, 0.343 mmol), and HATU (0.049 g, 0.128 mmol) in dry DMF (1.0 mL) to afford the titled compound as white solid (0.061 g, 66% yield) following purification by flash column chromatography on SiO₂ (DCM/MeOH, 95:5). ¹H NMR (400 MHz, CDCl₃): δ 7.94-7.86 (m, 1H), 7.57 (s, 1H), 7.34-7.13 (m, 11H), 6.94 (dd, J=16.8, 9.0 Hz, 1H), 6.50 (d, J=9.1 Hz, 1H), 6.18 (bs, 1H), 5.17 (t, J=9.1 Hz, 1H), 4.72-4.52 (m, 2H), 4.51-4.36 (m, 2H), 4.36-4.26 (m, 2H), 3.91-3.78 (m, 6H), 3.70-3.58 (m, 4H), 3.57-3.49 (m, 6H), 3.43-3.24 (m, 2H), 3.21-3.09 (m, 2H), 2.79 (s, 3H), 2.02-1.83 (m, 2H), 1.82-1.59 (m, 7H), 1.49 (s, 9H), 1.41-1.25 (m, 7H), 1.03-0.76 (m, 2H). HRMS (ESI) m/z [M+Na]+ calcd for $C_{56}H_{73}F_2N_7O_{10}S$ 1096.49999, found 1096.5010.

Tert-butyl ((S)-1-(((S)-1-cyclohexyl-2-((S)-2-(((S)-1-((4-(2-(2,3-difluoro-6-(2-morpholinothiazol-4-yl)phenoxy)acetamido)butyl)amino)-1-oxo-3,3-diphenylpropan-2-yl)carbamoyl)pyrrolidin-1-yl)-2-oxoethyl)amino)-1-oxopropan-2-yl)(methyl)carbamate (BY)

General Procedure III (overnight) was followed by using (S)-2-((S)-1-((S)-2-((S)-2-((tert-butoxycarbonyl)(methyl)amino)propanamido)-2-cyclohexylacetyl)pyrrolidine-2-carboxamido)-3,3-diphenylpropanoic acid (E3LB-5) (0.050 g, 0.075 mmol), tert-butyl (4-(2-(2,3-difluoro-6-(2-morpholinothiazol-4-yl)phenoxy)acetamido)butyl)carbamate (BI) (0.035 g, 0.075 mmol), DIPEA (0.05 mL, 0.302 mmol), and HATU (0.043 g, 0.113 mmol) in dry DMF (1.5 mL) to afford the titled compound as white solid (0.043 g, 53% yield) following purification by flash column chromatography on SiO$_2$ (DCM/MeOH, 95:5). $^1$H NMR (400 MHz, CDCl$_3$): δ 7.65-7.56 (m, 1H), 7.36-7.15 (m, 12H), 7.04-6.95 (m, 2H), 6.34-6.16 (m, 2H), 5.28-5.18 (m, 1H), 4.85-4.73 (m, 1H), 4.72-4.56 (m, 3H), 4.46-4.33 (m, 2H), 3.90-3.81 (m, 4H), 3.78-3.62 (m, 2H), 3.61-3.51 (m, 4H), 3.36-3.16 (m, 4H), 3.05-2.91 (m, 1H), 2.79 (s, 3H), 2.10-1.81 (m, 4H), 1.77-1.64 (m, 4H), 1.63-1.54 (m, 2H), 1.48 (s, 9H), 1.38-1.28 (m, 7H), 1.24-1.10 (m, 2H). IRMS (ESI) m/z [M+H]+ calcd for $C_{56}H_{72}F_2N_8O_9S$ 1071.51838, found 1071.51999.

Tert-butyl ((S)-1-(((S)-1-cyclohexyl-2-((S)-2-(((S)-1-((6-(2-(2,3-difluoro-6-(2-morpholinothiazol-4-yl)phenoxy)acetamido)hexyl)amino)-1-oxo-3,3-diphenylpropan-2-yl)carbamoyl)pyrrolidin-1-yl)-2-oxoethyl)amino)-1-oxopropan-2-yl)(methyl)carbamate (BZ)

General Procedure III (overnight) was followed by using (S)-2-((S)-1-((S)-2-((S)-2-((tert-butoxycarbonyl)(methyl)amino)propanamido)-2-cyclohexylacetyl)pyrrolidine-2-carboxamido)-3,3-diphenylpropanoic acid (E3LB-5) (0.038 g, 0.057 mmol), tert-butyl (6-(2-(2,3-difluoro-6-(2-morpholinothiazol-4-yl)phenoxy)acetamido)hexyl)carbamate (BJ) (0.028 g, 0.057 mmol), DIPEA (0.04 mL, 0.227 mmol), and HATU (0.032 g, 0.085 mmol) in dry DMF (0.5 mL) to afford the titled compound as white solid (0.031 g, 49% yield) following purification by flash column chromatography on SiO$_2$ (DCM/MeOH, 98:2 to 97:3). HRMS (ESI) m/z [M+H]+ calcd for $C_{58}H_{76}F_2N_8O_9S$ 1099.54968, found 1099.55025.

(S)-1-((S)-2-Cyclohexyl-2-((S)-2-(methylamino)propanamido)acetyl)-N—((S)-1-((2-(2-(2-(2,3-difluoro-6-(2-morpholinothiazol-4-yl)phenoxy)ethoxy)ethoxy)ethyl)amino)-1-oxo-3,3-diphenylpropan-2-yl)pyrrolidine-2-carboxamide (Example 24)

To the solution of tert-butyl ((S)-1-(((S)-1-cyclohexyl-2-((S)-2-(((S)-1-((2-(2-(2-(2,3-difluoro-6-(2-morpholinothiazol-4-yl)phenoxy)ethoxy)ethoxy)ethyl)amino)-1-oxo-3,3-diphenylpropan-2-yl)carbamoyl)pyrrolidin-1-yl)-2-oxoethyl)amino)-1-oxopropan-2-yl)(methyl)carbamate (BW) (0.060 g, 0.056 mmol) in dry DCM (0.5 mL) was added a solution of 4N HCl in dioxane (0.5 mL) and the mixture was stirred at rt for 4 h. The solvent was evaporated to dryness and the residue was diluted with saturated solution of NaHCO$_3$ (10 mL) and extracted with EA (6 mL×3). The reunited organic phases were washed with brine (10 mL), dried over Na$_2$SO$_4$, and evaporated under reduced pressure affording a crude residue which was purified by flash column chromatography on SiO$_2$ (DCM/MeOH, 95:5 to 94:6) yielding the titled compound (0.041 g, 75% yield) as white solid. HRMS (ESI) m/z [M+Na]+ calcd for $C_{51}H_{65}F_2N_7O_8S$ 996.44756, found 996.44769.

(S)-1-((S)-2-Cyclohexyl-2-((S)-2-(methylamino)propanamido)acetyl)-N—((S)-1-((4-(2-(2,3-difluoro-6-(2-morpholinothiazol-4-yl)phenoxy)acetamido)butyl)amino)-1-oxo-3,3-diphenylpropan-2-yl)pyrrolidine-2-carboxamide (Example 25)

To the solution of tert-butyl ((S)-1-(((S)-1-cyclohexyl-2-((S)-2-(((S)-1-((4-(2-(2,3-difluoro-6-(2-morpholinothiazol-4-yl)phenoxy)acetamido)butyl)amino)-1-oxo-3, 3-diphenylpropan-2-yl)carbamoyl)pyrrolidin-1-yl)-2-oxoethyl)amino)-1-oxopropan-2-yl)(methyl)carbamate (BY) (0.035 g, 0.033 mmol) in dry DCM (0.3 mL) was added a solution of 4N HCl in dioxane (0.3 mL) and the mixture was stirred at rt for 4 h. The solvent was evaporated to dryness and the residue was diluted with saturated solution of NaHCO$_3$ (10 mL) and extracted with EA (5 mL×3). The reunited organic phases were washed with brine (10 mL), dried over Na$_2$SO$_4$, and evaporated under reduced pressure affording a crude residue which was purified by flash column chromatography on SiO$_2$ (DCM/MeOH, 93:7 to 9:1) yielding the titled compound (0.010 g, 33% yield) as white solid. HRMS (ESI) m/z [M+Na]+ calcd for $C_{51}H_{64}F_2N_8O_7S$ 993.44789, found 993.44843.

(S)-1-((S)-2-Cyclohexyl-2-((S)-2-(methylamino)propanamido)acetyl)-N—((S)-1-((6-(2-(2,3-difluoro-6-(2-morpholinothiazol-4-yl)phenoxy)acetamido)hexyl)amino)-1-oxo-3,3-diphenylpropan-2-yl)pyrrolidine-2-carboxamide (Example 26)

To the solution of tert-butyl ((S)-1-(((S)-1-cyclohexyl-2-((S)-2-(((S)-1-((6-(2-(2,3-difluoro-6-(2-morpholinothiazol-4-yl)phenoxy)acetamido)hexyl)amino)-1-oxo-3, 3-diphenylpropan-2-yl)carbamoyl)pyrrolidin-1-yl)-2-oxoethyl)amino)-1-oxopropan-2-yl)(methyl)carbamate (BZ) (0.030 g, 0.027 mmol) in dry DCM (0.3 mL) was added a solution of 4N HCl in dioxane (0.3 mL) and the mixture was stirred at rt for 4 h. The solvent was evaporated to dryness and the residue was diluted with saturated solution of NaHCO$_3$ (10 mL) and extracted with EA (5 mL×3). The reunited organic phases were washed with brine (10 mL), dried over Na$_2$SO$_4$, and evaporated under reduced pressure affording a crude residue which was purified by flash column chromatography on SiO$_2$ (DCM/MeOH, 95:5 to 93:7) yielding the titled compound (0.017 g, 63% yield) as white solid. HRMS (ESI) m/z [M+H]+ calcd for $C_{53}H_{68}F_2N_8O_7S$ 999.49725, found 999.49979.

Scheme 14. Synthesis of Examples 27-29.

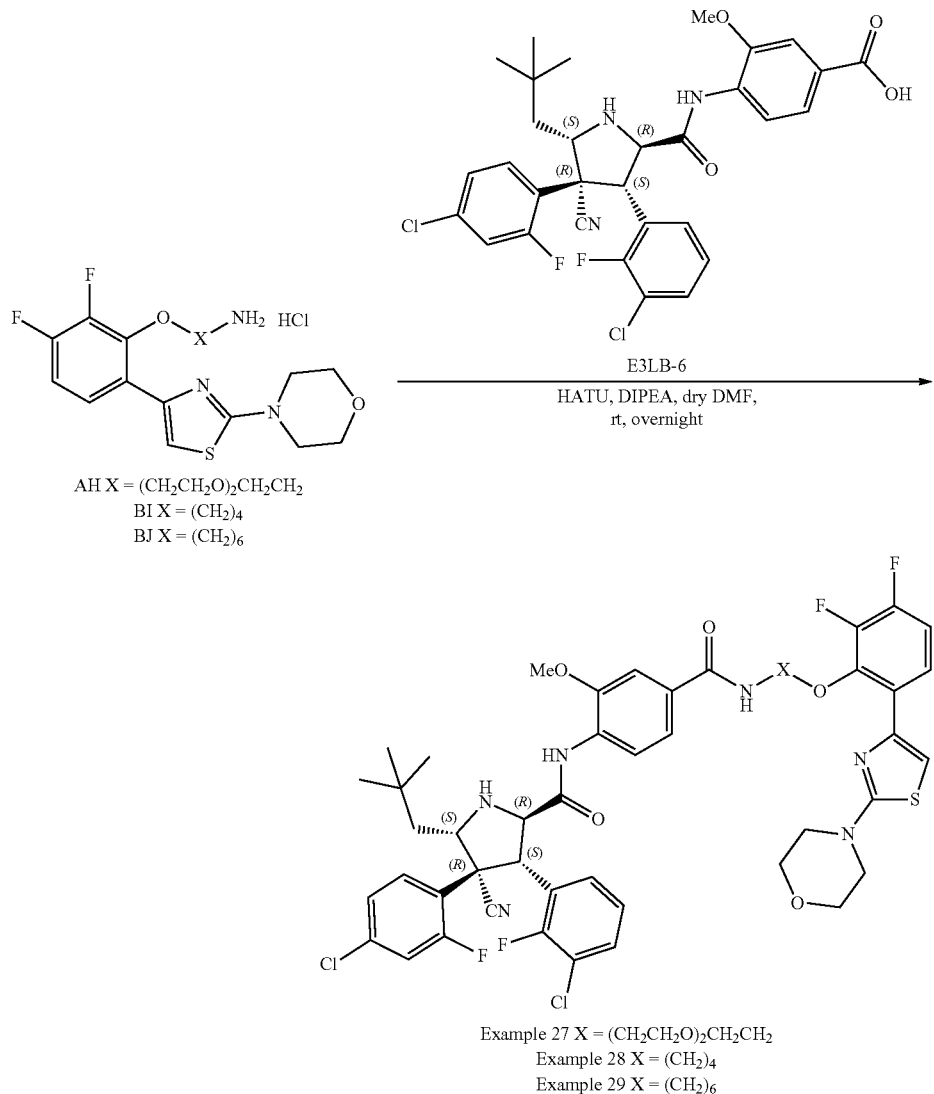

Example 27 X = (CH$_2$CH$_2$O)$_2$CH$_2$CH$_2$
Example 28 X = (CH$_2$)$_4$
Example 29 X = (CH$_2$)$_6$ (2R,3S,4R,5S)-3-(3-Chloro-2-fluorophenyl)-4-(4-chloro-2-fluorophenyl)-4-cyano-N-(4-((2-(2-(2-(2,3-difluoro-6-(2-morpholinothiazol-4-yl)phenoxy)ethoxy)ethoxy)ethyl)carbamoyl)-2-methoxyphenyl)-5-neopentylpyrrolidine-2-carboxamide (Example 27)

General Procedure III (5h) was followed by using 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (E3LB-6) (commercially available, for example, from Carbosynth) (0.021 g, 0.034 mmol), 2-(2-(2-(2,3-difluoro-6-(2-morpholinothiazol-4-yl)phenoxy)ethoxy)ethoxy)ethan-1-amine hydrochloride (AH) (0.016 g, 0.034 mmol), DIPEA (0.024 mL, 0.137 mmol), and HATU (0.016 g, 0.043 mmol) in dry DMF (0.5 mL) to afford the titled compound as white solid (0.030 g, 85% yield) following purification by flash column chromatography on SiO$_2$ (DCM/MeOH, 98:2). $^1$H NMR (400 MHz, CDCl$_3$): δ 10.35 (s, 1H), 8.40 (d, J=8.2 Hz, 1H), 7.88 (t, J=7.8 Hz, 1H), 7.57 (s, 1H), 7.56-7.51 (m, 1H), 7.49 (s, 1H), 7.35 (t, J=7.6 Hz, 1H), 7.28-7.24 (m, 1H), 7.23-7.10 (m, 4H), 6.92 (dd, J=17.3, 8.9 Hz, 1H), 6.64 (bs, 1H), 4.78 (d, J=8.5 Hz, 1H), 4.57 (bs, 1H), 4.28 (s, 2H), 4.16-4.07 (m, 1H), 3.93 (s, 3H), 3.86-3.79 (m, 6H), 3.70 (s, 8H), 3.56-3.50 (m, 4H), 2.80 (s, 1H), 1.70-1.54 (m, 2H), 1.04 (s, 9H). HRMS (ESI) m/z [M+Na]+ calcd for C$_{50}$H$_{52}$Cl$_2$F$_4$N$_6$O$_7$S 1049.28236, found 1049.28585.

(2R,3S,4R,5S)-3-(3-Chloro-2-fluorophenyl)-4-(4-chloro-2-fluorophenyl)-4-cyano-N-(4-((4-(2-(2,3-difluoro-6-(2-morpholinothiazol-4-yl)phenoxy)acetamido)butyl)carbamoyl)-2-methoxyphenyl)-5-neopentylpyrrolidine-2-carboxamide (Example 28)

General Procedure III (5h) was followed by using 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (E3LB-6) (0.030 g, 0.049 mmol), tert-butyl (4-(2-(2,3-difluoro-6-(2-morpholinothiazol-4-yl)phenoxy)acetamido)butyl)carbamate (BI) (0.022 g, 0.049 mmol), DIPEA (0.034 mL, 0.195 mmol), and HATU (0.023 g, 0.061 mmol) in dry DMF (1.0 mL) to afford the titled compound as white solid (0.033 g, 66% yield) following purification by flash column chromatography on SiO$_2$ (DCM/MeOH, 97:3). $^1$H NMR (400 MHz, CDCl$_3$): δ 10.37 (s, 1H), 8.44 (d, J=8.4 Hz, 1H), 7.60-7.45 (m, 3H), 7.35-7.29 (m, 1H), 7.29-7.26 (m, 1H), 7.24 (d, J=8.3 Hz, 1H), 7.19-7.07 (m, 3H), 6.97 (td, J=9.1, 7.5 Hz, 1H), 6.90 (s, 1H), 6.52 (bs, 1H), 4.76 (d, J=8.4 Hz, 1H), 4.60 (s, 2H), 4.54 (t, J=8.6 Hz, 1H), 4.09 (t, J=10.4 Hz, 1H), 3.94 (s, 3H), 3.86-3.77 (m, 4H), 3.55-3.49 (m, 4H), 3.42-3.34 (m, 2H), 2.84-2.73 (m, 1H), 1.70-1.54 (m, 6H), 1.01 (s, 9H). HRMS (ESI) m/z [M+Na]+ calcd for C$_{50}$H$_{51}$Cl$_2$F$_4$N$_7$O$_6$S 1046.28269, found 1046.28517.

(2R,3S,4R,5S)-3-(3-Chloro-2-fluorophenyl)-4-(4-chloro-2-fluorophenyl)-4-cyano-N-(4-((6-(2-(2,3-difluoro-6-(2-morpholinothiazol-4-yl)phenoxy)acetamido)hexyl)carbamoyl)-2-methoxyphenyl)-5-neopentylpyrrolidine-2-carboxamide (Example 29)

General Procedure III (4h) was followed by using 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (E3LB-6) (0.031 g, 0.051 mmol), tert-butyl (6-(2-(2,3-difluoro-6-(2-morpholinothiazol-4-yl)phenoxy)acetamido)hexyl)carbamate (BJ) (0.025 g, 0.051 mmol), DIPEA (0.035 mL, 0.204 mmol), and HATU (0.024 g, 0.063 mmol) in dry DMF (0.6 mL) to afford the titled compound as white solid (0.044 g, 82% yield) following purification by flash column chromatography on SiO$_2$ (DCM/MeOH, 99:1 to 98:2). $^1$H NMR (400 MHz, CDCl$_3$): δ 10.38 (s, 1H), 8.43 (d, J=8.3 Hz, 1H), 7.59-7.45 (m, 3H), 7.32 (t, J=6.8 Hz, 1H), 7.23 (d, J=8.3 Hz, 2H), 7.19-7.07 (m, 3H), 6.97 (dd, J=16.6, 9.2 Hz, 1H), 6.90 (s, 1H), 6.36 (bs, 1H), 4.76 (d, J=8.4 Hz, 1H), 4.57 (s, 2H), 4.54-4.48 (m, 1H), 4.09 (t, J=10.9 Hz, 1H), 3.94 (s, 3H), 3.88-3.78 (m, 4H), 3.57-3.50 (m, 4H), 3.45-3.38 (m, 2H), 3.39-3.28 (m, 2H), 2.85-2.74 (m, 1H), 1.70-1.49 (m, 6H), 1.47-1.32 (m, 4H), 1.01 (s, 9H). HRMS (ESI) m/z [M+Na]+ calcd for C$_{52}$H$_{55}$Cl$_2$F$_4$N$_7$O$_6$S 1074.31399, found 1074.31724.

Scheme 15. Synthesis of ARB-2 moiety.

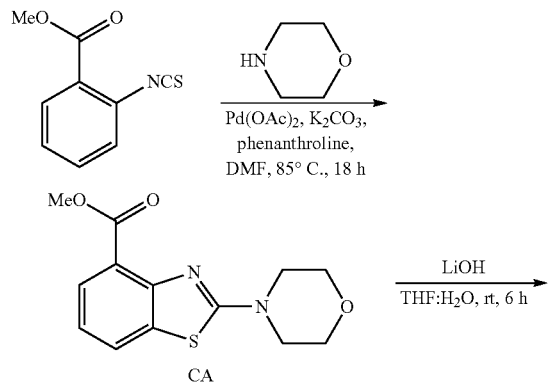

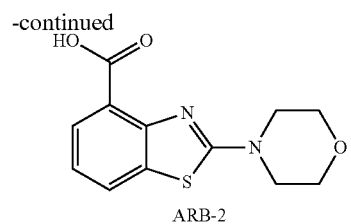

ARB-2

Methyl 2-morpholinobenzo[d]thiazole-4-carboxylate (CA)

Methyl 2-isothiocyanatobenzoate (0.20 g, 1.035 mmol) and morpholine (0.09 mL, 1.035 mmol) were stirred under solvent free condition for 15 min. Successively, DMF (4.0 mL) was added and the mixture was stirred for further 10 min. Then, K$_2$CO$_3$ (0.143 g, 1.035 mmol), phenanthroline (0.019 g, 0.103 mmol), and palladium (II) acetate (0.014 g, 0.062 mmol) were added and the reaction mixture was stirred at 85° C. for 24h. The reaction mixture was diluted with water (40 mL) and extracted with EA (20 mL×3). The reunited organic phases were washed with brine (30 mL), dried over anhydrous Na$_2$SO$_4$, and concentered under reduced pressure affording a crude residue which was purified by flash column chromatography on SiO$_2$ (PE/EA, 9:1 to 8:2) to give the titled compound (0.028 g, 10% yield) as light-yellow solid. $^1$H NMR (400 MHz, CDCl$_3$): δ 7.93 (dd, J=7.8, 1.3 Hz, 1H), 7.76 (dd, J=7.8, 1.3 Hz, 1H), 7.11 (t, J=7.8 Hz, 1H), 3.96 (s, 3H), 3.89-3.79 (m, 4H), 3.74-3.64 (m, 4H); $^{13}$C NMR (101 MHz, CDCl$_3$): δ 170.02, 16 6.82, 151.78, 132.76, 128.61, 124.88, 120.79, 120.67, 66.29 (2C), 52.12, 48.45 (2C).

2-Morpholinobenzo[d]thiazole-4-carboxylic acid (ARB-2)

To the solution of methyl 2-morpholinobenzo[d]thiazole-4-carboxylate (CA) (0.155 g, 0.557 mmol) in THF (2 mL) at 0° C. was added the solution of lithium hydroxide monohydrate (0.233 g, 5.569 mmol) in water (2.0 mL). The resulting mixture was stirred at rt for 6 h. The organic solvent was removed under vacuo, the residue was diluted with ice-water (4.0 mL) and the pH was slowly adjusted to 4-3 with 2N HCl yielding a solid which was collected by filtration and dried to afford the titled compound as light-yellow solid (0.122 g, 83% yield). $^1$H NMR (400 MHz, CDCl$_3$): δ 13.51 (bs, 1H), 8.16 (d, J=7.9 Hz, 1H), 7.78 (d, J=7.8 Hz, 1H), 7.25-7.20 (m, 1H), 3.92-3.83 (m, 4H), 3.73-3.65 (m, 4H); $^{13}$C NMR (101 MHz, CDCl$_3$): δ 169.97, 166.34, 150.83, 129.76, 129.23, 125.54, 122.25, 118.90, 65.97 (2C), 48.66 (2C).

Scheme 16. Synthesis of Examples 30.

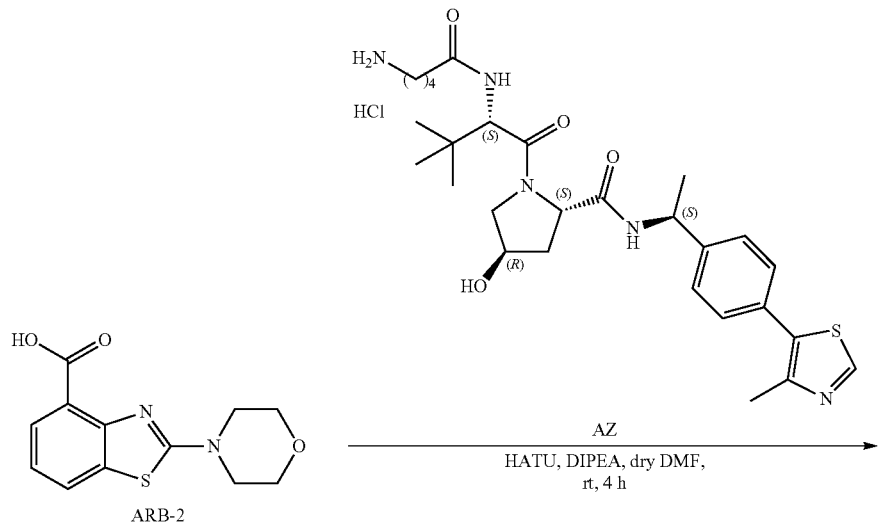

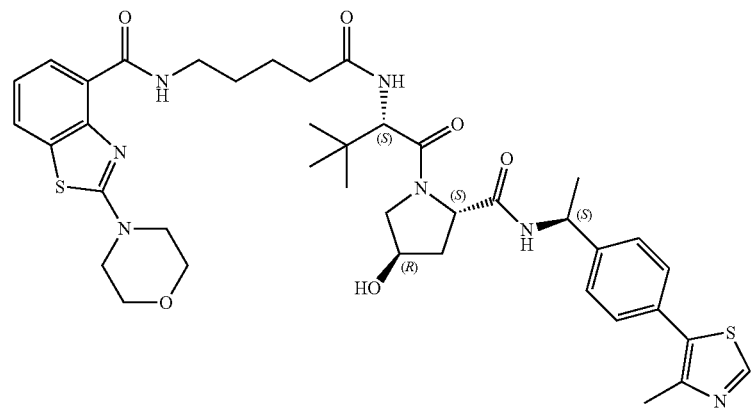

Example 30

N-(5-(((S)-1-((2S,4R)-4-Hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-5-oxopentyl)-2-morpholinobenzo[d]thiazole-4-carboxamide (Example 30)

General Procedure III (4h) was followed by using 2-morpholinobenzo[d]thiazole-4-carboxylic acid (ARB-2) (0.040 g, 0.151 mmol), (2S,4R)-1-((S)-2-(5-aminopentanamido)-3,3-dimethylbutanoyl)-4-hydroxy-N—((S)-1-(4-(4-methylthiazol-5-yl)phenyl)ethyl)pyrrolidine-2-carboxamide hydrochloride (AZ) (0.088 g, 0.151 mmol), DIPEA (0.079 mL, 0.454 mmol), and HATU (0.072 g, 0.189 mmol) in dry DMF (0.5 mL) to afford the titled compound as light-yellow solid (0.050 g, 42% yield) following purification by flash column chromatography on SiO$_2$ (DCM/MeOH, 98:2 to 95:5). $^1$H NMR (400 MHz, CDCl$_3$): δ 9.96-9.85 (m, 1H), 8.67 (s, 1H), 8.21 (d, J=7.7 Hz, 1H), 7.69 (d, J=7.7 Hz, 1H), 7.48-7.30 (m, 5H), 7.18 (t, J=7.8 Hz, 1H), 6.38 (d, J=8.5 Hz, 1H), 5.15-5.01 (m, 1H), 4.74 (t, J=7.9 Hz, 1H), 4.56 (d, J=8.6 Hz, 1H), 4.50 (s, 1H), 4.08 (d, J=11.4 Hz, 1H), 3.88 (t, J=4.6 Hz, 4H), 3.72-3.57 (m, 6H), 3.51 (d, J=2.7 Hz, 2H), 2.62-2.43 (m, 4H), 2.41-2.19 (m, 2H), 2.08 (dd, J=13.3, 8.3 Hz, 1H), 1.87-1.73 (m, 2H), 1.69-1.58 (m, 2H), 1.46 (d, J=6.9 Hz, 3H), 1.03 (s, 9H); $^{13}$C NMR (101 MHz, CDCl$_3$): δ 173.33, 172.17, 169.73, 169.51, 165.53, 150.28, 149.51, 148.51, 143.19, 131.60, 130.87, 130.75, 129.57 (2C), 128.04, 126.45 (2C), 123.84, 122.72, 121.64, 70.06, 66.12, 58.43, 57.68, 56.93, 48.81, 48.47, 38.92, 35.77, 35.51, 35.06, 29.23, 26.53, 23.02, 22.23, 16.12. HRMS (ESI) m/z [M+H]+ calcd for C$_{40}$H$_{51}$N$_7$O$_6$S$_2$ 790.34150, found 790.3412.

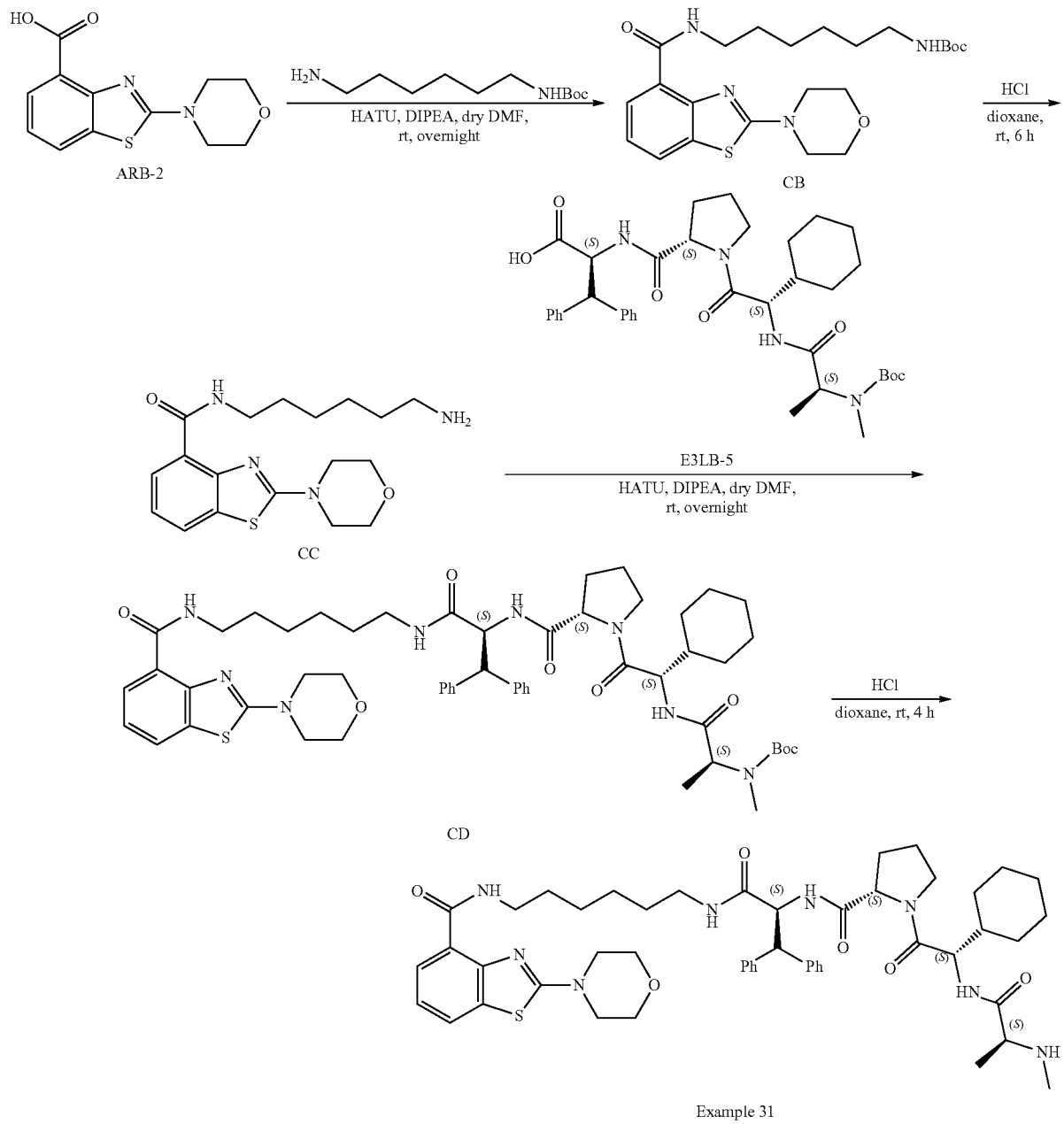

Scheme 17. Synthesis of Examples 31.

Example 31

Tert-butyl (6-(2-morpholinobenzo[d]thiazole-4-carboxamido)hexyl)carbamate (CB)

In an oven-dried round-bottom flask, under nitrogen atmosphere, to a stirred solution of 2-morpholinobenzo[d]thiazole-4-carboxylic acid (ARB-2) (0.050 g, 0.189 mmol), tert-butyl (6-aminohexyl)carbamate (0.041 g, 0.189 mmol), and DIPEA (0.099 mL, 0.567 mmol) in dry DMF (0.5 mL) was added HATU (0.090 g, 0.236 mmol). Stirring was continued at rt overnight. The reaction mixture was diluted with water (20 mL) and extracted with EA (10 mL×3). The reunited organic layers were washed with brine (15 mL), dried over anhydrous $Na_2SO_4$, and evaporated under reduced pressure to give a crude residue, which was purified by flash column chromatography on $SiO_2$ (DCM/MeOH, 97:3) affording a yellow film (0.062 g, 71% yield). $^1$H NMR (400 MHz, $CDCl_3$): δ 9.83 (s, 1H), 8.27 (d, J=7.8 Hz, 1H), 7.71 (d, J=7.6 Hz, 1H), 7.22 (t, J=7.6 Hz, 1H), 4.54 (bs, 1H), 3.95-3.82 (m, 4H), 3.70-0.59 (m, 4H), 3.53 (dd, J=11.9, 6.5 Hz, 2H), 3.18-3.01 (m, 2H), 1.73-1.64 (m, 2H), 1.54-1.41 (m, 13H), 1.41-1.31 (m, 2H).

N-(6-Aminohexyl)-2-morpholinobenzo[d]thiazole-4-carboxamide hydrochloride (CC)

To the solution of tert-butyl (6-(2-morpholinobenzo[d]thiazole-4-carboxamido)hexyl)carbamate (CB) (0.055 g, 0.119 mmol) in dry DCM (0.5 mL) at 0° C. was added dropwise the solution of 4N HCl in dioxane (0.5 mL). The mixture was stirred at rt for 6 h. The solvent was evaporated to dryness and the crude residue was triturated with DEE and filtered off to afford the titled compound as a light-yellow solid (0.044 g, 92% yield). $^1$H NMR (400 MHz, DMSO): δ 9.74 (t, J=5.4 Hz, 1H), 7.98 (dd, J=7.7, 4.1 Hz, 2H), 7.89 (bs, 3H), 7.20 (t, J=7.8 Hz, 1H), 3.87-3.74 (m, 4H), 3.70-3.56 (m, 4H), 3.40 (dd, J=12.4, 6.6 Hz, 2H), 2.75 (dd, J=13.8, 6.5 Hz, 2H), 1.67-1.49 (m, 4H), 1.43-1.28 (m, 4H).

Tert-butyl ((S)-1-(((S)-1-cyclohexyl-2-((S)-2-(((S)-1-((6-(2-morpholinobenzo[d]thiazole-4-carboxamido)hexyl)amino)-1-oxo-3,3-diphenylpropan-2-yl)carbamoyl)pyrrolidin-1-yl)-2-oxoethyl)amino)-1-oxopropan-2-yl)(methyl)carbamate (CD)

General Procedure III (overnight) was followed by using (S)-2-((S)-1-((S)-2-((S)-2-((tert-butoxycarbonyl)(methyl)amino)propanamido)-2-cyclohexylacetyl)pyrrolidine-2-carboxamido)-3,3-diphenylpropanoic acid (E3LB-5) (0.055 g, 0.083 mmol), N-(6-aminohexyl)-2-morpholinobenzo[d]thiazole-4-carboxamide hydrochloride (CC) (0.033 g, 0.083 mmol), DIPEA (0.058 mL, 0.331 mmol), and HATU (0.047 g, 0.124 mmol) in dry DMF (1.0 mL) to afford the titled compound as white solid (0.061 g, 73% yield) following purification by flash column chromatography on SiO$_2$ (DCM/MeOH, 97:3 to 96:4). HRMS (ESI) m/z [M+H]+ calcd for C$_{55}$H$_{74}$N$_8$O$_8$S 1007.54231, found 1007.54274.

N-(6-((S)-2-((S)-1-((S)-2-Cyclohexyl-2-((S)-2-(methylamino)propanamido)acetyl)pyrrolidine-2-carboxamido)-3,3-diphenylpropanamido)hexyl)-2-morpholinobenzo[d]thiazole-4-carboxamide (Example 31)

To the solution of tert-butyl ((S)-1-(((S)-1-cyclohexyl-2-((S)-2-(((S)-1-((6-(2-morpholinobenzo[d]thiazole-4-carboxamido)hexyl)amino)-1-oxo-3,3-diphenylpropan-2-yl)carbamoyl)pyrrolidin-1-yl)-2-oxoethyl)amino)-1-oxopropan-2-yl)(methyl)carbamate (CD) (0.050 g, 0.049 mmol) in dry DCM (0.5 mL) was added a solution of 4N HCl in dioxane (0.5 mL) and the mixture was stirred at rt for 4 h. The solvent was evaporated to dryness and the residue was diluted with saturated solution of NaHCO$_3$ (10 mL) and extracted with EA (6 mL×3). The reunited organic phases were washed with brine (10 mL), dried over Na$_2$SO$_4$, and evaporated under reduced pressure affording a crude residue which was purified by flash column chromatography on SiO$_2$ (DCM/MeOH, 97:3) yielding the titled compound (0.015 g, 33% yield) as white solid. HRMS (ESI) m/z [M+H]+ calcd for C$_{50}$H$_{66}$N$_8$O$_6$S 907.48988, found 907.48938.

Scheme 18. Synthesis of Examples 32-33.

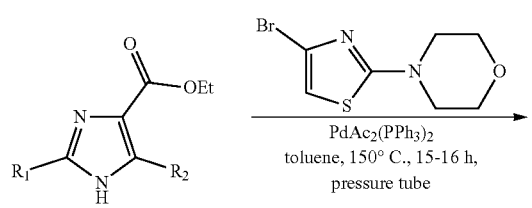

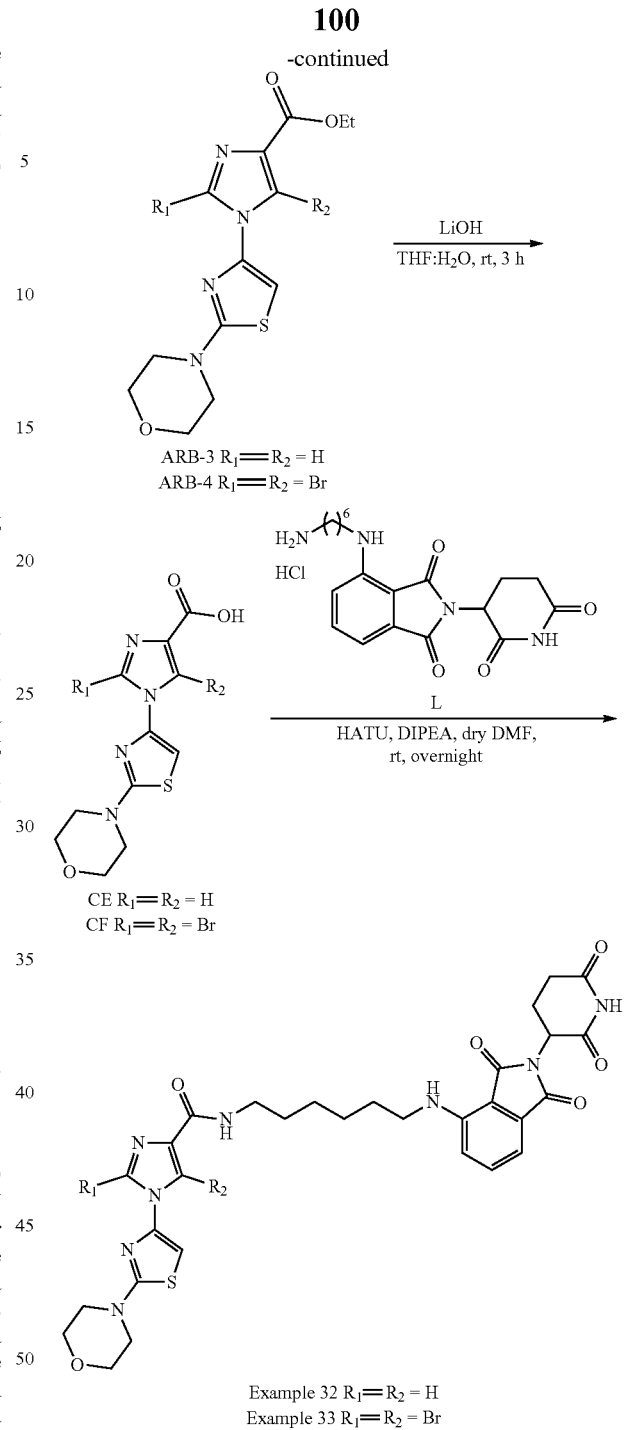

Ethyl 1-(2-morpholinothiazol-4-yl)-1H-imidazole-4-carboxylate (ARB-3)

The mixture of ethyl 1H-imidazole-4-carboxylate (commercially available from, for example, Sigma Aldrich) (0.24 g, 1.712 mmol), 4-(4-bromothiazol-2-yl)morpholine (commercially available from, for example, Fluorochem) (0.142 g, 0.571 mmol), and PdAc$_2$(PPh$_3$)$_2$ (0.022 g, 0.028 mmol) in dry and degassed toluene (3.0 mL) was stirred at 150° C. in an Ace pressure tube (charged under nitrogen atmosphere) for 15 h. After cooling, the reaction mixture was evaporated to dryness and purified by flash column chromatography on SiO$_2$ (PE/EA, 7:3 to 5:5) to afford the titled compound (0.105 g, 60% yield) as white solid. $^1$H NMR (400 MHz, CDCl$_3$): δ 8.09-7.96 (m, 2H), 6.36 (s, 1H), 4.39 (q, J=7.1 Hz, 2H), 3.91-3.74 (m, 4H), 3.57-3.46 (m, 4H), 1.39 (t, J=7.1 Hz, 3H). HRMS (ESI) m/z [M+H]+ calcd for C$_{13}$H$_{16}$N$_4$O$_3$S 309.10159, found 309.10191.

Ethyl 2,5-dibromo-1-(2-morpholinothiazol-4-yl)-1H-imidazole-4-carboxylate (ARB-4)

The mixture of ethyl 2,5-dibromo-1H-imidazole-4-carboxylate (0.437 g, 1.466 mmol), 4-(4-bromothiazol-2-yl)morpholine (commercially available from, for example, Fluorochem) (0.146 g, 0.586 mmol), and PdAc$_2$(PPh$_3$)$_2$ (0.044 g, 0.058 mmol) in dry and degassed toluene (3.0 mL) was stirred at 150° C. in an Ace pressure tube (charged under nitrogen atmosphere) for 16 h. After cooling, the reaction mixture was evaporated to dryness and purified by flash column chromatography on SiO$_2$ (PE/EA, 8:2) to afford the titled compound (0.036 g, 13% yield) as light-yellow solid. $^1$H NMR (400 MHz, CDCl$_3$): δ 6.62 (s, 1H), 4.25 (q, J=7.1 Hz, 2H), 3.99-3.62 (m, 4H), 3.62-3.22 (m, 4H), 1.26 (t, J=7.1 Hz, 3H). HRMS (ESI) m/z [M+H]+ calcd for C$_{13}$H$_{14}$Br$_2$N$_4$O$_3$S 464.92261, found 464.92235.

1-(2-Morpholinothiazol-4-yl)-1H-imidazole-4-carboxylic acid (CE)

To the solution of ethyl 1-(2-morpholinothiazol-4-yl)-1H-imidazole-4-carboxylate (ARB-3) (0.030 g, 0.097 mmol) in THF (0.2 mL) and EtOH (0.1 mL) at 0° C. was added the solution of lithium hydroxide monohydrate (0.008 g, 0.194 mmol) in water (0.3 mL). The resulting mixture was stirred at rt for 3 h. The organic solvent was removed under vacuo, the residue was diluted with ice-water (5.0 mL) and the pH was slowly adjusted to 3 with 2N HCl yielding a solid which was collected by filtration and dried to afford the titled compound as white solid (0.025 g, 92% yield). $^1$H NMR (400 MHz, MeOD): δ 8.26 (s, 1H), 8.08 (s, 1H), 6.87 (s, 1H), 3.97-3.74 (m, 4H), 3.68-3.43 (m, 4H).

N-(6-((2-(2,6-Dioxopiperidin-3-yl)-1,3-dioxoisoindolin-4-yl)amino)hexyl)-1-(2-morpholinothiazol-4-yl)-1H-imidazole-4-carboxamide (Example 32)

In an oven-dried round-bottom flask, under nitrogen atmosphere, to a stirred solution of 1-(2-morpholinothiazol-4-yl)-1H-imidazole-4-carboxylic acid (CE) (0.027 g, 0.098 mmol), 4-((6-aminohexyl)amino)-2-(2,6-dioxopiperidin-3-yl)isoindoline-1,3-dione hydrochloride (L) (0.044 g, 0.107 mmol), and DIPEA (0.055 mL, 0.318 mmol) in dry DMF (1.0 mL) was added HATU (0.046 g, 0.122 mmol). Stirring was continued at rt overnight. The reaction mixture was poured in ice-water yielding a precipitate collected by filtration and then purified by flash column chromatography on SiO$_2$ (DCM/MeOH, 98:2 to 97:3) affording a yellow film (0.011 g, 17% yield). $^1$H NMR (400 MHz, CDCl$_3$): δ 9.33 (s, 1H), 8.05 (s, 1H), 7.98 (s, 1H), 7.46 (t, J=7.6 Hz, 1H), 7.33 (s, 1H), 7.06 (d, J=6.8 Hz, 1H), 6.86 (d, J=8.4 Hz, 1H), 6.34 (s, 1H), 6.22 (s, 1H), 4.97-4.86 (m, 1H), 3.81 (s, 4H), 3.57-3.32 (m, 6H), 3.29-3.14 (m, 2H), 2.93-2.62 (m, 3H), 2.20-2.03 (m, 1H), 1.62 (d, J=6.5 Hz, 4H), 1.42 (s, 4H); $^{13}$C NMR (101 MHz, CDCl$_3$): δ 171.5, 170.5, 169.5, 168.8, 167.7, 162.2, 147.0, 142.5, 137.4, 136.1, 135.0, 132.5, 119.5, 116.8, 111.3, 109.9, 90.6, 66.0 (2C), 48.9, 48.0 (2C), 42.6, 38.9, 31.5, 29.6, 29.0, 26.6, 26.5, 22.9. HRMS (ESI) m/z [M+H]+ calcd for C$_{30}$H$_{34}$N$_8$O$_6$S 635.23948, found 635.23979.

2,5-Dibromo-N-(6-((2-(2,6-dioxopiperidin-3-yl)-1,3-dioxoisoindolin-4-yl)amino)hexyl)-1-(2-morpholinothiazol-4-yl)-1H-imidazole-4-carboxamide (Example 33)

To the solution of ethyl 2,5-dibromo-1-(2-morpholinothiazol-4-yl)-1H-imidazole-4-carboxylate (ARB-4) (0.036 g, 0.077 mmol) in THF (0.2 mL) and EtOH (0.1 mL) at 0° C. was added the solution of lithium hydroxide monohydrate (0.0065 g, 0.154 mmol) in water (0.3 mL). The resulting mixture was stirred at rt for 3 h. The organic solvent was removed under vacuo, the residue was diluted with ice-water (5.0 mL) and the pH was slowly adjusted to 3 with 2N HCl yielding a solid which was collected by filtration and dried to afford 2,5-dibromo-1-(2-morpholinothiazol-4-yl)-1H-imidazole-4-carboxylic acid (CF) as yellow solid (0.032 g, 94% yield). Then, in an oven-dried round-bottom flask, under nitrogen atmosphere, to a stirred solution of (CF) (0.031 g, 0.071 mmol), 4-((6-aminohexyl)amino)-2-(2,6-dioxopiperidin-3-yl)isoindoline-1,3-dione hydrochloride (L) (0.029 g, 0.107 mmol), and DIPEA (0.055 mL, 0.318 mmol) in dry DMF (1.0 mL) was added HATU (0.046 g, 0.071 mmol). Stirring was continued at rt overnight. The reaction mixture was diluted with water (20 mL) and extracted with EA (10 mL×3). The reunited organic layers were washed with brine (15 mL), dried over anhydrous Na$_2$SO$_4$, and evaporated under reduced pressure to give a crude residue, which was purified by flash column chromatography on SiO$_2$ (DCM/MeOH, 96:4) affording a yellow solid (0.004 g, 7% yield). $^1$H NMR (400 MHz, CDCl$_3$): δ 8.01 (s, 1H), 7.58-7.42 (m, 1H), 7.15-6.97 (m, 2H), 6.91 (d, J=8.5 Hz, 1H), 6.70 (s, 1H), 6.26 (t, J=5.2 Hz, 1H), 4.94 (dd, J=5.3, 12.2 Hz, 1H), 3.95-3.79 (m, 4H), 3.62-3.47 (m, 4H), 3.42 (q, J=6.8 Hz, 2H), 3.35-3.22 (m, 2H), 3.04-2.64 (m, 3H), 2.35-2.08 (m, 1H), 1.87-1.52 (m, 8H). HRMS (ESI) m/z [M+Na]+ calcd for C$_{13}$H$_{14}$Br$_2$N$_4$O$_3$S 813.04245, found 813.04210.

The human prostate cancer cell line, 22Rv1 has been reported to express a high level of AR-V7. Thus, 22Rv1 was seeded at 50,000 cells/well on a 24-well plate in quadruplicates and treated with test compound in concentrations ranging up to 20 µM for four days. Standard culture media was RPMI-1640 supplemented with 10% fetal bovine serum. The test compound initially was dissolved in DMSO at 50 mM. This stock solution was then diluted as needed for the indicated concentrations. At the end of the four-day period, cells were harvested using 1% trypsin and counted using an automated cell counter.

The results as shown in Table 1 below demonstrate that the test compounds decreased cell count in a concentration dependent manner.

TABLE 1

| 22Rv1 cell count decrease by compounds in the examples | |
|---|---|
| Examples | 22Rv1 cell count decrease at 10 uM for 48 hours |
| 1 | ++ |
| 2 | + |
| 3 | ++ |
| 4 | + |

TABLE 1-continued

22Rv1 cell count decrease by
compounds in the examples

| Examples | 22Rv1 cell count decrease at 10 uM for 48 hours |
|---|---|
| 5 | + |
| 6 | + |
| 7 | + |
| 8 | + |
| 9 | + |
| 10 | + |
| 11 | + |
| 12 | + |
| 13 | + |
| 14 | + |
| 15 | ++ |
| 16 | ++ |
| 17 | ++ |
| 18 | ++ |
| 19 | ++ |
| 20 | ++ |
| 21 | ++ |
| 22 | + |
| 23 | + |
| 24 | +++ |
| 25 | +++ |
| 26 | +++ |
| 27 | +++ |
| 28 | +++ |
| 29 | ++ |
| 30 | ++ |
| 31 | +++ |
| 32 | + |
| 33 | + |
| 34 | ++ |

+ - the cell count decreased between 0 and 20%
++ - the cell count decreased less than 50%
+++ - the cell count decreased by more than 50%

Immunoblot was carried out to determine the effect of the test compound on AR-V7. 22Rv1 was plated at 200,000 cell/well on a 6-well plate and cultured as described with 10 pM test compound. After four days of treatment, cells were harvested using a cell scraper and lysed in a standard fashion using SDS. After removing debris via centrifuge, 30 pg of protein were loaded onto SDS-PAGE gel. After electrophoresis, protein was transferred to a nylon membrane and ECL was carried out using primary antibody against AR-V7 (Thermofisher Scientific, cat #NC0752138). Protein bands were visualized using the commercially available Enhanced Chemiluminescence (ECL) kit (Thermofisher). As shown in FIG. 1, the results demonstrated a dramatically decreased level of AR-V7 protein.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present disclosure. In instances where a term is not specifically defined herein, that term is given an art-recognized meaning by those of ordinary skill applying that term in context to its use in describing the present invention.

The articles "a" and "an" as used herein and in the claims are used herein to refer to one or to more than one (i.e., to at least one) of the grammatical object of the article unless the context clearly indicates otherwise. By way of example, "an element" means one element or more than one element.

The phrase "and/of" as used herein and in the claims should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the term "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The term "about" and the like, as used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. In accordance with the above, the term "about" is normally used to encompass values within the standard deviation or standard error.

In the claims, as well as in the specification, all transitional phrases such as "comprising," "including," "carrying," "having," "containing," "involving," "holding," "composed of," and the like are to be understood to be open-ended, i.e., to mean "including without limitation". Only the transitional phrases "consisting of" and "consisting essentially of" shall be closed or semi-closed transitional phrases, respectively, as set forth in the United States Patent Office Manual of Patent Examining Procedures, Section 2111.03.

It should also be understood, that although various compounds, compositions, and methods are described in "open" terms of "comprising," "including," or "having" various components or steps (interpreted as meaning "including without limitation"), the compounds, compositions, methods, and devices can also "consist essentially of" or "consist of" the various components and steps, and such terminology should be interpreted as defining essentially closed-member groups. This paragraph is not meant in any way to limit the meaning of "comprising," "having," or "including" (and other verb forms thereof) which are to be interpreted as open-ended phrases meaning "including without limitation" consistent with patent law and custom. The intent of this paragraph is merely to indicate that the closed-member groups defined by the "consisting of" or "consisting essentially of" language are lesser included groups within the open-ended descriptions and to provide support for claims employing the "consisting of" or "consisting essentially of" language.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" can refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are co-administered in combination with at least one additional bioactive agent, especially including an anticancer agent. In particularly preferred aspects, the co-administration of compounds results in synergistic activity and/or therapy, including anticancer activity.

The term "effective" can mean, but is in no way limited to, that amount/dose of the active pharmaceutical ingredient, which, when used in the context of its intended use, effectuates or is sufficient to prevent, inhibit the occurrence, ameliorate, delay or treat (alleviate a symptom to some extent, preferably all) the symptoms of a condition, disorder or disease state in a subject in need of such treatment or receiving such treatment. The term effective subsumes all other effective amount or effective concentration terms, e.g., "effective amount/dose," "pharmaceutically effective amount/dose" or "therapeutically effective amount/dose," which are otherwise described or used in the present application.

The effective amount depends on the type and severity of disease, the composition used, the route of administration, the type of mammal being treated, the physical characteristics of the specific mammal under consideration, concurrent medication, and other factors which those skilled in the medical arts will recognize. The exact amount can be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington, *The Science and Practice of Pharmacy*, 20th Edition, 2003, Gennaro, Ed., Lippincott, Williams & Wilkins).

The term "pharmacological composition," "therapeutic composition," "therapeutic formulation" or "pharmaceutically acceptable formulation" can mean, but is in no way limited to, a composition or formulation that allows for the effective distribution of an agent provided by the present disclosure, which is in a form suitable for administration to the physical location most suitable for their desired activity, e.g., systemic administration.

The term "pharmaceutically acceptable" can mean, but is in no way limited to, entities and compositions that do not produce an adverse, allergic or other untoward reaction when administered to a patient or subject.

The term "pharmaceutically acceptable carrier" can mean, but is in no way limited to, any and all solvents, dispersion media, coatings, antibacterial and antifungal agents, isotonic and absorption delaying agents, and the like, compatible with pharmaceutical administration to a patient or subject. Suitable carriers are described in the most recent edition of Remington's *Pharmaceutical Sciences*, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" refers to a route of administration that is, e.g., enteral or parenteral, and results in the systemic distribution of an agent leading to systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect. Administration routes which lead to systemic absorption include, without limitations: intravenous, subcutaneous, intraperitoneal, inhalation, oral, intrapulmonary and intramuscular.

The rate of entry of a drug into the circulation has been shown to be a function of molecular weight or size. The use of a liposome or other drug carrier comprising the compounds of the instant disclosure can potentially localize the drug, for example, in certain tissue types, such as the tissues of the reticular endothelial system (RES). A liposome formulation which can facilitate the association of drug with the surface of cells, such as, lymphocytes and macrophages is also useful.

The terms "patient" and "subject" are used throughout the specification to describe a cell, tissue, or animal, preferably a mammal, e.g., a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "compound," as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. The term also refers to any specific chemical compound in which one or more atoms have been replaced with one or more different isotopes of the same element. It is noted that in describing the present compounds, numerous substituents and variables associated with same, among others, are described.

It is understood by those of ordinary skill that molecules which are described herein are stable compounds as generally described hereunder. When the bond is shown, both a double bond and single bond are represented or understood within the context of the compound shown and well-known rules for valence interactions.

As used herein, "derivatives" can mean compositions formed from the native compounds either directly, by modification, or by partial substitution. As used herein, "analogs" can mean compositions that have a structure similar to, but not identical to, the native compound.

The term "ubiquitin ligase" refers to a family of proteins that facilitate the transfer of ubiquitin to a specific substrate protein, targeting the substrate protein for degradation. For example, cereblon is an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase may be involved in polyubiquitination such that a second ubiquitin may be attached to the first; a third may be attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins may not be targeted to the proteasome for degradation, but may instead be altered in their cellular location or function, for example, via binding other proteins that have domains capable of binding ubiquitin. Further, different lysines on ubiquitin can be targeted by an E3 to make chains. The most common lysine is Lys48 on the ubiquitin chain. This is the lysine used to make polyubiquitin, which is recognized by the proteasome.

As used herein, the terms "halo" or "halogen" means fluoro (F), chloro (Cl), bromo (Br) or iodo (I).

As used herein, the term "hydrocarbyl" means a compound which contains carbon and hydrogen and which may be fully saturated, partially unsaturated or aromatic and includes aryl groups, alkyl groups, alkenyl groups and alkynyl groups.

As used herein, the term "alkyl" means within its context a linear, branch-chained, or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylmethyl, cyclopentylethyl, cyclohexylmethyl, cyclohexylethyl and cyclohexyl, among others.

As used herein, the term "alkenyl" refers to linear, branch-chained, or cyclic $C_2$-$C_{10}$ (preferably $C_2$-$C_6$) hydrocarbon radicals containing at least one C=C bond.

As used herein, the term "Alkynyl" refers to linear, branch-chained, or cyclic $C_2$-$C_{10}$ (preferably $C_2$-$C_6$) hydrocarbon radicals containing at least one C≡C bond.

As used herein, the term "alkylene" refers to a —$(CH_2)_n$— group (wherein n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), more preferably a methyl group, but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, (3-alanine, arginine, asparagine, aspartic acid, cysteine, cystine, glutamic acid, glutamine, glycine, phenylalanine, histidine, isoleucine, lysine, leucine, methionine, praline, serine, threonine, valine, tryptophan, or tyrosine.

As used herein, a range of carbon atoms which includes $C_0$ means that carbon is absent and is replaced with H (or deuterium). Thus, a range of carbon atoms which is $C_0$-$C_6$ includes carbons atoms of 1, 2, 3, 4, 5 and 6 and for $C_0$, H (or deuterium)stands in place of carbon.

As used herein, the term "unsubstituted" means substituted only with hydrogen atoms.

As used herein, the term "substituted" or "optionally substituted" means independently (i.e., where more than a single substitution occurs, each substituent is independent of another substituent) one or more substituents (independently up to five substituents, preferably up to three substituents, often 1 or 2 substituents on a moiety in a compound according to the present invention, and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted N($C_0$-$C_6$ alkyl)C(O)(O$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present invention may include, for example $SiR_1R_2R_3$ groups wherein each of $R_1$ and $R_2$ is as otherwise described herein, and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted —$(CH_2)_m$— or, alternatively, an optionally substituted —$(OCH_2)_m$—, —$(OCH_2CH_2)_m$— or —$(CH_2CH_2O)_m$— group, which may be substituted with any one or more of the above described substituents. Alkylene groups —$(CH_2)_m$— or —$(CH_2)_n$— groups or other chains such as ethylene glycol chains, as identified above, may be substituted anywhere on the chain. Preferred substituents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sidechain of an amino acid as otherwise described herein and optionally substituted amide (preferably carboxamide substituted as described above) or urethane groups (often with one or two $C_0$-$C_6$ alkyl substituents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present invention, a moiety in a molecule may be optionally substituted with up to five substituents, preferably up to three substituents. Most often, in the present invention moieties which are substituted are substituted with one or two substituents.

As used herein, the term "substituted" (each substituent being independent of any other substituent) also means within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene —$NR_1R_2$, a mono- or di-$C_1$-$C_6$ alkyl substituted amines which may be optionally substituted with one or two hydroxyl groups). Each of these groups contains unless otherwise indicated, within context, between 1 and 6 carbon atoms. In certain embodiments, preferred substituents will include, for example, NH, NHC(O), O, =O, $(CH_2)_m$ (here, m and n are in context, 1, 2, 3, 4, 5 or 6), S, S(O), $SO_2$ or NHC(O)NH, $(CH_2)_n$OH, $(CH2)_n$SH, $(CH2)_n$COOH, $C_1$-$C_6$ alkyl, $(CH_2)_n$O($C_1$-$C_6$ alkyl), $(CH_2)_n$C(O)($C_1$-$C_6$ alkyl), $(CH_2)_n$OC(O)($C_1$-$C_6$ alkyl), $(CH_2)_n$C(O)O($C_1$-$C_6$ alkyl), $(CH_2)_n$NHC(O)$R_1$, $(CH_2)_n$C(O)$NR_1R_2$, $(OCH_2)_n$OH, $(CH_2O)_n$COOH, $C_1$-$C_6$ alkyl, $(OCH_2)_n$O($C_1$-$C_6$ alkyl), $(CH_2O)_n$C(O)($C_1$-$C_6$ alkyl), $(OCH_2)_n$NHC(O)$R_1$, $(CH_2O)_n$C(O)$NR_1R_2$, $S(O)_2R_s$, $S(O)R_s$ ($R_s$ is $C_1$-$C_6$ alkyl or a $(CH_2)_m NR_1R_2$ group), $NO_2$, CN, or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine).

The term "substituted" also means, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group OC(O)$NR_1R_2$ group wherein $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

As used herein, the terms "aryl" and "aromatic," in context, refer to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present invention at any available stable position on the ring(s) or as otherwise indicated in the chemical structure presented. Other examples of aryl groups, in context, may include heterocyclic aromatic ring systems "heteroaryl" groups having one or more nitrogen, oxygen, or sulfur atoms in the ring (monocyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroiso-quinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur containing aromatic heterocycles such as thiophene and benzothiophene; oxygen containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadiazole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

As used herein, the term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: $(CH_2)_nOH$, $(CH_2)_nO(C_1-C_6)$alkyl, $(CH_2)_nO(CH_2)_n(C_1-C_6)$alkyl, $(CH_2)_nC(O)(C_0-C_6)$ alkyl, $(CH_2)_nC(O)O(C_0-C_6)$ alkyl, $(CH_2)_nOC(O)(C_0-C_6)$ alkyl, amine, mono- or di-$(C_1-C_6$ alkyl) amine wherein the alkyl group on the amine is optionally substituted with 1 or 2 hydroxyl groups or up to three halo (preferably F, Cl) groups, OH, COOH, $C_1-C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a ARB group, including a E3LB group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methyl substituted isoxazole, an optionally substituted oxazole including a methyl substituted oxazole, an optionally substituted thiazole including a methyl substituted thiazole, an optionally substituted isothiazole including a methyl substituted isothiazole, an optionally substituted pyrrole including a methyl substituted pyrrole, an optionally substituted imidazole including a methyl imidazole, an optionally substituted benzimidazole or methoxybenzyl-imidazole, an optionally substituted oximidazole or methyloximidazole, an optionally substituted diazole group, including a methyldiazole group, an optionally substituted triazole group, including a methyl substituted triazole group, an optionally substituted pyridine group, including a halo (preferably, F) or methyl substituted pyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

As used herein, the term "carboxyl" denotes the group C(O)OR, wherein R is hydrogen, alkyl, substituted alkyl, aryl, substituted aryl, heteroaryl or substituted heteroaryl, whereas these generic substituents have meanings which are identical with definitions of the corresponding groups defined herein.

As used herein, the terms "heteroaryl" and "hetaryl" include, without limitation, an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally sub-stituted imidazole, an optionally substituted isoxazole, an optionally substituted oxazole (preferably methyl substituted), an optionally substituted diazole, an optionally sub-stituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted $(CH_2)_mOC_1-C_6$ alkyl group or an optionally substituted $(CH_2)_mC(O)OC_1-C_6$ alkyl group), an optionally substituted pyridine (2-, 3-, or 4-pyridine) or a group according to the chemical structure:

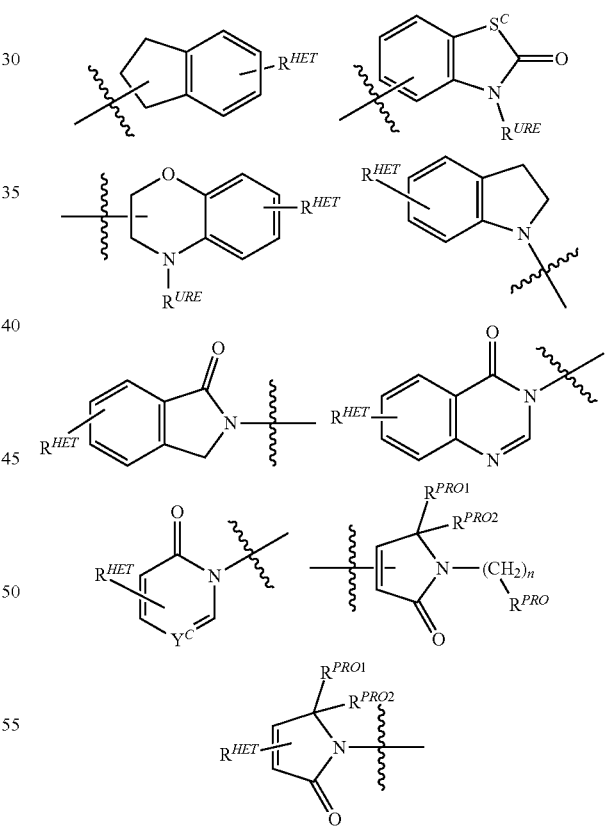

wherein $S^C$ is $CHR^{SS}$, $NR^{URE}$, or O;

$R^{HET}$ is H, CN, $NO_2$, halo (preferably Cl or F), optionally substituted $C_1-C_6$ alkyl (preferably substi-tuted with one or two hydroxyl groups or up to three halo groups (e.g. $CF_3$), optionally substituted $O(C_1-C_6$ alkyl) (preferably substituted with one or two hydroxyl groups or up to three halo groups) or an optionally substituted acetylenic group

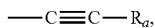

wherein $R_a$ is H or a $C_1$-$C_6$ alkyl group (preferably $C_1$-$C_3$ alkyl).

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted phenyl group, an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, wherein $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$, wherein $R_a$ is H or a $C_1$-$C_6$ alkyl group (preferably $C_1$-$C_3$ alkyl).

$R^{PRO}$ is H, optionally substituted $C_0$-$C_6$ alkyl or an optionally substituted aryl, heteroaryl or heterocyclic group selected from the group consisting of oxazole, isoxazole, thiazole, isothiazole, imidazole, diazole, oximidazole, pyrrole, pyrrolidine, furan, dihydrofuran, tetrahydrofuran, thiene, dihydrothiene, tetrahydrothiene, pyridine, piperidine, piperazine, morpholine, quinoline (each preferably substituted with a $C_0$-$C_3$ alkyl group, preferably methyl or a halo group preferably F or Cl), benzofuran, indole, indolizine, azaindolizine:

$R^{PRO1}$ and $R^{PRO2}$ are each independently H, an optionally substituted $C_0$-$C_3$ alkyl group or together form a keto group and each n is independently 0, 1, 2, 3, 4, 5 or 6 or an optionally substituted heterocycle, preferably tetrahydrofuran, tetrahydrothiene, piperidine, piperazine or morpholine (each of which groups when substituted are preferably substituted with a methyl or halo).

As used herein, the terms "arylkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

As used herein, the term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

As used herein, the terms "heterocycle" and "heterocyclic" refer to a cyclic group which contains at least one heteroatom, i.e., O, N or S, and may be aromatic (heteroaryl) or non-aromatic. Thus, the heteroaryl moieties are subsumed under the definition of heterocycle, depending on the context of its use. Exemplary heterocyclics include: azetidinyl, benzimidazolyl 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, and thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —$SO_2$-alkyl, —$SO_2$-substituted alkyl, —$SO_2$-aryl, oxo (=O), and —$SO_2$-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

As used herein, the term "cycloalkyl" includes, without limitation, univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like.

As used herein, the term "substituted cycloalkyl" includes, without limitation, a monocyclic or polycyclic alkyl group being substituted by one or more substituents, for example, amino, halogen, alkyl, substituted alkyl, carbyloxy, carbylmercapto, aryl, nitro, mercapto, or sulfa, whereas these generic substituent groups have meanings which are identical with definitions of the corresponding groups as defined herein.

As used herein, the term "heterocycloalkyl" refers to a monocyclic or polycyclic alkyl group in which at least one ring carbon atom of its cyclic structure being replaced with a heteroatom selected from the group consisting of N, O, S, or P.

As used herein, the term "substituted heterocycloalkyl" refers to a monocyclic or polycyclic alkyl group in which at least one ring carbon atom of its cyclic structure being replaced with a heteroatom selected from the group consisting of N, O, S, or P, and the group contains one or more substituents selected from the group consisting of halogen, alkyl, substituted alkyl, carbyloxy, carbylmercapto, aryl, nitro, mercapto, or sulfa, whereas these generic substituent group have meanings which are identical with definitions of the corresponding groups as defined herein.

What is claimed is:
1. A compound having a chemical structure:

ARB-Link-E3LB wherein ARB is an AR binding moiety that does not bind to a ligand binding domain, E3LB is an E3 ligase binding moiety, and Link is a linker coupling the AR binding moiety to the E3 ligase binding moiety; and
wherein the E3LB moiety is a structure selected from the group consisting of:

E3LB-a
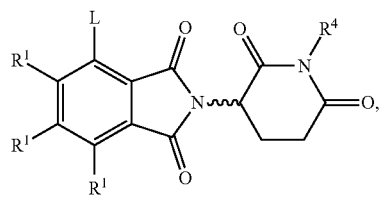

E3LB-b
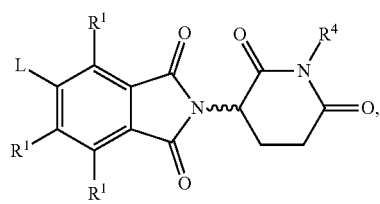

E3Lb-c
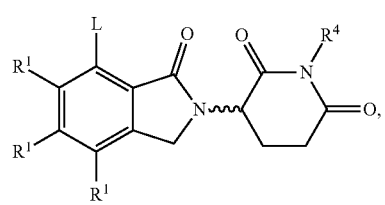

E3LB-d
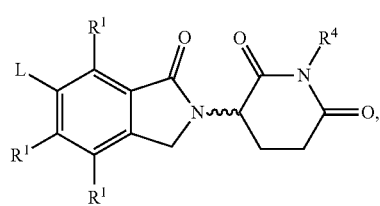

wherein "⁓" in the above structures, represents a bond that may be stereospecific ((R) or (S)), or non-stereospecific;

$R^1$ is each independently selected from H, OH, $CONH_2$, $CONR^2R^3$, $SONH_2$, $SONR^2R^3$, $SO_2NH_2$, $SO_2NR^2R^3$, $NHCOC_{1-3}$ alkyl, $NR^2COC_{1-3}$ alkyl, $NR^2SO_2C_{1-3}$ alkyl, $NR^2SOC_{1-3}$ alkyl, CN, C≡CH, NH, $NR^2R^3$, $OCH_3$, $OC_{1-3}$ alkyl, $CHF_2$, $CH_2F$, $CF_3$, halo, and $C_{1-6}$ alkyl wherein said alkyl is linear or branched and is optionally substituted by 1 or more halo or $C_{1-6}$ alkoxyl or, if applicable, taken together with an R on an adjacent bonded atom, together with the atoms they are attached to, form a 3-6 membered ring alicyclic, aryl, or heteroaryl system containing 0-2 heteroatoms;

$R^2$ and $R^3$ are independently H, halo, $C_{1-6}$ alkyl wherein said alkyl is optionally substituted by 1 or more F, or taken together with the atom they are attached to, form a 3-8 membered ring system containing 0-2 heteroatoms;

$R^4$ is selected from the group consisting of H, alkyl wherein said alkyl is linear or branched and is optionally substituted by 1 or more $R^5$, OH, $R^5OCOOR^6$, $R^5OCONR^5R^7$, $CH_2$-heterocyclyl optionally substituted with $R^5$, or benzyl optionally substituted with $R^5$;

$R^5$ and $R^7$ are each independently a bond, H, alkyl, cycloalkyl, aryl, hetaryl heterocyclyl, or —C(=O)$R^6$, each of which is optionally substituted;

$R^6$ is selected from $CONR^5R^7$, $OR^5$, $NR^5R^7$, $SR^5$, $SO_2R^5$, $SO_2NR^5R^7$, $CR^5R^7$, $CR^5NR^5R^7$, aryl, hetaryl, alkyl wherein said alkyl is linear or branched and is optionally substituted, cycloalkyl, heterocyclyl, $P(O)(OR^5)R^7$, $P(O)R^5R^7$, $OP(O)(OR^5)R^7$, $OP(O)R^5R^7$, Cl, F, Br, I, $CF_3$, $CHF_2$, $CH_2F$, CN, $NR^5SO_2NR^5R^7$, $NR^5CONR^5R^7$, $CONR^5COR^7$, $NR^5C(=N-CN)NR^5R^7$, $C(=N-CN)NR^5R^7$, $NR^5C(=N=CN)R^7$, $NR^5C(=C-NO_2)NR^5R^7$, $SO_2NR^5COR^7$, $NO_2$, $CO_2R^5$, $C(C=N-OR^5)R^7$, $CR^5$, $CR^5R^7$, $CCR^5$, $S(C=O)(C=N-R^5)R^7$, $SF_5$, $R^5NR^5R^7$, $(R^5O)_nR^7$, or $OCF_3$, where n is an integer from 1 to 10;

and wherein, the AR binding moiety is a structure selected from the group consisting of:

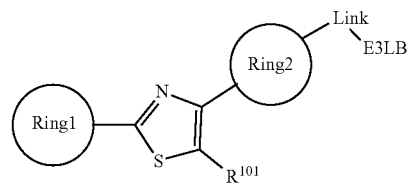 and

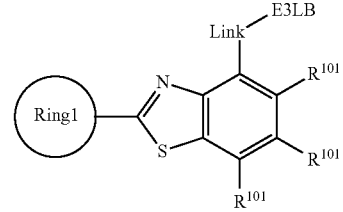

wherein:
Ring1 is 3-7 membered alicyclic with 0-4 heteroatoms and substituted by 1 or more halo, CN, C≡CH, $C_{1-6}$ alkyl wherein said alkyl is linear or branched and is optionally substituted by 1 or more $C_{1-6}$ alkoxy, $C_{1-6}$ alkoxy wherein said alkoxy is linear or branched and is optionally substituted by 1 or more halo, $C_{2-6}$ alkenyl, or $C_{2-6}$ alkynyl, bridged or spiro, bicyclic rings with 0-4 heteroatoms and substituted by 1 or more halo, CN, C≡CH, $C_{1-6}$ alkyl wherein said alkyl is linear or branched and is optionally substituted by 1 or more halo or $C_{1-6}$ alkoxy, $C_{1-6}$ alkoxy wherein said alkoxy is linear or branched and is optionally substituted by 1 or more halo, $C_{2-6}$ alkenyl, $C_{2-6}$ alkynyl, or

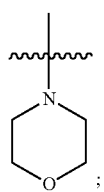 [SMILES: *N1CCOCC1]

Ring2 is aryl, 2-benzyloxy-3,4-difluoro, heteroaryl independently substituted by 1 or more halo, hydroxyl, CN, C≡CH, $NR^{102}R^{103}$, $OCH_3$, $OC_{1-3}$ alkyl wherein said alkyl is optionally substituted by 1 or more halo, $C_{1-6}$ alkyl wherein said alkyl is linear or branched and is optionally substituted by 1 or more halo or $C_{1-6}$ alkoxy, $C_{1-6}$ alkoxy wherein said alkoxy is linear or branched and is optionally substituted by 1 or more halo, $C_{2-6}$ alkenyl, $C_{2-6}$ alkynyl, 3-6 membered alicyclic with 0-4 heteroatoms and substituted with 1 or more halo, hydroxyl, CN, C≡CH, $C_{1-6}$ alkyl wherein said alkyl is linear or branched and is optionally substituted by 1 or more halo or $C_{1-6}$ alkoxy, $C_{1-6}$ alkoxy wherein said alkoxy is linear or branched and is optionally substituted by 1 or more halo or $C_{1-6}$ alkoxy $C_{2-6}$ alkenyl, or $C_{2-6}$ alkynyl, wherein $R^{102}$ and $R^{103}$ are independently H, halo, $C_{1-6}$ alkyl wherein said alkyl is optionally substituted by 1 or more F or, taken together with the atom they are attached to, form a 3-8 membered ring system containing 0-2 heteroatoms,

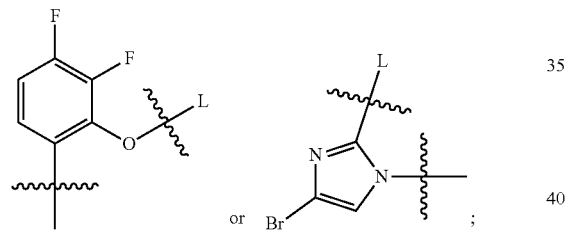

and $R^{101}$ is independently H, OH, $CONH_2$, $CONR^{102}R^{103}$, $SONH_2$, $SONR^{102}R^{103}$, $SO_2NH_2$, $SO_2NR^{102}R^{103}$, $NHCOC_{1-3}$ alkyl wherein said alkyl is optionally substituted by 1 or more halo, $NR^{102}COC_{1-3}$ alkyl wherein said alkyl is optionally substituted by 1 or more halo, $NR^{102}SO_2C_{1-3}$ alkyl wherein said alkyl is optionally substituted by 1 or more halo, $NR^{102}SO_2C_{1-3}$ alkyl wherein said alkyl is optionally substituted by 1 or more halo, CN, C≡CH, $NH_2$, $NR^{102}R^{103}$, $OCH_3$, $OC_{1-3}$ alkyl wherein said alkyl is optionally substituted by 1 or more halo, $CHF_2$, $CH_2F$, $CF_3$, halo, $C_{1-6}$ alkyl wherein said alkyl is linear or branched and is optionally substituted by 1 or more halo or $C_{1-6}$ alkoxy or, taken together with an $R^{101}$ on an adjacent bonded atom, together with the atoms they are attached to, form a 3-6 membered ring alicyclic, aryl, or heteroaryl system containing 0-2 heteroatoms, wherein $R^{102}$ and $R^{103}$ are independently H, halo, $C_{1-6}$ alkyl wherein said alkyl is optionally substituted by 1 or more F or, taken together with the atom they are attached to, form a 3-8 membered ring system containing 0-2 heteroatoms.

2. The compound of claim 1, wherein the AR binding moiety is a structure:

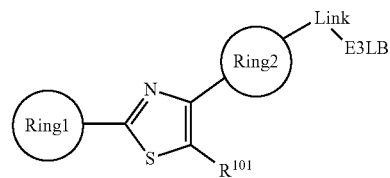

wherein:

Ring1 is 3-7 membered alicyclic with 0-4 heteroatoms and substituted by 1 or more halo, CN, C≡CH, $C_{1-6}$ alkyl wherein said alkyl is linear or branched and is optionally substituted by 1 or more $C_{1-6}$ alkoxy, $C_{1-6}$ alkoxy wherein said alkoxy is linear or branched and is optionally substituted by 1 or more halo, $C_{2-6}$ alkenyl, or $C_{2-6}$ alkynyl, bridged or spiro, bicyclic rings with 0-4 heteroatoms and substituted by 1 or more halo, CN, C≡CH, $C_{1-6}$ alkyl wherein said alkyl is linear or branched and is optionally substituted by 1 or more halo or $C_{1-6}$ alkoxy, $C_{1-6}$ alkoxy wherein said alkoxy is linear or branched and is optionally substituted by 1 or more halo, $C_{2-6}$ alkenyl, $C_{2-6}$ alkynyl, or

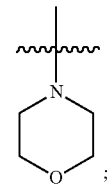 [SMILES: *N1CCOCC1]

Ring2 is aryl, 2-benzyloxy-3,4-difluoro, heteroaryl independently substituted by 1 or more halo, hydroxyl, CN, C≡CH, $NR^{102}R^{103}$, $OCH_3$, $OC_{1-3}$ alkyl wherein said alkyl is optionally substituted by 1 or more halo, $C_{1-6}$ alkyl wherein said alkyl is linear or branched and is optionally substituted by 1 or more halo or $C_{1-6}$ alkoxy, $C_{1-6}$ alkoxy wherein said alkoxy is linear or branched and is optionally substituted by 1 or more halo, $C_{2-6}$ alkynyl, 3-6 membered alicyclic with 0-4 heteroatoms and substituted with 1 or more halo, hydroxyl, CN, C≡CH, $C_{1-6}$ alkyl wherein said alkyl is linear or branched and is optionally substituted by 1 or more halo or $C_{1-6}$ alkoxy, $C_{1-6}$ alkoxy wherein said alkoxy is linear or branched and is optionally substituted by 1 or more halo or $C_{1-6}$ alkoxy, $C_{2-6}$ alkenyl, or $C_{2-6}$ alkynyl, wherein $R^{102}$ and $R^{103}$ are independently H, halo, $C_{1-6}$ alkyl wherein said alkyl is 1 optionally substituted by 1 or more F or, taken together with the atom they are attached to, form a 3-8 membered ring system containing 0-2 heteroatoms,

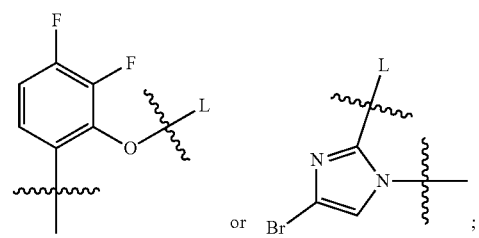

and

R$^{101}$ is independently H, OH, CONH$_2$, CONR$^{102}$R$^{103}$, SONH$_2$, SONR$^{102}$R$^{103}$, SO$_2$NH$_2$, SO$_2$NR$^{102}$R$^{103}$, NHCOC$_{1-3}$ alkyl wherein said alkyl is optionally substituted by 1 or more halo, NR$^{102}$COC$_{1-3}$ alkyl wherein said alkyl is optionally substituted by 1 or more halo, NR$^{102}$SO$_2$C$_{1-3}$ alkyl wherein said alkyl is optionally substituted by 1 or more halo, NR$^{102}$SO$_2$C$_{1-3}$ alkyl wherein said alkyl is optionally substituted by 1 or more halo, CN, C≡CH, NH$_2$, NR$^{102}$R$^{103}$, OCH$_3$, OC$_{1-3}$ alkyl wherein said alkyl is optionally substituted by 1 or more halo, CHF$_2$, CH$_2$F, CF$_3$, halo, C$_{1-6}$ alkyl wherein said alkyl is linear or branched and is optionally substituted by 1 or more halo or C$_{1-6}$ alkoxy or, taken together with an R$^{101}$ on an adjacent bonded atom, together with the atoms they are attached to, form a 3-6 membered ring alicyclic, aryl, or heteroaryl system containing 0-2 heteroatoms, wherein R$^{102}$ and R$^{103}$ are independently H, halo, C$_{1-6}$ alkyl wherein said alkyl is optionally substituted by 1 or more F or, taken together with the atom they are attached to, form a 3-8 membered ring system containing 0-2 heteroatoms.

3. The compound of claim 1, wherein the linker comprises a chemical structure represented by -A$_q$-, in which q is an integer greater than 1, and A is independently selected from the group consisting of a bond, CR$^{L1}$R$^{L2}$, O, S, SO, SO$_2$, NR$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, SiR$^{L1}$R$^{L2}$, P(O)R$^{L1}$, P(O)OR$^{L1}$, NR$^{L3}$C(=NCN)NR$^{L4}$, NR$^{L3}$C(=NCN), NR$^{L3}$C(=CNO$_2$)NR$^{L4}$, C$_{3-11}$ cycloalkyl wherein said cycloalkyl is optionally substituted with 0-6 R$^{L1}$ and/or R$^{L2}$ groups, and heteroaryl wherein said heteroaryl is optionally substituted with 0-6 R$^{L1}$ and/or R$^{L2}$ groups, wherein R$^{L1}$, R$^{L2}$, R$^{L3}$, R$^{L4}$ and R$^{L5}$ are each independently selected from the group consisting of H, halo, C$_{1-8}$ alkyl, OC$_{1-8}$ alkyl, SC$_{1-8}$ alkyl, NHC$_{1-8}$ alkyl, N(C$_{1-8}$ alkyl)$_2$, C$_{3-11}$ cycloalkyl, aryl, heteroaryl, C$_{3-11}$ heterocyclyl, OC$_{1-8}$ cycloalkyl, SC$_{1-8}$ cycloalkyl, NHC$_{1-8}$ cycloalkyl, N(C$_{1-8}$cycloalkyl)$_2$, N(C$_{1-8}$ cycloalkyl)(C$_{1-8}$ alkyl), OH, NH$_2$, SH, SO$_2$C$_{1-8}$ alkyl, P(O)(OC$_{1-8}$ alkyl)(C$_{1-8}$ alkyl), P(O)(OC$_{1-8}$ alkyl)$_2$, CC—C$_{1-8}$ alkyl, CCH, CH=CH(C$_{1-8}$ alkyl), C(C$_{1-8}$ alkyl)=CH(C$_{1-8}$ alkyl), C(C$_{1-8}$ alkyl)=C(C$_{1-8}$ alkyl)$_2$, Si(OH)$_3$, SiC(i-s alkyl)$_3$, Si(OH)(C$_{1-8}$ alkyl)$_2$, COC$_{1-8}$ alkyl, CO$_2$H, CN, CF$_3$, CHF$_2$, CH$_2$F, NO$_2$, SF$_5$, SO$_2$NHC$_{1-8}$ alkyl, SO$_2$NHC$_{1-8}$ alkyl, SO$_2$N(C$_{1-8}$ alkyl)$_2$, SONHC$_{1-8}$ alkyl, SON(C$_{1-8}$ alkyl)$_2$, CONHC$_{1-8}$ alkyl, CON(C$_{1-8}$ alkyl)$_2$, N(C$_{1-8}$ alkyl)CONH(C$_{1-8}$ alkyl), N(C$_{1-8}$ alkyl)CON(C$_{1-8}$ alkyl)$_2$, NHCONH(C$_{1-8}$ alkyl), NHCON(C$_{1-8}$ alkyl)$_2$, NHCONH$_2$, N(C$_{1-8}$ alkyl)SO$_2$NH(C$_{1-8}$ alkyl), N(C$_{1-8}$ alkyl)SO$_2$N(C$_{1-8}$ alkyl)$_2$, NHSO$_2$NH(C$_{1-8}$ alkyl), NHSO$_2$N(C$_{1-8}$ alkyl)$_2$ and NHSO$_2$NH$_2$, and wherein R$^{L1}$ and R$^{L2}$ each, independently may be linked to another A group to form a cycloalkyl and or heterocyclyl moiety that can be further substituted with 0-4 R$^{L5}$ groups.

4. The compound of claim 1, wherein the linker comprises a structure selected from the group consisting of:

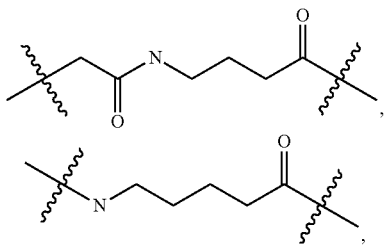

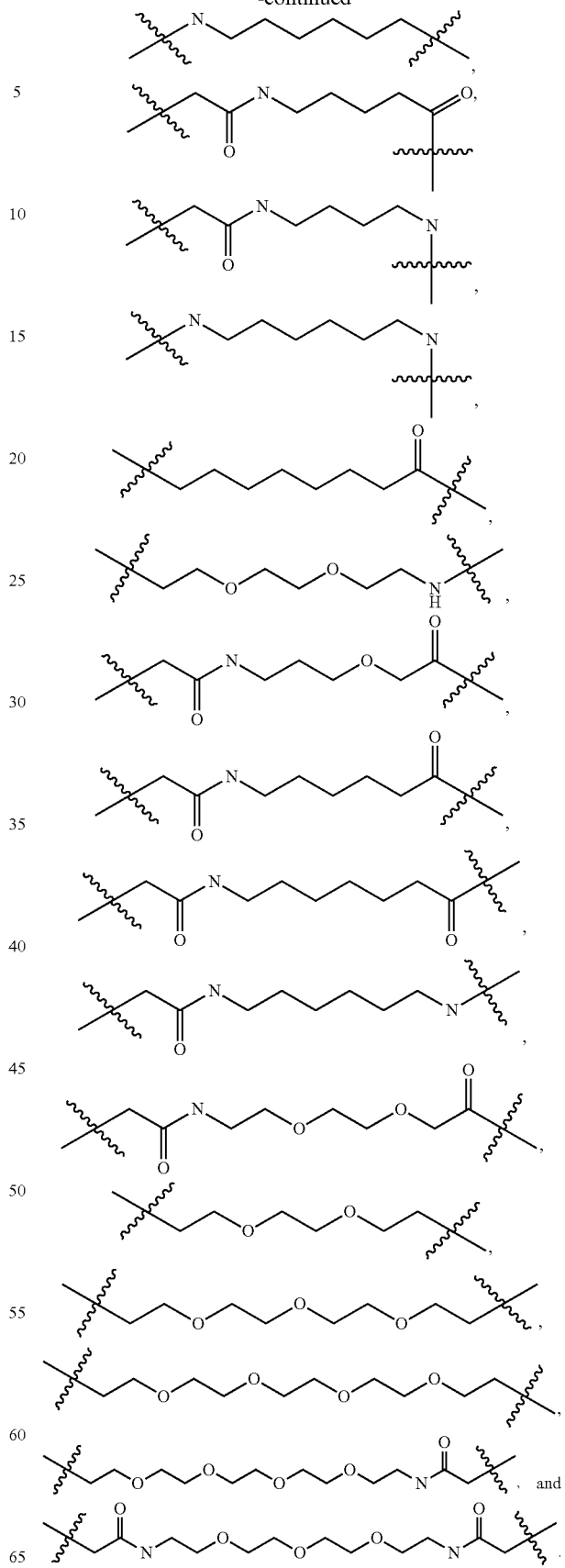

5. The compound according to claim 1, wherein the compound is selected from the group consisting of:
- 2-(2,3-difluoro-6-(2-morpholinothiazol-4-yl)phenoxy)-N-(6-((2-(2,6-dioxopiperidin-3-yl)-1,3-dioxoisoindolin-4-yl)amino)hexyl)acetamide,
- 2-(2,3-difluoro-6-(2-morpholinothiazol-4-yl)phenoxy)-N-(8-((2-(2,6-dioxopiperidin-3-yl)-1,3-dioxoisoindolin-4-yl)amino)octyl)acetamide,
- 2-(2,3-difluoro-6-(2-morpholinothiazol-4-yl)phenoxy)-N-(10-((2-(2,6-dioxopiperidin-3-yl)-1,3-dioxoisoindolin-4-yl)amino)decyl)acetamide,
- 2-(2,3-difluoro-6-(2-morpholinothiazol-4-yl)phenoxy)-N-(2-(2-(2-((2-(2,6-dioxopiperidin-3-yl)-1,3-dioxoisoindolin-4-yl)amino)ethoxy)ethoxy)ethyl)acetamide,
- 2-(2,3-difluoro-6-(2-morpholinothiazol-4-yl)phenoxy)-N-(2-(2-(2-(2-((2-(2,6-dioxopiperidin-3-yl)-1,3-dioxoisoindolin-4-yl)amino)ethoxy)ethoxy)ethoxy)ethyl)acetamide,
- 2-(2,3-difluoro-6-(2-morpholinothiazol-4-yl)phenoxy)-N-(14-((2-(2,6-dioxopiperidin-3-yl)-1,3-dioxoisoindolin-4-yl)amino)-3,6,9,12-tetraoxatetradecyl)acetamide,
- 2-(2,3-difluoro-6-(2-morpholinothiazol-4-yl)phenoxy)-N-(6-(2-((2-(2,6-dioxopiperidin-3-yl)-1,3-dioxoisoindolin-4-yl)oxy)acetamido)hexyl)acetamide,
- 2-(2,3-difluoro-6-(2-morpholinothiazol-4-yl)phenoxy)-N-(8-(2-((2-(2,6-dioxopiperidin-3-yl)-1,3-dioxoisoindolin-4-yl)oxy)acetamido)octyl)acetamide,
- 2-(2,3-difluoro-6-(2-morpholinothiazol-4-yl)phenoxy)-N-(10-(2-((2-(2,6-dioxopiperidin-3-yl)-1,3-dioxoisoindolin-4-yl)oxy)acetamido)decyl)acetamide,
- 2-(2,3-difluoro-6-(2-morpholinothiazol-4-yl)phenoxy)-N-(2-(2-(2-(2-((2-(2,6-dioxopiperidin-3-yl)-1,3-dioxoisoindolin-4-yl)oxy)acetamido)ethoxy)ethoxy)ethyl)acetamide,
- 2-(2,3-difluoro-6-(2-morpholinothiazol-4-yl)phenoxy)-N-(1-((2-(2,6-dioxopiperidin-3-yl)-1,3-dioxoisoindolin-4-yl)oxy)-2-oxo-6,9,12-trioxa-3-azatetradecan-14-yl)acetamide,
- 4-((2-(2-(2-(2,3-difluoro-6-(2-morpholinothiazol-4-yl)phenoxy)ethoxy)ethyl)amino)-2-(2,6-dioxopiperidin-3-yl)isoindoline-1,3-dione,
- 4-((2-(2-(2-(2-(2,3-difluoro-6-(2-morpholinothiazol-4-yl)phenoxy)ethoxy)ethoxy)ethoxy)ethyl)amino)-2-(2,6-dioxopiperidin-3-yl)isoindoline-1,3-dione,
- N-(14-(2,3-difluoro-6-(2-morpholinothiazol-4-yl)phenoxy)-3,6,9,12-tetraoxatetradecyl)-2-((2-(2,6-dioxopiperidin-3-yl)-1,3-dioxoisoindolin-4-yl)oxy)acetamide,
- N-(6-((2-(2,6-dioxopiperidin-3-yl)-1,3-dioxoisoindolin-4-yl)amino)hexyl)-1-(2-morpholinothiazol-4-yl)-1H-imidazole-4-carboxamide, and
- 2,5-dibromo-N-(6-((2-(2,6-dioxopiperidin-3-yl)-1,3-dioxoisoindolin-4-yl)amino)hexyl)-1-(2-morpholinothiazol-4-yl)-1H-imidazol-4-yl)-1H-imidazole-4-carboxamide.

6. A pharmaceutical composition, comprising:
an effective amount of the compound of claim 1, and
a pharmaceutically acceptable carrier, additive and/or excipient.

7. The pharmaceutical composition of claim 6, further comprising at least one additional anticancer agent.

8. A method for treating a disease state or condition in a patient wherein dysregulated protein activity is responsible for said disease or condition, said method comprising administering an effective amount of the compound according to claim 1.

9. The compound according to claim 1, wherein the AR binding moiety is the structure:

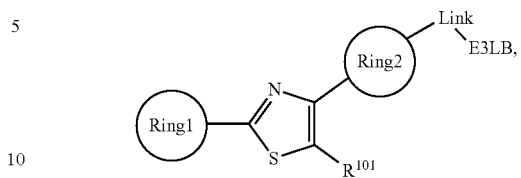

wherein Ring1 is:

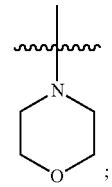 [SMILES: *N1CCOCC1]

Ring2 is:

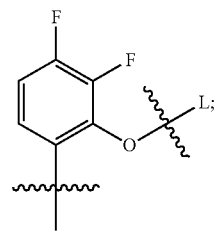

and
$R^{101}$ is H.

10. The compound according to claim 1, wherein the linker comprises a chemical structure represented by $-A_q-$, in which q is an integer greater than 1, and A is independently selected from the group consisting of a bond, $CR^{L1}R^{L2}$, O, $NR^{L3}$, $CONR^{L3}$, and CO, wherein $R^{L1}$, $R^{L2}$, and $R^{L3}$, are each independently selected from the group consisting of H, halo, $C_{1-8}$ alkyl, $OC_{1-8}$ alkyl, $NHC_{1-8}$ alkyl, $N(C_{1-8}$ alkyl$)_2$, $C_{3-11}$ cycloalkyl, $OC_{1-8}$ cycloalkyl, $NHC_{1-8}$ cycloalkyl, $CONHC_{1-8}$ alkyl, $N(C_{1-8}$ alkyl$)CONH(C_{1-8}$ alkyl), and $NHCONH(C_{1-8}$ alkyl).

11. The compound according to claim 10, wherein the linker comprises a chemical structure represented by $-A_q-$, in which q is an integer greater than 1, and A is independently selected from the group consisting of a bond, $CR^{L1}R^{L2}$, O, $NR^{L3}$ and $CONR^{L3}$, wherein $R^{L1}$ and $R^{L2}$, are each independently selected from the group consisting of H and $C_{1-8}$ alkyl, and wherein $R^{L3}$ is H.

12. The compound according to claim 1, wherein the E3LB moiety is a structure selected from E3LB-a, E3LB-b, E3LB-c and E3LB-d, wherein:
wherein " ∼∼∼ " in the above structures, represents a bond that may be stereospecific ((R) or (S)), or non-stereospecific;
$R^1$ is each independently selected from H, OH, CN, $NH_2$, $NR^2R^3$, $OCH_3$, $OC_{1-3}$ alkyl, $CHF_2$, $CH_2F$, $CF_3$, halo, and $C_{1-6}$ alkyl wherein said alkyl is linear or branched and is optionally substituted by 1 or more halo;
$R^2$ and $R^3$ are independently H, halo, $C_{1-6}$ alkyl wherein said alkyl is optionally substituted by 1 or more F, or taken together with the atom they are attached to, form a 3-8 membered ring system containing 0-2 heteroatoms; and $R^4$ is selected from the group consisting of H, and alkyl wherein said alkyl is linear or branched.

13. The compound according to claim 12, wherein
$R^1$ is each independently selected from H, $NH_2$, and halo; and
$R^4$ is H.

14. The compound according to claim 9, wherein the E3LB moiety is a structure selected from E3LB-a, E3LB-b, E3LB-c and E3LB-d, wherein:
wherein "〰" in the above structures, represents a bond that may be stereospecific ((R) or (S)), or non-stereospecific;

$R^1$ is each independently selected from H, OH, CN, $NH_2$, $NR^2R^3$, $OCH_3$, $OC_{1-3}$ alkyl, $CHF_2$, $CH_2F$, $CF_3$, halo, and $C_{1-6}$ alkyl wherein said alkyl is linear or branched and is optionally substituted by 1 or more halo;

$R^2$ and $R^3$ are independently H, halo, $C_{1-6}$ alkyl wherein said alkyl is optionally substituted by 1 or more F, or taken together with the atom they are attached to, form a 3-8 membered ring system containing 0-2 heteroatoms; and $R^4$ is selected from the group consisting of H, and alkyl wherein said alkyl is linear or branched.

15. The compound according to claim 14, wherein the linker comprises a chemical structure represented by -$A_q$-, in which q is an integer greater than 1, and A is independently selected from the group consisting of a bond, $CR^{L1}R^{L2}$, O, $NR^{L3}$, $CONR^{L3}$, and CO, wherein $R^{L1}$, $R^{L2}$, and $R^{L3}$, are each independently selected from the group consisting of H, halo, $C_{1-8}$ alkyl, $OC_{1-8}$ alkyl, $NHC_{1-8}$ alkyl, $N(C_{1-8}$ alkyl$)_2$, $C_{3-11}$ cycloalkyl, $OC_{1-8}$ cycloalkyl, $NHC_{1-8}$ cycloalkyl, $CONHC_{1-8}$ alkyl, $N(C_{1-8}$ alkyl$)CONH(C_{1-8}$ alkyl), and $NHCONH(C_{1-8}$ alkyl).

16. The compound according to claim 15, wherein the linker comprises a chemical structure represented by -$A_q$-, in which q is an integer greater than 1, and A is independently selected from the group consisting of a bond, $CR^{L1}R^{L2}$, O, $NR^{L3}$, and $CONR^{L3}$, wherein $R^{L1}$ and $R^{L2}$, are each independently selected from the group consisting of H and $C_{1-8}$ alkyl, and wherein $R^{L3}$ is H.

17. The compound according to claim 16, wherein
$R^1$ is each independently selected from H, $NH_2$, and halo; and
$R^4$ is H.

18. A pharmaceutical composition, comprising:
an effective amount of the compound of claim 16, and
a pharmaceutically acceptable carrier, additive and/or excipient.

19. A pharmaceutical composition, comprising:
an effective amount of the compound of claim 17, and
a pharmaceutically acceptable carrier, additive and/or excipient.

* * * * *

UNITED STATES PATENT AND TRADEMARK OFFICE
CERTIFICATE OF CORRECTION

PATENT NO. : 11,787,778 B2  
APPLICATION NO. : 17/331940  
DATED : October 17, 2023  
INVENTOR(S) : Jenny Desantis and Roy Joseph Vaz Page 1 of 4

It is certified that error appears in the above-identified patent and that said Letters Patent is hereby corrected as shown below:

In the Specification

Column 8, Lines 30-38, " 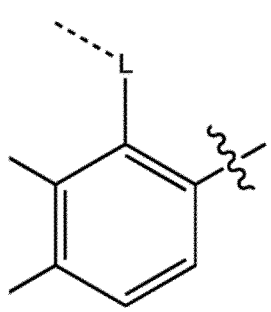 " should be changed to " 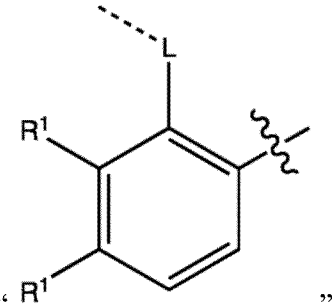 "

Column 9, Lines 2-3, "$NR^{L3}$ $SO_2NR^{L3}$ $SONR^{L3}$ $CONR^{L3}$," should be changed to "$NR^{L3}$, $SO_2NR^{L3}$, $SONR^{L3}$, $CONR^{L3}$,"

Column 9, Lines 17-18, "SiC(i-s alkyl)$_3$," should be changed to "Si($C_{1-8}$ alkyl)$_3$,"

Column 10, Lines 47-60, " 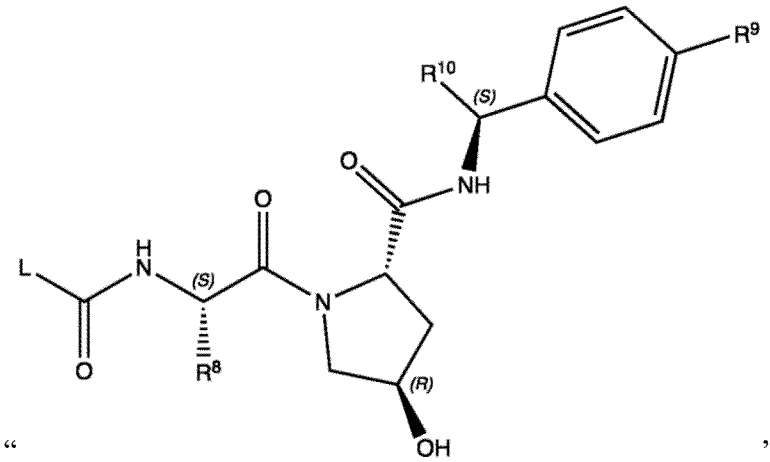 " should be

Signed and Sealed this  
Thirtieth Day of January, 2024

Katherine Kelly Vidal  
*Director of the United States Patent and Trademark Office*

CERTIFICATE OF CORRECTION (continued)
U.S. Pat. No. 11,787,778 B2 changed to " 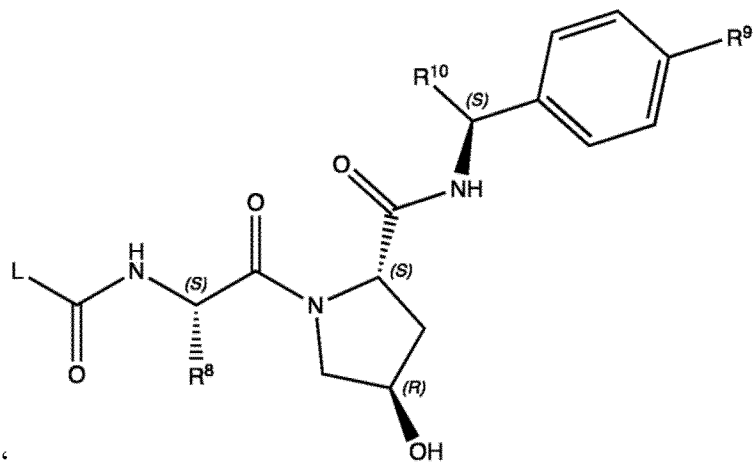 "

Column 13, Line 41-42, "(R) wherein $R^{22}$" should be changed to "wherein $R^{22}$"

Column 21-22, Example 20 the structure

" 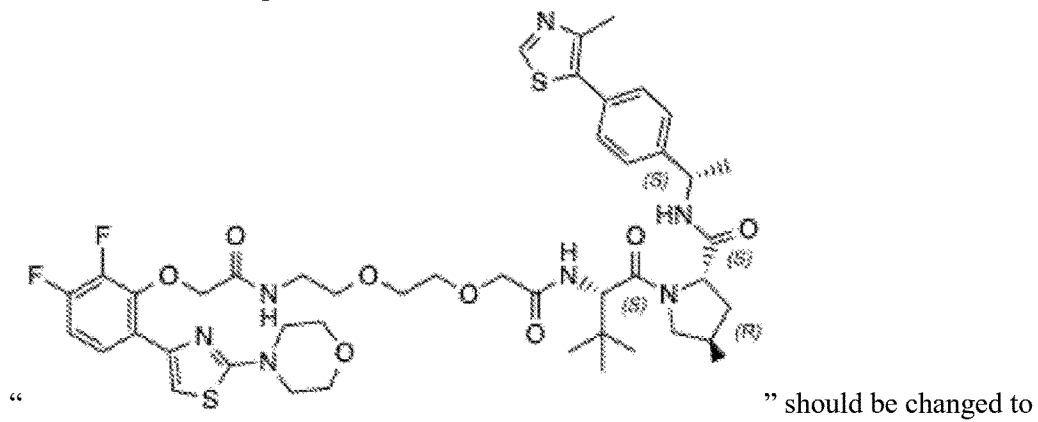 " should be changed to

" 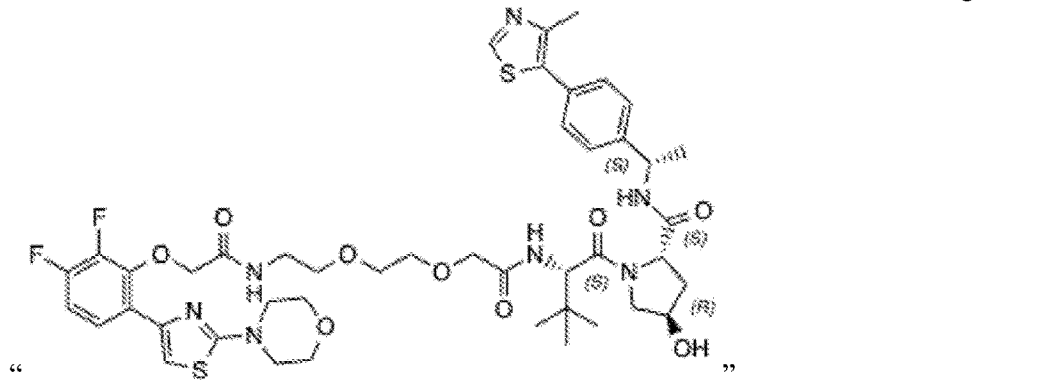 "

Column 23-24, Example 22 the structure " 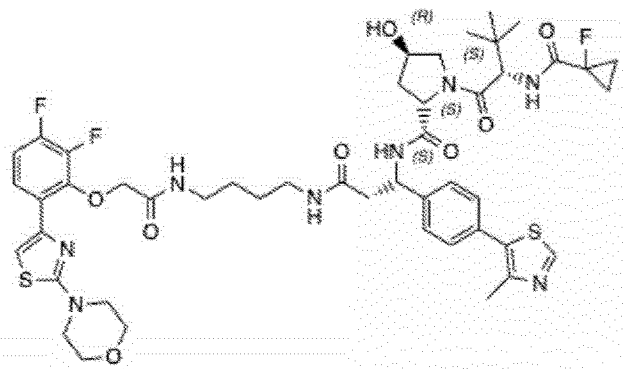 "
should be changed to " 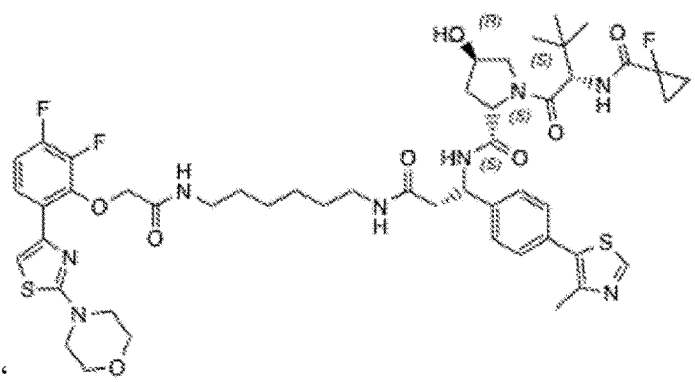 "
Column 27-28, Example 30 the structure
" 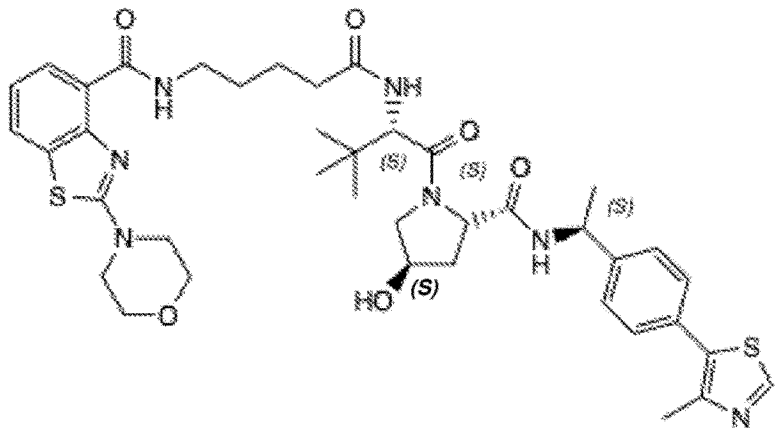 " should be changed to "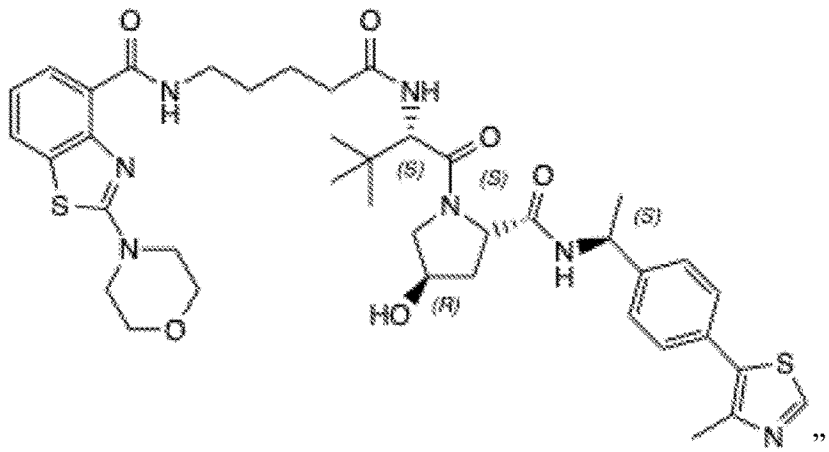"

Column 41, Line 25, "(5 m)" should be changed to "(5 μm)"

Column 42, Line 22, "(5 m)" should be changed to "(5 μm)"

Column 42, Line 58, "IRMS" should be changed to "HRMS"

Column 56, Line 31, "(5 m)" should be changed to "(5 μm)"

Column 89, Line 34, "IRMS" should be changed to "HRMS"

Column 103, Line 37-38, "10 pM" should be changed to "10 μM"

Column 103, Line 40, "30 pg" should be changed to "30 μg"

In the Claims

Claim 1, Column 115, Line 63, "NH" should be changed to "NH$_2$"

Claim 1, Column 115, Line 67, "an R on" should be changed to "an R$^1$ on"

Claim 1, Column 117, Line 52, "NR$^{102}$SO$_2$C$_{1-3}$ alkyl" should be changed to "NR$^{102}$SOC$_{1-3}$ alkyl"

Claim 2, Column 118, Line 43, "halo, C$_{2-6}$ alkynyl," should be changed to "halo, C$_{2-6}$ alkenyl, C$_{2-6}$ alkynyl,"

Claim 2, Column 118, Line 52, "said alkyl is 1 optionally" should be changed to "said alkyl is optionally"

Claim 2, Column 119, Line 8, "NR$^{102}$SO$_2$C$_{1-3}$ alkyl" should be changed to "NR$^{102}$SOC$_{1-3}$ alkyl"

Claim 3, Column 119, Line 41-42, "SiC(i-s alkyl)$_3$," should be changed to "Si(C$_{1-8}$ alkyl)$_3$,"